(12) United States Patent
Chen et al.

(10) Patent No.: US 10,493,070 B2
(45) Date of Patent: Dec. 3, 2019

(54) AZADECALIN DERIVATIVES AS INHIBITORS OF HUMAN IMMUNODEFICIENCY VIRUS REPLICATION

(71) Applicant: VIIV HEALTHCARE UK (NO. 5) LIMITED, Brentford, Middlesex (GB)

(72) Inventors: Jie Chen, Wallingford, CT (US); Nicholas A. Meanwell, Wallingford, CT (US); Alicia Regueiro-Ren, Wallingford, CT (US); Sing-Yuen Sit, Wallingford, CT (US); Jacob Swidorski, Wallingford, CT (US); Yan Chen, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 0 days.

(21) Appl. No.: 16/307,632

(22) PCT Filed: Jun. 28, 2017

(86) PCT No.: PCT/IB2017/053879
§ 371 (c)(1),
(2) Date: Dec. 6, 2018

(87) PCT Pub. No.: WO2018/002848
PCT Pub. Date: Jan. 4, 2018

(65) Prior Publication Data
US 2019/0209550 A1    Jul. 11, 2019

Related U.S. Application Data

(60) Provisional application No. 62/356,829, filed on Jun. 30, 2016.

(51) Int. Cl.
| | | |
|---|---|---|
| C07D 217/06 | (2006.01) | |
| C07D 401/12 | (2006.01) | |
| C07D 401/14 | (2006.01) | |
| C07D 405/12 | (2006.01) | |
| C07D 407/12 | (2006.01) | |
| C07D 413/12 | (2006.01) | |
| C07D 417/12 | (2006.01) | |
| C07D 453/00 | (2006.01) | |
| C07D 471/04 | (2006.01) | |
| C07D 471/08 | (2006.01) | |
| C07D 473/28 | (2006.01) | |
| C07D 487/04 | (2006.01) | |
| C07D 487/08 | (2006.01) | |
| C07D 491/056 | (2006.01) | |
| C07D 495/04 | (2006.01) | |
| A61K 31/4725 | (2006.01) | |
| A61K 31/496 | (2006.01) | |
| A61K 31/522 | (2006.01) | |
| A61K 31/53 | (2006.01) | |
| A61K 31/5365 | (2006.01) | |
| A61K 31/54 | (2006.01) | |

(Continued)

(52) U.S. Cl.
CPC ...... *A61K 31/4725* (2013.01); *A61K 31/4748* (2013.01); *A61K 31/496* (2013.01); *A61K 31/522* (2013.01); *A61K 31/53* (2013.01); *A61K 31/5365* (2013.01); *A61K 31/541* (2013.01); *A61K 45/06* (2013.01); *A61P 31/18* (2018.01); *C07D 217/06* (2013.01); *C07D 401/12* (2013.01); *C07D 401/14* (2013.01); *C07D 405/12* (2013.01); *C07D 407/12* (2013.01); *C07D 413/12* (2013.01); *C07D 417/12* (2013.01); *C07D 417/14* (2013.01); *C07D 453/00* (2013.01); *C07D 471/04* (2013.01); *C07D 471/08* (2013.01); *C07D 473/28* (2013.01); *C07D 487/04* (2013.01); *C07D 487/08* (2013.01); *C07D 491/056* (2013.01); *C07D 495/04* (2013.01)

(58) Field of Classification Search
CPC .. C07D 217/06; C07D 401/12; C07D 401/14; C07D 405/12; C07D 407/12; C07D 413/12; C07D 417/12; C07D 417/14; C07D 453/00; C07D 471/04; C07D 471/08; C07D 473/28; C07D 487/04; C07D 487/08; C07D 491/056; C07D 495/04; A61K 31/4725; A61K 31/4728; A61K 31/496; A61K 31/522; A61K 31/53; A61K 31/53645; A61K 31/54; A61K 45/06; A61P 31/18
See application file for complete search history.

(56) References Cited

U.S. PATENT DOCUMENTS

| | | | |
|---|---|---|---|
| 2012/0142707 A1 | 6/2012 | Regueiro-Ren | |
| 2014/0221361 A1 | 8/2014 | Swidorski | |
| 2016/0168100 A1* | 6/2016 | Atuegbu | ............. C07D 217/02 514/307 |

* cited by examiner

*Primary Examiner* — Timothy R Rozof
(74) *Attorney, Agent, or Firm* — Robert H. Brink; Kathryn A. Lutomski; Edward R. Gimmi

(57) ABSTRACT

Compounds having drug and bio-affecting properties, their pharmaceutical compositions and methods of use are set forth. In particular, azadecaline derivatives that possess unique antiviral activity are provided as HIV maturation inhibitors, as represented by compounds of Formula I:

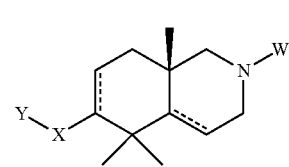

Formula I (Continued)

These compounds are useful for the treatment of HIV and AIDS.

8 Claims, No Drawings

(51) Int. Cl.
    *A61K 45/06*       (2006.01)
    *A61P 31/18*       (2006.01)
    *A61K 31/541*     (2006.01)
    *C07D 417/14*    (2006.01)
    *A61K 31/4748*   (2006.01)

AZADECALIN DERIVATIVES AS INHIBITORS OF HUMAN IMMUNODEFICIENCY VIRUS REPLICATION

This application is a § 371 of International Application No. PCT/IB2017/053879, filed 28 Jun. 2017, which claims the benefit of U.S. Provisional Application No. 62/356,829, filed 30 Jun. 2016.

FIELD OF THE INVENTION

The invention relates to compounds, compositions, and methods for the treatment of human immunodeficiency virus (HIV) infection. More particularly, the invention provides novel azadecalin derivatives as inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV infection remains a major medical problem, with an estimated 45-50 million people infected worldwide at the end of 2011, 3.3 million of them under the age of 15. In 2011, there were 2.5 million new infections, and 1.7 million deaths from complications due to HIV/AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads >500 copies/mL (Oette, M, Kaiser, R, Daumer, M, et al. Primary HIV Drug Resistance and Efficacy of First-Line Antiretroviral Therapy Guided by Resistance Testing. J Acq Imm Def Synd 2006; 41(5):573-581). Among these patients, 76% had viruses that were resistant to one or more classes of antiretroviral agents. As a result, new drugs are needed that are easier to take, have high genetic barriers to the development of resistance and have improved safety over current agents. In this panoply of choices, novel MOAs that can be used as part of the preferred highly active antiretroviral therapy (HAART) regimen can still have a major role to play since they should be effective against viruses resistant to current agents.

Certain therapeutic compounds are disclosed in WO 2013/006738, WO 2014/110298, and WO 2014/134566.

What is now needed in the art are additional compounds which are novel and useful in the treatment of HIV. Additionally, these compounds may desirably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

In one aspect of the invention, there is provided a compound of Formula I, including pharmaceutically acceptable salts thereof:

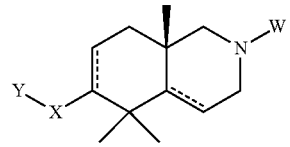

Formula I wherein X is a phenyl or heteroaryl ring optionally substituted with $R_1$;

$R_1$ is —H, -halo, -hydroxyl, —$C_{1-6}$alkyl, —$C_{1-6}$ alkoxy, —$CF_3$, and —$COOR_2$;

$R_2$ is —H, —$C_{1-6}$ alkyl, -alkylsubstituted $C_{1-6}$ alkyl or -arylsubstituted $C_{1-6}$ alkyl;

Y is selected from —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_2$— alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and —$CONHOH$, wherein n is 1-6;

W is selected from —$C_{1-6}$alkyl, -substituted $C_{1-6}$alkyl, —$C_{3-16}$ carbocycle, -substituted $C_{3-16}$ carbocycle, —$C_{3-16}$ heterocycle, -substituted $C_{3-16}$ hetereocycle, -aryl, -substituted aryl, -heteroaryl, -substituted heteroaryl, —$COC_{1-6}$alkyl, —$CO$substituted$C_{1-6}$alkyl, —$CO$—$C_{3-16}$ carbocycle, —$CO$substituted $C_{3-16}$ carbocycle, —$COC_{3-16}$ heterocycle, —$CO$substituted $C_{3-16}$ hetereocycle, —$CO$aryl, —$CO$substituted aryl, —$CO$heteroaryl, —$CO$substituted heteroaryl, —$COCOC_{1-6}$alkyl, —$COCO$substituted $C_{1-6}$alkyl, —$COCO$—$C_{3-16}$ carbocycle, —$COCO$substituted $C_{3-16}$ carbocycle, —$COCOC_{3-16}$ heterocycle, —$CO$-$CO$substituted $C_{3-16}$ hetereocycle, —$COCO$aryl, —$COCO$-substituted aryl, —$COCO$heteroaryl, —$COCO$substituted heteroaryl, wherein said carbocycles, heterocycles, aryls, and heteroaryls defined herein for W are further selected from monocyclic, bicyclic, and tricyclic systems, wherein the bicyclic and tricyclic systems are further selected from fused, non-fused, and spiro systems and wherein said substituents on those that are substituted are further selected from —H, -halo, -hydroxyl, —NO$_2$, —CN, —C$_{1-6}$ alkyl, —OQ$_1$, —C$_{1-6}$ alkoxy, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O—C$_{1-6}$ alkyl Q$_1$ Q$_1$ is selected from C$_{3-16}$ carbocycle, substituted C$_{3-16}$ carbocycle, C$_{3-16}$ heterocycle, substituted C$_{3-16}$ hetereocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and Spiro systems and wherein said substituents are further selected from —H, -halo, -hydroxyl, —NO$_2$, —CN, —C$_{1-6}$ alkyl, —C$_{1-6}$ alkoxy, —CF$_3$, —COOR$_2$, —NR$_3$R$_4$; —COR, —COOR, —SO$_2$, and —SO$_2$NR$_3$R$_4$;

alternatively, W is selected from —CO—V, wherein V is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$-hetereocycle, -aryl, -substituted aryl, -heteroaryl, -substituted heteroaryl, wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —OQ$_1$, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO—C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$;

and R$_3$ and R$_4$ are independently selected from —H, —C$_{1-6}$ alkyl, —C$_{1-6}$ substituted alkyl, aryl, heteroaryl, substituted aryl, substituted heteroaryl, and —COOR$_2$;

alternatively R$_3$ and R$_4$ are taken together with the adjacent N to form a cycle selected from:

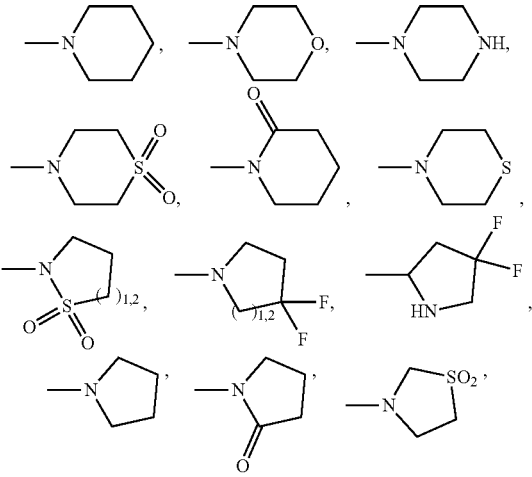

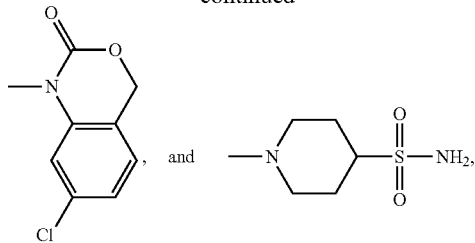

with the proviso that only one of R$_3$ or R$_4$ can be —COOR$_2$.

The invention also relates to pharmaceutical compositions comprising the compounds of the invention, including pharmaceutically acceptable salts thereof, and a pharmaceutically acceptable carrier, excipient, and/or diluent.

In addition, the invention provides one or more methods of treating HIV infection comprising administering a therapeutically effective amount of the compounds of the invention to a patient.

Also provided as part of the invention are one or more methods for making the compounds of the invention.

The present invention is directed to these, as well as other important ends, hereinafter described.

DETAILED DESCRIPTION OF THE INVENTION

The singular forms "a", "an", and "the" include plural reference unless the context dictates otherwise.

Unless otherwise expressly set forth elsewhere in the application, the following terms shall have the following meanings:

"Alkenyl" means a straight or branched alkyl group comprised of 2 to 10 carbons with at least one double bond and optionally substituted with 0-3 halo or alkoxy group.

"Alkenyloxy" means an alkenyl group attached to the parent structure by an oxygen atom.

"Alkoxy" means an alkyl group attached to the parent structure by an oxygen atom.

"Alkoxycarbonyl" means an alkoxy group attached to the parent structure by a carbonyl moiety.

"Alkyl" means a straight or branched saturated hydrocarbon comprised of 1 to 10 carbons, and preferably 1 to 6 carbons.

"Alkylthioxy" means an alkyl group attached to the parent structure through a sulfur atom.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of C$_3$ to C$_7$ alkyl group. Examples of aromatic group include, but are not limited to, phenyl, biphenyl, cyclopropylphenyl, indane, naphthalene, and tetrahydronaphthalene. The aryl group can be attached to the parent structure through any substitutable carbon atom in the group.

"Arylalkyl" is a C$_1$-C$_5$ alkyl group attached to 1 to 2 aryl groups and linked to the parent structure through the alkyl moiety. Examples include, but are not limited to, —(CH$_2$)$_n$Ph with n is 1-5, —CH(CH$_3$)Ph, —CH(Ph)$_2$.

"Aryloxy" is an aryl group attached to the parent structure by oxygen.

"Azaindole" means one of the "CH" moieties in the 6-member ring of an indole is substituted with a nitrogen atom.

"Azaindoline" means one of the aromatic "CH" moieties of an indoline is substituted with a nitrogen atom.

"Azatetrahydroquinoline" means any aromatic CH moiety of tetrahydroquinoline is substituted with a nitrogen atom.

"Benzyloxy" means a benzyl group is attached to the parent structure through an oxygen atom. The phenyl group of the benzyl moiety could be optionally substituted by 1-3 moieties independently selected from alkyl, alkoxy, halo, haloalkyl, haloalkoxy and cyano.

"$C_x$-$C_y$" notation indicates a structural element comprised of carbons numbering between 'x' and 'y'. For example, "$C_5$-$C_{10}$ bicycloalkyl" means a bicyclic ring system comprised of 5 to 10 carbons, where the rings are attached in a fused, Spiro or bridged manner; an example of $C_5$-$C_{10}$ bicycloalkyl include, but is not limited to, bicyclo[2.2.2]octane. Similarly, "$C_3$-$C_4$ cycloalkyl" is a subset of monocyclic ring system comprised of 3 to 4 carbons.

"Cycloalkyl" means a monocyclic ring system comprised of 3 to 7 carbons.

"Cyano" refers to —CN.

"Diazaindole" means any two "CH" moieties in the 6-member ring of an indole are substituted with nitrogen atoms.

"Diazaindoline" means any two aromatic "CH" moieties of an indoline are substituted with a nitrogen atom.

"Diazatetrahydroquinoline" means any two aromatic CH moieties of tetrahydroquinoline are substituted with nitrogen atoms.

"Halo" or "halogen" refers to —F, —Cl, —Br, or —I.

"Haloalkyl" means an alkyl group substituted by any combination of one to six halogen atoms.

"Haloalkoxy" or "Haloalkyloxy" means a haloalkyl group attached to the parent structure through an oxygen atom.

"Hydroxy" refers to —OH.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or Spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo [2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —(CH$_2$)$_n$—R$^Z$ or —CH(CH$_3$)—(R$^Z$) where n is 1-5 and that R$^Z$ is chosen from benzimidazole, imidazole, indazole, isooxazole, phenylpyrazole, pyridine, quinoline, thiazole, triazole, triazolone, oxadiazole.

The compounds of the present invention can be referred to as azadecalin derivatives, as they generally contain a fused 10-membered ring structure containing a nitrogen atom. The structures for decalin and an azadecalin are shown for reference immediately below.

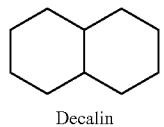 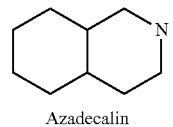

Decalin      Azadecalin

With respect to the azadecalin derviatives of the present invention, it should be noted that for Formula I, the structures are represented with dotted lines for some of the bonds. This convention with the dotted lines is to indicate that the bond at the indicated site can independently be selected from a single bond or a double bond. See, below the representation for Formula I where these bonds are shown with the dotted line notation.

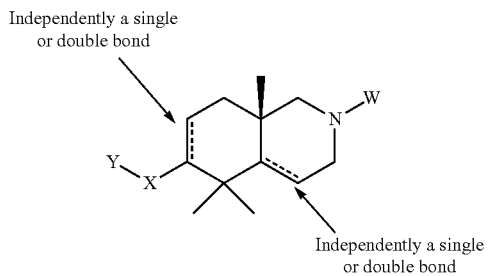

Formula I

Independently a single or double bond

Independently a single or double bond

"Tetrahydroquinoline" means 1,2,3,4-tetrahydroquinoline.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

For the sake of efficiency some ring structures are shown with a variable number of members in the ring. For example, the following ring substituent

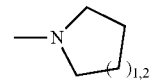

having the parenthetical "$()_{1,2}$" is intended to encompass both a single carbon group, —($CH_2$)—, and a two carbon group, —($CH_2CH_2$)—. The intended ring structures could individually be depicted as:

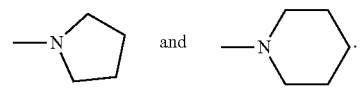

The compounds of the invention also include "prodrugs". The term "prodrug" as used herein encompasses both the term "prodrug esters" and the term "prodrug ethers".

In an aspect of the invention, there is provided a compound of Formula I, including pharmaceutically acceptable salts thereof:

Formula I

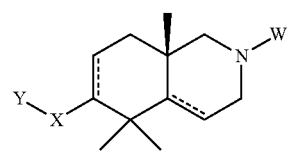

wherein X is a phenyl or heteroaryl ring optionally substituted with $R_1$;
$R_1$ is —H, -halo, -hydroxyl, —$C_{1-6}$ alkyl, —$C_{1-6}$ alkoxy, —$CF_3$, and —$COOR_2$;
$R_2$ is —H, —$C_{1-6}$ alkyl, -alkylsubstituted $C_{1-6}$ alkyl or -arylsubstituted $C_{1-6}$ alkyl;
Y is selected from —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and —$CONHOH$, wherein n is 1-6;
W is selected from —$C_{1-6}$alkyl, -substituted $C_{1-6}$alkyl, —$C_{3-16}$ carbocycle, -substituted $C_{3-16}$ carbocycle, —$C_{3-16}$ heterocycle, -substituted $C_{3-16}$ hetereocycle, -aryl, -substituted aryl, -heteroaryl, -substituted heteroaryl, —$COC_{1-6}$alkyl, —$COsubstitutedC_{1-6}$alkyl, —$CO$—$C_{3-16}$ carbocycle, —$CO$substituted $C_{3-16}$ carbocycle, —$COC_{3-16}$ heterocycle, —$CO$substituted $C_{3-16}$ hetereocycle, —$CO$aryl, —$CO$substituted aryl, —$CO$heteroaryl, —$CO$substituted heteroaryl, —$COCOC_{1-6}$alkyl, —$COCO$substituted $C_{1-6}$alkyl, —$COCO$—$C_{3-16}$ carbocycle, —$COCO$substituted $C_{3-16}$ carbocycle, —$COCOC_{3-16}$ heterocycle, —$CO$-$CO$substituted $C_{3-16}$ hetereocycle, —$COCO$aryl, —$COCO$-substituted aryl, —$COCO$heteroaryl, —$COCO$substituted heteroaryl,
wherein said carbocycles, heterocycles, aryls, and heteroaryls defined herein for W are further selected from monocyclic, bicyclic, and tricyclic systems, wherein the bicyclic and tricyclic systems are further selected from fused, non-fused, and spiro systems and wherein said substituents on those that are substituted are further selected from —H, -halo, -hydroxyl, —NO$_2$, —CN, —C$_{1-6}$ alkyl, —OQ$_1$, —C$_{1-6}$ alkoxy, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O—C$_{1-6}$ alkyl Q$_1$ Q$_1$ is selected from C$_{3-16}$ carbocycle, substituted C$_{3-16}$ carbocycle, C$_{3-16}$ heterocycle, substituted C$_{3-16}$ hetereocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —CF$_3$, —COOR$_2$, —NR$_3$R$_4$; —COR, —COOR, —SO$_2$, and —SO$_2$NR$_3$R$_4$;

alternatively, W is selected from —CO—V, wherein V is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$-hetereocycle, -aryl, -substituted aryl, -heteroaryl, -substituted heteroaryl, wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —OQ$_1$, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$;

and R$_3$ and R$_4$ are independently selected from —H, —C$_{1-6}$ alkyl, —C$_{1-6}$ substituted alkyl, aryl, heteroaryl, substituted aryl, substituted heteroaryl, and —COOR$_2$;

alternatively R$_3$ and R$_4$ are taken together with the adjacent N to form a cycle selected from:

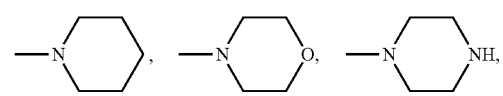

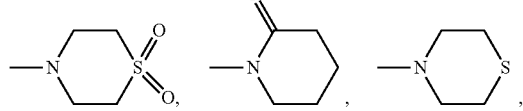

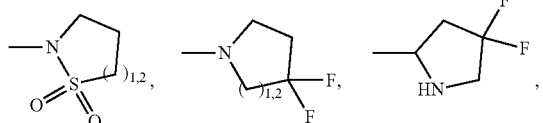

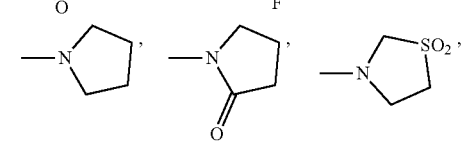

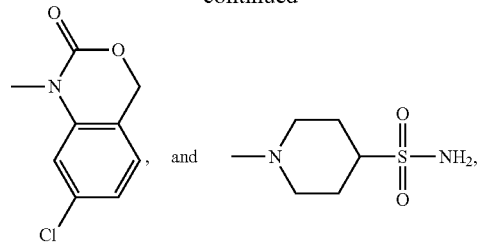

with the proviso that only one of R$_3$ or R$_4$ can be —COOR$_2$.

In an aspect of the invention, there is provided a compound of Formula I, wherein X is phenyl.

In an aspect of the invention, there is provided a compound of Formula I, wherein Y is —COOR$_2$.

In an aspect of the invention, there is provided a compound of Formula I, wherein Y is —COOH.

In an aspect of the invention, there is provided a compound of Formula I, wherein R$_1$ is H.

In an aspect of the invention, there is provided a compound of Formula I, wherein W is —COV.

In an aspect of the invention, there is provided a compound of

Formula II,

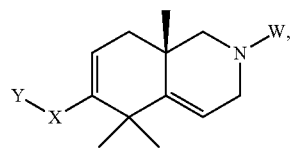

Formula II

Formula III,

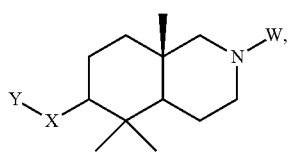

Formula III

Formula IV,

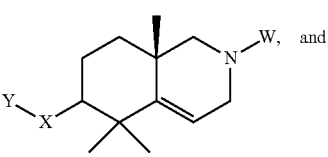

Formula IV, and

Formula V

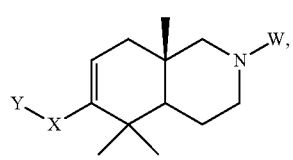

Formula V including pharmaceutically acceptable salts thereof:
wherein X is a phenyl or heteroaryl ring optionally substituted with R$_1$;
R$_1$ is —H, -halo, -hydroxyl, —C$_{1-6}$alkyl, —C$_{1-6}$ alkoxy, —CF$_3$, and —COOR$_2$;
R$_2$ is —H, —C$_{1-6}$ alkyl, -alkylsubstituted C$_{1-6}$ alkyl or -arylsubstituted C$_{1-6}$alkyl;

Y is selected from —COOR$_2$, —C(O)NR$_2$SO$_2$R$_3$,—C(O) NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, and —CONHOH, wherein n is 1-6;

W is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$ hetereocycle, -aryl, -substituted aryl, -heteroaryl, -substituted heteroaryl, —COC$_{1-6}$alkyl, —COsubstitutedC$_{1-6}$alkyl, —CO—C$_{3-16}$ carbocycle, —COsubstituted C$_{3-16}$ carbocycle, —COC$_{3-16}$ heterocycle, —COsubstituted C$_{3-16}$ hetereocycle, —COaryl, —COsubstituted aryl, —COheteroaryl, —COsubstituted heteroaryl, —COCOC$_{1-6}$alkyl, —COCOsubstituted C$_{1-6}$alkyl, —COCO—C$_{3-16}$ carbocycle, —COCOsubstituted C$_{3-16}$ carbocycle, —COCOC$_{3-16}$ heterocycle, —CO-COsubstituted C$_{3-16}$ hetereocycle, —COCOaryl, —COCO-substituted aryl, —COCOheteroaryl, —COCOsubstituted heteroaryl,
wherein said carbocycles, heterocycles, aryls, and heteroaryls defined herein for W are further selected from monocyclic, bicyclic, and tricyclic systems, wherein the bicyclic and tricyclic systems are further selected from fused, non-fused, and spiro systems and wherein said substituents on those that are substituted are further selected from —H, -halo, -hydroxyl, —NO$_2$, —CN, —C$_{1-6}$alkyl, —OQ$_1$, —C$_{1-6}$ alkoxy, —CF$_3$, —COOR$_2$, —NR$_3$R$_4$; —COR, —COOR, —SO$_2$, —SO$_2$NR$_3$R$_4$, and —C$_{1-6}$alkylQ$_1$, —C$_{1-6}$ alkyl-CO— C$_{1-6}$ alkyl Q$_1$, —C$_{1-6}$alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO—C$_{1-6}$ alkyl Q$_1$, —C$_{1-6}$ alkyl-CONR$_3$— C$_{1-6}$ alkyl Q$_1$, —C$_{2-6}$ alkyl-O—C$_{1-6}$ alkyl Q$_1$ Q$_1$ is selected from C$_{3-16}$ carbocycle, substituted C$_{3-16}$ carbocycle, C$_{3-16}$ heterocycle, substituted C$_{3-16}$ hetereocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$alkyl, —C$_{1-6}$ alkoxy, —CF$_3$, —COOR$_2$, —NR$_3$R$_4$; —COR, —COOR, —SO$_2$, and —SO$_2$NR$_3$R$_4$;

alternatively, W is selected from —CO—V, wherein V is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$-hetereocycle, -aryl, -substituted aryl, -heteroaryl, -substituted heteroaryl,
wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$alkyl, —C$_{1-6}$ alkoxy, —OQ$_1$, —CF$_3$, —COOR$_2$, —NR$_3$R$_4$; —COR, —COOR, —SO$_2$, —SO$_2$NR$_3$R$_4$, and —C$_{1-6}$alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$;

and R$_3$ and R$_4$ are independently selected from —H, —C$_{1-6}$ alkyl, —C$_{1-6}$ substituted alkyl, aryl, heteroaryl, substituted aryl, substituted heteroaryl, and —COOR$_2$;

alternatively R$_3$ and R$_4$ are taken together with the adjacent N to form a cycle selected from:

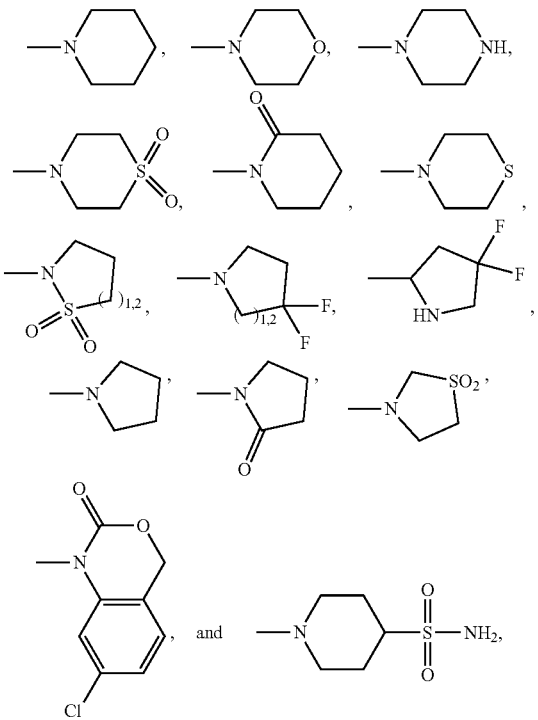

with the proviso that only one of R$_3$ or R$_4$ can be —COOR$_2$.

In an aspect of the invention, there is provided a compound of Formula II, including pharmaceutically acceptable salts thereof:

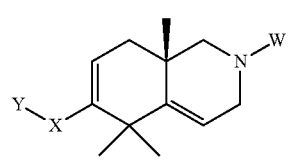

Formula II wherein X is a phenyl or heteroaryl ring optionally substituted with R$_1$;

R$_1$ is —H, -halo, -hydroxyl, —C$_{1-6}$ alkyl, —C$_{1-6}$ alkoxy, —CF$_3$, and —COOR$_2$;

R$_2$ is —H, —C$_{1-6}$ alkyl, -alkylsubstituted C$_{1-6}$ alkyl or -arylsubstituted C$_{1-6}$ alkyl;

Y is selected from —COOR$_2$, —C(O)NR$_2$SO$_2$R$_3$,—C(O) NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, and —CONHOH, wherein n is 1-6;

W is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$ hetereocycle, -aryl, -substituted aryl, -heteroaryl, -substituted heteroaryl, —COC$_{1-6}$alkyl, —COsubstitutedC$_{1-6}$alkyl, —CO—C$_{3-16}$ carbocycle, —COsubstituted C$_{3-16}$ carbocycle, —COC$_{3-16}$ heterocycle, —COsubstituted C$_{3-16}$ hetereocycle, —COaryl, —COsubstituted aryl, —COheteroaryl, —COsubstituted heteroaryl, —COCOC$_{1-6}$alkyl, —COCOsubstituted C$_{1-6}$alkyl, —COCO—C$_{3-16}$ carbocycle, —COCOsubstituted C$_{3-16}$ carbocycle, —COCOC$_{3-16}$ heterocycle, —COCOsubstituted C$_{3-16}$ hetereocycle, —COCOaryl, —COCOsubstituted aryl, —COCOheteroaryl, —COCOsubstituted heteroaryl, wherein said carbocycles, heterocycles, aryls, and heteroaryls defined herein for W are further selected from monocyclic, bicyclic, and tricyclic systems, wherein the bicyclic and tricyclic systems are further selected from fused, non-fused, and spiro systems and wherein said substituents on those that are substituted are further selected from —H, -halo, -hydroxyl, —NO$_2$, —CN, —C$_{1-6}$ alkyl, —OQ$_1$, —C$_{1-6}$ alkoxy, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$—C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$ Q$_1$ is selected from C$_{3-16}$ carbocycle, substituted C$_{3-16}$ carbocycle, C$_{3-16}$ heterocycle, substituted C$_{3-16}$ hetereocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —CF$_3$, —COOR$_2$, —NR$_3$R$_4$; —COR, —COOR, —SO$_2$, and —SO$_2$NR$_3$R$_4$;

alternatively, W is selected from —CO—V, wherein V is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$-hetereocycle, -aryl, -substituted aryl, -heteroaryl, -substituted heteroaryl, wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —OQ$_1$, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$;

and R$_3$ and R$_4$ are independently selected from —H, —C$_{1-6}$ alkyl, —C$_{1-6}$ substituted alkyl, aryl, heteroaryl, substituted aryl, substituted heteroaryl, and —COOR$_2$;

alternatively R$_3$ and R$_4$ are taken together with the adjacent N to form a cycle selected from:

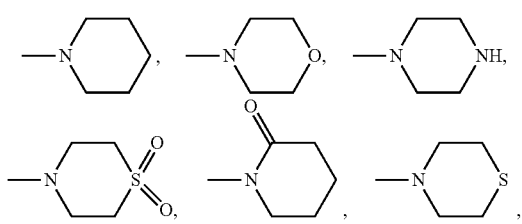

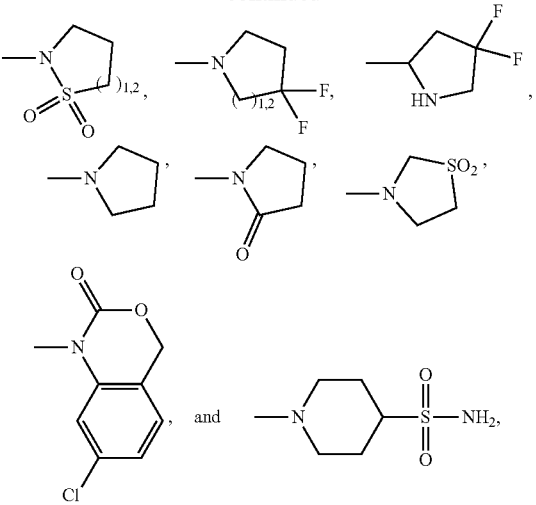

with the proviso that only one of R$_3$ or R$_4$ can be —COOR$_2$.

In an aspect of the invention, there is provided a compound of

Formula VI,

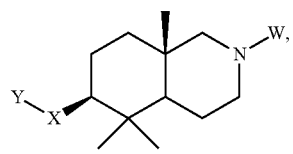

Formula VI

Formula VII,

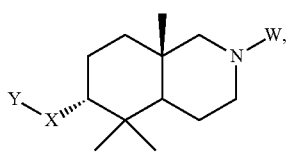

Formula VII

Formula VIII,

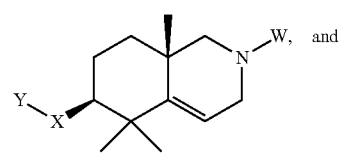

Formula VIII and

Formula IX,

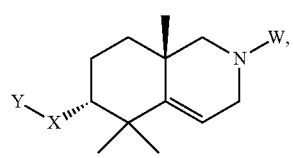

Formula IX including pharmaceutically acceptable salts thereof:

wherein X is a phenyl or heteroaryl ring optionally substituted with R$_1$;

R$_1$ is —H, -halo, -hydroxyl, —C$_{1-6}$ alkyl, —C$_{1-6}$ alkoxy, —CF$_3$, and —COOR$_2$;

R$_2$ is —H, —C$_{1-6}$ alkyl, -alkylsubstituted C$_{1-6}$ alkyl or -arylsubstituted C$_{1-6}$ alkyl;

Y is selected from —COOR$_2$, —C(O)NR$_2$SO$_2$R$_3$, —C(O)NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, and —CONHOH, wherein n is 1-6;

W is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$ hetereocycle, -aryl, -substituted aryl, -heteroaryl, -substituted heteroaryl, —COC$_{1-6}$alkyl, —COsubstitutedC$_{1-6}$alkyl, —CO—C$_{3-16}$ carbocycle, —COsubstituted C$_{3-16}$ carbocycle, —COC$_{3-16}$ heterocycle, —COsubstituted C$_{3-16}$ hetereocycle, —COaryl, —COsubstituted aryl, —COheteroaryl, —COsubstituted heteroaryl, —COCOC$_{1-6}$alkyl, —COCOsubstitutedC$_{1-6}$alkyl, —COCO—C$_{3-16}$ carbocycle, —COCOsubstituted C$_{3-16}$ carbocycle, —COCOC$_{3-16}$ heterocycle, —COCOsubstituted C$_{3-16}$ hetereocycle, —COCOaryl, —COCOsubstituted aryl, —COCOheteroaryl, —COCOsubstituted heteroaryl, wherein said carbocycles, heterocycles, aryls, and heteroaryls defined herein for W are further selected from monocyclic, bicyclic, and tricyclic systems, wherein the bicyclic and tricyclic systems are further selected from fused, non-fused, and spiro systems and wherein said substituents on those that are substituted are further selected from —H, -halo, -hydroxyl, —NO$_2$, —CN, —C$_{1-6}$ alkyl, —OQ$_1$, —C$_{1-6}$ alkoxy, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$—C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO—C$_{1-6}$ alkyl Q$_1$, —C$_{1-6}$ alkyl-CONR$_3$—C$_{1-6}$ alkyl Q$_1$, —C$_{2-6}$ alkyl-O—C$_{1-6}$ alkyl Q$_1$ Q$_1$ is selected from C$_{3-16}$ carbocycle, substituted C$_{3-16}$ carbocycle, C$_{3-16}$ heterocycle, substituted C$_{3-16}$ hetereocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —CF$_3$, —COOR$_2$, —NR$_3$R$_4$; —COR, —COOR, —SO$_2$, and —SO$_2$NR$_3$R$_4$;

alternatively, W is selected from —CO—V, wherein V is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$-hetereocycle, -aryl, -substituted aryl, -heteroaryl, -substituted heteroaryl, wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and Spiro systems and wherein said substituents are further selected from —H, -halo, -hydroxyl, —NO$_2$, —CN, —C$_{1-6}$ alkyl, —C$_{1-6}$ alkoxy, —OQ$_1$, —CF$_3$, —COOR$_2$, —NR$_3$R$_4$; —COR, —COOR, —SO$_2$, —SO$_2$NR$_3$R$_4$, and —C$_{1-6}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO—C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$;

and R$_3$ and R$_4$ are independently selected from —H, —C$_{1-6}$ alkyl, —C$_{1-6}$ substituted alkyl, aryl, heteroaryl, substituted aryl, substituted heteroaryl, and —COOR$_2$;

alternatively R$_3$ and R$_4$ are taken together with the adjacent N to form a cycle selected from:

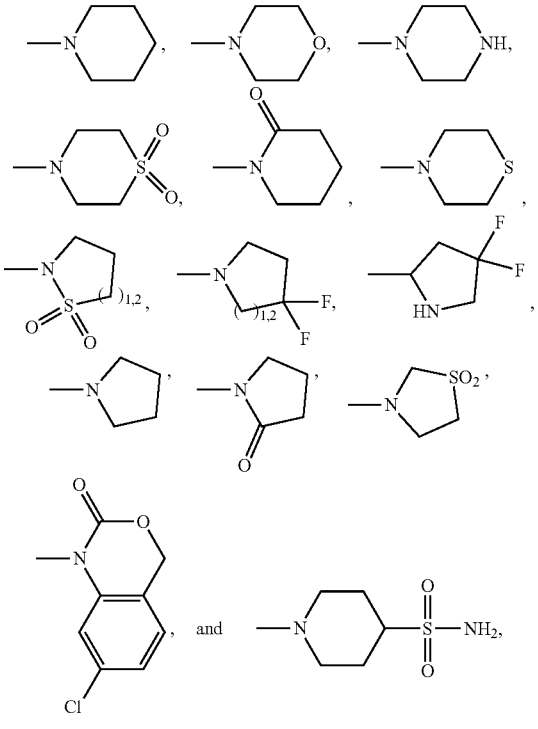

with the proviso that only one of R$_3$ or R$_4$ can be —COOR$_2$.

In an aspect of the invention, there is provided a compound of Formula X, including pharmaceutically acceptable salts thereof:

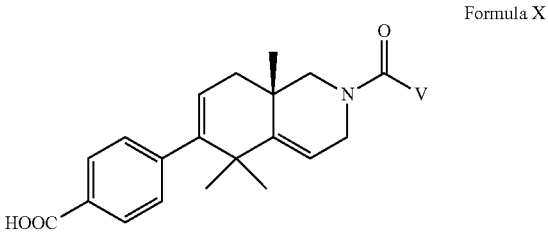

Formula X wherein V is selected from —C$_{1-6}$alkyl, -substituted C$_{1-6}$alkyl, —C$_{3-16}$ carbocycle, -substituted C$_{3-16}$ carbocycle, —C$_{3-16}$ heterocycle, -substituted C$_{3-16}$-hetereocycle, -aryl, -substituted aryl, -heteroaryl, -substituted heteroaryl, wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —NO$_2$, —CN, —C$_{1-6}$ alkyl, —C$_{1-6}$ alkoxy, —OQ$_1$, —CF$_3$, —COOR$_2$, —NR$_3$R$_4$; —COR, —COOR, —SO$_2$, —SO$_2$NR$_3$R$_4$, and —C$_{1-5}$ alkylQ$_1$, —C$_{1-6}$ alkyl-CO— C$_{1-6}$ alkyl Q$_1$, —C$_{1-6}$ alkyl-NR$_3$— C$_{1-6}$ alkyl Q$_1$, —C$_{1-6}$ alkyl-SO$_2$C$_{1-6}$ alkyl Q$_1$, —C$_{1-6}$ alkyl-SO$_2$NR$_3$— C$_{1-6}$ alkyl Q$_1$, —C$_{1-6}$ alkyl-NR$_3$SO$_2$— C$_{1-6}$ alkyl Q$_1$, —C$_{1-6}$ alkyl-NR$_3$CO— C$_{1-6}$ alkyl Q$_1$, —C$_{1-6}$ alkyl-CONR$_3$— C$_{1-6}$ alkyl Q$_1$, —C$_{2-6}$ alkyl-O— C$_{1-6}$ alkyl Q$_1$;

$Q_1$ is selected from $C_{3-16}$ carbocycle, substituted $C_{3-16}$ carbocycle, $C_{3-16}$ heterocycle, substituted $C_{3-16}$ hetereocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —$NO_2$, —CN, —$C_{1-6}$ alkyl, —$C_{1-6}$ alkoxy, —$CF_3$, —$COOR_2$, —$NR_3R_4$; —COR, —COOR, —$SO_2$, and —$SO_2NR_3R_4$;

and $R_3$ and $R_4$ are independently selected from —H, —$C_{1-6}$ alkyl, —$C_{1-6}$ substituted alkyl, aryl, heteroaryl, substituted aryl, substituted heteroaryl, and —$COOR_2$;

alternatively $R_3$ and $R_4$ are taken together with the adjacent N to form a cycle selected from:

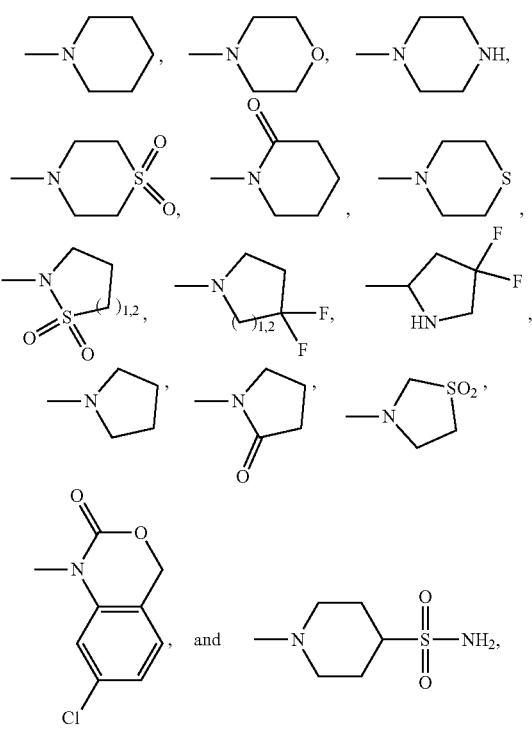

with the proviso that only one of $R_3$ or $R_4$ can be —$COOR_2$.

In an aspect of the invention, there is provided a compound, including pharmaceutically acceptable salts thereof, which is selected from a compound as disclosed in Table 11, Table 12, Table 13, or Table 17.

In an aspect of the invention, there is provided a composition useful for treating HIV infection comprising a therapeutic amount of a compound of Formula I-X and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, $CXCR_4$ inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I-X, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I-X.

Pharmaceutical Compositions and Methods of Use

The compounds of the invention herein described and set forth are generally given as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 mg/kg body weight daily. Generally, more compound is required orally and less parenterally. The specific dosing regimen, however, will be determined by a physician using sound medical judgment.

The compounds of this invention desirably have activity against HIV. Accordingly, another aspect of the invention is a method for treating HIV infection in a human patient comprising administering a therapeutically effective amount of a compound of Formula I, including a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, $CXCR_4$ inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

"Combination," "coadministration," "concurrent" and similar terms referring to the administration of a compound of Formula I with at least one anti-HIV agent mean that the components are part of a combination antiretroviral therapy or HAART as understood by practitioners in the field of AIDS and HIV infection.

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRALS | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |

-continued

| Drug Name | Manufacturer | Indication |
|---|---|---|
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA®) (-)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium | Astra Pharm. | CMV retinitis, HIV |

-continued

| Drug Name | Manufacturer | Indication |
|---|---|---|
| Phosphonoformate | Products, Inc. | infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |

-continued

| Drug Name | Manufacturer | Indication |
|---|---|---|
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon | Hoffman-La Roche | Kaposi's sarcoma |

| Drug Name | Manufacturer | Indication |
|---|---|---|
| Alfa 2a | | AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

"Therapeutically effective" means the amount of agent required to provide a meaningful patient benefit as understood by practitioners in the field of AIDS and HIV infection. In general, the goals of therapeutically effective treatment include suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

Methods of Synthesis

The compounds of the invention according to the various aspects can be made by various methods available in the art, including those of the following schemes in the specific examples which follow. The structure numbering and variable numbering shown in the synthetic schemes may be distinct from, and should not be confused with, the structure or variable numbering in the claims or the rest of the specification. The variables in the schemes are meant only to illustrate how to make some of the compounds of the invention.

Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "4" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

EXAMPLES

The following examples illustrate typical syntheses of the compounds of Formulas I to X, as described generally above. These examples are illustrative only and are not intended to limit the disclosure in any way. The reagents and starting materials are readily available to one of ordinary skill in the art.

Chemistry
Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: $CDCl_3$ ($δ_H$ 7.26), $CD_3OD$ ($δ_H$ 3.30), Acetic-d4 (Acetic Acid $d_4$) ($δ_H$ 11.6, 2.07), DMSO mix or DMSO-D6_$CDCl_3$ (($_H$ 2.50 and 8.25) (ratio 75%:25%), and DMSO-D6 ($δ_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

Section 1
LCMS Methods:
Method 1
Start % B=0, Final % B=100
Gradient Time=0.5 min hold at 0% B, 0-100% B over 4 min, 0.5 min hold at 100% B
Flow Rate=0.5 ml/min
Wavelength=220
Solvent A=5% MeOH—95% $H_2O$—10 mM Ammonium Acetate
Solvent B=95% MeOH—5% $H_2O$—10 mM Ammonium Acetate
Column=Waters BEH C18 2.0×50 mm 1.7 um
Method 2
Start % B=30, Final % B=100
Gradient Time=2 min
Flow Rate=0.8 ml/min
Wavelength=220
Solvent A=10% MeOH—90% $H_2O$—0.1% TFA
Solvent B=90% MeOH-10% $H_2O$-0.1% TFA
Column=Xbridge C8 2.1×50 mm 2.5 um
Method 3
Start % B=30, Final % B=100
Gradient Time=2 min
Flow Rate=1 ml/min
Wavelength=220
Solvent A=5% MeOH: 95% Water: 10 mM Ammonium Actetate
Solvent B=95% MeOH: 5% Water: 10 mM Ammonium Actetate
Column=Phenomenex LUNA C18, 30×2, 3 u
Method 4
Start % B=30, Final % B=100
Gradient Time=2 min
Flow Rate=1 ml/min
Wavelength=220
Solvent A=10% MeOH-90% $H_2O$-0.1% TFA
Solvent B=90% MeOH-10% $H_2O$-0.1% TFA
Column=PHENOMENEX-LUNA 2.0×30 mm 3 um
Method 5
Start % B=0, Final % B=100
Gradient Time=2 min
Flow Rate=1 ml/min
Wavelength=220
Solvent A=10% MeOH-90% $H_2O$-0.1% TFA
Solvent B=90% MeOH-10% $H_2O$-0.1% TFA
Column=PHENOMENEX-LUNA 2.0×30 mm 3 um
Method 6
Start % B=30, Final % B=100
Gradient Time=2 min
Flow Rate=8 ml/min
Wavelength=220
Solvent A=10% MeOH-90% $H_2O$-0.1% TFA
Solvent B=90% MeOH-10% $H_2O$-0.1% TFA
Column=Xbridge Phenyl 2.1×50 mm 2.5 um
Method 7
Waters Acquity SDS; Run Time: 5.00 min
Solvent Name A: Water; Solvent Name B: Methanol

| [Gradient Table] | Time(min) | Flow Rate | % A | % B | Curve |
|---|---|---|---|---|---|
| 1 | Initial | 0.500 | 100.0 | 0.00 | |
| 2 | 0.50 | 0.500 | 100.0 | 0.00 | 6 |
| 3 | 4.50 | 0.500 | 0.00 | 100.0 | 6 |
| 4 | 5.00 | 0.500 | 0.00 | 100.0 | 6 |
| 5 | 5.02 | 0.500 | 100.00 | 0.00 | 6 |
| 6 | 5.50 | 0.500 | 100.0 | 0.00 | |

Method 8
Start % B=0, Final % B=100
Gradient Time=2 min
Flow Rate=1 ml/min
Wavelength=220
Solvent A=5% MeOH-95% $H_2O$-10 mM Ammonium Acetate
Solvent B=95% MeOH-5% $H_2O$-10 mM Ammonium Acetate
Column=Phenomenex LUNA C18, 30×2, 3 u
Method 9
Start % B=10, Final % B=100
Gradient Time=2 min
Flow Rate=0.8 ml/min
Wavelength=220
Solvent A=10% MeOH-90% $H_2O$-0.1% TFA Solvent B=90% MeOH-10% H$_2$O-0.1% TFA
Column=Xbridge Phenyl 2.1×50 mm 2.5 um

PREPARATION OF INTERMEDIATES

Intermediate 1: Methyl (S)-4-(5,5,8a-trimethyl-1,2,3,5,8,8a-hexahydroisoquinolin-6-yl)benzoate hydrochloride

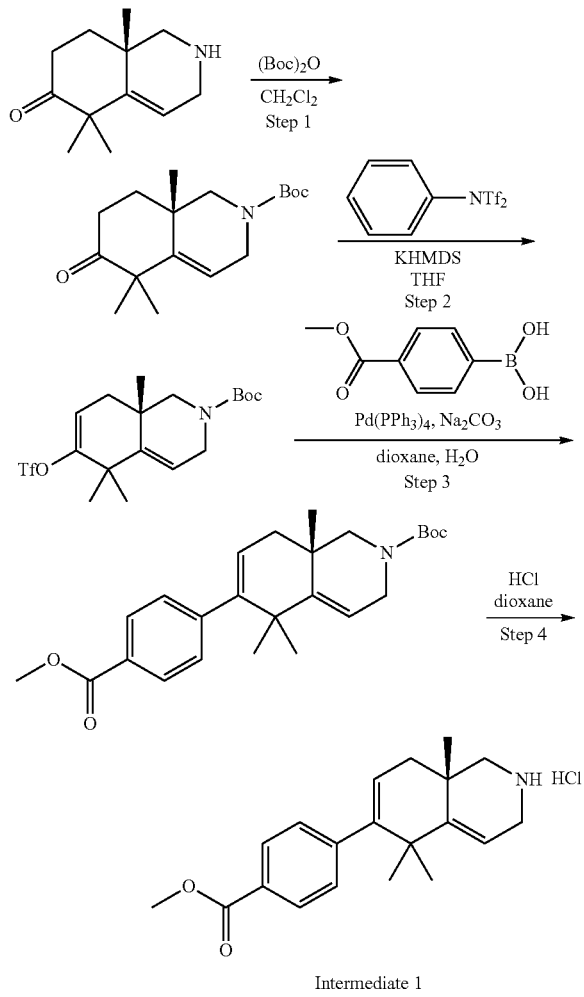

Intermediate 1

Step 1: Preparation of tert-butyl (S)-5,5,8a-trimethyl-6-oxo-3,5,6,7,8,8a-hexahydroisoquinoline-2(1H)-carboxylate To a solution of (S)-5,5,8a-trimethyl-1,3,5,7,8,8a-hexahydroisoquinolin-6(2H)-one (20.0 g, 87 mmol) (prepared as described in J. Med. Chem. 1996, 20, 2302-2312) and Boc$_2$O (22.8 g, 104 mmol) in CH$_2$Cl$_2$ (250 ml) was added Et$_3$N (24.3 ml, 174 mmol) slowly. The reaction mixture was stirred at RT overnight. The reaction mixture was diluted with CH$_2$Cl$_2$ (100 ml), washed with H$_2$O (2×100 ml) followed by brine (100 ml), dried over Na$_2$SO$_4$, and concentrated in vacuo. The crude product was purified by silica gel column eluted with 20% EtOAc/hexanes to give the desired product (25.0 g, 98%) as a solid. $^1$H NMR (400 MHz, CHLOROFORM-d) δ 5.61-5.43 (m, 1H), 4.44-4.13 (m, 1H), 3.97-3.72 (m, 1H), 3.70-3.55 (m, 1H), 2.76-2.43 (m, 3H), 1.86-1.69 (m, 2H), 1.49 (s, 9H), 1.26 (s, 6H), 1.09 (s, 3H).

Step 2: Preparation of tert-butyl (S)-5,5,8a-trimethyl-6-(((trifluoromethyl)sulfonyl)oxy)-3,5,8,8a-tetrahydroisoquinoline-2(1H)-carboxylate To a solution of tert-butyl (S)-5,5,8a-trimethyl-6-oxo-3,5,6,7,8,8a-hexahydroisoquinoline-2(1H)-carboxylate (25.0 g, 85 mmol) in THF (300 ml) at −78° C. was added KHMDS (0.5M in toluene) (341 ml, 170 mmol). The yellow-orange solution was stirred at −78° C. for 1 h. A solution of N-phenyl bis-(trifluoromethanesulfonamide) (33.5 g, 94 mmol) in THF (120 ml) was added. The resulted reaction mixture was stirred at −78° C. for 2 h, then warmed to RT and stirred overnight. The reaction was quenched with H$_2$O (500 ml). The separated aqueous layer was extracted with EtOAc (3×250 ml). The combined organic layers were washed with brine (250 ml), dried over MgSO$_4$, and concentrated in vacuo. The crude product was purified by silica gel column eluted with 20% EtOAc/hexanes to give the desired product (20.6 g, 57%) as an oil. $^1$H NMR (400 MHz, CHLOROFORM-d) δ 5.79 (dd, J=6.0, 3.3 Hz, 1H), 5.69-5.56 (m, 1H), 4.45-4.17 (m, 1H), 4.01-3.78 (m, 1H), 3.75-3.58 (m, 1H), 2.76-2.54 (m, 1H), 2.09-2.01 (m, 2H), 1.49 (s, 9H), 1.30 (s, 3H), 1.27 (br. s., 3H), 1.20 (s, 3H).

Step 3: Preparation of tert-butyl (S)-6-(4-(methoxycarbonyl)phenyl)-5,5,8a-trimethyl-3,5,8,8a-tetrahydroisoquinoline-2(1H)-carboxylate To a solution of tert-butyl (S)-5,5,8a-trimethyl-6-(((trifluoromethyl)sulfonyl)oxy)-3,5,8,8a-tetrahydroisoquinoline-2(1H)-carboxylate (20.6 g, 48.4 mmol) in dioxane (250 ml) was added Na$_2$CO$_3$ (15.4 g, 145 mmol) in H$_2$O (50 ml), (4-(methoxycarbonyl)phenyl)boronic acid (11.3 g, 63 mmol) and Pd(Ph$_3$P)$_4$ (2.8 g, 2.42 mmol). The resulted mixture was refluxed under nitrogen for 4 h. The reaction mixture was diluted with H$_2$O (250 ml), extracted with ethyl acetate (3×250 ml). The combined organic layers were dried over Na$_2$SO$_4$, and concentrated in vacuo. The crude product was purified by silica gel column eluted with 5% EtOAc/hexanes to give the desired product (13.4 g, 67%) as a solid. $^1$H NMR (400 MHz, CHLOROFORM-d) δ 7.97 (d, J=8.3 Hz, 2H), 7.24 (d, J=8.5 Hz, 2H), 5.68-5.50 (m, 2H), 4.46-4.19 (m, 1H), 3.93 (s, 3H), 3.91-3.64 (m, 2H), 2.78-2.60 (m, 1H), 2.01 (br. s., 2H), 1.50 (s, 9H), 1.23 (s, 3H), 1.20 (s, 3H), 1.11 (s, 3H).

Step 4

To a solution of tert-butyl (S)-6-(4-(methoxycarbonyl)phenyl)-5,5,8a-trimethyl-3,5,8,8a-tetrahydroisoquinoline-2(1H)-carboxylate (7.7 g, 18.7 mmol) in dioxane (100 ml) was added HCl (4M in dioxane) (23.4 ml, 94 mmol) and the mixture was stirred at RT for 2 days. Hexanes (100 ml) was added into the reaction mixture. The white solid was collected by filtration, washed with hexanes (2×50 ml), and dried under vacuum to give the title compound (5.93 g, 91%) as HCl salt. $^1$H NMR (400 MHz, METHANOL-d$_4$) δ 7.98 (d, J=8.3 Hz, 2H), 7.31 (d, J=8.3 Hz, 2H), 5.81 (dd, J=3.8, 2.8 Hz, 1H), 5.56 (dd, J=5.8, 3.0 Hz, 1H), 3.91 (s, 3H), 3.77 (qd, J=16.7, 3.1 Hz, 2H), 3.33 (d, J=12.5 Hz, 1H), 3.05 (d, J=12.5 Hz, 1H), 2.19-2.14 (m, 2H), 1.48 (s, 3H), 1.24 (s, 3H), 1.23 (s, 3H).

Intermediate 2: Methyl (S)-4-(5,5,8a-trimethyl-2-(4-phenylpiperidine-4-carbonyl)-1,2,3,5,8,8a-hexahydroisoquinolin-6-yl)benzoate hydrochloride

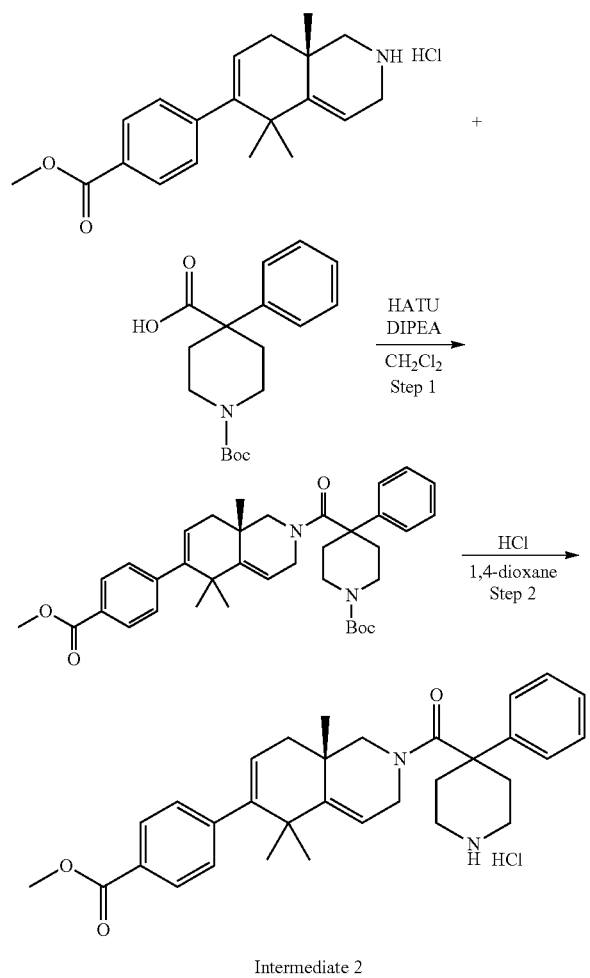

Intermediate 2

Step 1: Preparation of tert-butyl (S)-4-(6-(4-(methoxycarbonyl)phenyl)-5,5,8a-trimethyl-1,2,3,5,8,8a-hexahydroisoquinoline-2-carbonyl)-4-phenylpiperidine-1-carboxylate To a solution of methyl (S)-4-(5,5,8a-trimethyl-1,2,3,5,8,8a-hexahydroisoquinolin-6-yl)benzoate hydrochloride (1.82 g, 5.2 mmol) and 1-(tert-butoxycarbonyl)-4-phenylpiperidine-4-carboxylic acid (1.92 g, 6.3 mmol) in $CH_2Cl_2$ (100 ml) was added DIPEA (9 ml, 52 mmol) followed by HATU (2.98 g, 7.9 mmol). The resulted solution was stirred at RT for 3 h. The reaction mixture was diluted with $CH_2Cl_2$ (150 ml) and washed with $H_2O$ (2×100 ml) followed by brine (100 ml), dried over $Na_2SO_4$ and concentrated in vacuo. The crude product was purified by silica gel column eluted with 20% EtOAc/hexane to give the desired product (2.88 g, 92%) as a solid.

LC/MS m/z 621.40 (M+Na)$^+$, 2.71 min (Method 2).

Step 2

To a solution of tert-butyl (S)-4-(6-(4-(methoxycarbonyl)phenyl)-5,5,8a-trimethyl-1,2,3,5,8,8a-hexahydroisoquinoline-2-carbonyl)-4-phenylpiperidine-1-carboxylate (2.88 g, 4.8 mmol) in dioxane (30 ml) was added HCl (4M in 1,4-dioxane) (6 ml, 24 mmol) and the mixture was stirred at RT overnight. The reaction mixture was concentrated in vacuo, and the residue was triturated with ether. The ether was decanted and residue was concentrated in vacuo to give the title compound (2.53 g, 98%) as HCl salt without purification. LC/MS m/z 499.35 (M+H)$^+$, 2.18 min (Method 2).

Intermediate 3: Methyl (S)-4-(2-(2-formylbenzoyl)-5,5,8a-trimethyl-1,2,3,5,8,8a-hexahydroisoquinolin-6-yl)benzoate

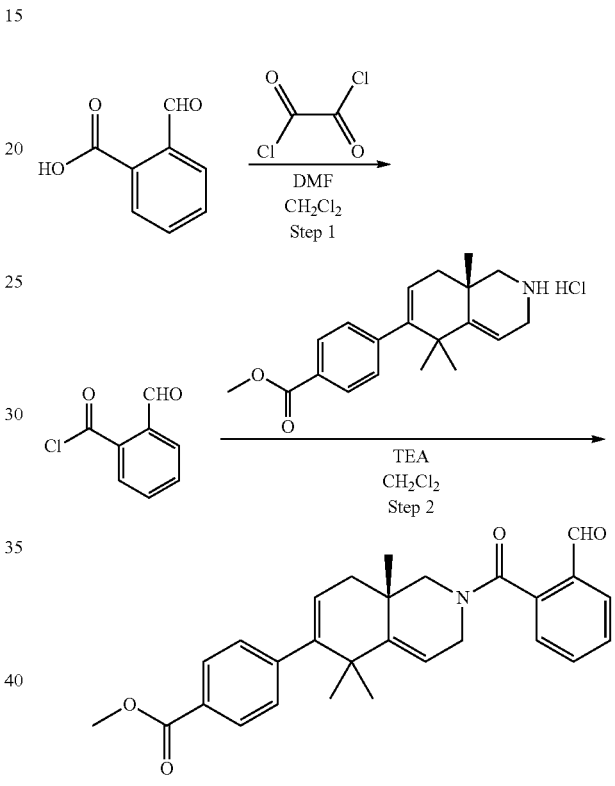

Intermediate 3

Step 1: Preparation of 2-formylbenzoyl Chloride

To a solution of 2-formylbenzoic acid (210 mg, 1.4 mmol) in $CH_2Cl_2$ (10 ml) at 0° C. was added oxalyl chloride (2M in DCM) (0.7 ml, 1.4 mmol) followed by DMF (11 μl, 0.14 mmol). The reaction mixture was warmed to RT and stirred overnight. The reaction mixture was concentrated in vacuo to give the crude product.

Step 2

To a solution of methyl (S)-4-(5,5,8a-trimethyl-1,2,3,5,8,8a-hexahydroisoquinolin-6-yl)benzoate hydrochloride (400 mg, 1.15 mmol) in $CH_2Cl_2$ (10 ml) was added TEA (0.24 ml, 1.73 mmol) followed by crude 2-formylbenzoyl chloride. The reaction mixture was stirred at 0° C. for 2 h then warmed to RT and stirred for 3 days (over weekend). The reaction mixture was concentrated in vacuo. The crude product was purified by silica gel column eluted with 35%

EtOAc/hexanes to give the desired product (403 mg, 79%) as a solid. LC/MS m/z 444.25 (M+H)+, 2.47 min (Method 2).

Example 1

Preparation of (S)-4-(2-benzoyl-5,5,8a-trimethyl-1,2,3,5,8,8a-hexahydroisoquinolin-6-yl)benzoic acid

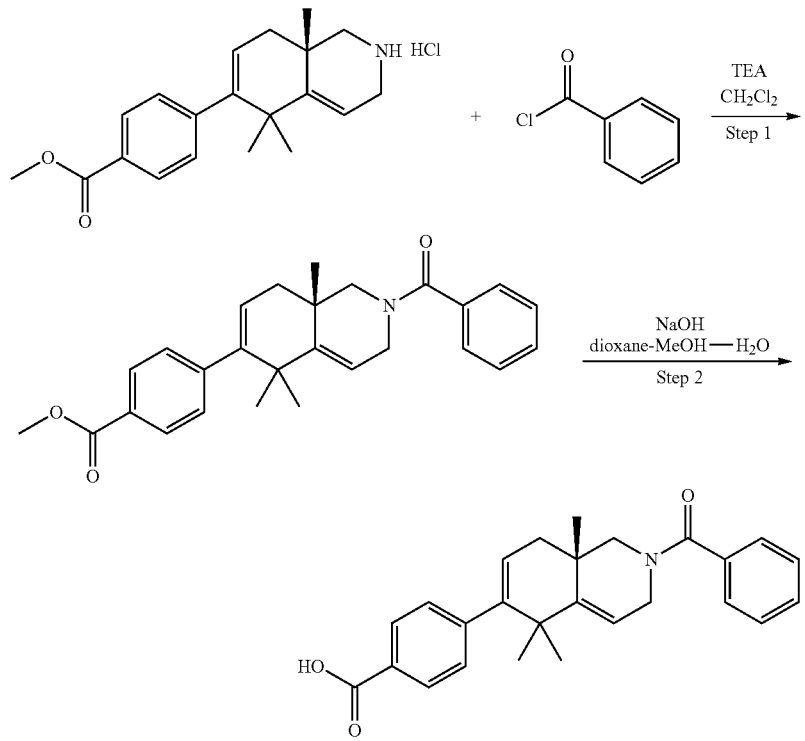

Example 1

Step 1: Preparation of methyl (S)-4-(2-benzoyl-5,5,8a-trimethyl-1,2,3,5,8,8a-hexahydroisoquinolin-6-yl)benzoate To a solution of methyl (S)-4-(5,5,8a-trimethyl-1,2,3,5,8,8a-hexahydroisoquinolin-6-yl)benzoate hydrochloride (30 mg, 0.096 mmol) in CH$_2$Cl$_2$ (2 ml) was added benzoyl chloride (16 mg, 0.12 mmol), Et3N (0.13 ml, 0.96 mmol) and DMAP (1.2 mg, 9.6 μmop. The resulted mixture was stirred at RT for 3 h. The reaction was quenched with 1N HCl (1 ml) and the mixture was extracted with CH$_2$Cl$_2$ (2 ml). The organic layer was washed with brine (2 ml) then concentrated in vacuo to give the crude product without purification. LC/MS m/z 416.02 (M+H)+, 2.48 min (Method 2).

Step 2

To a solution of crude methyl (S)-4-(2-benzoyl-5,5,8a-trimethyl-1,2,3,5,8,8a-hexahydroisoquinolin-6-yl)benzoatein dioxane (2 ml) and MeOH (1 ml) was added 1N NaOH (1 ml). The mixture was stirred at 50° C. for 2 h. The reaction mixture was purified by Prep HPLC to give the desired product (22 mg, 56%) as a solid. $^1$H NMR (300 MHz, DMSO-d6, 100° C.) δ 7.90 (d, J=8.1 Hz, 2H), 7.50-7.37 (m, 5H), 7.29 (d, J=6.6 Hz, 2H), 5.69 (br. s., 1H), 5.54 (dd, J=6.4, 2.7 Hz, 1H), 3.90 (d, J=17.9 Hz, 2H), 2.95 (d, J=12.4 Hz, 2H), 2.12-1.96 (m, 2H), 1.24 (s, 3H), 1.19 (s, 3H), 1.13 (s, 3H).

LC/MS m/z 402.24 (M+H)+, 2.34 min (Method 2).

The examples in Table 1 were prepared from intermediate 1 by the procedure described for the preparation of Example 1 using the reagent indicated in the table instead of benzoyl chloride:

TABLE 1

| Ex | Reagent | MW | Obs (M + 1)+ | RT | Met |
|---|---|---|---|---|---|
| 2 | 3-fluorobenzoyl chloride | 419.2 | 420.22 | 2.46 | 2 |
| 3 | 4-fluorobenzoyl chloride | 419.2 | 420.28 | 2.43 | 2 |
| 4 | 2,3-difluorobenzoyl chloride | 437.2 | 438.26 | 2.46 | 2 |
| 5 | 2,4-difluorobenzoyl chloride | 437.2 | 438.33 | 2.45 | 2 |
| 6 | 2,5-difluorobenzoyl chloride | 437.2 | 438.33 | 2.41 | 2 |
| 7 | 3,4-difluorobenzoyl chloride | 437.2 | 438.26 | 2.45 | 2 |
| 8 | 3,5-difluorobenzoyl chloride | 437.2 | 438.19 | 2.46 | 2 |
| 9 | oxalyl chloride | 648.3 | 649.4 | 2.75 | 6 |
| 10 | oxalyl chloride | 369.2 | 370.3 | 1.33 | 8 |

Ex = Example;
MW = Molecular weight;
Obs = Observed;
RT = Retention time;
Met = LC/MS Method.

Example 11

Preparation of (S)-4-(2-(2-(4-(tert-butoxycarbonyl)piperazin-1-yl)benzoyl)-5,5,8a-trimethyl-1,2,3,5,8,8a-hexahydroisoquinolin-6-yl)benzoic acid

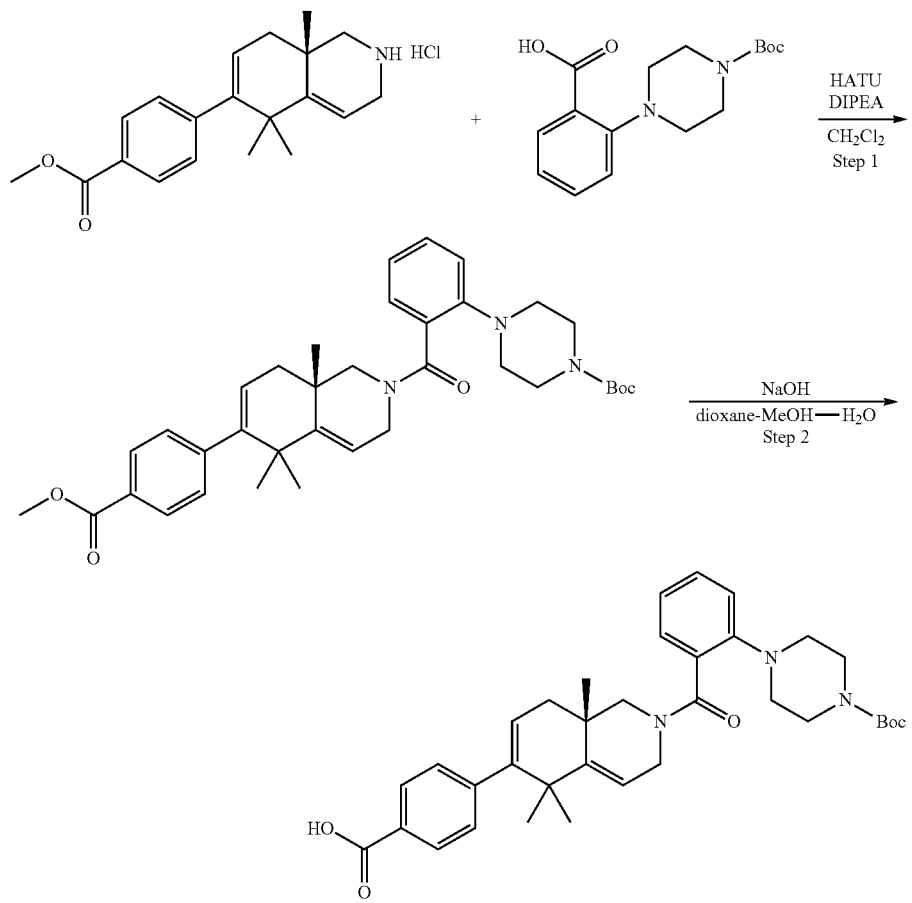

Example 11

Step 1: Preparation of tert-butyl (S)-4-(2-(6-(4-(methoxycarbonyl)phenyl)-5,5,8a-trimethyl-1,2,3,5,8,8a-hexahydroisoquinoline-2-carbonyl)phenyl)piperazine-1-carboxylate To a solution of methyl (S)-4-(5,5,8a-trimethyl-1,2,3,5,8,8a-hexahydroisoquinolin-6-yl)benzoate hydrochloride (30 mg, 0.086 mmol) and 2-(4-(tert-butoxycarbonyl)piperidin-1-yl)benzoic acid (40 mg, 0.13 mmol) in CH$_2$Cl$_2$ (2 ml) was added DIPEA (0.15 ml, 0.86 mmol) followed by HATU (49 mg, 0.13 mmol). The resulted solution was stirred at RT for 2 h. The solvent was evaporated to give the crude product without purification.

LC/MS m/z 600.47 (M+H)$^+$, 2.48 min (Method 2).

Step 2

To a solution of crude tert-butyl (S)-4-(2-(6-(4-(methoxycarbonyl)phenyl)-5,5,8a-trimethyl-1,2,3,5,8,8a-hexahydroisoquinoline-2-carbonyl)phenyl)piperazine-1-carboxylate in dioxane (2 ml) and MeOH (1 ml) was added 1N NaOH (1 ml). The mixture was stirred at 50° C. for 3 h. The reaction mixture was purified by Prep HPLC to give the desired product (27 mg, 53%) as a solid. LC/MS m/z 586.317 (M+H)$^+$, 2.20 min (Method 2).

The examples in Table 2 were prepared from intermediate 1 by the procedure described for the preparation of Example 11 using the reagent indicated in the table instead of 2-(4-(tert-butoxycarbonyl)piperidin-1-yl)benzoic acid:

TABLE 2

| Ex | Reagent | MW | Obs (M + 1)$^+$ | RT | Met |
|---|---|---|---|---|---|
| 12 | isophthalic acid | 445.2 | 446.34 | 1.76 | 2 |
| 13 | terephthalic acid | 445.2 | 445.86 | 1.72 | 2 |
| 14 | phthalic acid | 445.2 | 446.24 | 2.63 | 2 |
| 15 | (1S,4S)-4-(tert-butoxycarbonylamino)cyclohexanecarboxylic acid | 522.3 | 523.49 | 2.52 | 2 |
| 16 | (1R,4R)-4-(tert-butoxycarbonylamino)cyclohexanecarboxylic acid | 522.3 | 523.49 | 2.47 | 2 |
| 17 | 2-methoxybenzoic acid- | 431.2 | 432.29 | 2.77 | 3 |
| 18 | 3-methoxybenzoic acid | 431.2 | 432.29 | 2.82 | 2 |
| 19 | 4-methoxybenzoic acid | 431.2 | 432.29 | 2.8 | 2 |
| 20 | 2-carbamoylbenzoic acid | 444.2 | 449.28 (M-H$_2$O + Na)$^+$ | 2.72 | 2 |
| 21 | 3-carbamoylbenzoic acid | 444.2 | 445.28 | 2.51 | 2 |
| 22 | 4-carbamoylbenzoic acid | 444.2 | 445.28 | 2.52 | 2 |

TABLE 2-continued

| Ex | Reagent | MW | Obs (M + 1)+ | RT | Met |
|---|---|---|---|---|---|
| 23 | 2-(dimethylamino)benzoic acid | 444.2 | 445.28 | 2.64 | 2 |
| 24 | 3-(dimethylamino)benzoic acid | 444.2 | 445.28 | 2.57 | 2 |
| 25 | 4-(dimethylamino)benzoic acid | 444.2 | 445.34 | 2.64 | 2 |
| 26 | 2-morpholinobenzoic acid | 486.3 | 487.29 | 2.74 | 2 |
| 27 | 3-morpholinobenzoic acid | 486.3 | 487.29 | 2.68 | 2 |
| 28 | 4-morpholinobenzoic acid | 486.3 | 487.29 | 2.64 | 2 |
| 29 | 3-(4-methylpiperazin-1-yl)benzoic acid | 499.3 | 500.35 | 2.36 | 2 |
| 30 | 4-(4-methylpiperazin-1-yl)benzoic acid | 499.3 | 500.35 | 2.32 | 2 |
| 31 | 4-((1,1-dioxidothiomorpholino)methyl)benzoic acid | 548.2 | 549.34 | 2.35 | 2 |
| 32 | 5-(benzylsulfonyl)-2-methoxybenzoic acid | 585.2 | 586.17 | 2.55 | 2 |
| 33 | 4-(((tert-butoxycarbonyl)amino)methyl)benzoic acid | 530.3 | 531.37 | 2.68 | 2 |
| 34 | 3-(dimethylamino)propanoic acid hydrochloride | 396.2 | 397.26 | 2.06 | 2 |
| 35 | 2-(dimethylamino)acetic acid hydroxychloride | 382.2 | 384.41 | 2.03 | 2 |
| 36 | 3-(1,1-dioxidothiomorpholino)propanoic acid | 486.2 | 487.25 | 1.687 | 6 |
| 37 | 2-(1,1-dioxidothiomorpholino)acetic acid | 472.2 | 473.25 | 1.788 | 6 |
| 38 | 3-((1,1-dioxidothiomorpholino)methyl)benzoic acid | 548.2 | 549.17 | 1.55 | 4 |
| 39 | 1H-indole-6-carboxylic acid | 440.2 | 441.2 | 1.59 | 3 |
| 40 | 1H-benzo[d]imidazole-5-carboxylic acid | 441.2 | 442.2 | 1.21 | 3 |
| 41 | 2-methyl-1H-benzo[d]imidazole-5-carboxylic acid | 455.2 | 456.3 | 1.28 | 3 |
| 42 | 1H-benzo[d][1,2,3]triazole-5-carboxylic acid | 442.2 | 443.2 | 1.19 | 3 |
| 43 | 1H-indole-5-carboxylic acid | 440.2 | 463.31 (M + Na)+ | 2.6 | 2 |
| 44 | 2-(4-(2-(1,1-dioxidothiomorpholino)ethyl)piperazin-1-yl)benzoic acid | 646.3 | 647.34 | 2.92 | 2 |
| 45 | pyridine-3,5-dicarboxylic acid | 446.2 | 447.22 | 1.59 | 4 |
| 46 | 1-(tert-butoxycarbonyl)-4-phenylpiperidine-4-carboxylic acid | 584.3 | 583.5 (M − 1)− | 2.08 | 3 |
| 47 | 4-benzyl-1-(tert-butoxycarbonyl)piperidine-4-carboxylic acid | 598.3 | 597.6 (M − 1)− | 2.06 | 3 |
| 48 | 1-(tert-butoxycarbonyl)-4-methylpiperidine-4-carboxylic acid | 522.3 | 523.31 | 4.01 | 7 |
| 49 | 1-(tert-butoxycarbonyl)-4-isopropylpiperidine-4-carboxylic acid | 550.3 | 551.34 | 4.23 | 7 |
| 50 | 1-(tert-butoxycarbonyl)-4-cyclohexylpiperidine-4-carboxylic acid | 590.4 | 591.37 | 4.49 | 7 |

Ex = Example;
MW = Molecular weight;
Obs = Observed;
RT = Retention time;
Met = LC/MS Method.

Example 51

Preparation of (S)-4-(5,5,8a-trimethyl-2-(2-(piperazin-1-yl)benzoyl)-1,2,3,5,8,8a-hexahydroisoquinolin-6-yl)benzoic acid

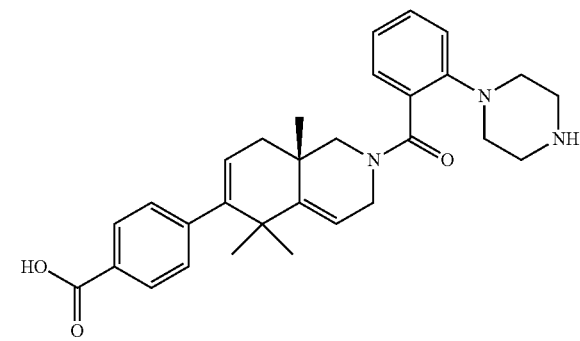 [SMILES: CC1(C)C(c2ccc(C(=O)O)cc2)=CC[C@]2(C)CN(C(=O)c3ccccc3N3CCNCC3)CC=C12]

To a solution of (S)-4-(2-(2-(4-(tert-butoxycarbonyl)piperazin-1-yl)benzoyl)-5,5,8a-trimethyl-1,2,3,5,8,8a-hexahydroisoquinolin-6-yl)benzoic acid (25 mg, 0.043 mmol) in CH$_2$Cl$_2$ (2 ml) was added TFA (0.5 ml). The resulted solution was stirred at RT for 30 min. The reaction mixture was concentrated in vacuo. The crude product was purified by Prep HPLC to give the desired product (20 mg, 94%) as a solid. LC/MS m/z 486.38 (M+H)+, 2.27 min (Method 2).

The examples in Table 3 were prepared by the procedure described in Example 51 using the using the starting materials indicated in the table instead of S)-4-(2-(2-(4-(tert-butoxycarbonyl)piperazin-1-yl)benzoyl)-5,5,8a-trimethyl-1,2,3,5,8,8a-hexahydroisoquinolin-6-yl)benzoic acid:

TABLE 3

| Ex | Reagent | MW | Obs M + 1 | RT | Met |
|---|---|---|---|---|---|
| 52 | 4-((S)-2-((1R,2S)-4-((tert-butoxycarbonyl)amino)cyclohexane-1-carbonyl)-5,5,8a-trimethyl-1,2,3,5,8,8a-hexahydroisoquinolin-6-yl)benzoic acid | 422.3 | 421.3 (M − 1)− | 0.9 | 3 |
| 53 | (S)-4-(2-(4-(((tert-butoxycarbonyl)amino)methyl)benzoyl)5,5,8a-trimethyl-1,2,3,5,8,8a-hexahydroisoquinolin-6-yl)benzoic acid | 430.2 | 431.33 | 2.37 | 2 |
| 54 | (S)-4-(2-(1-(tert-butoxycarbonyl)-4-phenylpiperidine-4-carbonyl)-5,5,8a-trimethyl-1,2,3,5,8,8a-hexahydroisoquinolin-6-yl)benzoic acid | 484.3 | 485.35 | 2.021 | 6 |
| 55 | (S)-4-(2-(4-benzyl-1-(tert-butoxycarbonyl)piperidine-4-carbonyl)-5,5,8a-trimethyl-1,2,3,5,8,8a-hexahydroisoquinolin-6-yl)benzoic acid | 498.3 | 499.35 | 2.035 | 6 |
| 56 | 4-((S)-2-(1-((tert-butoxycarbonyl)-L-leucyl)-4-phenylpiperidine-4-carbonyl)-5,5,8a-trimethyl-1,2,3,5,8,8a-hexahydroisoquinolin-6-yl)benzoic acid | 597.4 | 598.35 | 2.36 | 6 |
| 57 | 4-((S)-2-(1-((tert-butoxycarbonyl)-D-leucyl)-4-phenylpiperidine-4-carbonyl)-5,5,8a-trimethyl-1,2,3,5,8,8a-hexahydroisoquinolin-6-yl)benzoic acid | 597.4 | 598.35 | 2.36 | 6 |

Ex = Example;
MW = Molecular weight;
Obs = Observed;
RT = Retention time;
Met = LC/MS Method.

Example 58

Preparation of 4,4'-((8aS,8a'S)-isophthaloylbis(5,5,8a-trimethyl-1,2,3,5,8,8a-hexahydroisoquinoline-2,6-diyl))dibenzoic acid

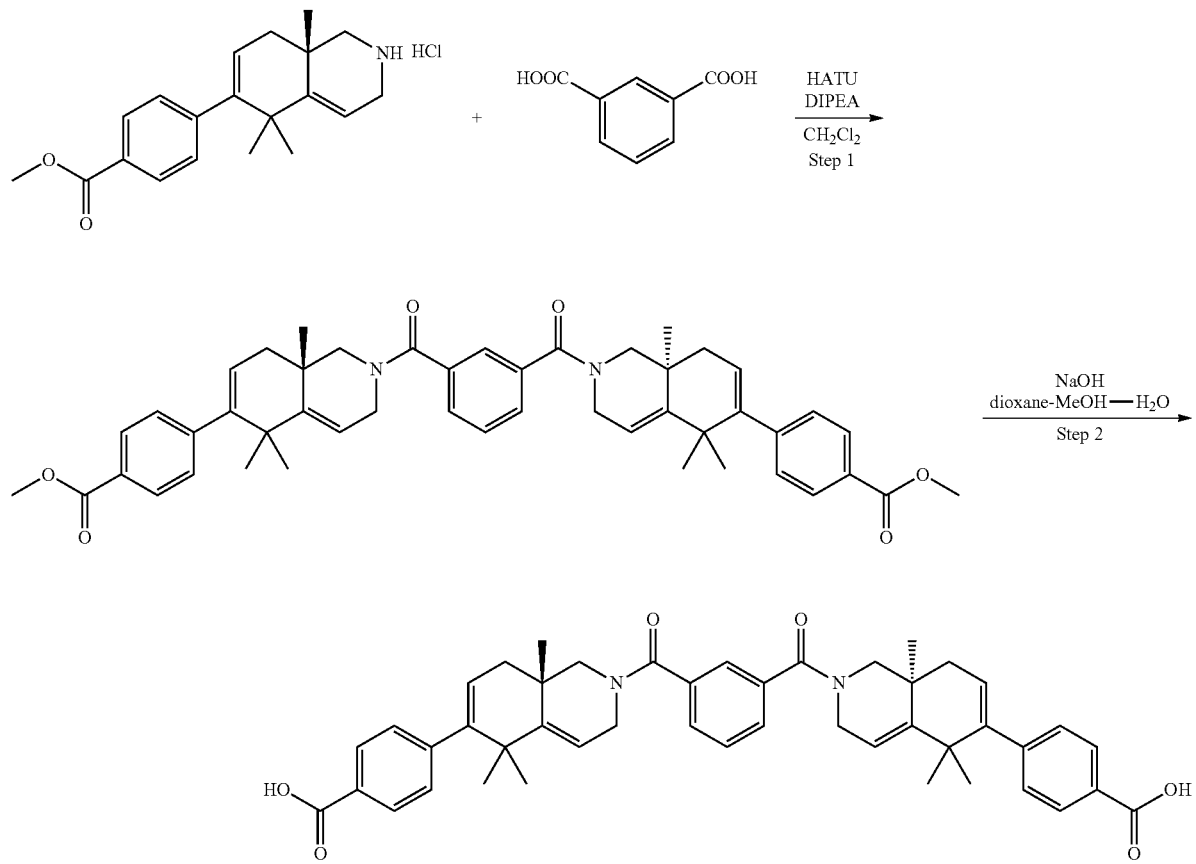

Example 58

Step 1: Preparation of dimethyl 4,4'-((8aS,8a'S)-isophthaloylbis(5,5,8a-trimethyl-1,2,3,5,8,8a-hexahydroisoquinoline-2,6-diyl))dibenzoate To a solution of methyl (S)-4-(5,5,8a-trimethyl-1,2,3,5,8,8a-hexahydroisoquinolin-6-yl)benzoate hydrochloride (50 mg, 0.16 mmol) and isophthalic acid (13 mg, 0.08 mmol) in CH$_2$Cl$_2$ (2 ml) was added DIPEA (0.14 ml, 0.80 mmol) followed by HATU (92 mg, 0.24 mmol). The resulted solution was stirred at RT for 2 h. The reaction mixture was concentrated in vacuo to give crude product without purification. LC/MS m/z 753.30 (M+H)$^+$, 2.41 min (Method 2).

Step 2

To a solution of crude dimethyl 4,4'-((8aS,8a'S)-isophthaloylbis(5,5,8a-trimethyl-1,2,3,5,8,8a-hexahydroisoquinoline-2,6-diyl))dibenzoate in dioxane (5 ml) was added 1N NaOH (1 ml). The mixture was stirred at 50° C. for 4 h. The reaction mixture was purified by Prep HPLC to give the desired product (16 mg, 24%) as a solid. LC/MS m/z 725.26 (M+H)$^+$, 2.17 min (Method 2).

The examples in Table 4 were prepared from intermediate 1 by the procedure described in Example 58 using the reagents indicated in Table 4:

TABLE 4

| Ex | Reagent | MW | Obs (M + 1)$^+$ | RT | Met |
|---|---|---|---|---|---|
| 59 | terephthalic acid | 724.4 | 725.19 | 2.22 | 2 |
| 60 | phthalic acid | 724.4 | 725.19 | 2.55 | 2 |
| 61 | pyridine-2,6-dicarboxylic acid | 725.4 | 726.4 | 2.35 | 5 |
| 62 | thiophene-2,5-dicarboxylic acid | 730.3 | 731.36 | 2.37 | 5 |
| 63 | pyridine-3,5-dicarboxylic acid | 725.4 | 726.38 | 2.35 | 5 |
| 64 | thiophene-3,4-dicarboxylic acid | 730.3 | 731.49 | 2.14 | 4 |
| 65 | bicyclo[2.2.1]heptane-2,3-dicarboxylic acid | 742.4 | 743.7 | 1.73 | 3 |

Ex = Example;
MW = Molecular weight;
Obs = Observed;
RT = Retention time;
Met = LC/MS Method.

Example 66

Preparation of (S)-4-(2-(3-(1,1-dioxidothiomorpholine-4-carbonyl)benzoyl)-5,5,8a-trimethyl-1,2,3,5,8,8a-hexahydroisoquinolin-6-yl)benzoic acid

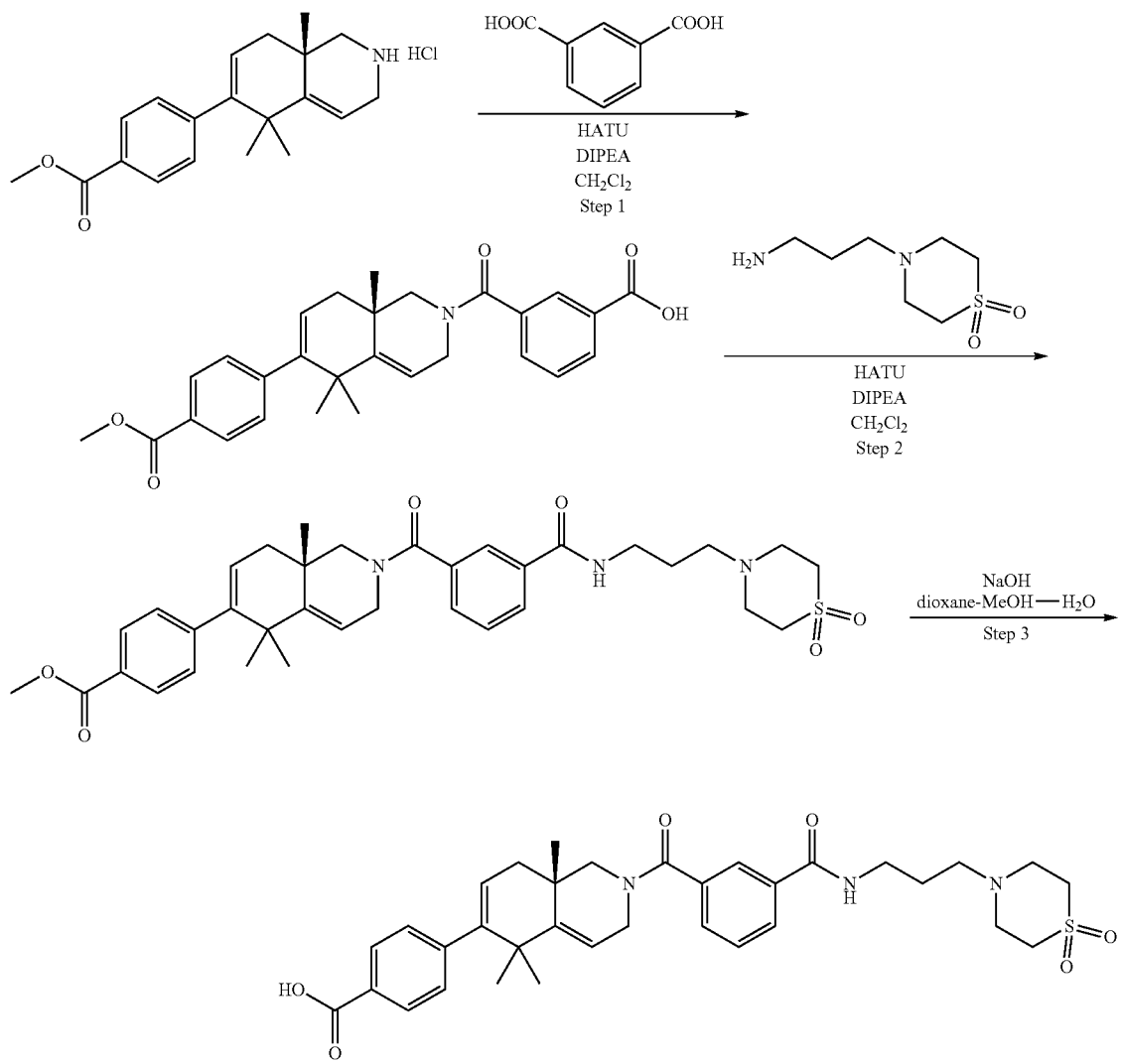

Example 66

Step 1: Preparation of (S)-3-(6-(4-(methoxycarbonyl)phenyl)-5,5,8a-trimethyl-1,2,3,5,8,8a-hexahydroisoquinoline-2-carbonyl)benzoic acid To a solution of methyl (S)-4-(5,5,8a-trimethyl-1,2,3,5,8,8a-hexahydroisoquinolin-6-yl)benzoate hydrochloride (50 mg, 0.144 mmol) and isophthalic acid (48 mg, 0.29 mmol) in $CH_2Cl_2$ (5 ml) was added DIPEA (0.13 ml, 0.72 mmol) followed by HATU (164 mg, 0.43 mmol). The resulted solution was stirred at RT for 3 h. The reaction mixture was diluted with $CH_2Cl_2$ (5 ml), washed with $NaHCO_3$(5 ml) followed by brine (5 ml), dried over $Na_2SO_4$, and concentrated in vacuo to give crude product without purification.

LC/MS m/z 460.30 (M+H)$^+$, 1.70 min (Method 3).

Step 2: Preparation of methyl (S)-4-(2-(3-((3-(1,1-dioxidothiomorpholino)propyl)carbamoyl)benzoyl)-5,5,8a-trimethyl-1,2,3,5,8,8a-hexahydroisoquinolin-6-yl)benzoate To a solution of crude (S)-3-(6-(4-(methoxycarbonyl)phenyl)-5,5,8a-trimethyl-1,2,3,5,8,8a-hexahydroisoquinoline-2-carbonyl)benzoic acid and 4-(3-aminopropyl)thiomorpholine 1,1-dioxide (41 mg, 0.215 mmol) in $CH_2Cl_2$ (5 ml) was added DIPEA (0.125 ml, 0.72 mmol) followed by HATU (82 mg, 0.215 mmol). The resulted solution was stirred at RT for 2 h. The reaction mixture was diluted with $CH_2Cl_2$ (10 ml), washed with $H_2O$ (10 ml) followed by brine (10 ml), dried over $Na_2SO_4$, and concentrated in vacuo to give crude product without purification. LC/MS m/z 634.45 (M+H)$^+$, 2.09 min (Method 2).

Step 3

To a solution of crude methyl (S)-4-(2-(3-((3-(1,1-dioxidothiomorpholino)propyl)carbamoyl)benzoyl)-5,5,8a-trimethyl-1,2,3,5,8,8a-hexahydroisoquinolin-6-yl)benzoate in dioxane (2 ml) and MeOH (1 ml) was added 1N NaOH (1 ml). The mixture was stirred at 50° C. for 4 h. The reaction mixture was purified by Prep HPLC to give the desired product (39 mg, 42%) as a solid. $^1$H NMR (400 MHz, METHANOL-d4) δ 8.00-7.91 (m, 4H), 7.67-7.58 (m, 2H), 7.27 (t, J=8.2 Hz, 2H), 5.85-5.80 (m, 0.5H), 5.62-5.56 (m, 1H), 5.53-5.47 (m, 0.5H), 4.85-4.77 (m, 0.5H), 4.50 (d, J=12.5 Hz, 0.5H), 4.16-4.07 (m, 0.5H), 3.95-3.84 (m. 0.5H), 3.66-3.59 (m, 4H), 3.51 (t, J=6.5 Hz, 2H), 3.46-3.40 (m, 4H), 3.32-3.24 (m, 1H), 3.21-3.12 (m, 2.5H), 2.93-2.85 (m, 0.5H), 2.19-2.13 (m, 1H), 2.06-1.96 (m, 2.5H), 1.86-1.78 (m, 0.5H), 1.35 (s, 1.5H), 1.27 (s, 1.5H), 1.22 (s, 1.5H), 1.18 (s, 1.5H), 1.16 (s, 1.5H), 1.12 (s, 1.5H). LC/MS m/z 620.40 (M+H)$^+$, 1.84 min (Method 2).

The examples in Table 5 were prepared from intermediate 1 by the procedure described in Example 66 using the reagents indicated in the table:

TABLE 5

| Ex | Reagent | MW | Obs (M + 1)$^+$ | RT | Met |
|---|---|---|---|---|---|
| 67 | phthalic acid followed by thiomorpholine 1,1-dioxide | 562.2 | 563.3 | 2.52 | 2 |
| 68 | isophthalic acid followed by thiomorpholine 1,1-dioxide | 562.2 | 563.37 | 2.51 | 2 |
| 69 | terephthalic acid followed by thiomorpholine 1,1-dioxide | 562.2 | 563.37 | 2.5 | 2 |
| 70 | pyridine-2,6-dicarboxylic acid | 620.3 | 621.27 | 1.34 | 4 |
| 71 | pyridine-3,5-dicarboxylic acid | 620.3 | 621.4 | 1.32 | 4 |
| 72 | thiophene-2,5-dicarboxylic acid | 625.2 | 626.26 | 1.41 | 4 |
| 73 | thiophene-3,4-dicarboxylic acid | 625.2 | 626.35 | 1.875 | 6 |

Ex = Example;
MW = Molecular weight;
Obs = Observed;
RT = Retention time;
Met = LC/MS Method.

Example 74

Preparation of (S)-4-(2-(4-((3-(1,1-dioxidothiomorpholino)propyl)amino)-1,3,5-triazin-2-yl)-5,5,8a-trimethyl-1,2,3,5,8,8a-hexahydroisoquinolin-6-yl)benzoic acid

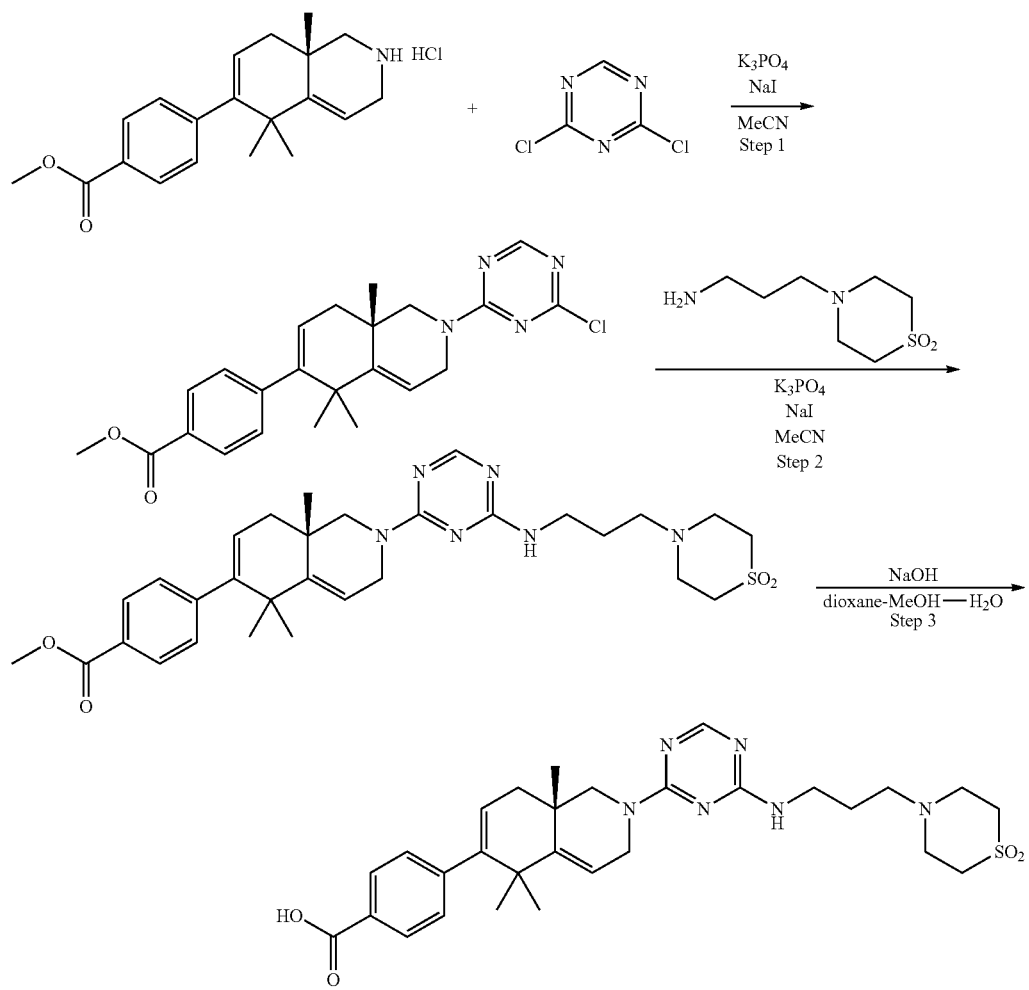

Example 74

Step 1: Preparation of methyl (S)-4-(2-(4-chloro-1,3,5-triazin-2-yl)-5,5,8a-trimethyl-1,2,3,5,8,8a-hexahydroisoquinolin-6-yl)benzoate In a sealed tube, a suspension of methyl (S)-4-(5,5,8a-trimethyl-1,2,3,5,8,8a-hexahydroisoquinolin-6-yl)benzoate hydrochloride (50 mg, 0.144 mmol), 2,4-dichloro-1,3,5-triazine (43 mg, 0.287 mmol), $K_3PO_4$ (122 mg, 0.575 mmol) and NaI (43 mg, 0.287 mmol) in MeCN (5 ml) was heated at 125° C. overnight. The reaction mixture was cooled to RT, diluted with $CH_2Cl_2$ (20 ml), washed with $H_2O$ (20 ml), dried over $Na_2SO_4$, and concentrated. The crude product was purified by silica gel column eluted with 10% Hex/EtOAc) to give the desired product (33 mg, 54%) as a solid. $^1$H NMR (400 MHz, CHLOROFORM-d) δ 8.38 (d, J=9.3 Hz, 1H), 7.98 (d, J=8.3 Hz, 2H), 7.24 (d, J=8.5 Hz, 2H), 5.69-5.66 (m, 1H), 5.58 (dt, J=5.1, 3.7 Hz, 1H), 4.80 (dt, J=18.6, 4.1 Hz, 1H), 4.61 (dd, J=17.8, 12.8 Hz, 1H), 3.93 (s, 3H), 3.93-3.86 (m, 1H), 2.93 (dd, J=12.7, 9.2 Hz, 1H), 2.14-2.09 (m, 2H), 1.25 (s, 3H), 1.23 (s, 1.5H), 1.22 (s, 1.5H), 1.13 (s, 1.5H), 1.12 (s, 1.5H). LC/MS m/z 425.22 $(M+H)^+$, 2.93 min (Method 2).

Step 2: Preparation of methyl (S)-4-(2-(4-((3-(1,1-dioxidothiomorpholino)propyl)amino)-1,3,5-triazin-2-yl)-5,5,8a-trimethyl-1,2,3,5,8,8a-hexahydroisoquinolin-6-yl)benzoate In a sealed tube, a suspension of methyl (S)-4-(2-(4-chloro-1,3,5-triazin-2-yl)-5,5,8a-trimethyl-1,2,3,5,8,8a-hexahydroisoquinolin-6-yl)benzoate (33 mg, 0.078 mmol), 4-(3-aminopropyl)thiomorpholine 1,1-dioxide (30 mg, 0.155 mmol), K3PO4 (66 mg, 0.311 mmol) and NaI (23 mg, 0.155 mmol) in DMF (5 ml) was heated at 125° C. The reaction mixture was cooled to RT, diluted with $CH_2Cl_2$ (20 ml), washed with $H_2O$ (20 ml), dried over $Na_2SO_4$, and concentrated in vacuo to give crude product as solid. LC/MS m/z 581.33 $(M+H)^+$, 2.77 min (Method 2).

Step 3

To a solution of crude methyl (S)-4-(2-(4-((3-(1,1-dioxidothiomorpholino)propyl)amino)-1,3,5-triazin-2-yl)-5,5,8a-trimethyl-1,2,3,5,8,8a-hexahydroisoquinolin-6-yl)benzoate in dioxane (2 ml) and MeOH (1 ml) was added 1N NaOH (1 ml). The mixture was stirred at 50° C. for 2 h. The reaction mixture was purified by Prep HPLC to give the desired product (40 mg, 84%) as a solid. $^1$H NMR (400 MHz, METHANOL-d4) δ 8.31 (d, J=4.5 Hz, 1H), 7.96 (d, J=8.3 Hz, 2H), 7.28 (d, J=8.3 Hz, 2H), 5.79 (t, J=3.0 Hz, 1H), 5.59 (t, J=3.9 Hz, 1H), 4.86 (t, J=3.8 Hz, 1H), 4.65 (dd, J=12.7, 8.2 Hz, 1H), 4.07-3.95 (m, 1H), 3.69-3.54 (m, 6H), 3.49-3.40 (m, 4H), 3.23-3.18 (m, 2H), 3.06 (dd, J=12.7, 8.9 Hz, 1H), 2.20-2.01 (m, 4H), 1.30-1.22 (m, 6H), 1.14 (s, 3H). LC/MS m/z 567.30 $(M+H)^+$, 2.52 min (Method 2).

The examples in Table 6 were prepared from intermediate 1 by the procedure described in Example 74 using the reagents indicated in the table:

Table 6

Ex=Example; MW=Molecular weight; Obs=Observed; RT=Retention time; Met=LC/MS Method.

TABLE 6

| Ex | Reagent | MW | Obs $(M + 1)^+$ | RT | Met |
|---|---|---|---|---|---|
| 75 | 2,4-dichloro-1,3,5-triazine | 671.4 | 672.34 | 2.19 | 4 |
| 76 | 2,6-dibromopyridine, step 1 and step 3 | 452.1 | 453.14 | 3.68 | 2 |
| 77 | 2,5-dibromothiazole, step 1 and step 3 | 458.1 | 459.2 | 2.484 | 6 |
| 78 | 2,5-dibromothiazole, step 1 and step 3 | 380.2 | 381.25 | 1.745 | 6 |
| 79 | 4-(2-chloroethyl)thiomorpholine 1,1-dioxide, step 1 and step 3 | 458.2 | 459.22 | 2.66 | 7 |
| 80 | 2-bromobenzo[d]thiazole | 430.2 | 431.17 | 4.28 | 7 |
| 81 | methyl (S)-4-(2-(2-(1H-benzo[d]imidazol-2-yl)benzoyl)-5,5,8a-trimeethyl-1,2,3,5,8,8a-hexahydroisoquinolin-6-tl)benzoate and 4-(2-chloroethyl)thiomorpholine 1,1-dioxide | 678.3 | 679.3 | 2.13 | 6 |
| 82 | methyl (S)-4-(2-(2-(1H-benzo[d]imidazol-2-yl)benzoyl)-5,5,8a-trimethyl-1,2,3,5,8,8a-hexahydroisoquinolin-6-yl)benzoate and 4-(2-chloroethyl)thiomorpholine 1,1-dioxide | 840.4 | 858.35 $(M + MH4)^+$ | 2.39 | 6 |

Ex = Example;
MW = Molecular weight;
Obs = Observed;
RT = Retention time;
Met = LC/MS Method.

Examples 83

Preparation of 4-((8aS)-2-(2-(4-(tert-butoxycarbonyl)piperazin-1-yl)benzoyl)-5,5,8a-trimethyldecahydroisoquinolin-6-yl)benzoic acid

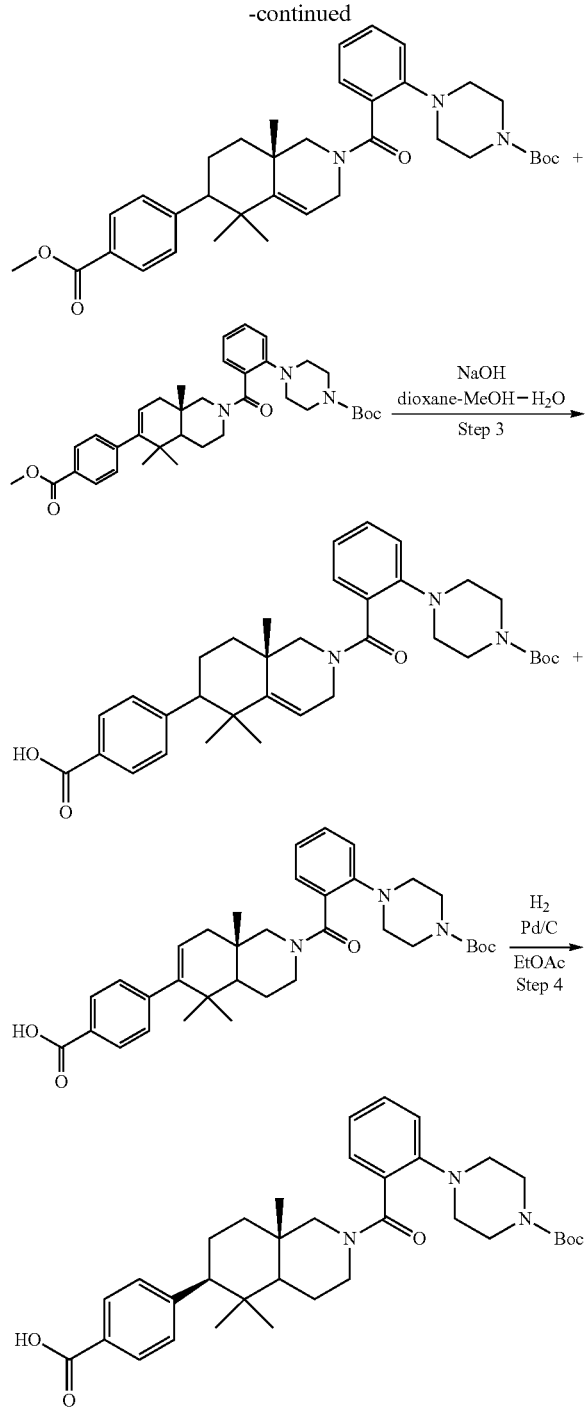

Example 83 with H$_2$ (50 psi) and on Parr shaker for 3 days. The reaction mixture was filtered through Celite and the filtrate was concentrated in vacuo to give the crude product. LC/MS m/z 314.25 (M+H)$^+$, 1.67 min (Method 2).

Step 2: Preparation of a Mixture of tert-butyl 4-(2-((8aS)-6-(4-(methoxycarbonyl)phenyl)-5,5,8a-trimethyl-1,2,3,5,6,7,8,8a-octahydroisoquinoline-2-carbonyl)phenyl)piperazine-1-carboxylate and tert-butyl 4-(2-((8aS)-6-(4-(methoxycarbonyl)phenyl)-5,5,8a-trimethyl-1,2,3,4,4a,5,8,8a-octahydroisoquinoline-2-carbonyl)phenyl)piperazine-1-carboxylate To a solution of crude mixture from step 1 (33 mg, 0.094 mmol) and 2-(4-(tert-butoxycarbonyl)piperazin-1-yl)benzoic acid (43 mg, 0.14 mmol) in CH$_2$Cl$_2$ (5 ml) was added DIPEA (0.08 ml, 0.47 mmol) followed by HATU (54 mg, 0.14 mmol). The resulted solution was stirred at RT for 2 h. The reaction mixture was diluted with CH$_2$Cl$_2$ (10 ml) and washed with H$_2$O (2×10 ml) followed by brine (10 ml), dried over Na$_2$SO$_4$, and concentrated in vacuo to give crude product without purification. LC/MS m/z 602.50 (M+H)$^+$, 2.63 min (Method 2).

Step 3: Preparation of a Mixture of 4-((8aS)-2-(2-(4-(tert-butoxycarbonyl)piperazin-1-yl)benzoyl)-5,5,8a-trimethyl-1,2,3,5,6,7,8,8a-octahydroisoquinolin-6-yl)benzoic acid and 4-((8aS)-2-(2-(4-(tert-butoxycarbonyl)piperazin-1-yl)benzoyl)-5,5,8a-trimethyl-1,2,3,4,4a,5,8,8a-octahydroisoquinolin-6-yl)benzoic acid To a solution of crude mixture from step 2 in dioxane (2 ml) and MeOH (1 ml) was added 1N NaOH (1 ml). The mixture was stirred at 50° C. for 4 h. The reaction mixture was purified by Prep HPLC to give the desired product as a solid. LC/MS m/z 588.45 (M+H)$^+$, 2.45 min (Method 2).

Step 4

To a solution of a mixture from step 3 in MeOH (10 ml) under nitrogen was added 10% Pd/C (30 mg, 0.028 mmol). The mixture was charged with H2 (50 psi) and on Parr shaker for 3 days. The reaction mixture was filtered through Celite and the filtrate was concentrated in vacuo. The crude product was purified by Prep HPLC to give the title compound as a solid. LC/MS m/z 590.45 (M+H)$^+$, 2.48 min (Method 2).

The examples in Table 7 were prepared from intermediate 1 by the procedure described in Examples 83 using the reagents indicated in the table:

Step 1: Preparation of a Mixture of methyl 4-((8aS)-5,5,8a-trimethyl-1,2,3,5,6,7,8,8a-octahydroisoquinolin-6-yl)benzoate hydrochloride and methyl 4-((8aS)-5,5,8a-trimethyl-1,2,3,4,4a,5,8,8a-octahydroisoquinolin-6-yl)benzoate hydrochloride To a solution of methyl (S)-4-(5,5,8a-trimethyl-1,2,3,5,8,8a-hexahydroisoquinolin-6-yl)benzoate hydrochloride (100 mg, 0.29 mmol) in MeOH (20 ml) under nitrogen was added 10% Pd/C (15 mg, 0.014 mmol). The mixture was charged

TABLE 7

| Ex | Reagent | MW | Obs (M + 1)$^+$ | RT | Met |
|---|---|---|---|---|---|
| 84 | 1-(tert-butoxycarbonyl)-4-phenylpiperidine-4-carboxylic acid | 588.36 | 589.36 | 4.39 | 7 |
| 85 | 2-(1H-benzo[d]imidazol-2-yl)benzoic acid | 521.27 | 522.27 | 3.6 | 7 |
| 86 | Boc-D-Leu-OH | 701.44 | 702.5 | 2.89 | 6 |
| 87 | Boc-L-Leu-OH | 701.44 | 702.5 | 2.88 | 6 |

TABLE 7-continued

| Ex | Reagent | MW | Obs (M + 1)+ | RT | Met |
|---|---|---|---|---|---|
| 88 | Boc-D-Leu-OH and 5% Rhodium on alumina as catalyst | 699.42 | 700.45 | 2.94 | 6 |
| 89 | Boc-L-Leu-OH and 5% Rhodium on alumina as catalyst | 699.42 | 700.45 | 2.85 | 6 |

Ex = Example;
MW = Molecular weight;
Obs = Observed;
RT = Retention time;
Met = LC/MS Method.

Examples 90 and Example 91

Preparation of 4-((6R,8aS)-2,5,5,8a-tetramethyl-decahydroisoquinolin-6-yl)benzoic acid and 4-((6S,8aS)-2,5,5,8a-tetramethyldecahydroisoquinolin-6-yl)benzoic acid

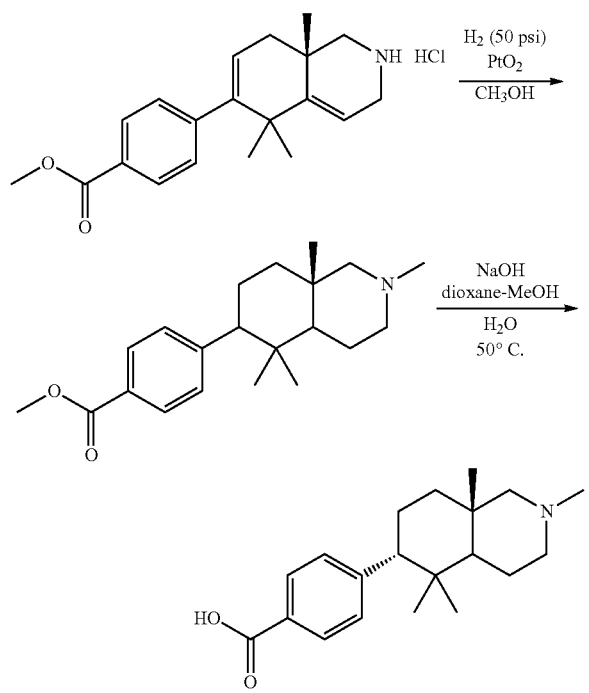

Example 90

Example 91

Step 1: Preparation of methyl 4-((8aS)-2,5,5,8a-tetramethyldecahydroisoquinolin-6-yl)benzoate To a solution of methyl (S)-4-(5,5,8a-trimethyl-1,2,3,5,8,8a-hexahydroisoquinolin-6-yl)benzoate hydrochloride (50 mg, 0.144 mmol) in MeOH (20 ml) under nitrogen was added platinum(IV) oxide (29 mg, 0.13 mmol). The mixture was charged with H2 (50 psi) and on Parr shaker for 2 days. The reaction mixture was filtered through Celite and the filtrate was concentrated in vacuo to give the crude product. LC/MS m/z 330.20 (M+H)+, 1.56 min (Method 2).

Step 2

To a solution of crude methyl 4-((8aS)-2,5,5,8a-tetramethyldecahydroisoquinolin-6-yl)benzoate in dioxane (2 ml) and MeOH (1 ml) was added 1N NaOH (1 ml). The mixture was stirred at 50° C. for 4 h. The crude mixture was purified by Prep HPLC to give the isomers respectively as solids.

Example 90: Isomer 1

$^1$H NMR (500 MHz, DMSO-d6) δ 7.83 (d, J=8.2 Hz, 2H), 7.31 (d, J=8.2 Hz, 2H), 2.95-2.89 (m, 1H), 2.48 (dd, J=13.4, 2.1 Hz, 1H), 2.33 (d, J=9.8 Hz, 1H), 2.27-2.17 (m, 1H), 2.11 (s, 3H), 1.83-1.76 (m, 1H), 1.56 (d, J=10.4 Hz, 1H), 1.54-1.48 (m, 2H), 1.44-1.37 (m, 2H), 1.27-1.18 (m, 1H), 1.13 (s, 3H), 1.01-0.95 (m, 1H), 0.71 (s, 3H), 0.66 (s, 3H). LC/MS m/z 316.30 (M+H)+, 1.78 min (Method 1).

Example 91: Isomer 2

$^1$H NMR (500 MHz, DMSO-d6) δ 7.79 (d, J=7.9 Hz, 2H), 7.28 (d, J=7.9 Hz, 2H), 2.85-2.79 (m, 1H), 2.76-2.70 (m, 1H), 2.30-2.11 (m, 3H), 2.08 (s, 3H), 1.84-1.73 (m, 1H), 1.68-1.60 (m, 2H), 1.59-1.52 (m, 1H), 1.45-1.37 (m, 1H), 1.08 (s, 3H), 1.10-1.02 (m, 2H), 0.98 (s, 3H), 0.66 (s, 3H). LC/MS m/z 316.30 (M+H)+, 2.12 min (Method 1).

Example 92

Preparation of 4-((S)-2-(1-((tert-butoxycarbonyl)-D-leucyl)-4-phenylpiperidine-4-carbonyl)-5,5,8a-trimethyl-1,2,3,5,8,8a-hexahydroisoquinolin-6-yl)benzoic acid

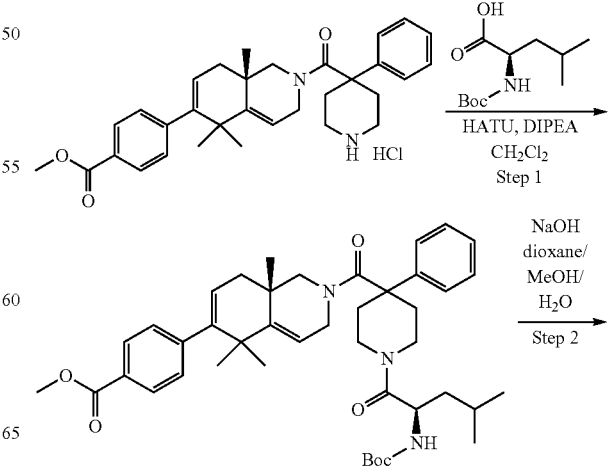

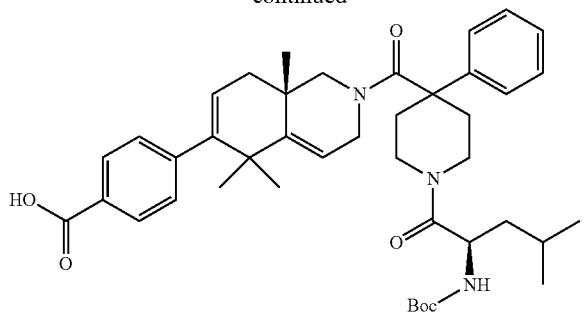

Example 92

Step 1: Preparation of methyl 4-((S)-2-(1-((tert-butoxycarbonyl)-D-leucyl)-4-phenylpiperidine-4-carbonyl)-5,5,8a-trimethyl-1,2,3,5,8,8a-hexahydroisoquinolin-6-yl)benzoate To a solution of methyl (S)-4-(5,5,8a-trimethyl-2-(4-phenylpiperidine-4-carbonyl)-1,2,3,5,8,8a-hexahydroisoquinolin-6-yl)benzoate hydrochloride (100 mg, 0.187 mmol) and Boc-D-Leu-OH (86 mg, 0.374 mmol) in CH$_2$C12 (10 ml) was added DIPEA (0.33 ml, 1.87 mmol) followed by HATU (142 mg, 0.374 mmol). The resulted solution was stirred at RT overnight. The reaction mixture was concentrated in vacuo. The crude product was purified by silica gel column eluted with 25% EtOAc/hexanes to give the desired product (115 mg, 86%) as a solid. LC/MS m/z 712.40 (M+H)$^+$, 2.92 min (Method 2).

Step 2

To a solution of methyl 4-((S)-2-(1-((tert-butoxycarbonyl)-D-leucyl)-4-phenylpiperidine-4-carbonyl)-5,5,8a-trimethyl-1,2,3,5,8,8a-hexahydroisoquinolin-6-yl)benzoate (46 mg, 0.065 mmol) in dioxane (2 ml) and MeOH (1 ml) was added 1N NaOH (1 ml). The mixture was stirred at 50° C. for 4 h. The reaction mixture was purified by Prep HPLC to give the desired product (29 mg, 64%) as a solid. LC/MS m/z 698.45 (M+H)$^+$, 2.72 min (Method 2).

The examples in Table 8 were prepared from intermediate 2 by the procedure described in Example 92 using the reagents indicated in the table:

TABLE 8

| Ex | Reagent | MW | Obs (M + 1)$^+$ | RT | Met |
|---|---|---|---|---|---|
| 93 | Boc-L-Leu-OH | 697.4 | 698.45 | 2.76 | 6 |
| 94 | 2-(1,1-dioxidothiomorpholino)acetic acid | 659.3 | 660.35 | 2.244 | 6 |
| 95 | 3-(1,1-dioxidothiomorpholino)propanoic acid | 673.3 | 674.35 | 2.171 | 6 |

Ex = Example;
MW = Molecular weight;
Obs = Observed;
RT = Retention time;
Met = LC/MS Method.

Example 96

Preparation of (S)-4-(2-(1-(2-(1,1-dioxidothiomorpholino)ethyl)-4-phenylpiperidine-4-carbonyl)-5,5,8a-trimethyl-1,2,3,5,8,8a-hexahydroisoquinolin-6-yl)benzoic acid

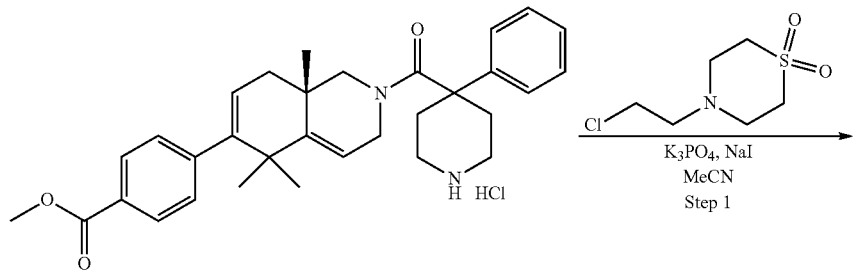

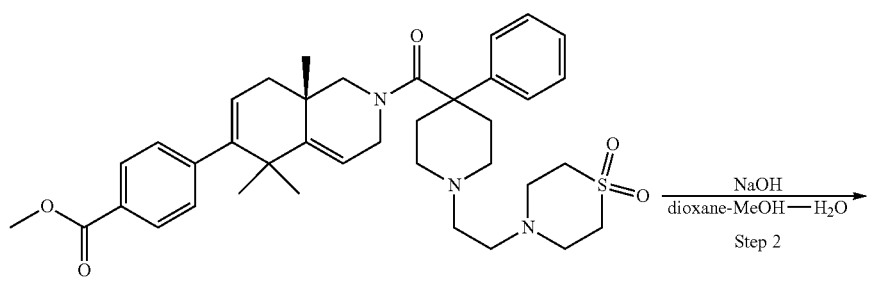

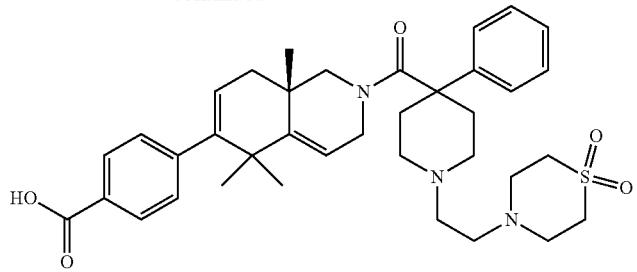

Example 96

Step 1: Preparation of methyl (S)-4-(2-(1-(2-(1,1-dioxidothiomorpholino)ethyl)-4-phenylpiperidine-4-carbonyl)-5,5,8a-trimethyl-1,2,3,5,8,8a-hexahydroisoquinolin-6-yl)benzoate A suspension of methyl (S)-4-(5,5,8a-trimethyl-2-(4-phenylpiperidine-4-carbonyl)-1,2,3,5,8,8a-hexahydroisoquinolin-6-yl)benzoate hydrochloride (25 mg, 0.047 mmol), 4-(2-chloroethyl)thiomorpholine 1,1-dioxide (55 mg, 0.28 mmol), K3PO4 (80 mg, 0.38 mmol) and NaI (28 mg, 0.19 mmol) in MeCN (3 ml) was heated at 100° C. overnight. The reaction mixture was diluted with $CH_2Cl_2$ (10 ml), washed with $H_2O$ (10 ml), dried over $Na_2SO_4$ and concentrated in vacuo to give the crude product without purification. LC/MS m/z 660.40 (M+H)+, 2.22 min (Method 2).

Step 2

To a solution of crude methyl (S)-4-(2-(1-(2-(1,1-dioxidothiomorpholino)ethyl)-4-phenylpiperidine-4-carbonyl)-5,5,8a-trimethyl-1,2,3,5,8,8a-hexahydroisoquinolin-6-yl)benzoate in dioxane (2 ml) and MeOH (1 ml) was added 1N NaOH (1 ml). The mixture was stirred at 50° C. for 4 h. The reaction mixture was purified by Prep HPLC to give the desired product (16 mg, 54%) as a solid. LC/MS m/z 646.40 (M+H)+, 2.05 min (Method 2).

Example 97

Preparation of (S)-4-(2-(2-(5,6-dimethyl-1H-benzo[d]imidazol-2-yl)benzoyl)-5,5,8a-trimethyl-1,2,3,5,8,8a-hexahydroisoquinolin-6-yl)benzoic acid

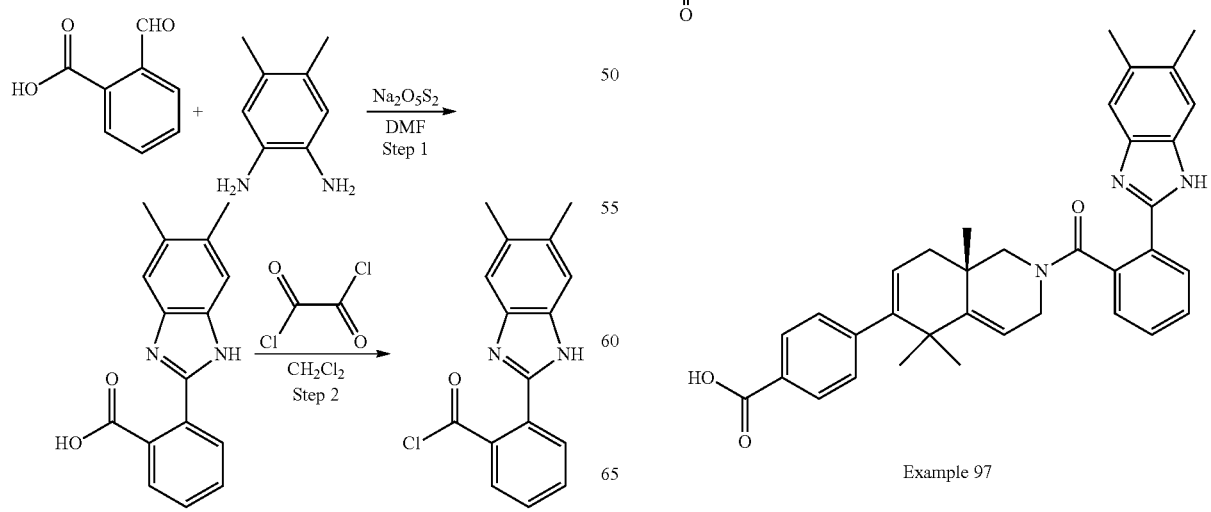

Example 97

Step 1: Preparation of 2-(5,6-dimethyl-1H-benzo[d]imidazol-2-yl)benzoic acid

To a solution of 2-formylbenzoic acid (500 mg, 3.33 mmol) and 4,5-dimethylbenzene-1,2-diamine (454 mg, 3.33 mmol) in DMF (50 ml) was added sodium metabisulfite (696 mg, 3.66 mmol). The mixture was stirred at 60° C. overnight. The mixture was concentrated in vacuo. The residue was partitioned between EtOAc (20 ml) and 1N NaOH (20 ml). The separated aqueous layer was neutralized with 1N HCl to pH~7. The precipitated solid was collected by filtration, washed with $H_2O$, and dried to give the desired product (886 mg, 100%). $^1H$ NMR (400 MHz, DMSO-d6) δ 8.09 (d, J=6.5 Hz, 1H), 7.77 (dd, J=7.7, 1.1 Hz, 1H), 7.54-7.47 (m, 1H), 7.47-7.42 (m, 1H), 7.34 (s, 2H), 2.32 (s, 6H). LC/MS m/z 267.10 $(M+H)^+$, 1.80 min (Method 9).

Step 2: Preparation of 2-(5,6-dimethyl-1H-benzo[d]imidazol-2-yl)benzoyl chloride To a suspension of 2-(5,6-dimethyl-1H-benzo[d]imidazol-2-yl)benzoic acid (85 mg, 0.32 mmol) in $CH_2Cl_2$ (5 ml) was added oxalyl chloride (2 M in $CH_2Cl_2$) (0.24 ml, 0.48 mmol). The reaction mixture was stirred at RT for 2 h and concentrated in vacuo to give the crude product as solid.

Step 3: Preparation of methyl (S)-4-(2-(2-(5,6-dimethyl-1H-benzo[d]imidazol-2-yl)benzoyl)-5,5,8a-trimethyl-1,2,3,5,8,8a-hexahydroisoquinolin-6-yl)benzoate To a solution of methyl (S)-4-(5,5,8a-trimethyl-1,2,3,5,8,8a-hexahydroisoquinolin-6-yl)benzoate hydrochloride (111 mg, 0.32 mmol) and crude 2-(5,6-dimethyl-1H-benzo[d]imidazol-2-yl)benzoyl chloride in $CH_2Cl_2$ (5 ml) was added TEA (0.07 ml, 0.48 mmol). The reaction mixture was stirred at RT overnight. The reaction mixture was concentrated in vacuo. The crude product was purified by silica gel column eluted with 35% EtOAc/hexanes to give the desired product (66 mg, 89%) as a solid. LC/MS m/z 560.35 $(M+H)^+$, 2.37 min (Method 2).

Step 4

To a solution of methyl (S)-4-(2-(2-(5,6-dimethyl-1H-benzo[d]imidazol-2-yl)benzoyl)-5,5,8a-trimethyl-1,2,3,5,8,8a-hexahydroisoquinolin-6-yl)benzoate (26 mg, 0.05 mmol) in dioxane (2 ml) and MeOH (1 ml) was added 1N NaOH (1 ml). The mixture was stirred at 50° C. for 4 h. The crude product was purified by Prep HPLC to give the desired product (19 mg, 75%) as a solid. LC/MS m/z 546.30 $(M+H)^+$, 2.19 min (Method 2).

The example in Table 9 was prepared by the procedure described in Example 97 using the starting material indicated in the table instead of 4,5-dimethylbenzene-1,2-diamine

TABLE 9

| Ex | Reagent | MW | Obs $(M + 1)^+$ | RT | Met |
|---|---|---|---|---|---|
| 98 | 3,4-dimethylbenzene-1,2-diamine | 545.3 | 546.3 | 2.27 | 6 |

Ex = Example;
MW = Molecular weight;
Obs = Observed;
RT = Retention time;
Met = LC/MS Method.

Example 99

Preparation of (S)-4-(2-(2-(5,6-dibromo-1H-benzo[d]imidazol-2-yl)benzoyl)-5,5,8a-trimethyl-1,2,3,5,8,8a-hexahydroisoquinolin-6-yl)benzoic acid

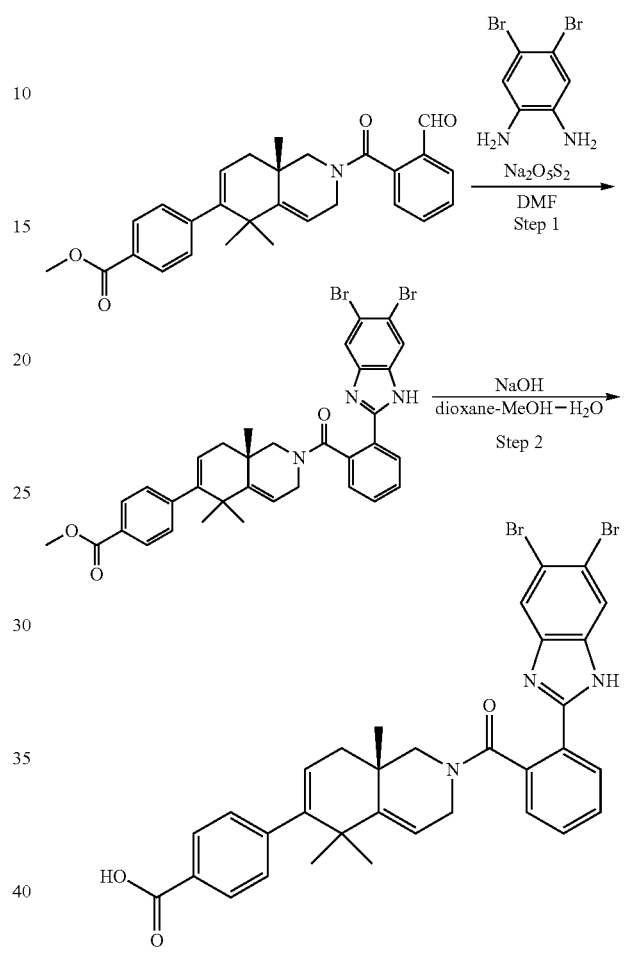

Example 99

Step 1: Preparation of methyl (S)-4-(2-(2-(5,6-dibromo-1H-benzo[d]imidazol-2-yl)benzoyl)-5,5,8a-trimethyl-1,2,3,5,8,8a-hexahydroisoquinolin-6-yl)benzoate To a solution of methyl (S)-4-(2-(2-formylbenzoyl)-5,5,8a-trimethyl-1,2,3,5,8,8a-hexahydroisoquinolin-6-yl)benzoate (50 mg, 0.113 mmol) and 4,5-dibromobenzene-1,2-diamine (30 mg, 0.113 mmol) in DMF (2 ml) was added sodium metabisulfite (24 mg, 0.124 mmol). The mixture was stirred at 60° C. overnight. The mixture was concentrated in vacuo. The residue was partitioned between EtOAc (20 ml) and $H_2O$ (20 ml). The separated aqueous layer was extracted with EtOAc (20 ml). The combined organic layers were washed brine (20 ml), dried over $Na_2SO_4$, and concentrated in vacuo. The crude product was purified by silica gel column eluted with 35% EtOAc/hexanes to give the desired product (62 mg, 80%) as a solid. LC/MS m/z 688.10 $(M+H)^+$, 2.91 min (Method 2).

Step 2

To a solution of methyl (S)-4-(2-(2-(5,6-dibromo-1H-benzo[d]imidazol-2-yl)benzoyl)-5,5,8a-trimethyl-1,2,3,5,8, 8a-hexahydroisoquinolin-6-yl)benzoate (53 mg, 0.077 mmol) in 1,4-dioxane (2 ml) and MeOH (1 ml) was added 1N NaOH (1 ml). The mixture was stirred at 50° C. for 2 h. The crude product was purified by Prep HPLC to give the desired product (43 mg, 81%) as a solid. LC/MS m/z 674.10 (M+H)$^+$, 2.73 min (Method 2).

The examples in Table 10 were prepared from intermediate 3 by the procedure described in Example 99 using the reagents indicated in the table instead of 4,5-dibromobenzene-1,2-diamine:

TABLE 10

| Ex | Reagent | MW | Obs (M + 1)$^+$ | RT | Met |
|---|---|---|---|---|---|
| 100 | 2-methyl-4-phenyl-1,2,3,4-tetrahydroisoquinoline-7,8-diamine | 662.3 | 663.4 | 2.38 | 6 |
| 101 | 2-methyl-4-phenyl-1,2,3,4-tetrahydroisoquinoline-7,8-diamine | 662.3 | 663.4 | 2.49 | 6 |

Ex = Example;
MW = Molecular weight;
Obs = Observed;
RT = Retention time;
Met = LC/MS Method.

Section 2
LCMS Methods:
Method-A:
Column: Waters BEH C18, 2.0×50 mm, 1.7-μm particles
Mobile Phase A: 5:95 acetonitrile:water with 10 mM ammonium acetate
Mobile Phase B: 95:5 acetonitrile:water with 10 mM ammonium acetate
Temperature: 40° C.
Gradient: 0.5 min hold at 0% B, 0-100% B over 4 minutes, then a 0.5-minute hold at 100% B
Flow: 1 mL/min
Method-M:
Column: Waters BEH C18, 2.0×50 min, 1.7-μm particles
Mobile Phase A: 5:95 methanol:water with 10 mM ammonium acetate
Mobile Phase B: 95:5 methanol:water with 10 mM ammonium acetate
Temperature: 40° C.
Gradient: 0.5 min hold at 0% B, 0-100% B over 4 minutes, then a 0.5-minute hold at 100% B
Flow: 0.5 mL/min.

Examples A1-A126 were prepared from intermediate 1 and commercially available carboxylic acids by the following general method:

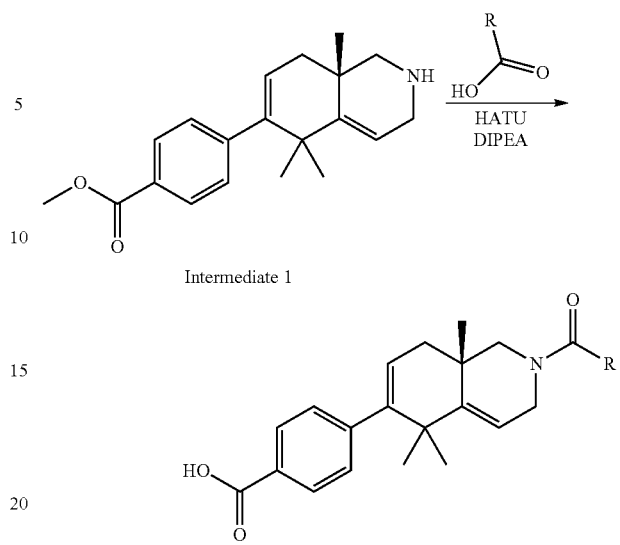

Prepared a solution of HATU (684 mg, 1.8 mmol) in DMF (12.0 mL). To each of the carboxylic acids weighed into 16×48 mm threaded vials was added 0.5 mL of the HATU solution. The reactions were agitated at 350 rpm on an Innova platform shaker at room temperature for 10 minutes. Prepared a solution of the (S)-methyl 4-(5,5,8a-trimethyl-1,2,3,5,8,8a-hexahydroisoquinolin-6-yl)benzoate (417 mg, 1.2 mmol) and DIPEA (840 μL, 4.8 mmol). Added 0.5 mL of the (S)-methyl 4-(5,5,8a-trimethyl-1,2,3,5,8,8a-hexahydroisoquinolin-6-yl)benzoate/DIPEA solution to each of the reaction vials. Capped vials and agitated at 350 rpm on an Innova platform shaker at room temperature for 18 hrs. Samples were blown down in the Zymark tabletop dryer at 35° C. for 3 hours. Prepared a solution of lithium hydroxide Monohydrate (403 mg, 9.6 mmol) in water (4.8 mL). To each of the reaction vials was added 0.8 mL dioxane and 0.2 mL of the lithium hydroxide solution. Capped vials and agitated at 350 rpm on an Innova platform shaker at 70° C. for 18 hrs. Samples were blown down in the Zymark tabletop dryer at 35° C. for 3 hours. Added 1.0 mL DMF to each vial. Transferred contents to a 96 well 2 mL filter plate, collecting into a 96 well deepwell plate. Rinsed reaction vials w/500 DMF each and transferred rinses to the appropriate wells of the filter plate. Transferred contents to 16×48 mm threaded vials, followed by automated HPLC purification and LCMS analyses. See Table 11.

TABLE 11

| Ex | Structure | MW | Obs Ion | RT | Met |
|---|---|---|---|---|---|
| A1 | 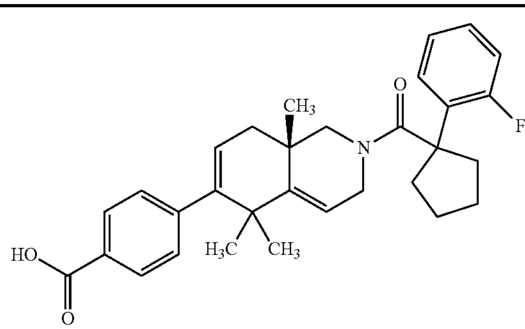 | 487.61 | 488.3 | 2.66 | A |

TABLE 11-continued

| Ex | Structure | MW | Obs Ion | RT | Met |
|---|---|---|---|---|---|
| A2 | 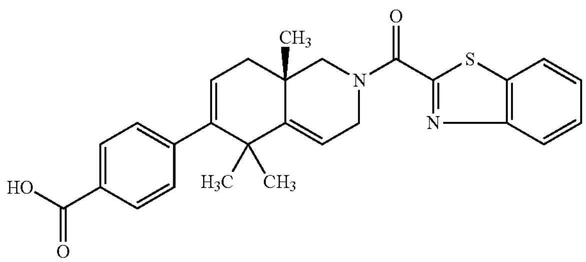 [SMILES: CC1(C)C(c2ccc(C(=O)O)cc2)=CC[C@]2(C)CN(C(=O)c3nc4ccccc4s3)CC=C12] | 458.57 | 459.1 | 2.55 | A |
| A3 | 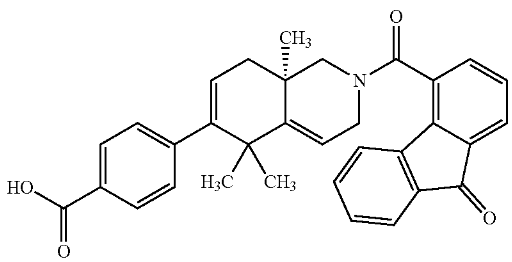 [SMILES: CC1(C)C(c2ccc(C(=O)O)cc2)=CC[C@@]2(C)CN(C(=O)c3cccc4c3-c3ccccc3C4=O)CC=C12] | 503.59 | 502.3 | 2.34 | A |
| A4 | 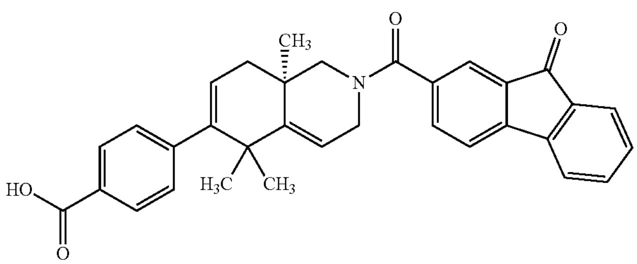 [SMILES: CC1(C)C(c2ccc(C(=O)O)cc2)=CC[C@@]2(C)CN(C(=O)c3ccc4c(c3)C(=O)c3ccccc3-4)CC=C12] | 503.59 | 504.2 | 3.83 | M |
| A5 | 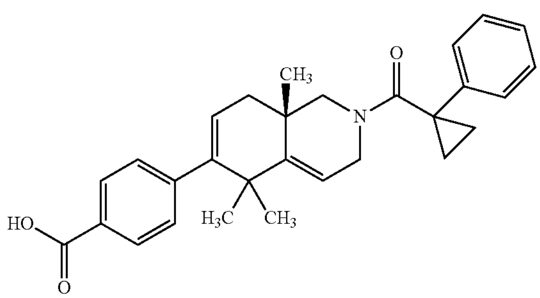 [SMILES: CC1(C)C(c2ccc(C(=O)O)cc2)=CC[C@]2(C)CN(C(=O)C3(c4ccccc4)CC3)CC=C12] | 441.56 | 440.3 | 3.84 | M |
| A6 | 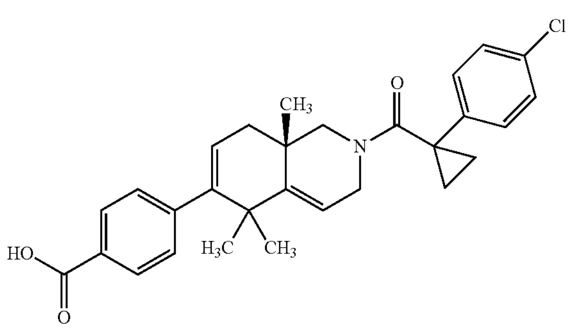 [SMILES: CC1(C)C(c2ccc(C(=O)O)cc2)=CC[C@]2(C)CN(C(=O)C3(c4ccc(Cl)cc4)CC3)CC=C12] | 476.01 | 476.2 | 4.00 | M |

TABLE 11-continued

| Ex | Structure | MW | Obs Ion | RT | Met |
|---|---|---|---|---|---|
| A7 | 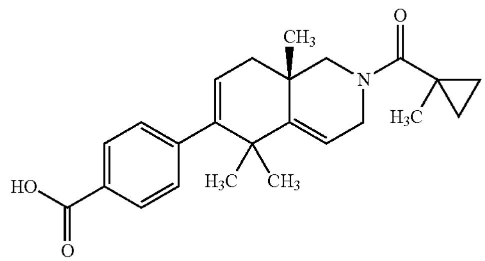 [SMILES: CC1(C(=O)N2CC=C3C(C)(C)C(c4ccc(C(=O)O)cc4)=CC[C@]3(C)C2)CC1] | 379.49 | 380.2 | 2.08 | A |
| A8 | 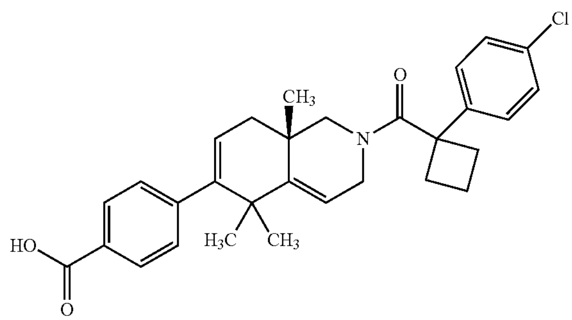 [SMILES: CC1(C)C(c2ccc(C(=O)O)cc2)=CC[C@]2(C)CN(C(=O)C3(c4ccc(Cl)cc4)CCC3)CC=C12] | 490.03 | 490.3 | 2.75 | A |
| A9 | 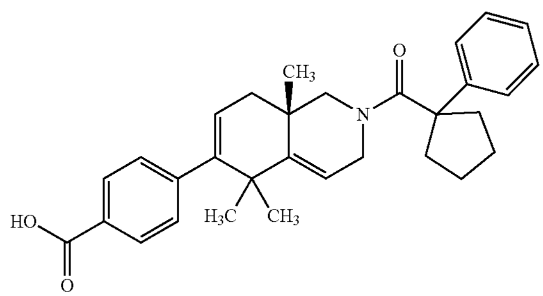 [SMILES: CC1(C)C(c2ccc(C(=O)O)cc2)=CC[C@]2(C)CN(C(=O)C3(c4ccccc4)CCCC3)CC=C12] | 469.61 | 470.3 | 2.77 | A |
| A10 | 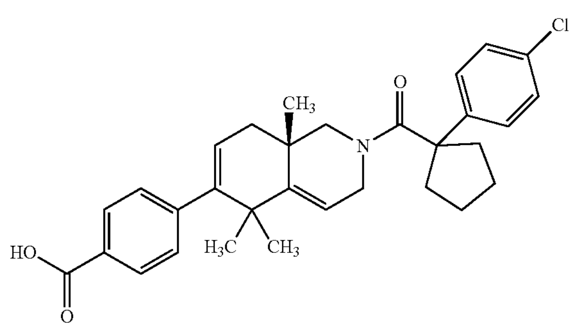 [SMILES: CC1(C)C(c2ccc(C(=O)O)cc2)=CC[C@]2(C)CN(C(=O)C3(c4ccc(Cl)cc4)CCCC3)CC=C12] | 504.06 | 504.3 | 2.94 | A |
| A11 | 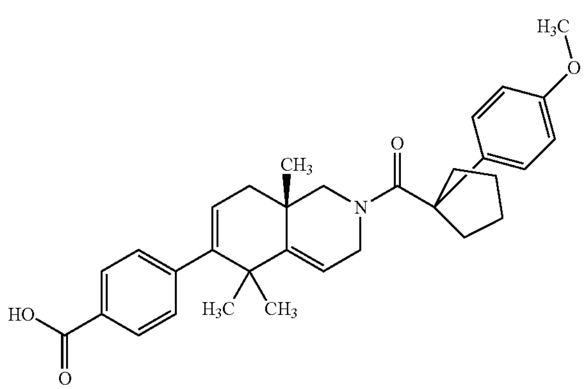 [SMILES: COc1ccc(C2(C(=O)N3CC=C4C(C)(C)C(c5ccc(C(=O)O)cc5)=CC[C@]4(C)C3)CCCC2)cc1] | 499.64 | 500.3 | 2.71 | A |

TABLE 11-continued

| Ex | Structure | MW | Obs Ion | RT | Met |
|---|---|---|---|---|---|
| A12 | 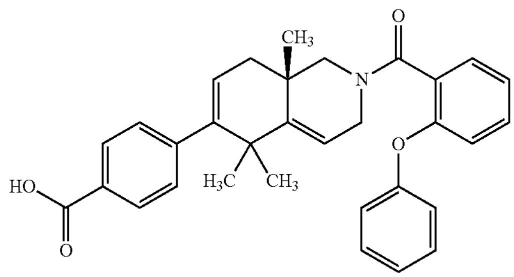 [SMILES: CC1(C)C(c2ccc(C(=O)O)cc2)=CC[C@]2(C)CN(C(=O)c3ccccc3Oc3ccccc3)CC=C12] | 493.59 | 494.3 | 3.93 | M |
| A13 | 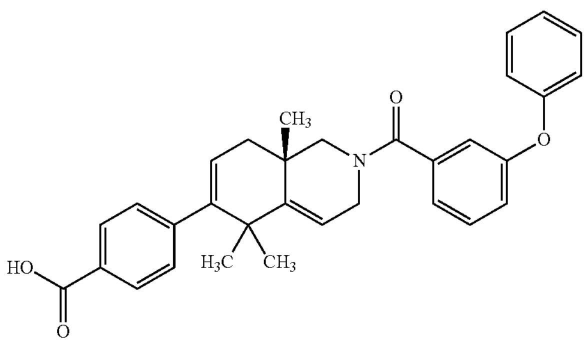 [SMILES: CC1(C)C(c2ccc(C(=O)O)cc2)=CC[C@]2(C)CN(C(=O)c3cccc(Oc4ccccc4)c3)CC=C12] | 493.59 | 494.3 | 2.58 | A |
| A14 | 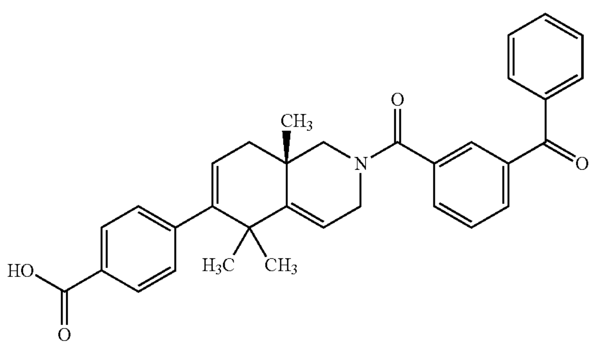 [SMILES: CC1(C)C(c2ccc(C(=O)O)cc2)=CC[C@]2(C)CN(C(=O)c3cccc(C(=O)c4ccccc4)c3)CC=C12] | 505.60 | 506.3 | 3.75 | M |
| A15 | 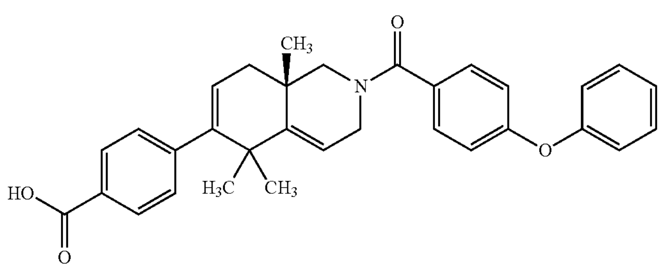 [SMILES: CC1(C)C(c2ccc(C(=O)O)cc2)=CC[C@]2(C)CN(C(=O)c3ccc(Oc4ccccc4)cc3)CC=C12] | 493.59 | 494.3 | 4.05 | M |
| A16 | 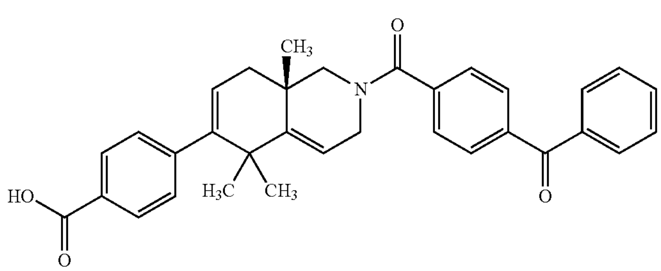 [SMILES: CC1(C)C(c2ccc(C(=O)O)cc2)=CC[C@]2(C)CN(C(=O)c3ccc(C(=O)c4ccccc4)cc3)CC=C12] | 505.60 | 506.3 | 3.78 | M |

TABLE 11-continued

| Ex | Structure | MW | Obs Ion | RT | Met |
|---|---|---|---|---|---|
| A17 | 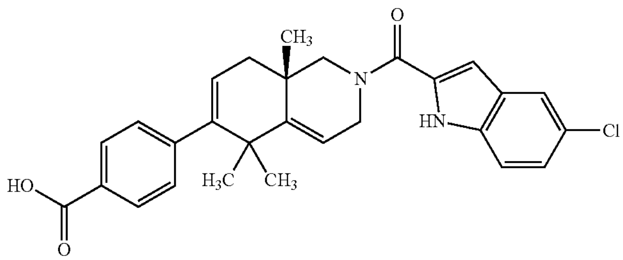 [SMILES: CC1(C)C(c2ccc(C(=O)O)cc2)=CC[C@]2(C)CN(C(=O)c3cc4cc(Cl)ccc4[nH]3)CC=C12] | 474.98 | 475.3 | 4.07 | M |
| A18 | 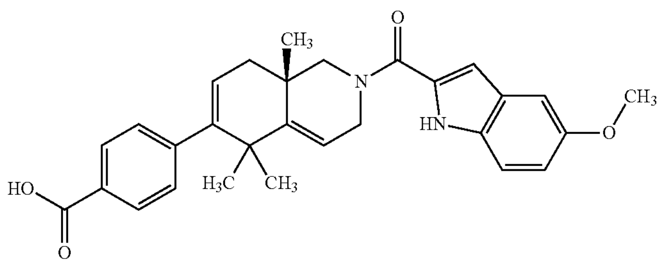 [SMILES: COc1ccc2[nH]c(C(=O)N3CC=C4C(C)(C)C(c5ccc(C(=O)O)cc5)=CC[C@]4(C)C3)cc2c1] | 470.56 | 471.2 | 3.73 | M |
| A19 | 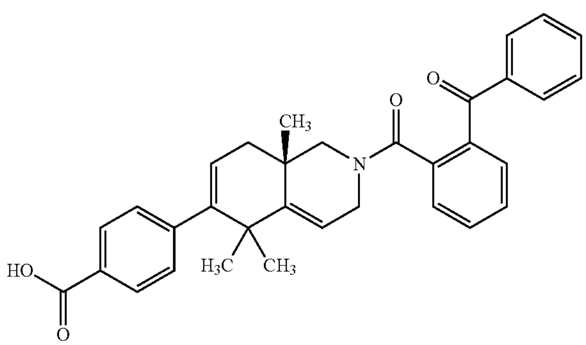 [SMILES: CC1(C)C(c2ccc(C(=O)O)cc2)=CC[C@]2(C)CN(C(=O)c3ccccc3C(=O)c3ccccc3)CC=C12] | 505.60 | 506.3 | 3.76 | M |
| A20 | 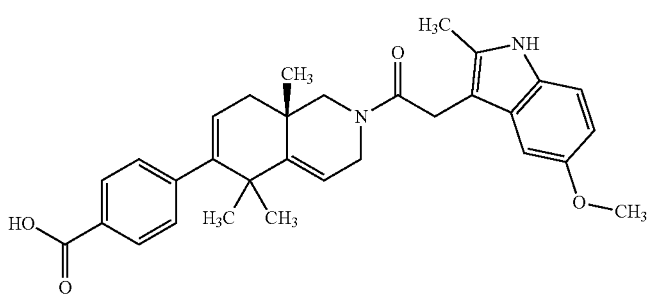 [SMILES: COc1ccc2[nH]c(C)c(CC(=O)N3CC=C4C(C)(C)C(c5ccc(C(=O)O)cc5)=CC[C@]4(C)C3)c2c1] | 498.61 | 499.2 | 2.12 | M |
| A21 | 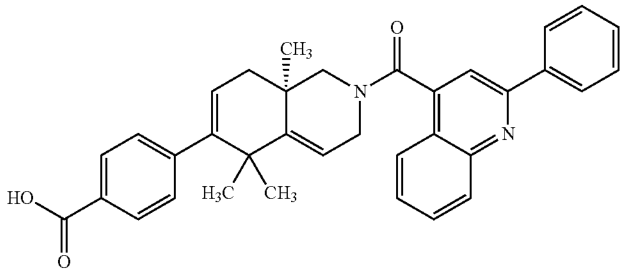 [SMILES: CC1(C)C(c2ccc(C(=O)O)cc2)=CC[C@@]2(C)CN(C(=O)c3cc(-c4ccccc4)nc4ccccc34)CC=C12] | 528.64 | 527.3 | 2.64 | A |

TABLE 11-continued

| Ex | Structure | MW | Obs Ion | RT | Met |
|---|---|---|---|---|---|
| A22 | 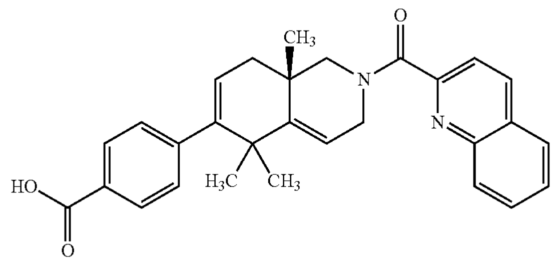 [SMILES: CC1(C)C(c2ccc(C(=O)O)cc2)=CC[C@]2(C)CN(C(=O)c3ccc4ccccc4n3)CC=C12] | 452.54 | 453.2 | 3.60 | M |
| A23 | 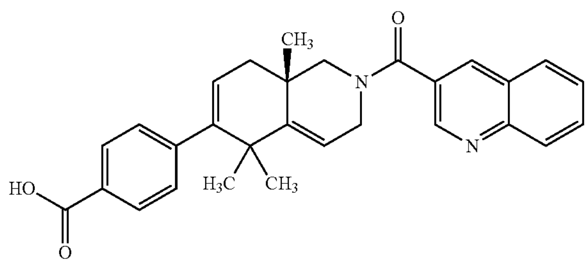 [SMILES: CC1(C)C(c2ccc(C(=O)O)cc2)=CC[C@]2(C)CN(C(=O)c3cnc4ccccc4c3)CC=C12] | 452.54 | 453.2 | 3.43 | M |
| A24 | 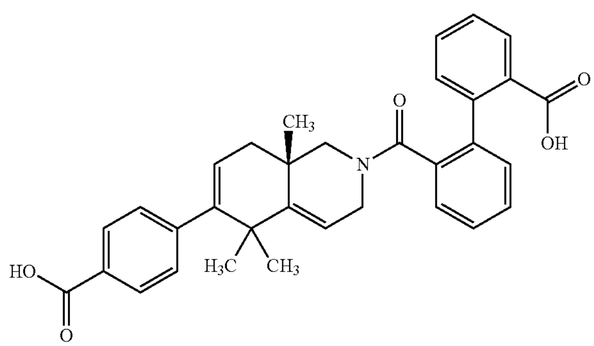 [SMILES: CC1(C)C(c2ccc(C(=O)O)cc2)=CC[C@]2(C)CN(C(=O)c3ccccc3-c3ccccc3C(=O)O)CC=C12] | 521.60 | 522.3 | 3.07 | M |
| A25 | 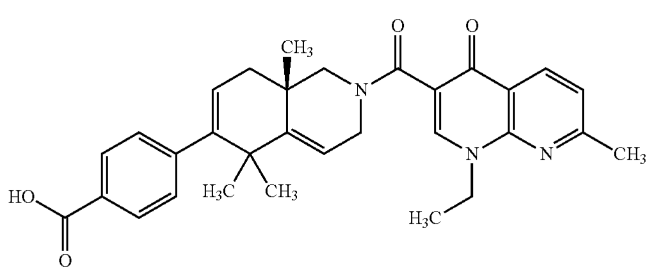 [SMILES: CCn1cc(C(=O)N2CC=C3C(C)(C)C(c4ccc(C(=O)O)cc4)=CC[C@]3(C)C2)c(=O)c2ccc(C)nc21] | 511.61 | 510.4 | 3.46 | M |
| A26 | 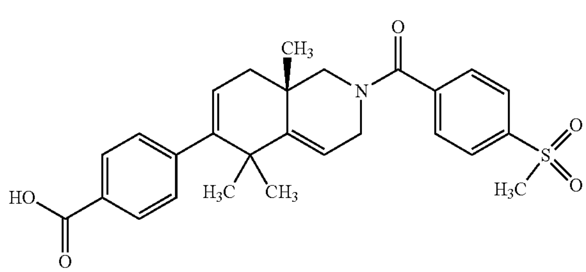 [SMILES: CC1(C)C(c2ccc(C(=O)O)cc2)=CC[C@]2(C)CN(C(=O)c3ccc(S(C)(=O)=O)cc3)CC=C12] | 479.59 | 480.3 | 2.99 | M |

TABLE 11-continued

| Ex | Structure | MW | Obs Ion | RT | Met |
|---|---|---|---|---|---|
| A27 | 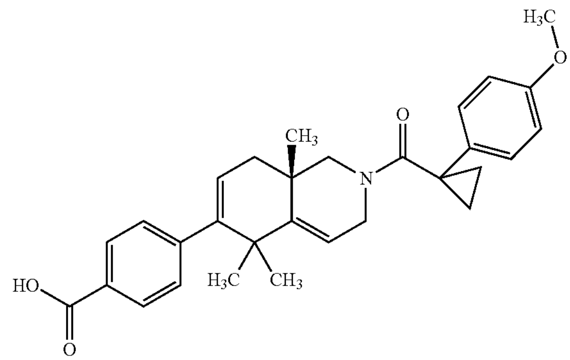 [SMILES: COc1ccc(C2(C(=O)N3CC=C4C(C)(C)C(c5ccc(C(=O)O)cc5)=CC[C@]4(C)C3)CC2)cc1] | 471.59 | 472.3 | 2.32 | A |
| A28 | 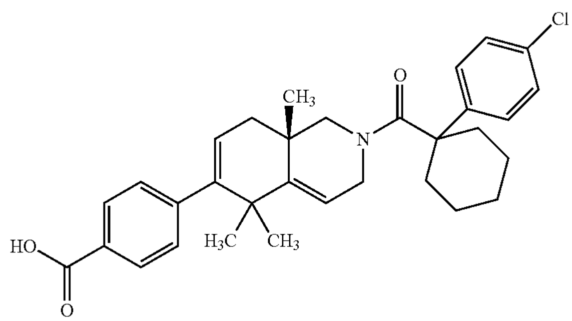 [SMILES: CC1(C)C(c2ccc(C(=O)O)cc2)=CC[C@]2(C)CN(C(=O)C3(c4ccc(Cl)cc4)CCCCC3)CC=C12] | 518.09 | 518.4 | 3.17 | A |
| A29 | 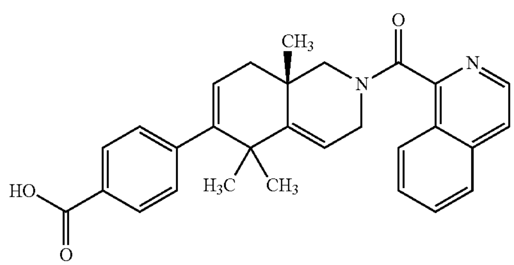 [SMILES: CC1(C)C(c2ccc(C(=O)O)cc2)=CC[C@]2(C)CN(C(=O)c3nccc4ccccc34)CC=C12] | 452.54 | 453.3 | 3.42 | M |
| A30 | 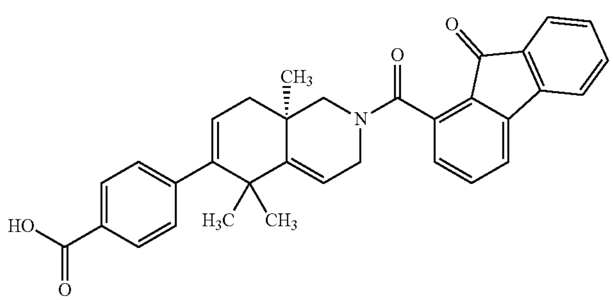 [SMILES: CC1(C)C(c2ccc(C(=O)O)cc2)=CC[C@@]2(C)CN(C(=O)c3cccc4c3C(=O)c3ccccc3-4)CC=C12] | 503.59 | 504.3 | 3.77 | M |
| A31 | 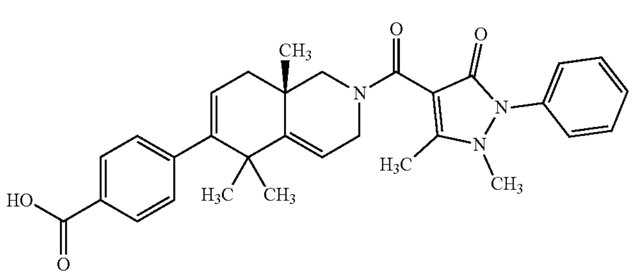 [SMILES: Cc1c(C(=O)N2CC=C3C(C)(C)C(c4ccc(C(=O)O)cc4)=CC[C@]3(C)C2)c(=O)n(-c2ccccc2)n1C] | 511.61 | 512.3 | 1.74 | A |

TABLE 11-continued

| Ex | Structure | MW | Obs Ion | RT | Met |
|---|---|---|---|---|---|
| A32 | 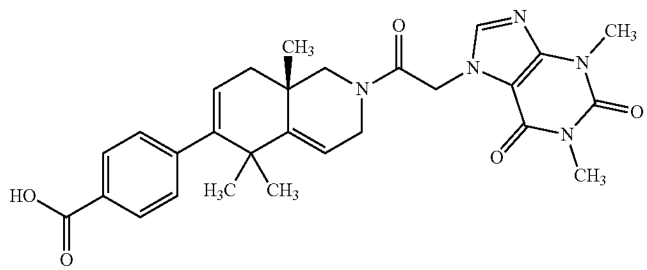 [SMILES: Cn1c(=O)c2c(ncn2CC(=O)N2CC=C3C(C)(C)C(c4ccc(C(=O)O)cc4)=CC[C@]3(C)C2)n(C)c1=O] | 517.58 | 518.3 | 2.95 | M |
| A33 | 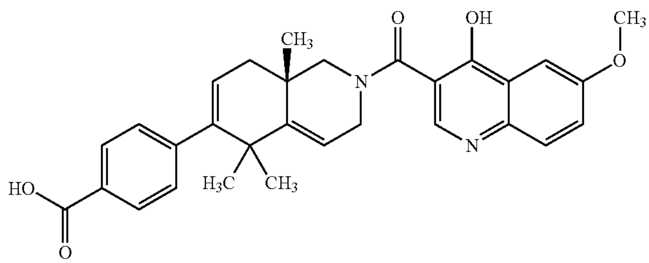 [SMILES: COc1ccc2ncc(C(=O)N3CC=C4C(C)(C)C(c5ccc(C(=O)O)cc5)=CC[C@]4(C)C3)c(O)c2c1] | 498.57 | 499.3 | 3.11 | M |
| A34 | 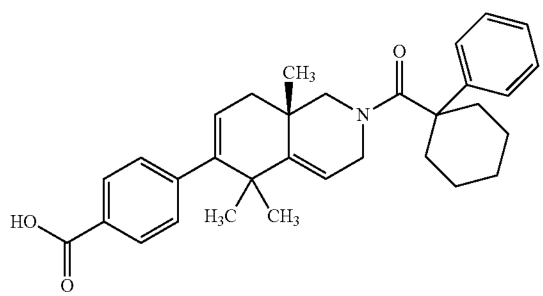 [SMILES: CC1(C)C(c2ccc(C(=O)O)cc2)=CC[C@]2(C)CN(C(=O)C3(c4ccccc4)CCCCC3)CC=C12] | 483.64 | 484.3 | 4.41 | M |
| A35 | 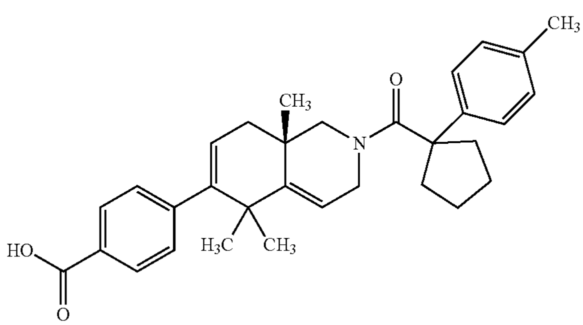 [SMILES: Cc1ccc(C2(C(=O)N3CC=C4C(C)(C)C(c5ccc(C(=O)O)cc5)=CC[C@]4(C)C3)CCCC2)cc1] | 483.64 | 484.3 | 4.39 | M |
| A36 | 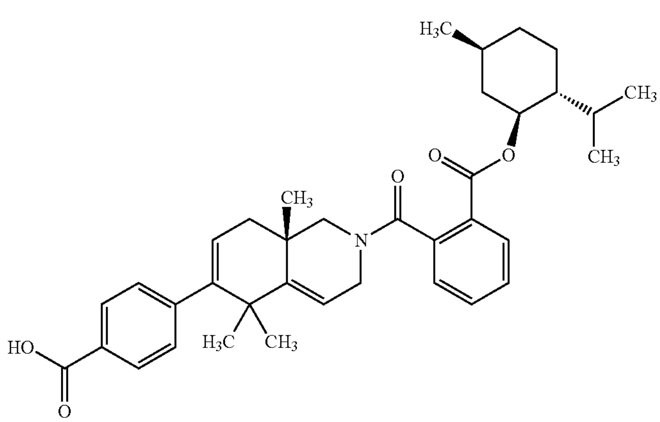 [SMILES: CC(C)[C@H]1CC[C@H](C)C[C@@H]1OC(=O)c1ccccc1C(=O)N1CC=C2C(C)(C)C(c3ccc(C(=O)O)cc3)=CC[C@]2(C)C1] | 583.77 | 584.4 | 4.54 | M |

TABLE 11-continued

| Ex | Structure | MW | Obs Ion | RT | Met |
|---|---|---|---|---|---|
| A37 | 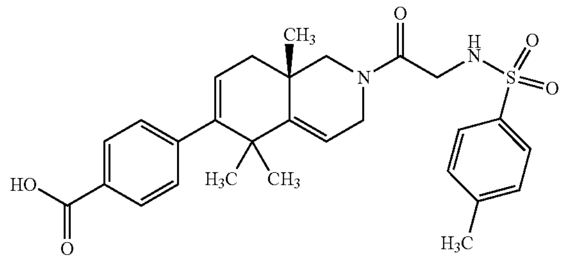 [SMILES: Cc1ccc(S(=O)(=O)NCC(=O)N2CC=C3C(C)(C)C(c4ccc(C(=O)O)cc4)=CC[C@]3(C)C2)cc1] | 508.63 | 509.3 | 3.37 | M |
| A38 | 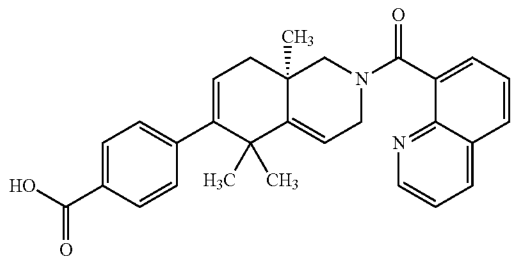 [SMILES: CC1(C)C(c2ccc(C(=O)O)cc2)=CC[C@@]2(C)CN(C(=O)c3cccc4cccnc34)CC=C12] | 452.54 | 453.3 | 3.34 | M |
| A39 | 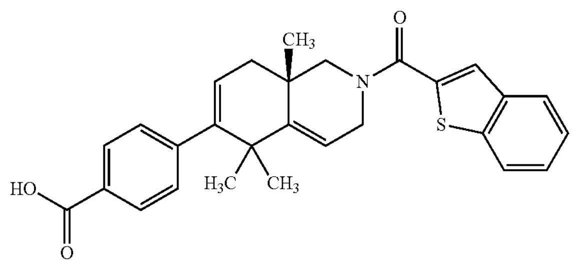 [SMILES: CC1(C)C(c2ccc(C(=O)O)cc2)=CC[C@]2(C)CN(C(=O)c3cc4ccccc4s3)CC=C12] | 457.58 | 458.3 | 3.92 | M |
| A40 | 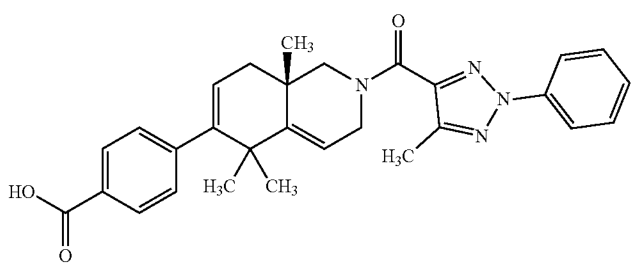 [SMILES: Cc1nn(-c2ccccc2)nc1C(=O)N1CC=C2C(C)(C)C(c3ccc(C(=O)O)cc3)=CC[C@]2(C)C1] | 482.58 | 483.3 | 4.16 | M |
| A41 | 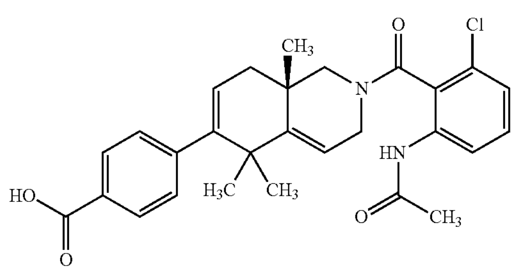 [SMILES: CC(=O)Nc1cccc(Cl)c1C(=O)N1CC=C2C(C)(C)C(c3ccc(C(=O)O)cc3)=CC[C@]2(C)C1] | 492.99 | 493.2 | 2.52 | M |
| A42 | 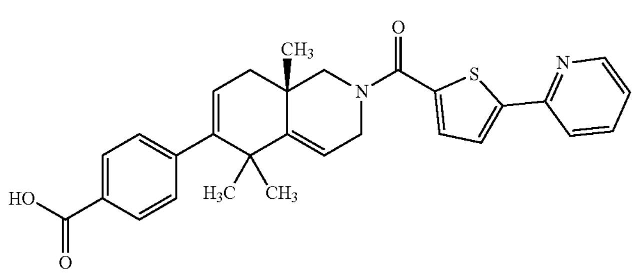 [SMILES: CC1(C)C(c2ccc(C(=O)O)cc2)=CC[C@]2(C)CN(C(=O)c3ccc(-c4ccccn4)s3)CC=C12] | 484.61 | 485.3 | 3.63 | M |

TABLE 11-continued

| Ex | Structure | MW | Obs Ion | RT | Met |
|---|---|---|---|---|---|
| A43 | 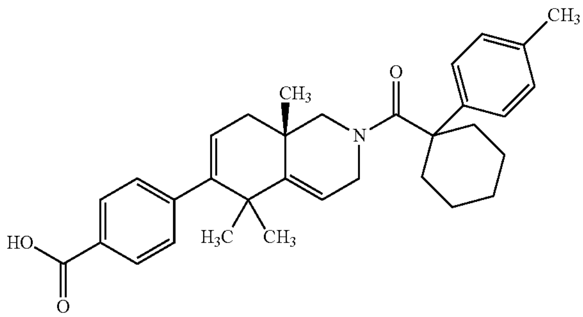 [SMILES: Cc1ccc(C2(C(=O)N3CC=C4C(C)(C)C(c5ccc(C(=O)O)cc5)=CC[C@]4(C)C3)CCCCC2)cc1] | 497.67 | 498.3 | 3.18 | A |
| A44 | 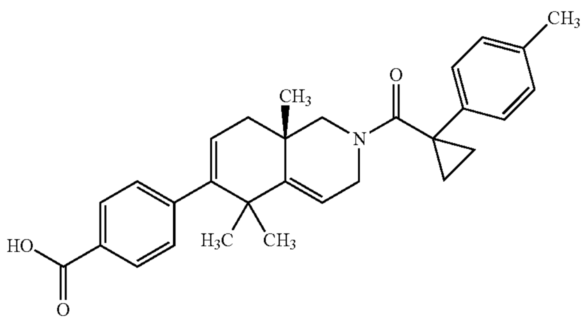 [SMILES: Cc1ccc(C2(C(=O)N3CC=C4C(C)(C)C(c5ccc(C(=O)O)cc5)=CC[C@]4(C)C3)CC2)cc1] | 455.59 | 456.3 | 4.02 | M |
| A45 | 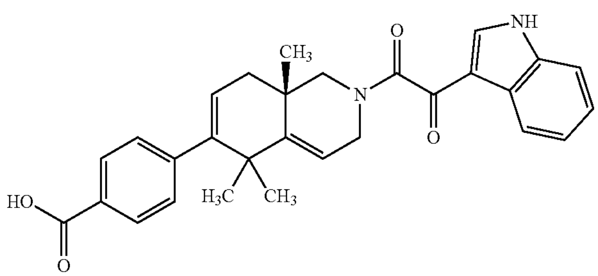 [SMILES: CC1(C)C(c2ccc(C(=O)O)cc2)=CC[C@]2(C)CN(C(=O)C(=O)c3c[nH]c4ccccc34)CC=C12] | 468.54 | 469.3 | 2.06 | A |
| A46 | 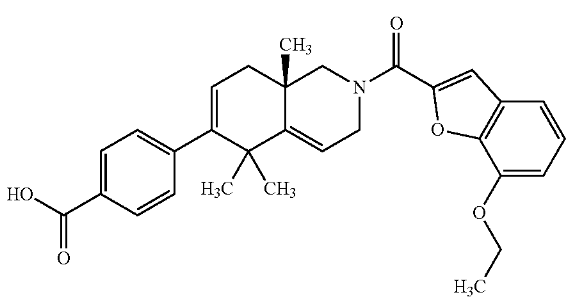 [SMILES: CCOc1cccc2cc(C(=O)N3CC=C4C(C)(C)C(c5ccc(C(=O)O)cc5)=CC[C@]4(C)C3)oc12] | 485.58 | 486.3 | 2.57 | A |
| A47 | 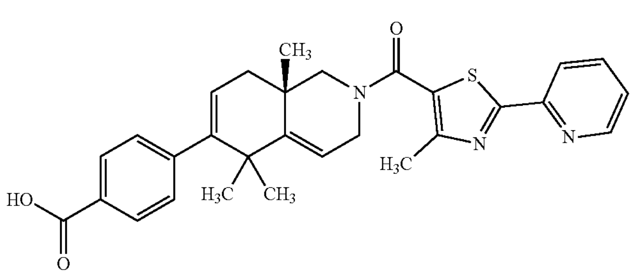 [SMILES: Cc1nc(-c2ccccn2)sc1C(=O)N1CC=C2C(C)(C)C(c3ccc(C(=O)O)cc3)=CC[C@]2(C)C1] | 499.62 | 500.3 | 2.09 | A |

TABLE 11-continued

| Ex | Structure | MW | Obs Ion | RT | Met |
|---|---|---|---|---|---|
| A48 | 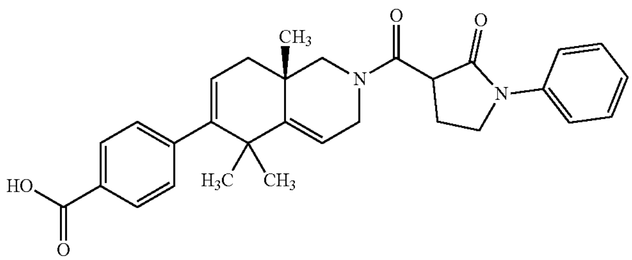 [SMILES: CC1(C)C(c2ccc(C(=O)O)cc2)=CC[C@]2(C)CN(C(=O)C3CCN(c4ccccc4)C3=O)CC=C12] | 484.59 | 485.3 | 2.02 | A |
| A49 | 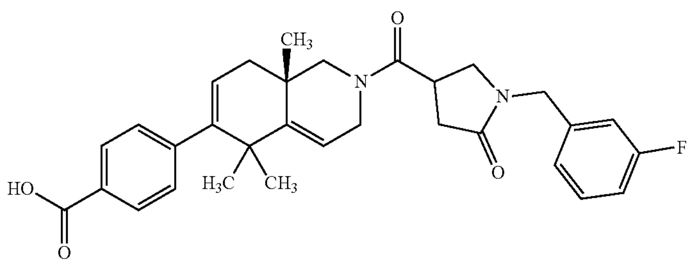 [SMILES: CC1(C)C(c2ccc(C(=O)O)cc2)=CC[C@]2(C)CN(C(=O)C3CC(=O)N(Cc4cccc(F)c4)C3)CC=C12] | 515.60 | 517.3 | 1.94 | A |
| A50 | 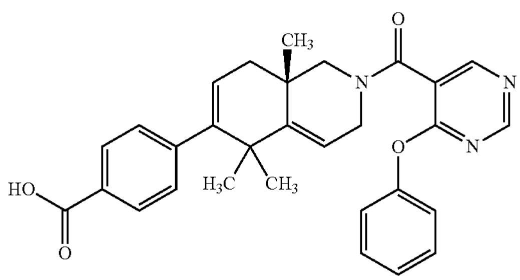 [SMILES: CC1(C)C(c2ccc(C(=O)O)cc2)=CC[C@]2(C)CN(C(=O)c3cncnc3Oc3ccccc3)CC=C12] | 495.57 | 496.3 | 2.07 | A |
| A51 | 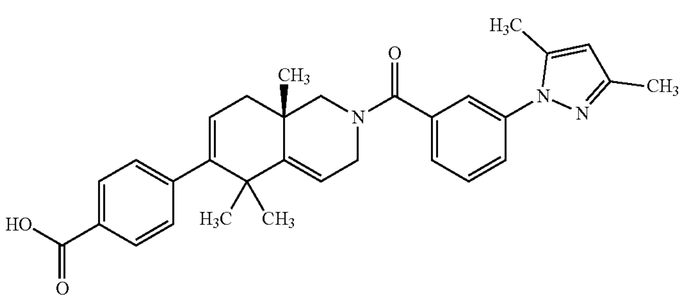 [SMILES: Cc1cc(C)n(-c2cccc(C(=O)N3CC=C4C(C)(C)C(c5ccc(C(=O)O)cc5)=CC[C@]4(C)C3)c2)n1] | 495.61 | 496.3 | 1.94 | A |
| A52 | 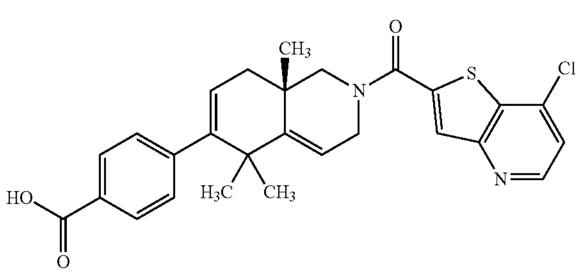 [SMILES: CC1(C)C(c2ccc(C(=O)O)cc2)=CC[C@]2(C)CN(C(=O)c3cc4nccc(Cl)c4s3)CC=C12] | 493.02 | 493.3 | 2.21 | A |

TABLE 11-continued

| Ex | Structure | MW | Obs Ion | RT | Met |
|---|---|---|---|---|---|
| A53 | 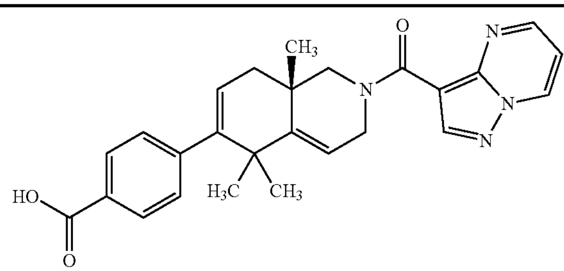 | 442.51 | 443.3 | 2.76 | M |
| A54 | 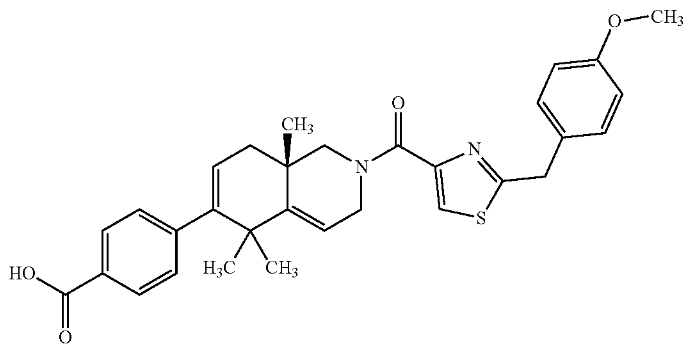 [SMILES: COc1ccc(Cc2nc(C(=O)N3CC=C4C(C)(C)C(c5ccc(C(=O)O)cc5)=CC[C@]4(C)C3)cs2)cc1] | 528.66 | 529.3 | 2.27 | A |
| A55 | 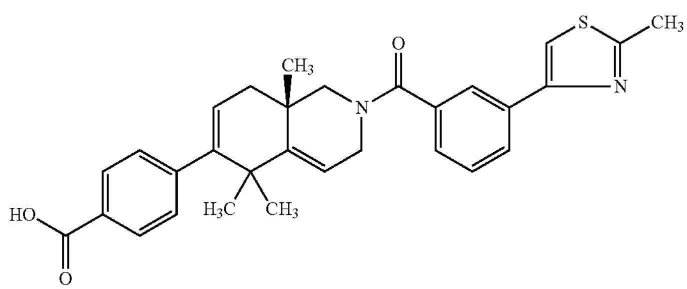 [SMILES: Cc1nc(-c2cccc(C(=O)N3CC=C4C(C)(C)C(c5ccc(C(=O)O)cc5)=CC[C@]4(C)C3)c2)cs1] | 498.64 | 499.3 | 2.17 | A |
| A56 | 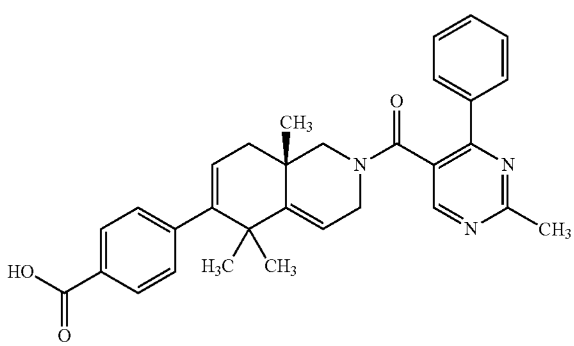 [SMILES: Cc1ncc(C(=O)N2CC=C3C(C)(C)C(c4ccc(C(=O)O)cc4)=CC[C@]3(C)C2)c(-c2ccccc2)n1] | 493.60 | 494.3 | 1.98 | A |
| A57 | 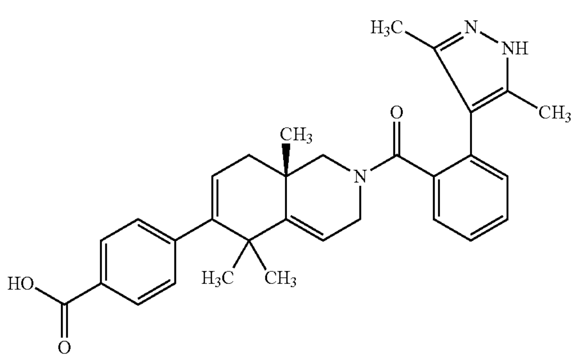 [SMILES: Cc1n[nH]c(C)c1-c1ccccc1C(=O)N1CC=C2C(C)(C)C(c3ccc(C(=O)O)cc3)=CC[C@]2(C)C1] | 495.61 | 496.4 | 1.95 | A |

TABLE 11-continued
| Ex | Structure | MW | Obs Ion | RT | Met |
|---|---|---|---|---|---|
| A58 | 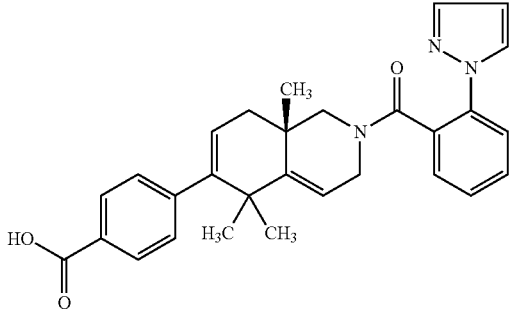 [SMILES: CC1(C)C(c2ccc(C(=O)O)cc2)=CC[C@]2(C)CN(C(=O)c3ccccc3-n3cccn3)CC=C12] | 467.57 | 468.3 | 1.93 | A |
| A59 | 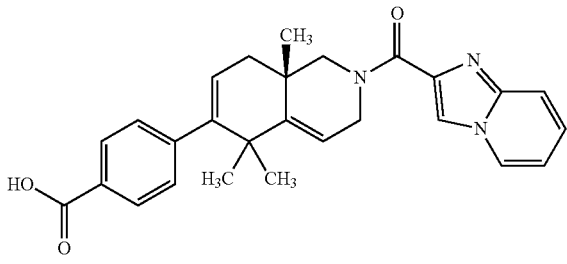 [SMILES: CC1(C)C(c2ccc(C(=O)O)cc2)=CC[C@]2(C)CN(C(=O)c3cn4ccccc4n3)CC=C12] | 441.52 | 442.3 | 1.71 | A |
| A60 | 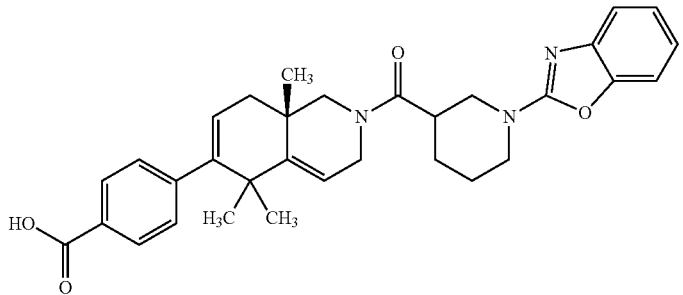 [SMILES: CC1(C)C(c2ccc(C(=O)O)cc2)=CC[C@]2(C)CN(C(=O)C3CCCN(c4nc5ccccc5o4)C3)CC=C12] | 525.64 | 526.4 | 3.69 | M |
| A61 | 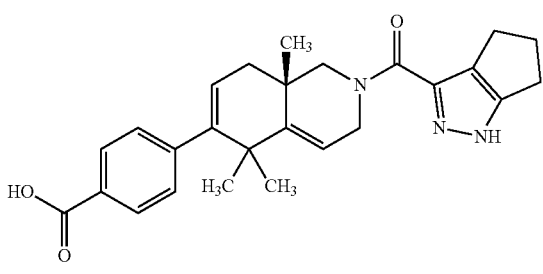 [SMILES: CC1(C)C(c2ccc(C(=O)O)cc2)=CC[C@]2(C)CN(C(=O)c3n[nH]c4c3CCC4)CC=C12] | 431.53 | 432.3 | 1.80 | A |
| A62 | 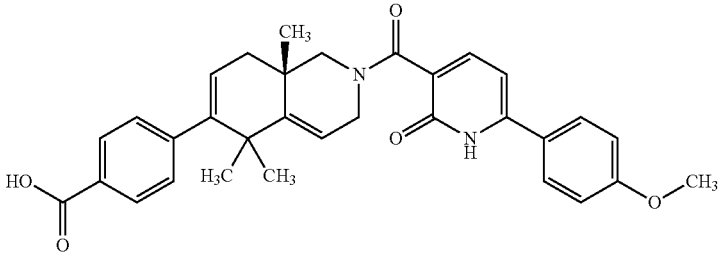 [SMILES: COc1ccc(-c2ccc(C(=O)N3CC=C4C(C)(C)C(c5ccc(C(=O)O)cc5)=CC[C@]4(C)C3)c(=O)[nH]2)cc1] | 524.61 | 525.3 | 1.84 | A |

TABLE 11-continued

| Ex | Structure | MW | Obs Ion | RT | Met |
|---|---|---|---|---|---|
| A63 | 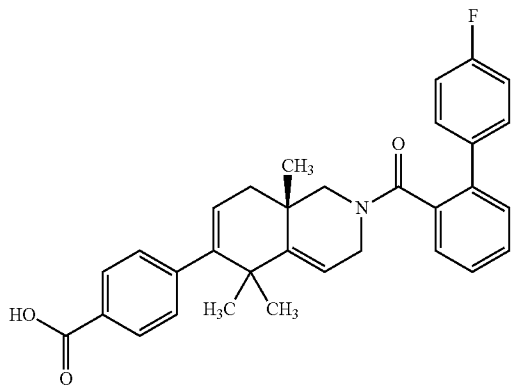 [SMILES: CC1(C)C(c2ccc(C(=O)O)cc2)=CC[C@]2(C)CN(C(=O)c3ccccc3-c3ccc(F)cc3)CC=C12] | 495.58 | 496.3 | 2.39 | A |
| A64 | 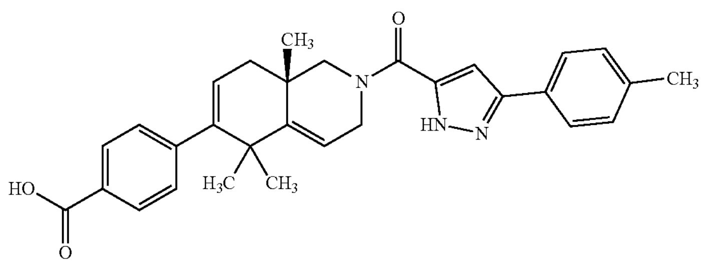 [SMILES: Cc1ccc(-c2cc(C(=O)N3CC=C4C(C)(C)C(c5ccc(C(=O)O)cc5)=CC[C@]4(C)C3)[nH]n2)cc1] | 481.59 | 482.3 | 2.19 | A |
| A65 | 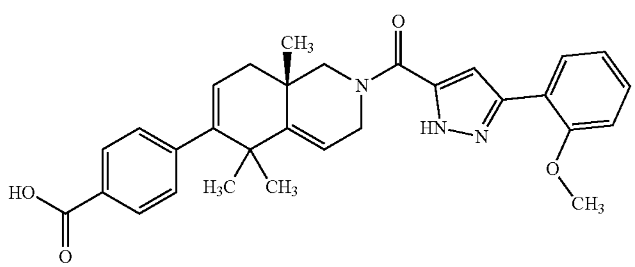 [SMILES: COc1ccccc1-c1cc(C(=O)N2CC=C3C(C)(C)C(c4ccc(C(=O)O)cc4)=CC[C@]3(C)C2)[nH]n1] | 497.58 | 498.3 | 2.17 | A |
| A66 | 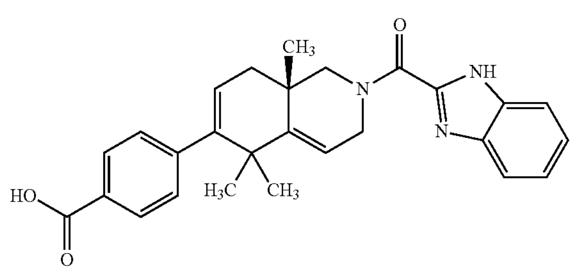 [SMILES: CC1(C)C(c2ccc(C(=O)O)cc2)=CC[C@]2(C)CN(C(=O)c3nc4ccccc4[nH]3)CC=C12] | 441.53 | 442.3 | 2.08 | A |
| A67 | 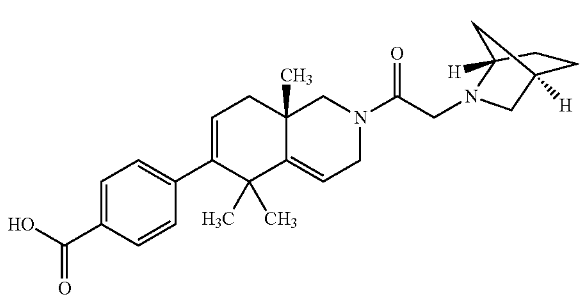 [SMILES: CC1(C)C(c2ccc(C(=O)O)cc2)=CC[C@]2(C)CN(C(=O)CN3C[C@@H]4CC[C@H]3C4)CC=C12] | 434.57 | 435.3 | 1.37 | A |

TABLE 11-continued
| Ex | Structure | MW | Obs Ion | RT | Met |
|---|---|---|---|---|---|
| A68 | 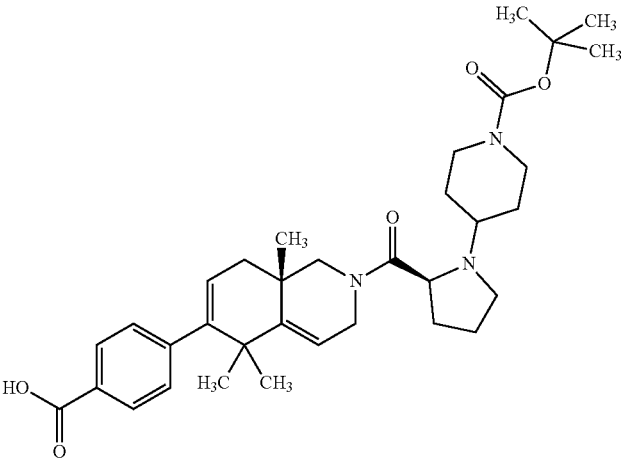 [SMILES: CC(C)(C)OC(=O)N1CCC(N2CCC[C@H]2C(=O)N2CC=C3C(C)(C)C(c4ccc(C(=O)O)cc4)=CC[C@]3(C)C2)CC1] | 577.75 | 578.4 | 1.87 | A |
| A69 | 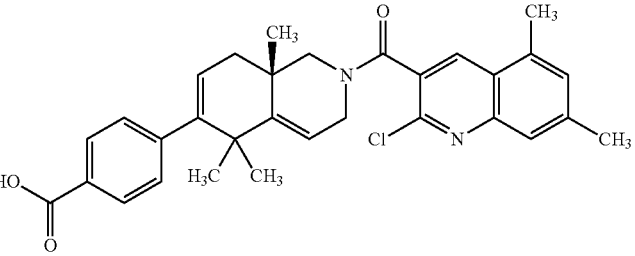 | 515.04 | 515.3 | 3.74 | M |
| A70 | 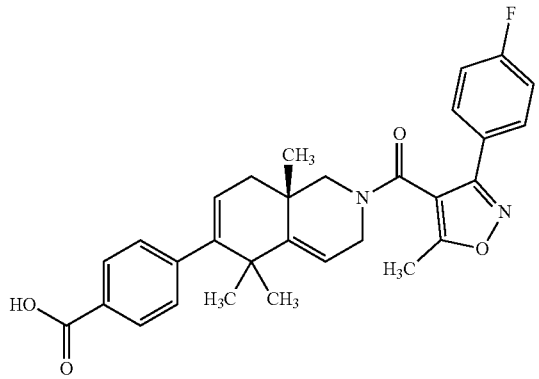 [SMILES: Cc1onc(-c2ccc(F)cc2)c1C(=O)N1CC=C2C(C)(C)C(c3ccc(C(=O)O)cc3)=CC[C@]2(C)C1] | 500.56 | 499.4 | 2.20 | A |
| A71 | 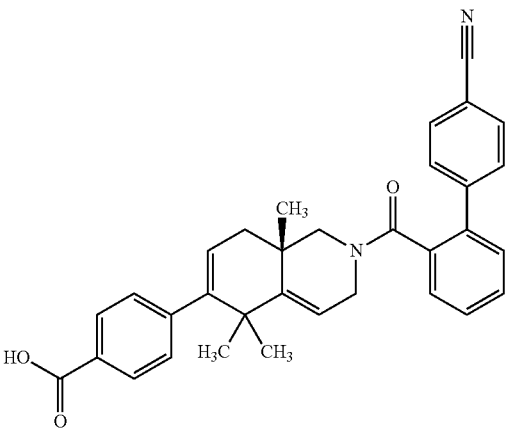 [SMILES: CC1(C)C(c2ccc(C(=O)O)cc2)=CC[C@]2(C)CN(C(=O)c3ccccc3-c3ccc(C#N)cc3)CC=C12] | 502.61 | 503.4 | 2.23 | A |

TABLE 11-continued

| Ex | Structure | MW | Obs Ion | RT | Met |
|---|---|---|---|---|---|
| A72 | 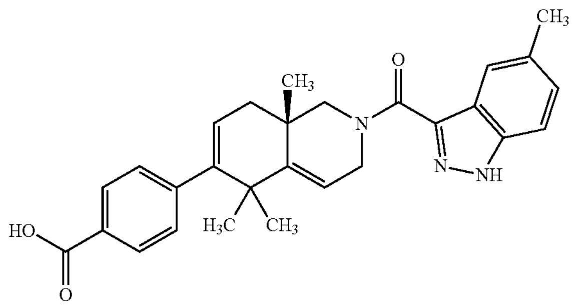 [SMILES: Cc1ccc2[nH]nc(C(=O)N3CC=C4C(C)(C)C(c5ccc(C(=O)O)cc5)=CC[C@]4(C)C3)c2c1] | 455.55 | 456.3 | 2.02 | A |
| A73 | 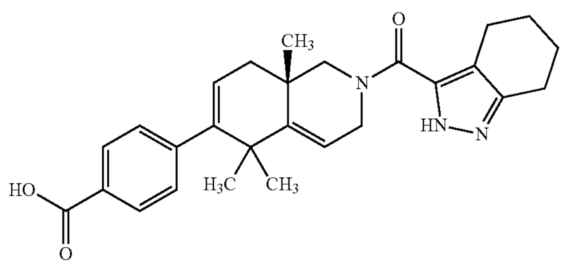 [SMILES: CC1(C)C(c2ccc(C(=O)O)cc2)=CC[C@]2(C)CN(C(=O)c3[nH]nc4c3CCCC4)CC=C12] | 445.55 | 446.3 | 1.85 | A |
| A74 | 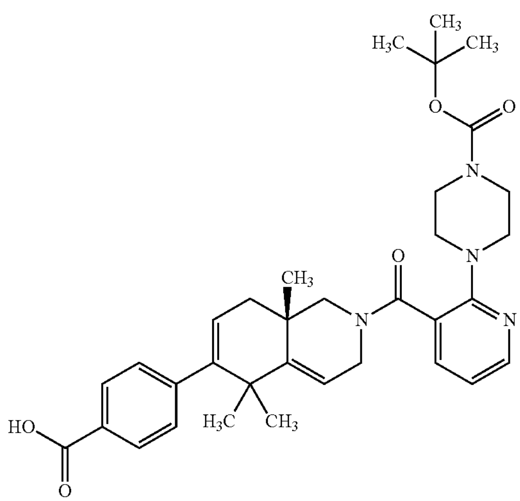 [SMILES: CC(C)(C)OC(=O)N1CCN(c2ncccc2C(=O)N2CC=C3C(C)(C)C(c4ccc(C(=O)O)cc4)=CC[C@]3(C)C2)CC1] | 586.72 | 587.4 | 2.27 | A |
| A75 | 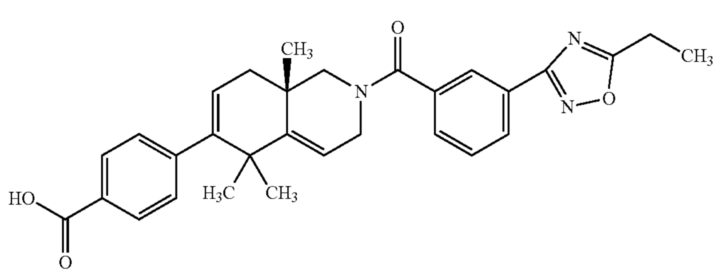 [SMILES: CCc1nc(-c2cccc(C(=O)N3CC=C4C(C)(C)C(c5ccc(C(=O)O)cc5)=CC[C@]4(C)C3)c2)no1] | 497.58 | 498.3 | 3.56 | M |

TABLE 11-continued

| Ex | Structure | MW | Obs Ion | RT | Met |
|---|---|---|---|---|---|
| A76 | 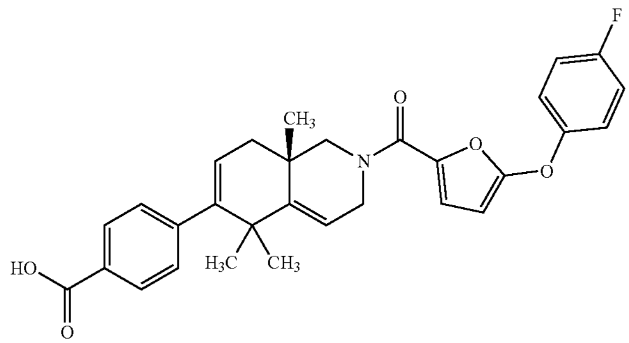 [SMILES: CC1(C)C(c2ccc(C(=O)O)cc2)=CC[C@]2(C)CN(C(=O)c3ccc(Oc4ccc(F)cc4)o3)CC=C12] | 501.55 | 502.3 | 3.77 | M |
| A77 | 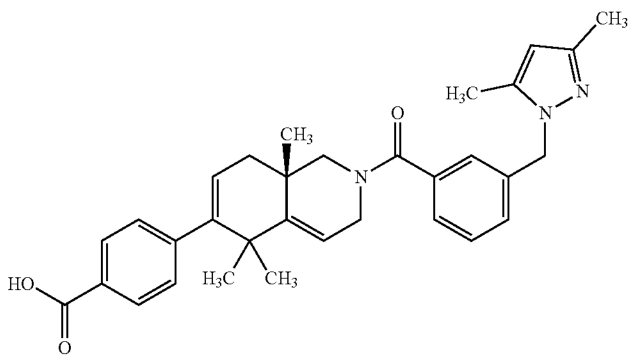 [SMILES: Cc1cc(C)n(Cc2cccc(C(=O)N3CC=C4C(C)(C)C(c5ccc(C(=O)O)cc5)=CC[C@]4(C)C3)c2)n1] | 509.64 | 510.4 | 2.04 | A |
| A78 | 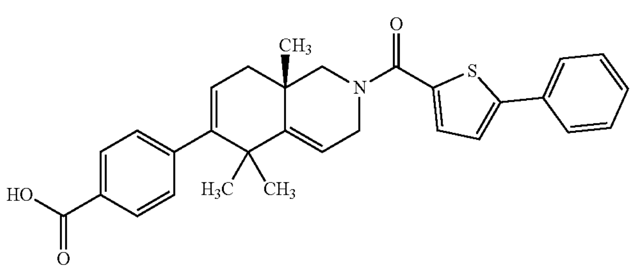 [SMILES: CC1(C)C(c2ccc(C(=O)O)cc2)=CC[C@]2(C)CN(C(=O)c3ccc(-c4ccccc4)s3)CC=C12] | 483.62 | 484.3 | 2.55 | A |
| A79 | 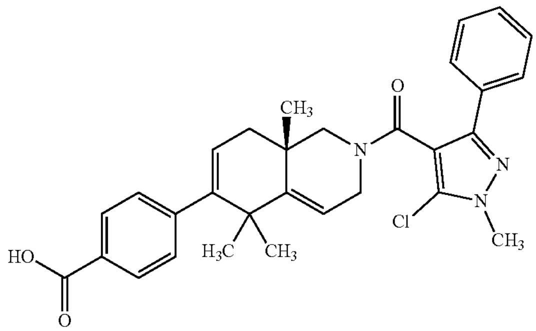 [SMILES: Cn1nc(-c2ccccc2)c(C(=O)N2CC=C3C(C)(C)C(c4ccc(C(=O)O)cc4)=CC[C@]3(C)C2)c1Cl] | 516.04 | 516.3 | 2.15 | A |

TABLE 11-continued

| Ex | Structure | MW | Obs Ion | RT | Met |
|---|---|---|---|---|---|
| A80 | 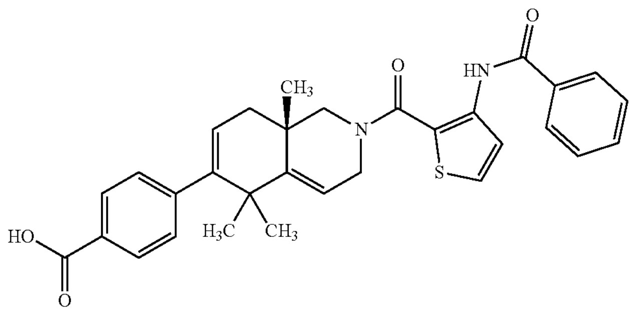 [SMILES: CC1(C)C(c2ccc(C(=O)O)cc2)=CC[C@]2(C)CN(C(=O)c3sccc3NC(=O)c3ccccc3)CC=C12] | 526.65 | 527.3 | 3.78 | M |
| A81 | 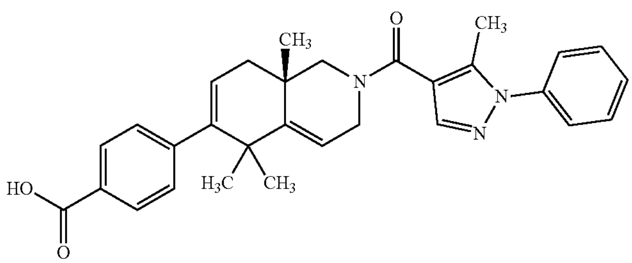 [SMILES: Cc1c(C(=O)N2CC=C3C(C)(C)C(c4ccc(C(=O)O)cc4)=CC[C@]3(C)C2)cnn1-c1ccccc1] | 481.59 | 482.4 | 2.03 | A |
| A82 | 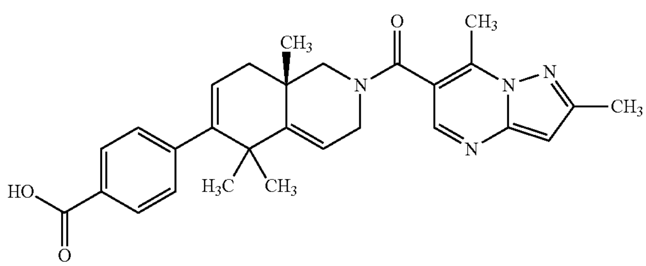 [SMILES: Cc1cc2ncc(C(=O)N3CC=C4C(C)(C)C(c5ccc(C(=O)O)cc5)=CC[C@]4(C)C3)c(C)n2n1] | 470.56 | 471.3 | 1.78 | A |
| A83 | 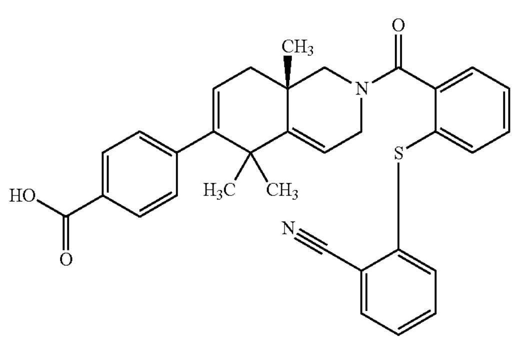 [SMILES: CC1(C)C(c2ccc(C(=O)O)cc2)=CC[C@]2(C)CN(C(=O)c3ccccc3Sc3ccccc3C#N)CC=C12] | 534.67 | 535.3 | 3.54 | M |
| A84 | 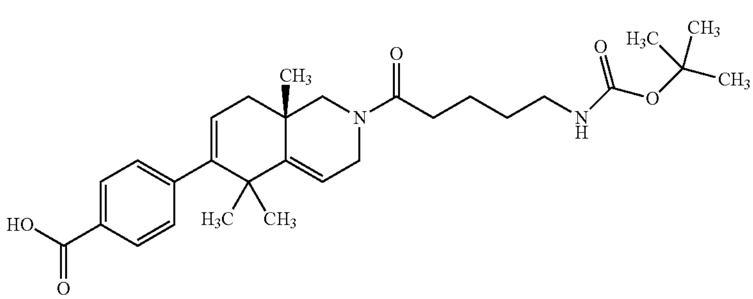 [SMILES: CC(C)(C)OC(=O)NCCCCC(=O)N1CC=C2C(C)(C)C(c3ccc(C(=O)O)cc3)=CC[C@]2(C)C1] | 496.64 | 497.4 | 3.49 | M |

TABLE 11-continued

| Ex | Structure | MW | Obs Ion | RT | Met |
|---|---|---|---|---|---|
| A85 | 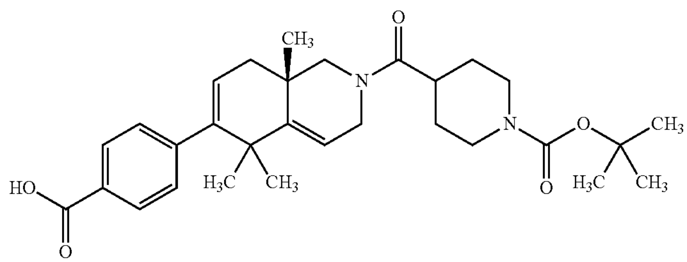 [SMILES: CC(C)(C)OC(=O)N1CCC(C(=O)N2CC=C3C(C)(C)C(c4ccc(C(=O)O)cc4)=CC[C@]3(C)C2)CC1] | 508.65 | 509.4 | 2.24 | A |
| A86 | 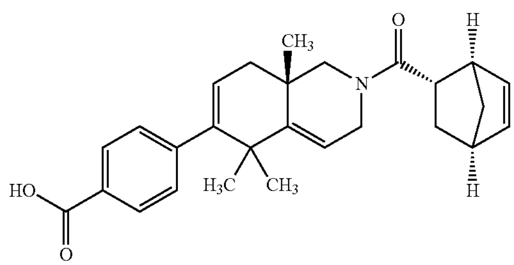 [SMILES: CC1(C)C(c2ccc(C(=O)O)cc2)=CC[C@]2(C)CN(C(=O)[C@H]3C[C@@H]4C=C[C@H]3C4)CC=C12] | 417.55 | 418.3 | 2.28 | A |
| A87 | 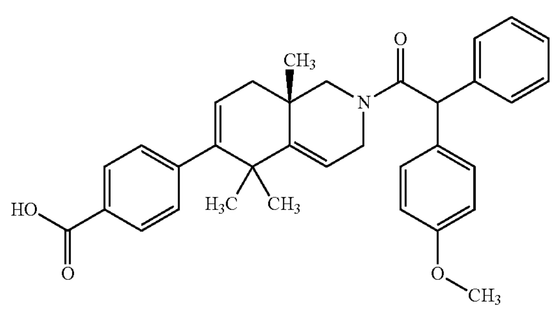 [SMILES: COc1ccc(C(C(=O)N2CC=C3C(C)(C)C(c4ccc(C(=O)O)cc4)=CC[C@]3(C)C2)c2ccccc2)cc1] | 521.65 | 522.4 | 3.80 | M |
| A88 | 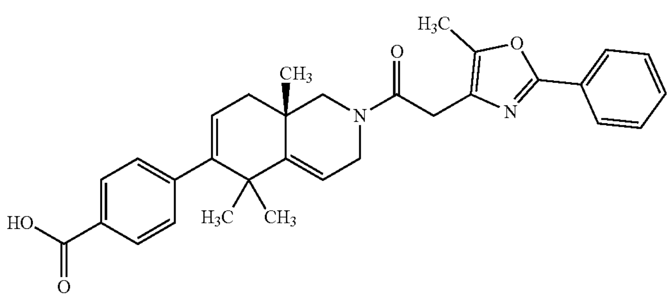 [SMILES: Cc1oc(-c2ccccc2)nc1CC(=O)N1CC=C2C(C)(C)C(c3ccc(C(=O)O)cc3)=CC[C@]2(C)C1] | 496.60 | 497.4 | 2.28 | A |
| A89 | 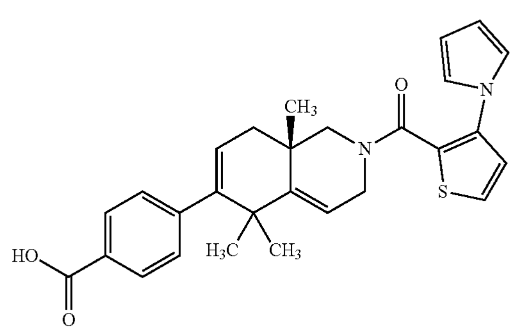 [SMILES: CC1(C)C(c2ccc(C(=O)O)cc2)=CC[C@]2(C)CN(C(=O)c3sccc3-n3cccc3)CC=C12] | 472.60 | 473.3 | 2.26 | A |

TABLE 11-continued

| Ex | Structure | MW | Obs Ion | RT | Met |
|---|---|---|---|---|---|
| A90 | 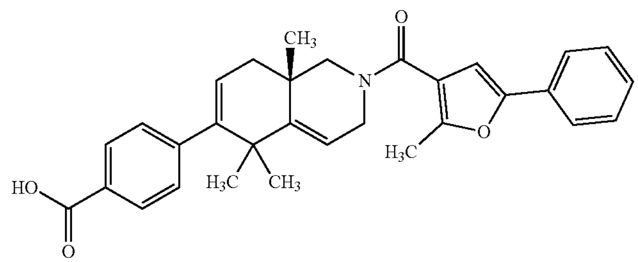 [SMILES: Cc1oc(-c2ccccc2)cc1C(=O)N1CC=C2C(C)(C)C(c3ccc(C(=O)O)cc3)=CC[C@]2(C)C1] | 481.58 | 482.3 | 3.90 | M |
| A91 | 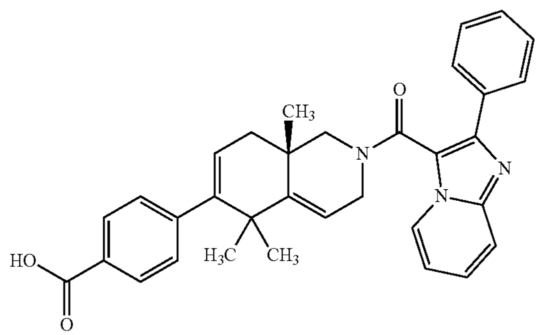 [SMILES: CC1(C)C(c2ccc(C(=O)O)cc2)=CC[C@]2(C)CN(C(=O)c3c(-c4ccccc4)nc4ccccn34)CC=C12] | 517.63 | 518.4 | 3.48 | M |
| A92 | 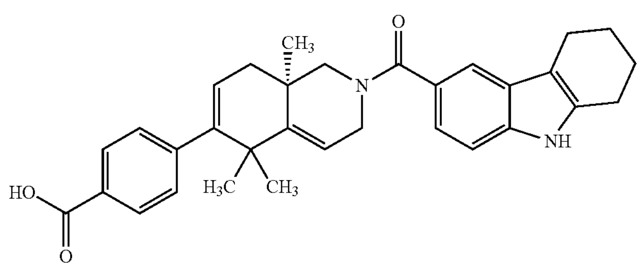 [SMILES: CC1(C)C(c2ccc(C(=O)O)cc2)=CC[C@@]2(C)CN(C(=O)c3ccc4[nH]c5c(c4c3)CCCC5)CC=C12] | 494.62 | 495.4 | 2.34 | A |
| A93 | 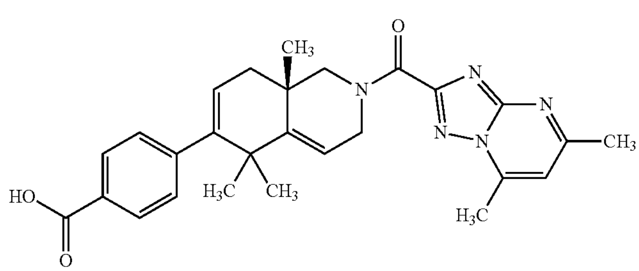 [SMILES: Cc1cc(C)n2nc(C(=O)N3CC=C4C(C)(C)C(c5ccc(C(=O)O)cc5)=CC[C@]4(C)C3)nc2n1] | 471.55 | 472.3 | 1.67 | A |
| A94 | 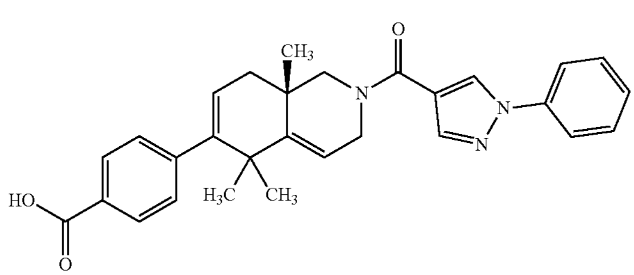 [SMILES: CC1(C)C(c2ccc(C(=O)O)cc2)=CC[C@]2(C)CN(C(=O)c3cnn(-c4ccccc4)c3)CC=C12] | 467.56 | 468.3 | 2.11 | A |

TABLE 11-continued

| Ex | Structure | MW | Obs Ion | RT | Met |
|---|---|---|---|---|---|
| A95 | 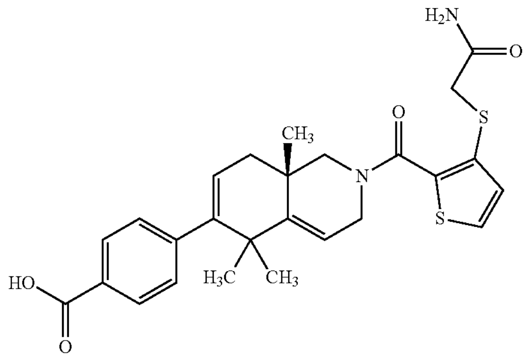 [SMILES: CC1(C)C(c2ccc(C(=O)O)cc2)=CC[C@]2(C)CN(C(=O)c3sccc3SCC(N)=O)CC=C12] | 496.64 | 497.3 | 1.71 | A |
| A96 | 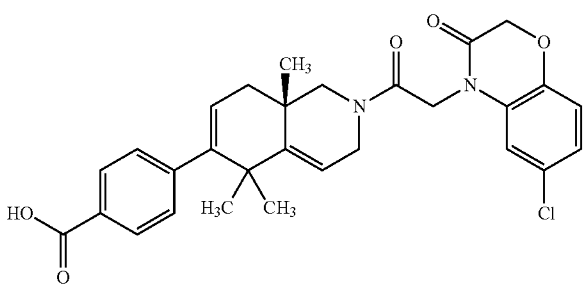 [SMILES: CC1(C)C(c2ccc(C(=O)O)cc2)=CC[C@]2(C)CN(C(=O)CN3C(=O)COc4ccc(Cl)cc43)CC=C12] | 521.00 | 521.3 | 2.18 | A |
| A97 | 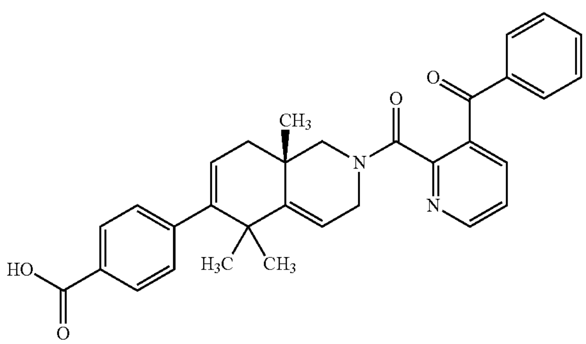 [SMILES: CC1(C)C(c2ccc(C(=O)O)cc2)=CC[C@]2(C)CN(C(=O)c3ncccc3C(=O)c3ccccc3)CC=C12] | 506.59 | 507.3 | 2.03 | A |
| A98 | 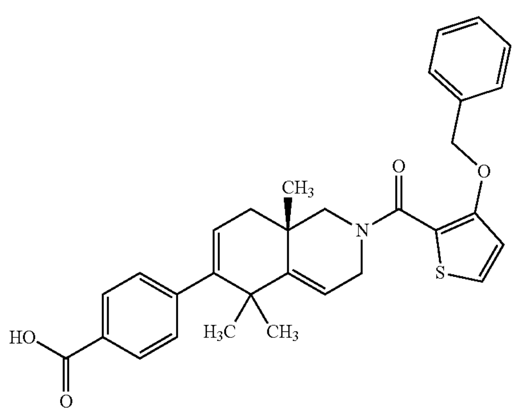 [SMILES: CC1(C)C(c2ccc(C(=O)O)cc2)=CC[C@]2(C)CN(C(=O)c3sccc3OCc3ccccc3)CC=C12] | 513.65 | 514.3 | 3.68 | M |

TABLE 11-continued

| Ex | Structure | MW | Obs Ion | RT | Met |
|---|---|---|---|---|---|
| A99 | 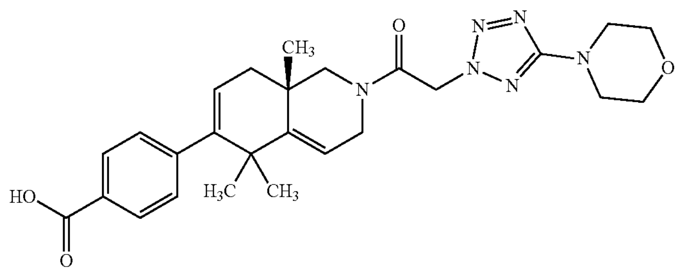 [SMILES: CC1(C)C(c2ccc(C(=O)O)cc2)=CC[C@]2(C)CN(C(=O)Cn3nnc(N4CCOCC4)n3)CC=C12] | 492.57 | 493.4 | 2.82 | M |
| A100 | 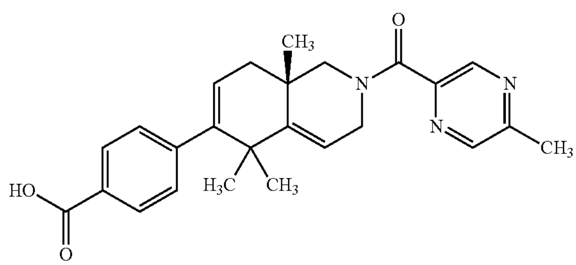 [SMILES: Cc1cnc(C(=O)N2CC=C3C(C)(C)C(c4ccc(C(=O)O)cc4)=CC[C@]3(C)C2)cn1] | 417.50 | 418.3 | 1.70 | A |
| A101 | 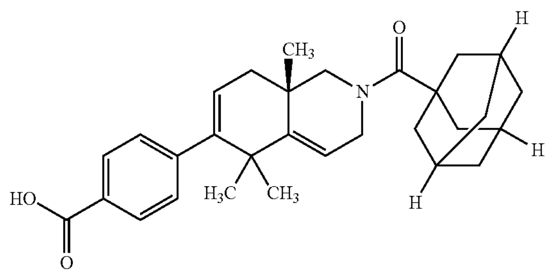 [SMILES: CC1(C)C(c2ccc(C(=O)O)cc2)=CC[C@]2(C)CN(C(=O)C34CC5CC(CC(C5)C3)C4)CC=C12] | 459.62 | 460.4 | 2.71 | A |
| A102 | 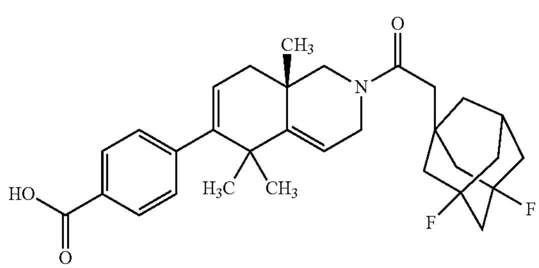 [SMILES: CC1(C)C(c2ccc(C(=O)O)cc2)=CC[C@]2(C)CN(C(=O)CC34CC5CC(F)(CC(F)(C5)C3)C4)CC=C12] | 473.65 | 474.4 | 2.76 | A |
| A103 | 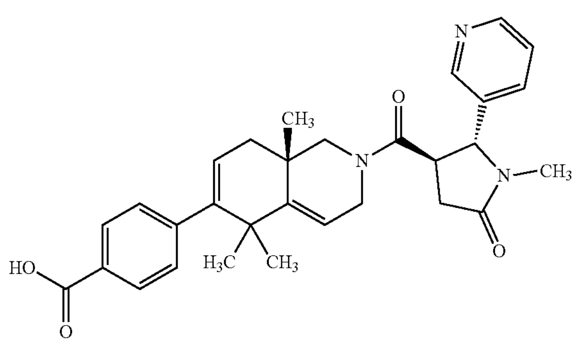 [SMILES: CN1C(=O)C[C@@H](C(=O)N2CC=C3C(C)(C)C(c4ccc(C(=O)O)cc4)=CC[C@]3(C)C2)[C@@H]1c1cccnc1] | 499.60 | 500.4 | 2.63 | A |

TABLE 11-continued

| Ex | Structure | MW | Obs Ion | RT | Met |
|---|---|---|---|---|---|
| A104 | 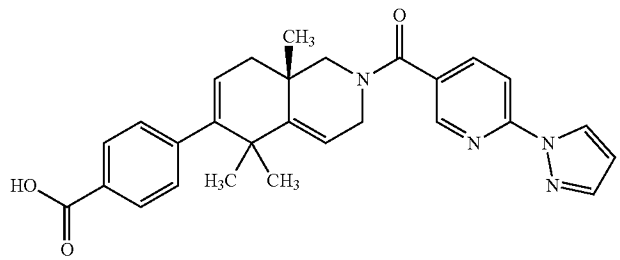 [SMILES: CC1(C)C(c2ccc(C(=O)O)cc2)=CC[C@]2(C)CN(C(=O)c3ccc(-n4cccn4)nc3)CC=C12] | 468.55 | 469.3 | 2.01 | A |
| A105 | 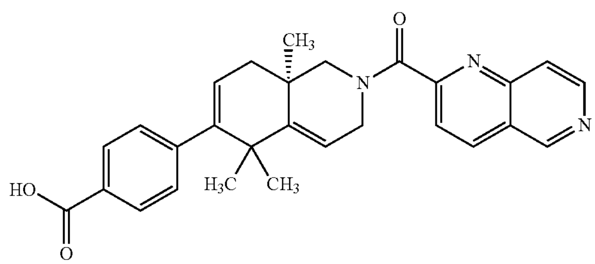 [SMILES: CC1(C)C(c2ccc(C(=O)O)cc2)=CC[C@@]2(C)CN(C(=O)c3ccc4cnccc4n3)CC=C12] | 453.53 | 454.3 | 1.70 | A |
| A106 | 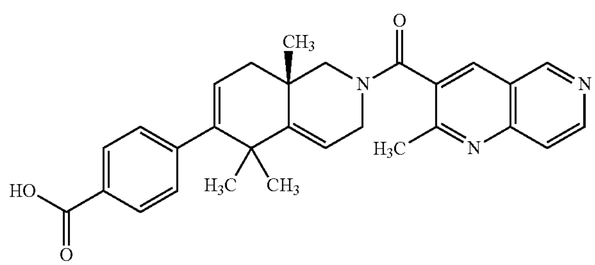 [SMILES: Cc1nc2ccncc2cc1C(=O)N1CC=C2C(C)(C)C(c3ccc(C(=O)O)cc3)=CC[C@]2(C)C1] | 467.56 | 468.3 | 1.67 | A |
| A107 | 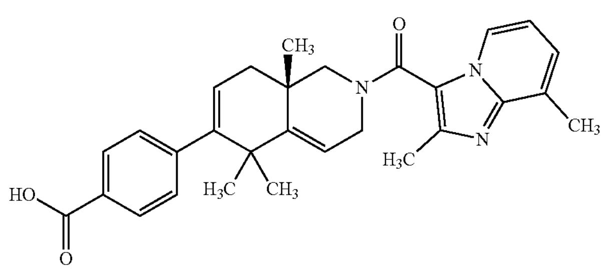 [SMILES: Cc1nc2c(C)cccn2c1C(=O)N1CC=C2C(C)(C)C(c3ccc(C(=O)O)cc3)=CC[C@]2(C)C1] | 469.57 | 470.24 | 1.85 | A |
| A108 | 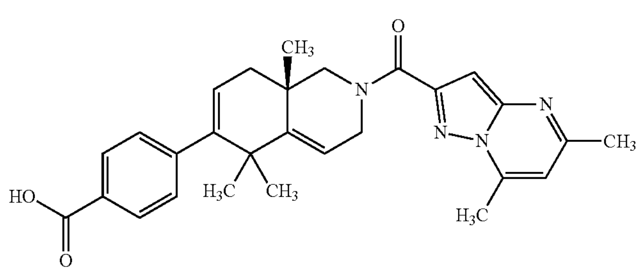 [SMILES: Cc1cc(C)n2nc(C(=O)N3CC=C4C(C)(C)C(c5ccc(C(=O)O)cc5)=CC[C@]4(C)C3)cc2n1] | 470.56 | 471.3 | 1.88 | A |
| A109 | 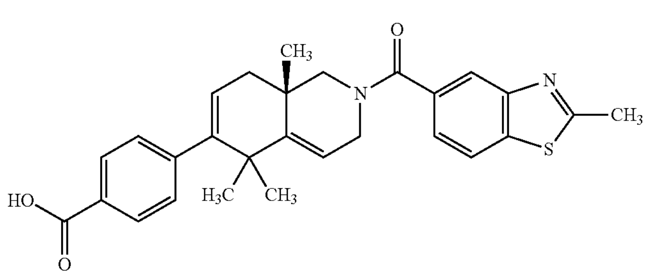 [SMILES: Cc1nc2cc(C(=O)N3CC=C4C(C)(C)C(c5ccc(C(=O)O)cc5)=CC[C@]4(C)C3)ccc2s1] | 472.60 | 473.3 | 2.01 | A |

TABLE 11-continued

| Ex | Structure | MW | Obs Ion | RT | Met |
|---|---|---|---|---|---|
| A110 | 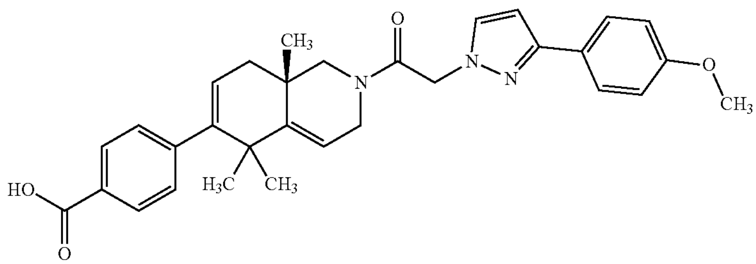 [SMILES: COc1ccc(-c2ccn(CC(=O)N3CC=C4C(C)(C)C(c5ccc(C(=O)O)cc5)=CC[C@]4(C)C3)n2)cc1] | 511.61 | 512.4 | 3.34 | M |
| A111 | 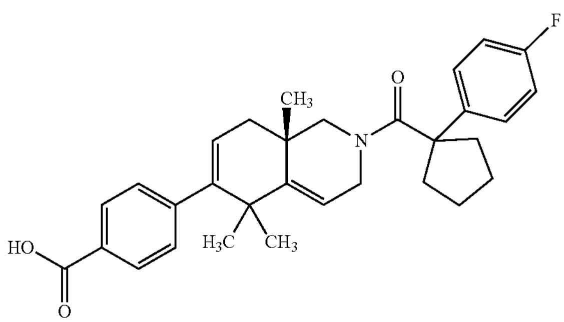 [SMILES: CC1(C)C(c2ccc(C(=O)O)cc2)=CC[C@]2(C)CN(C(=O)C3(c4ccc(F)cc4)CCCC3)CC=C12] | 487.61 | 488.4 | 2.67 | A |
| A112 | 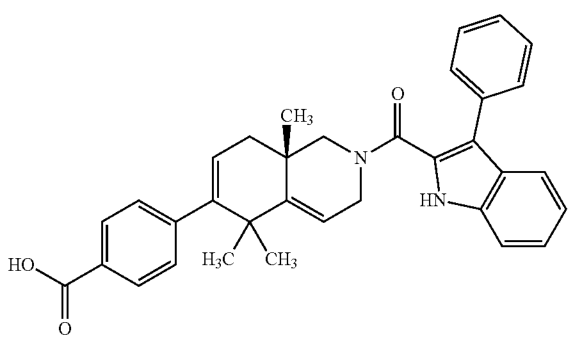 [SMILES: CC1(C)C(c2ccc(C(=O)O)cc2)=CC[C@]2(C)CN(C(=O)c3[nH]c4ccccc4c3-c3ccccc3)CC=C12] | 516.64 | 517.4 | 2.60 | A |
| A113 | 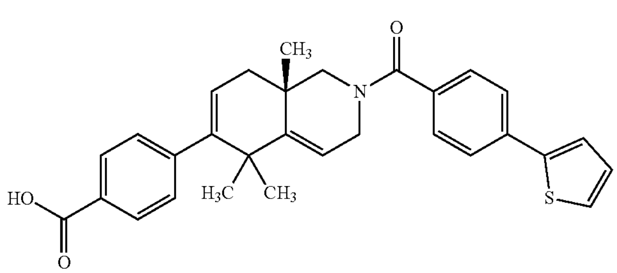 [SMILES: CC1(C)C(c2ccc(C(=O)O)cc2)=CC[C@]2(C)CN(C(=O)c3ccc(-c4cccs4)cc3)CC=C12] | 483.62 | 484.3 | 2.46 | A |

TABLE 11-continued
| Ex | Structure | MW | Obs Ion | RT | Met |
|---|---|---|---|---|---|
| A114 | 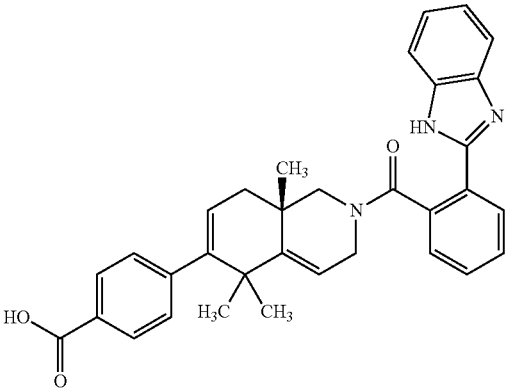 [SMILES: CC1(C)C(c2ccc(C(=O)O)cc2)=CC[C@]2(C)CN(C(=O)c3ccccc3-c3nc4ccccc4[nH]3)CC=C12] | 517.63 | 518.4 | 2.00 | A |
| A115 | 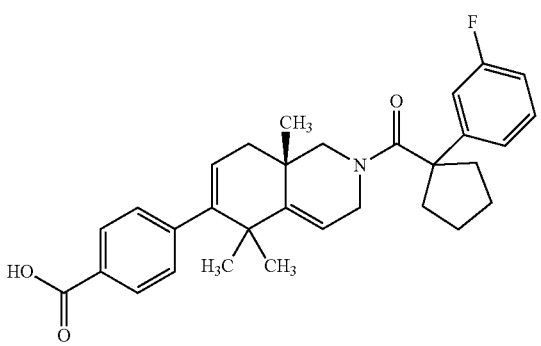 [SMILES: CC1(C)C(c2ccc(C(=O)O)cc2)=CC[C@]2(C)CN(C(=O)C3(c4cccc(F)c4)CCCC3)CC=C12] | 487.61 | 488.3 | 2.68 | A |
| A116 | 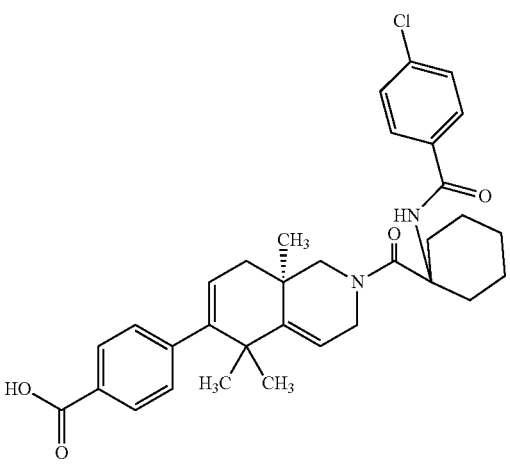 [SMILES: CC1(C)C(c2ccc(C(=O)O)cc2)=CC[C@@]2(C)CN(C(=O)C3(NC(=O)c4ccc(Cl)cc4)CCCCC3)CC=C12] | 561.11 | 559.4 | 3.82 | M |
| A117 | 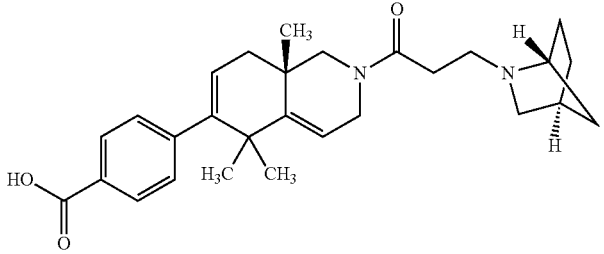 [SMILES: CC1(C)C(c2ccc(C(=O)O)cc2)=CC[C@]2(C)CN(C(=O)CCN3C[C@H]4CC[C@@H]3C4)CC=C12] | 448.60 | 449.3 | 2.52 | M |

TABLE 11-continued

| Ex | Structure | MW | Obs Ion | RT | Met |
|---|---|---|---|---|---|
| A118 | 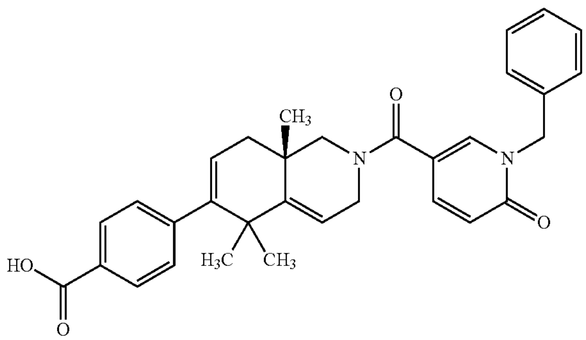 [SMILES: CC1(C)C(c2ccc(C(=O)O)cc2)=CC[C@]2(C)CN(C(=O)c3ccc(=O)n(Cc4ccccc4)c3)CC=C12] | 508.61 | 509.4 | 3.14 | M |
| A119 | 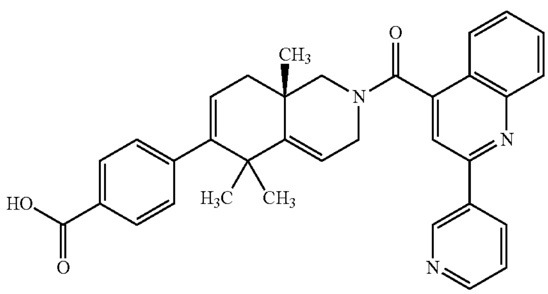 [SMILES: CC1(C)C(c2ccc(C(=O)O)cc2)=CC[C@]2(C)CN(C(=O)c3cc(-c4cccnc4)nc4ccccc34)CC=C12] | 529.63 | 530.3 | 3.48 | M |
| A120 | 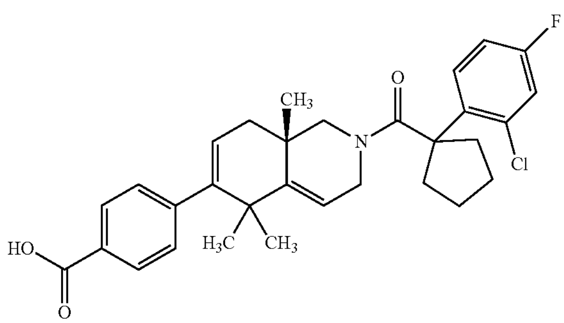 [SMILES: CC1(C)C(c2ccc(C(=O)O)cc2)=CC[C@]2(C)CN(C(=O)C3(c4ccc(F)cc4Cl)CCCC3)CC=C12] | 522.05 | 522.3 | 4.05 | M |
| A121 | 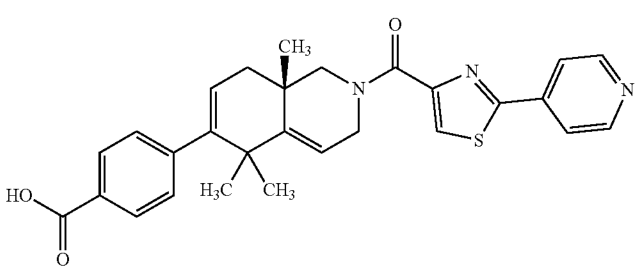 [SMILES: CC1(C)C(c2ccc(C(=O)O)cc2)=CC[C@]2(C)CN(C(=O)c3csc(-c4ccncc4)n3)CC=C12] | 485.60 | 486.3 | 3.25 | M |

TABLE 11-continued

| Ex | Structure | MW | Obs Ion | RT | Met |
|---|---|---|---|---|---|
| A122 | 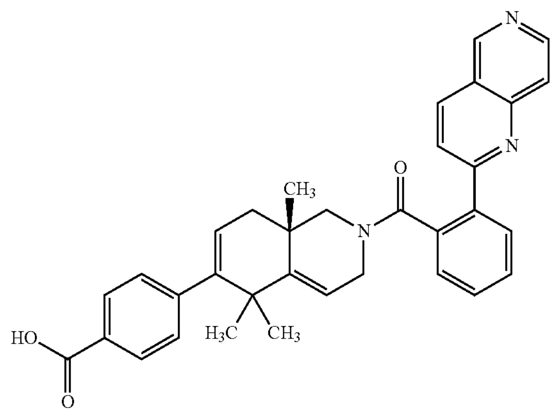 [SMILES: CC1(C)C(c2ccc(C(=O)O)cc2)=CC[C@]2(C)CN(C(=O)c3ccccc3-c3ccc4cnccc4n3)CC=C12] | 529.63 | 530.4 | 3.56 | M |
| A123 | 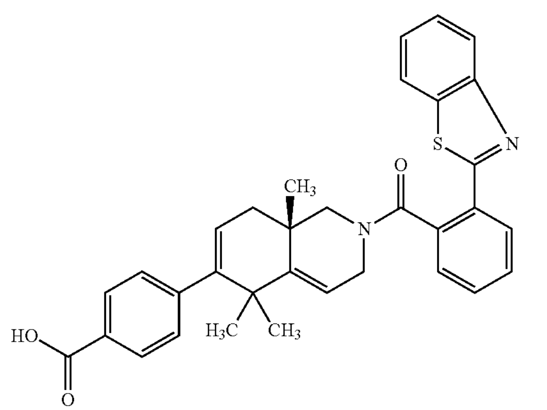 [SMILES: CC1(C)C(c2ccc(C(=O)O)cc2)=CC[C@]2(C)CN(C(=O)c3ccccc3-c3nc4ccccc4s3)CC=C12] | 534.67 | 535.4 | 2.71 | A |
| A124 | 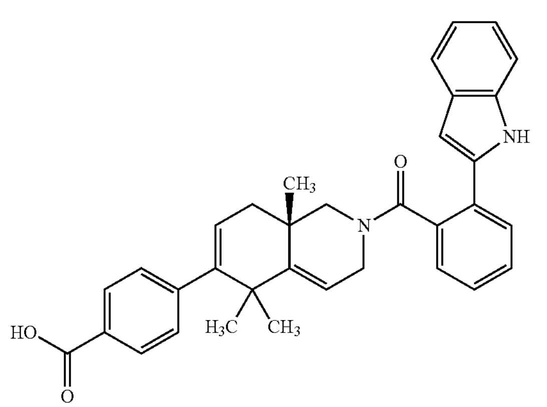 [SMILES: CC1(C)C(c2ccc(C(=O)O)cc2)=CC[C@]2(C)CN(C(=O)c3ccccc3-c3cc4ccccc4[nH]3)CC=C12] | 516.63 | 517.5 | 2.64 | A |

TABLE 11-continued

| Ex | Structure | MW | Obs Ion | RT | Met |
|---|---|---|---|---|---|
| A125 | 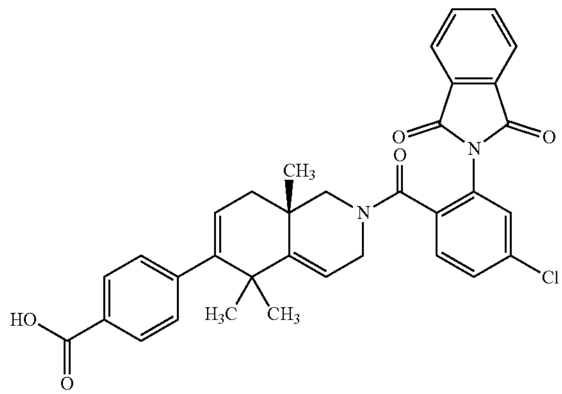 [SMILES: CC1(C)C(c2ccc(C(=O)O)cc2)=CC[C@]2(C)CN(C(=O)c3ccc(Cl)cc3N3C(=O)c4ccccc4C3=O)CC=C12] | 581.06 | 579.5 | 2.55 | A |
| A126 | 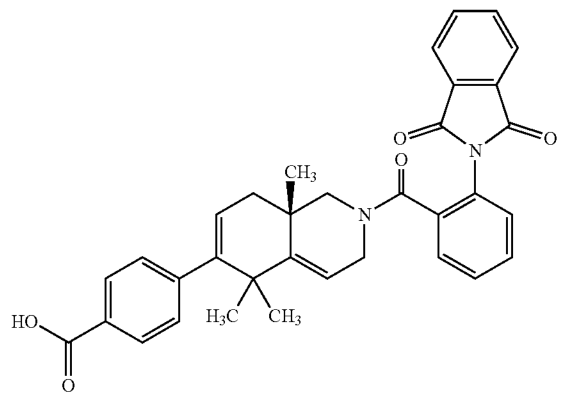 [SMILES: CC1(C)C(c2ccc(C(=O)O)cc2)=CC[C@]2(C)CN(C(=O)c3ccccc3N3C(=O)c4ccccc4C3=O)CC=C12] | 546.61 | 547.4 | 2.22 | A |

Examples A127-A253 were prepared from intermediate 2 and commercially available carboxylic acids by the following general method:

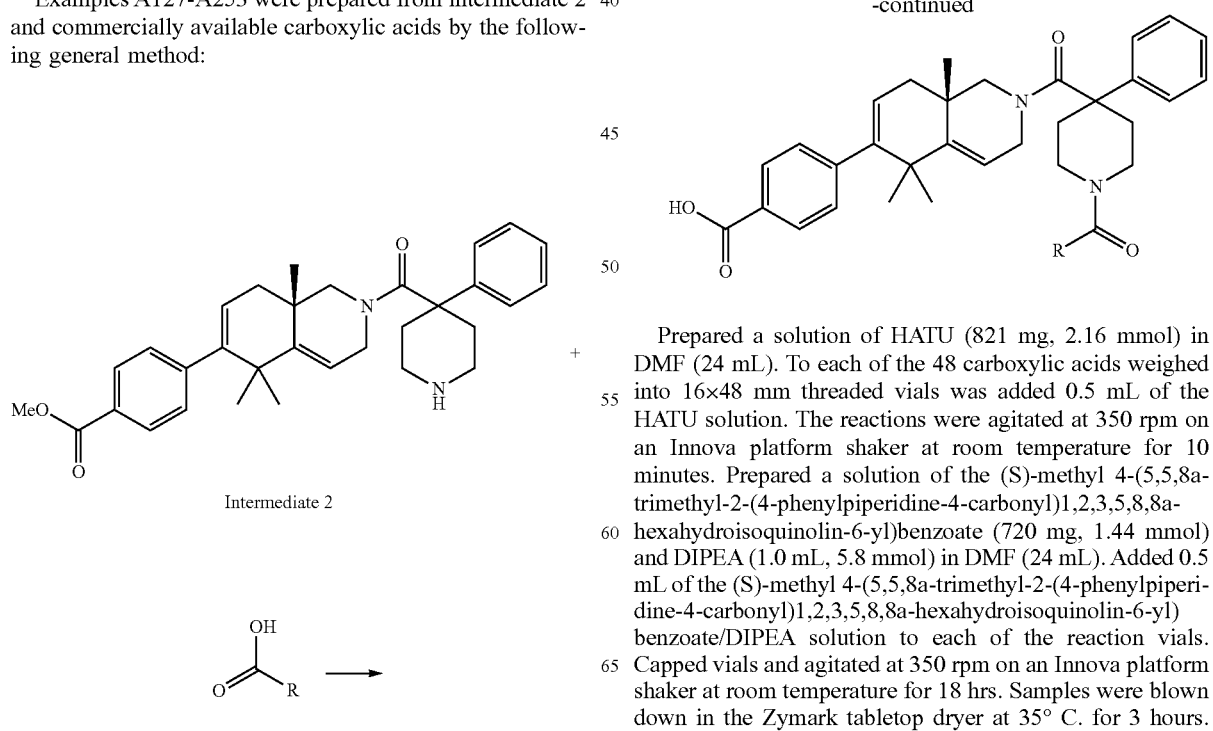

Prepared a solution of HATU (821 mg, 2.16 mmol) in DMF (24 mL). To each of the 48 carboxylic acids weighed into 16×48 mm threaded vials was added 0.5 mL of the HATU solution. The reactions were agitated at 350 rpm on an Innova platform shaker at room temperature for 10 minutes. Prepared a solution of the (S)-methyl 4-(5,5,8a-trimethyl-2-(4-phenylpiperidine-4-carbonyl)1,2,3,5,8,8a-hexahydroisoquinolin-6-yl)benzoate (720 mg, 1.44 mmol) and DIPEA (1.0 mL, 5.8 mmol) in DMF (24 mL). Added 0.5 mL of the (S)-methyl 4-(5,5,8a-trimethyl-2-(4-phenylpiperidine-4-carbonyl)1,2,3,5,8,8a-hexahydroisoquinolin-6-yl)benzoate/DIPEA solution to each of the reaction vials. Capped vials and agitated at 350 rpm on an Innova platform shaker at room temperature for 18 hrs. Samples were blown down in the Zymark tabletop dryer at 35° C. for 3 hours.

Prepared a solution of Lithium Hydroxide Monohydrate (483 mg, 11.5 mmol) in water (9.6 mL). To each of the reaction vials was added 0.8 mL dioxane and 0.2 mL of the lithium hydroxide solution. Capped vials and agitated at 350 rpm on an Innova platform shaker at 70° C. for 18 hrs. Added 100 μL glacial acetic acid to each vial. Samples were blown down in the Zymark tabletop dryer at 35° C. for 3 hours. Added 1.0 mL DMF to each vial. Transferred contents to a 96 well 2-mL filter plate, collecting into a 96 well deepwell plate. Rinsed reaction vials w/500 μL DMF each and transferred rinses to the appropriate wells of the filter plate. Transferred contents to 16×48 mm threaded vials. Submitted for HPLC purification, and LCMS analyses, results are shown in the spreadsheet. See Table 12.

TABLE 12

| Ex | Structure | MW | Obs Ion | RT | Met |
|---|---|---|---|---|---|
| A127 | 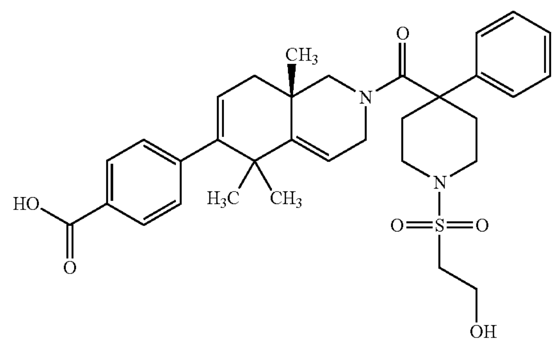 [SMILES: CC1(C)C(c2ccc(C(=O)O)cc2)=CC[C@]2(C)CN(C(=O)C3(c4ccccc4)CCN(S(=O)(=O)CCO)CC3)CC=C12] | 592.75 | 593.3 | 1.78 | A |
| A128 | 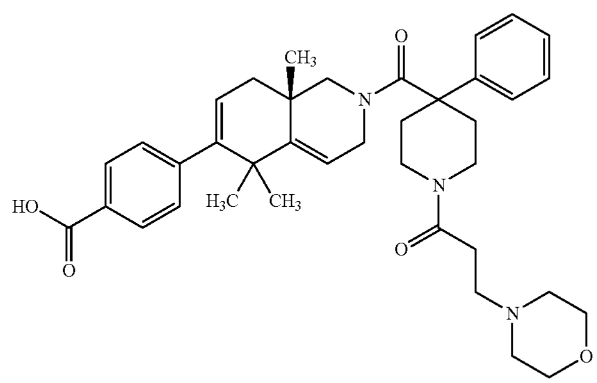 [SMILES: CC1(C)C(c2ccc(C(=O)O)cc2)=CC[C@]2(C)CN(C(=O)C3(c4ccccc4)CCN(C(=O)CCN4CCOCC4)CC3)CC=C12] | 625.80 | 626.5 | 2.11 | A |
| A129 | 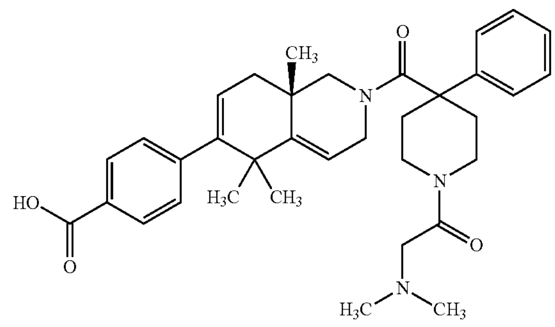 [SMILES: CN(C)CC(=O)N1CCC(C(=O)N2CC=C3C(C)(C)C(c4ccc(C(=O)O)cc4)=CC[C@]3(C)C2)(c2ccccc2)CC1] | 569.73 | 570.5 | 3.49 | M |

татяне 12-continued

| Ex | Structure | MW | Obs Ion | RT | Met |
|---|---|---|---|---|---|
| A130 | 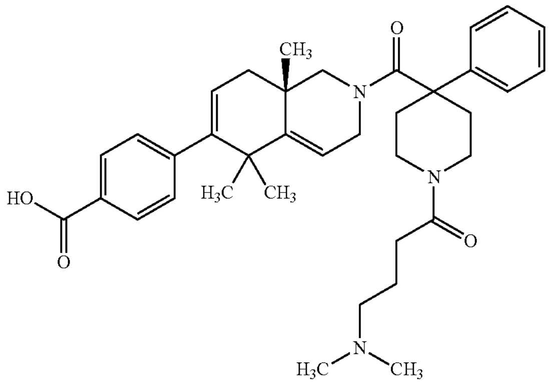 [SMILES: CN(C)CCCC(=O)N1CCC(C(=O)N2CC=C3C(C)(C)C(c4ccc(C(=O)O)cc4)=CC[C@]3(C)C2)(c2ccccc2)CC1] | 597.79 | 598.5 | 1.98 | A |
| A131 | 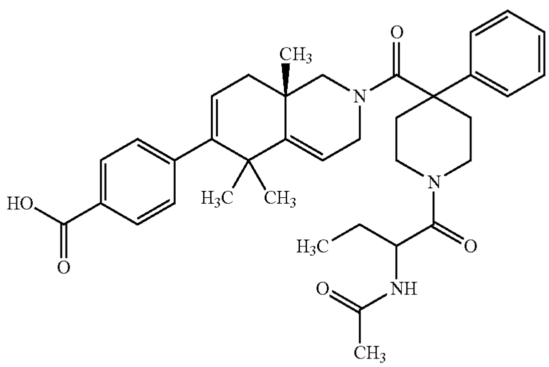 [SMILES: CCC(NC(C)=O)C(=O)N1CCC(C(=O)N2CC=C3C(C)(C)C(c4ccc(C(=O)O)cc4)=CC[C@]3(C)C2)(c2ccccc2)CC1] | 611.77 | 612.5 | 2.17 | A |
| A132 | 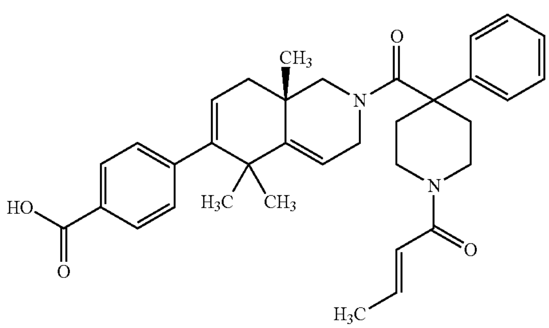 | 552.70 | 553.5 | 3.85 | M |
| A133 | 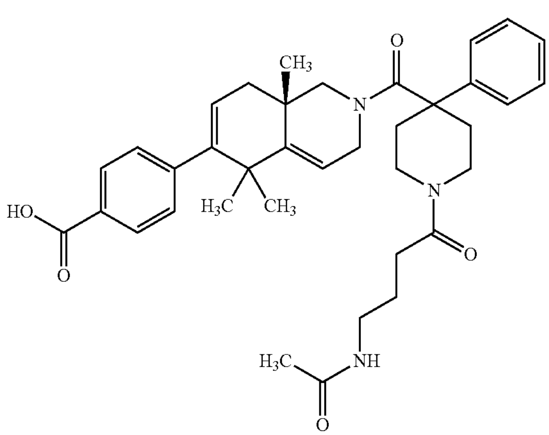 [SMILES: CC(=O)NCCCC(=O)N1CCC(C(=O)N2CC=C3C(C)(C)C(c4ccc(C(=O)O)cc4)=CC[C@]3(C)C2)(c2ccccc2)CC1] | 611.77 | 612.5 | 3.55 | M |

TABLE 12-continued

| Ex | Structure | MW | Obs Ion | RT | Met |
|---|---|---|---|---|---|
| A134 | 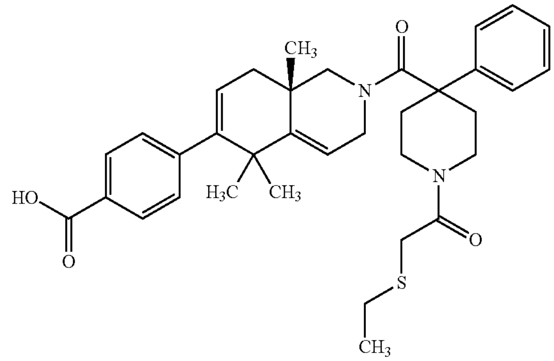 [SMILES: CCSCC(=O)N1CCC(C(=O)N2CC=C3C(C)(C)C(c4ccc(C(=O)O)cc4)=CC[C@]3(C)C2)(c2ccccc2)CC1] | 586.78 | 587.5 | 3.96 | M |
| A135 | 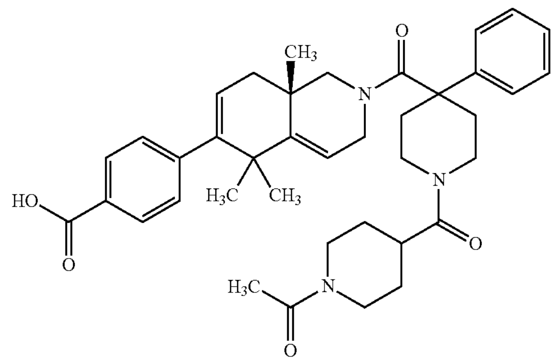 [SMILES: CC(=O)N1CCC(C(=O)N2CCC(C(=O)N3CC=C4C(C)(C)C(c5ccc(C(=O)O)cc5)=CC[C@]4(C)C3)(c3ccccc3)CC2)CC1] | 637.81 | 638.5 | 2.16 | A |
| A136 | 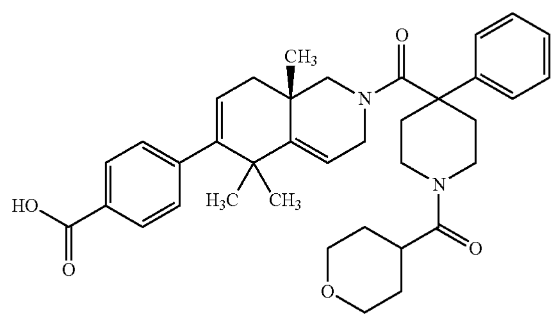 [SMILES: CC1(C)C(c2ccc(C(=O)O)cc2)=CC[C@]2(C)CN(C(=O)C3(c4ccccc4)CCN(C(=O)C4CCOCC4)CC3)CC=C12] | 596.76 | 595.5 | 3.71 | M |
| A137 | 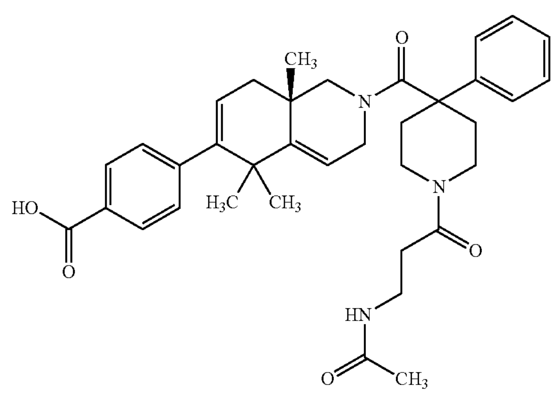 [SMILES: CC(=O)NCCC(=O)N1CCC(C(=O)N2CC=C3C(C)(C)C(c4ccc(C(=O)O)cc4)=CC[C@]3(C)C2)(c2ccccc2)CC1] | 597.74 | 598.4 | 2.03 | A |

TABLE 12-continued

| Ex | Structure | MW | Obs Ion | RT | Met |
|---|---|---|---|---|---|
| A138 | 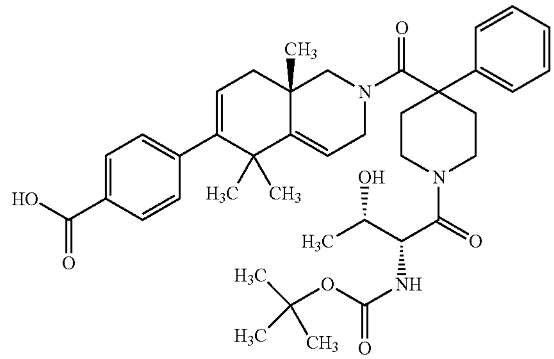 [SMILES: C[C@H](O)[C@@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 685.85 | 686.6 | 3.93 | M |
| A139 | 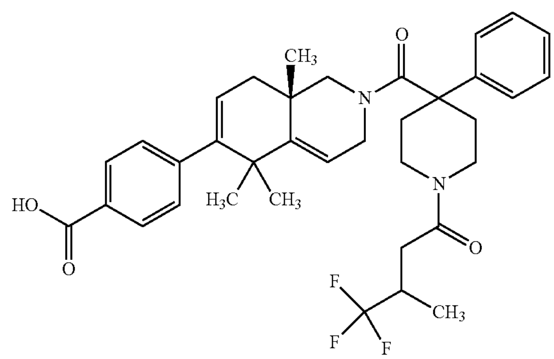 [SMILES: CC(CC(=O)N1CCC(C(=O)N2CC=C3C(C)(C)C(c4ccc(C(=O)O)cc4)=CC[C@]3(C)C2)(c2ccccc2)CC1)C(F)(F)F] | 622.72 | 623.5 | 4.09 | M |
| A140 | 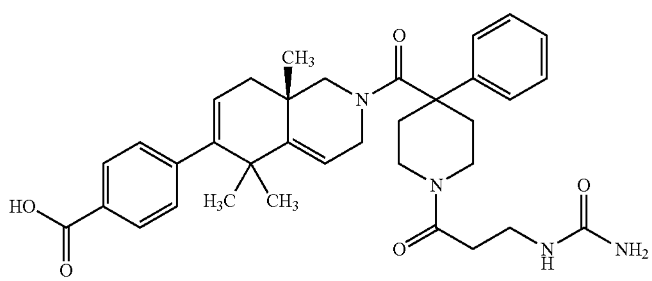 [SMILES: CC1(C)C(c2ccc(C(=O)O)cc2)=CC[C@]2(C)CN(C(=O)C3(c4ccccc4)CCN(C(=O)CCNC(N)=O)CC3)CC=C12] | 598.73 | 599.5 | 3.41 | M |
| A141 | 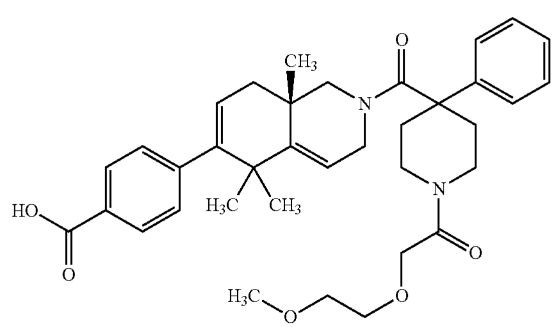 [SMILES: COCCOCC(=O)N1CCC(C(=O)N2CC=C3C(C)(C)C(c4ccc(C(=O)O)cc4)=CC[C@]3(C)C2)(c2ccccc2)CC1] | 600.74 | 601.5 | 3.64 | M |

TABLE 12-continued

| Ex | Structure | MW | Obs Ion | RT | Met |
|---|---|---|---|---|---|
| A142 | 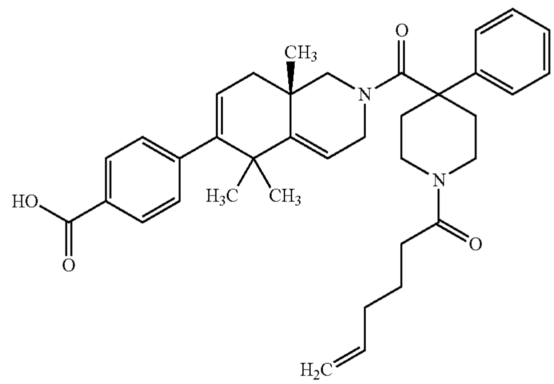 [SMILES: C=CCCCC(=O)N1CCC(C(=O)N2CC=C3C(C)(C)C(c4ccc(C(=O)O)cc4)=CC[C@]3(C)C2)(c2ccccc2)CC1] | 580.76 | 581.5 | 4.09 | M |
| A143 | 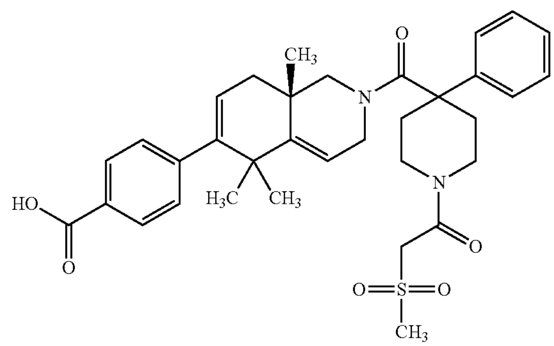 [SMILES: CC1(C)C(c2ccc(C(=O)O)cc2)=CC[C@]2(C)CN(C(=O)C3(c4ccccc4)CCN(C(=O)CS(C)(=O)=O)CC3)CC=C12] | 604.76 | 605.5 | 3.45 | M |
| A144 | 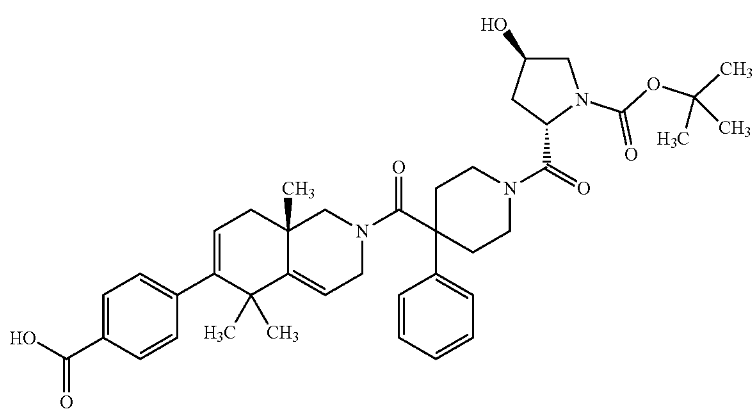 [SMILES: CC(C)(C)OC(=O)N1C[C@H](O)C[C@H]1C(=O)N1CCC(C(=O)N2CC=C3C(C)(C)C(c4ccc(C(=O)O)cc4)=CC[C@]3(C)C2)(c2ccccc2)CC1] | 697.86 | 698.7 | 3.82 | M |
| A145 | 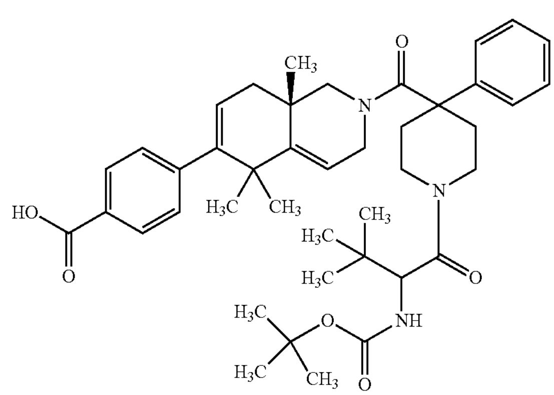 [SMILES: CC(C)(C)OC(=O)NC(C(=O)N1CCC(C(=O)N2CC=C3C(C)(C)C(c4ccc(C(=O)O)cc4)=CC[C@]3(C)C2)(c2ccccc2)CC1)C(C)(C)C] | 697.90 | 698.7 | 4.30 | M |

TABLE 12-continued

| Ex | Structure | MW | Obs Ion | RT | Met |
|---|---|---|---|---|---|
| A146 | 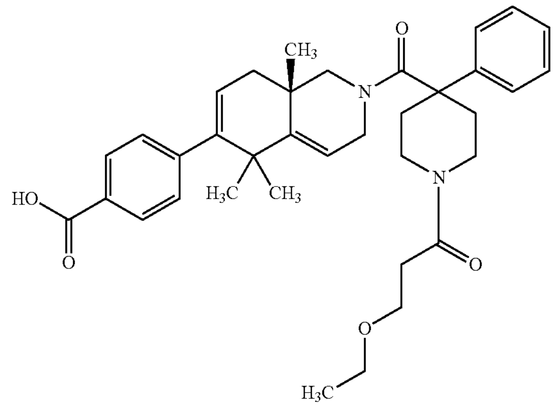 [SMILES: CCOCCC(=O)N1CCC(C(=O)N2CC=C3C(C)(C)C(c4ccc(C(=O)O)cc4)=CC[C@]3(C)C2)(c2ccccc2)CC1] | 584.75 | 585.5 | 2.35 | A |
| A147 | 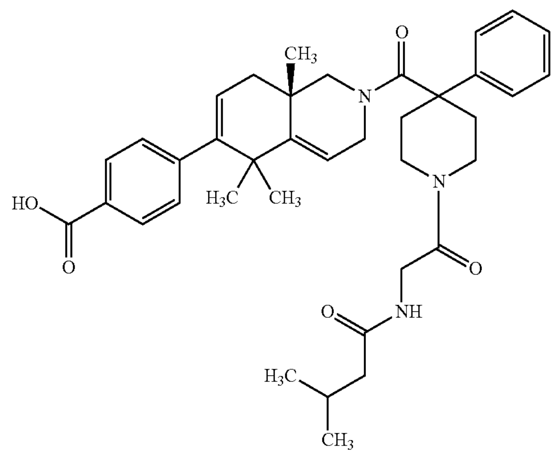 [SMILES: CC(C)CC(=O)NCC(=O)N1CCC(C(=O)N2CC=C3C(C)(C)C(c4ccc(C(=O)O)cc4)=CC[C@]3(C)C2)(c2ccccc2)CC1] | 625.80 | 626.5 | 3.78 | M |
| A148 | 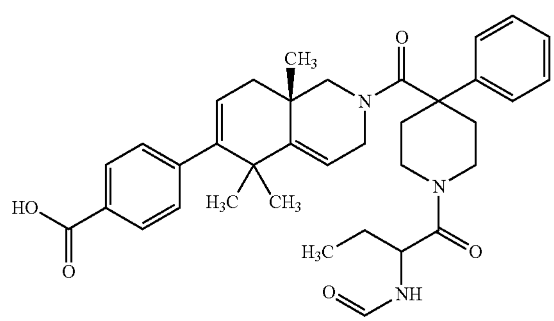 [SMILES: CCC(NC=O)C(=O)N1CCC(C(=O)N2CC=C3C(C)(C)C(c4ccc(C(=O)O)cc4)=CC[C@]3(C)C2)(c2ccccc2)CC1] | 597.74 | 598.4 | 2.17 | A |
| A149 | 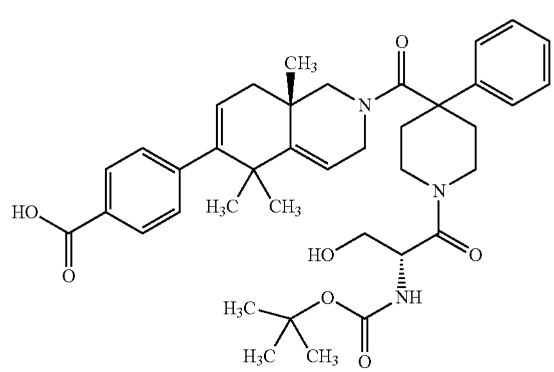 [SMILES: CC(C)(C)OC(=O)N[C@H](CO)C(=O)N1CCC(C(=O)N2CC=C3C(C)(C)C(c4ccc(C(=O)O)cc4)=CC[C@]3(C)C2)(c2ccccc2)CC1] | 671.82 | 672.6 | 3.85 | M |

TABLE 12-continued

| Ex | Structure | MW | Obs Ion | RT | Met |
|---|---|---|---|---|---|
| A150 | 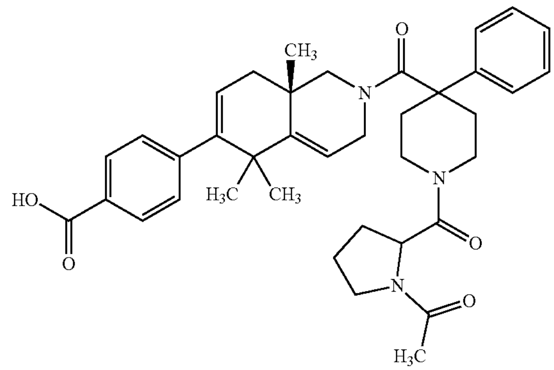 [SMILES: CC(=O)N1CCCC1C(=O)N1CCC(C(=O)N2CC=C3C(C)(C)C(c4ccc(C(=O)O)cc4)=CC[C@]3(C)C2)(c2ccccc2)CC1] | 623.78 | 624.5 | 3.58 | M |
| A151 | 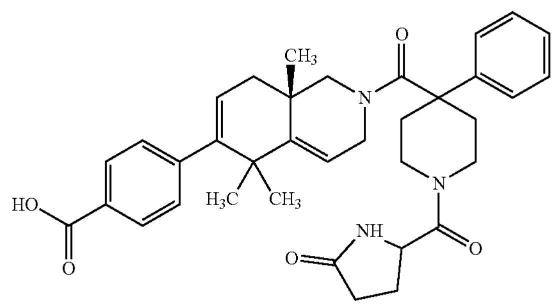 [SMILES: CC1(C)C(c2ccc(C(=O)O)cc2)=CC[C@]2(C)CN(C(=O)C3(c4ccccc4)CCN(C(=O)C4CCC(=O)N4)CC3)CC=C12] | 595.73 | 596.5 | 2.04 | A |
| A152 | 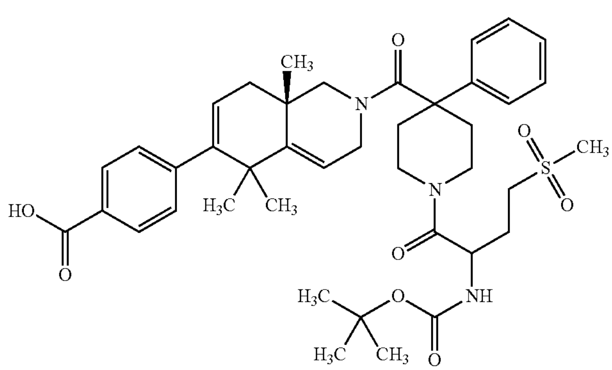 [SMILES: CC(C)(C)OC(=O)NC(CCS(C)(=O)=O)C(=O)N1CCC(C(=O)N2CC=C3C(C)(C)C(c4ccc(C(=O)O)cc4)=CC[C@]3(C)C2)(c2ccccc2)CC1] | 747.94 | 748.7 | 3.83 | M |
| A153 | 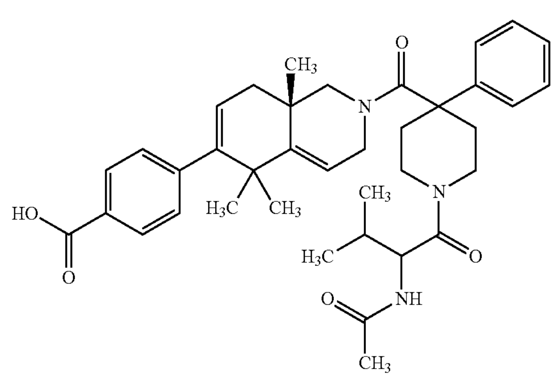 [SMILES: CC(=O)NC(C(=O)N1CCC(C(=O)N2CC=C3C(C)(C)C(c4ccc(C(=O)O)cc4)=CC[C@]3(C)C2)(c2ccccc2)CC1)C(C)C] | 625.80 | 626.6 | 3.80 | M |

TABLE 12-continued

| Ex | Structure | MW | Obs Ion | RT | Met |
|---|---|---|---|---|---|
| A154 | 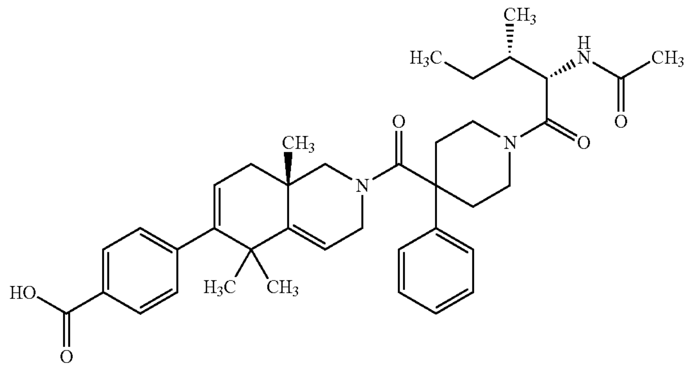 [SMILES: CC[C@H](C)[C@H](NC(C)=O)C(=O)N1CCC(C(=O)N2CC=C3C(C)(C)C(c4ccc(C(=O)O)cc4)=CC[C@]3(C)C2)(c2ccccc2)CC1] | 639.82 | 640.5 | 2.40 | A |
| A155 | 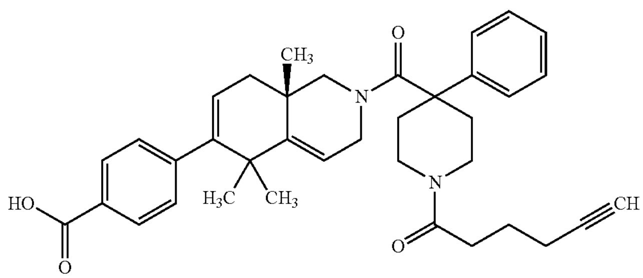 [SMILES: C#CCCCC(=O)N1CCC(C(=O)N2CC=C3C(C)(C)C(c4ccc(C(=O)O)cc4)=CC[C@]3(C)C2)(c2ccccc2)CC1] | 578.74 | 579.5 | 2.57 | A |
| A156 | 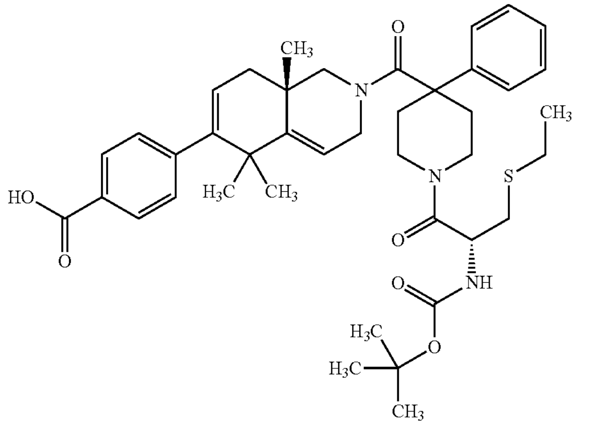 [SMILES: CCSC[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 715.94 | 716.6 | 4.20 | M |
| A157 | 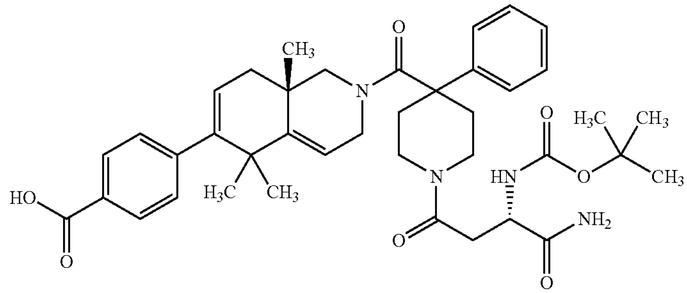 [SMILES: CC(C)(C)OC(=O)N[C@@H](CC(=O)N1CCC(C(=O)N2CC=C3C(C)(C)C(c4ccc(C(=O)O)cc4)=CC[C@]3(C)C2)(c2ccccc2)CC1)C(N)=O] | 698.85 | 699.6 | 3.80 | M |

TABLE 12-continued

| Ex | Structure | MW | Obs Ion | RT | Met |
|---|---|---|---|---|---|
| A158 | 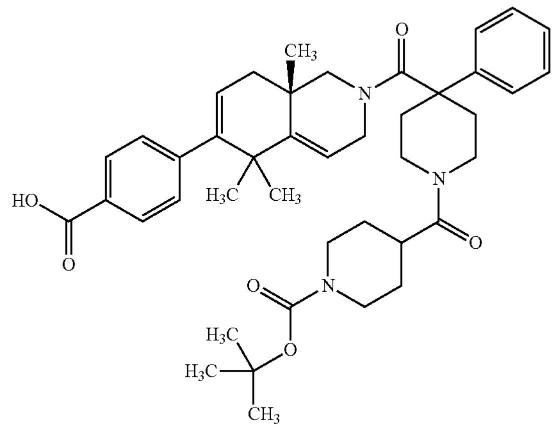 [SMILES: CC(C)(C)OC(=O)N1CCC(C(=O)N2CCC(C(=O)N3CC=C4C(C)(C)C(c5ccc(C(=O)O)cc5)=CC[C@]4(C)C3)(c3ccccc3)CC2)CC1] | 695.89 | 696.6 | 4.11 | M |
| A159 | 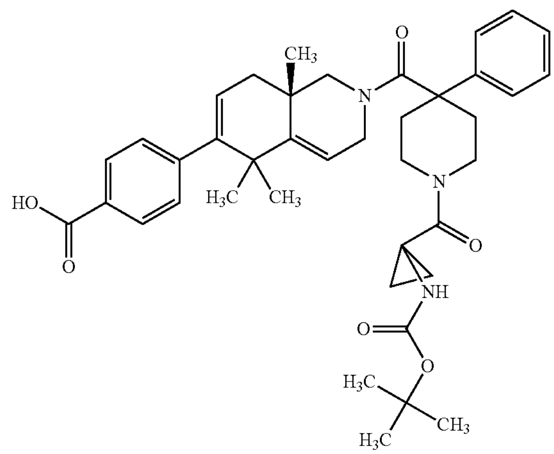 [SMILES: CC(C)(C)OC(=O)NC1(C(=O)N2CCC(C(=O)N3CC=C4C(C)(C)C(c5ccc(C(=O)O)cc5)=CC[C@]4(C)C3)(c3ccccc3)CC2)CC1] | 667.83 | 666.8 | 3.89 | M |
| A160 | 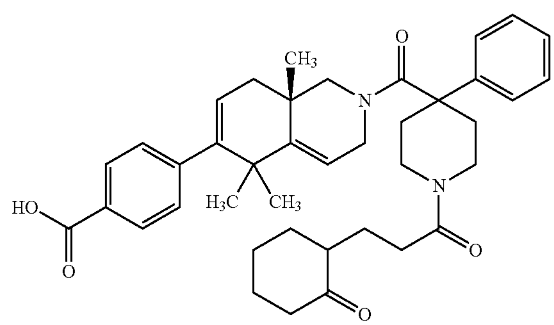 [SMILES: CC1(C)C(c2ccc(C(=O)O)cc2)=CC[C@]2(C)CN(C(=O)C3(c4ccccc4)CCN(C(=O)CCC4CCCCC4=O)CC3)CC=C12] | 636.82 | 635.5 | 3.96 | M |
| A161 | 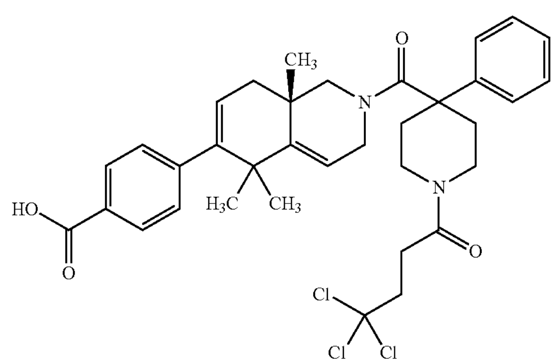 [SMILES: CC1(C)C(c2ccc(C(=O)O)cc2)=CC[C@]2(C)CN(C(=O)C3(c4ccccc4)CCN(C(=O)CCC(Cl)(Cl)Cl)CC3)CC=C12] | 658.05 | 657.3 | 2.90 | A |

TABLE 12-continued

| Ex | Structure | MW | Obs Ion | RT | Met |
|---|---|---|---|---|---|
| A162 | 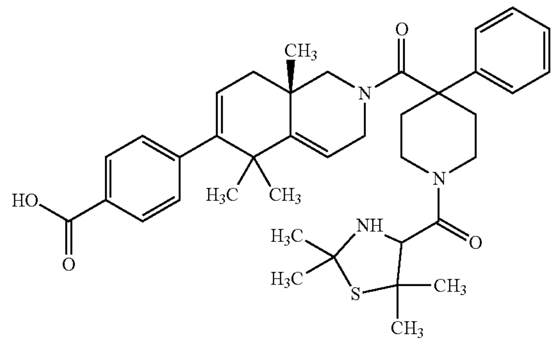 [SMILES: CC1(C)NC(C(=O)N2CCC(C(=O)N3CC=C4C(C)(C)C(c5ccc(C(=O)O)cc5)=CC[C@]4(C)C3)(c3ccccc3)CC2)C(C)(C)S1] | 655.89 | 656.6 | 4.16 | M |
| A163 | 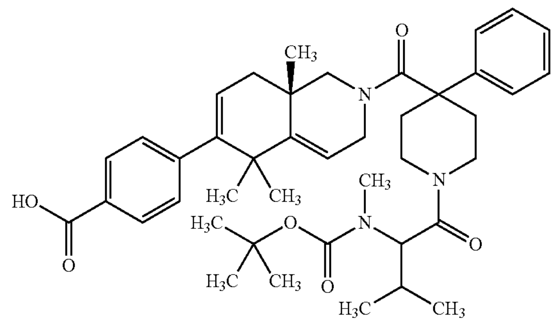 [SMILES: CC(C)C(C(=O)N1CCC(C(=O)N2CC=C3C(C)(C)C(c4ccc(C(=O)O)cc4)=CC[C@]3(C)C2)(c2ccccc2)CC1)N(C)C(=O)OC(C)(C)C] | 697.90 | 698.6 | 3.03 | A |
| A164 | 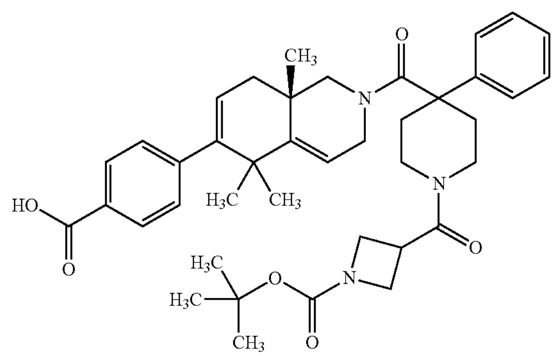 [SMILES: CC(C)(C)OC(=O)N1CC(C(=O)N2CCC(C(=O)N3CC=C4C(C)(C)C(c5ccc(C(=O)O)cc5)=CC[C@]4(C)C3)(c3ccccc3)CC2)C1] | 667.83 | 668.6 | 2.67 | A |
| A165 | 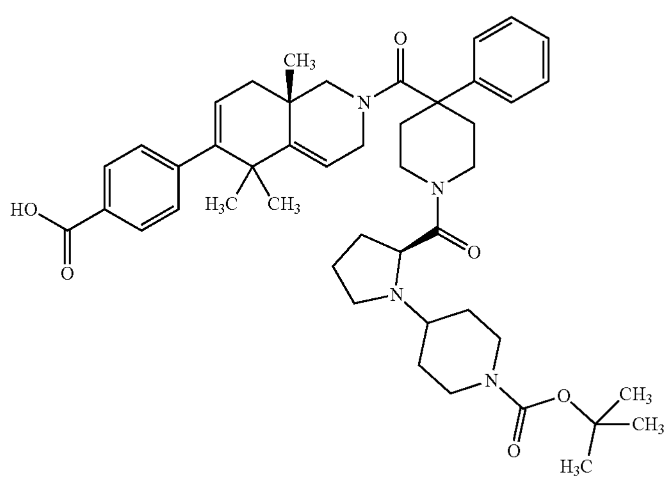 [SMILES: CC(C)(C)OC(=O)N1CCC(N2CCC[C@H]2C(=O)N2CCC(C(=O)N3CC=C4C(C)(C)C(c5ccc(C(=O)O)cc5)=CC[C@]4(C)C3)(c3ccccc3)CC2)CC1] | 764.99 | 765.8 | 2.50 | A |

TABLE 12-continued
| Ex | Structure | MW | Obs Ion | RT | Met |
|---|---|---|---|---|---|
| A166 | 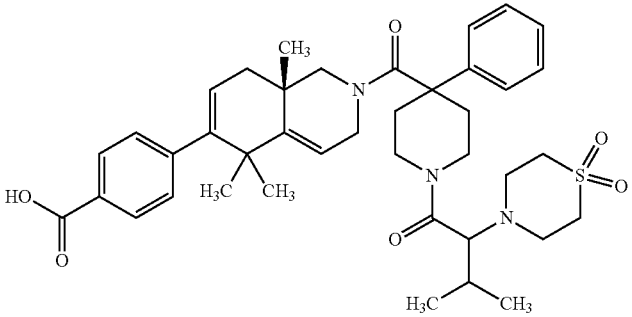 [SMILES: CC(C)C(C(=O)N1CCC(C(=O)N2CC=C3C(C)(C)C(c4ccc(C(=O)O)cc4)=CC[C@]3(C)C2)(c2ccccc2)CC1)N1CCS(=O)(=O)CC1] | 701.91 | 702.5 | 3.81 | M |
| A167 | 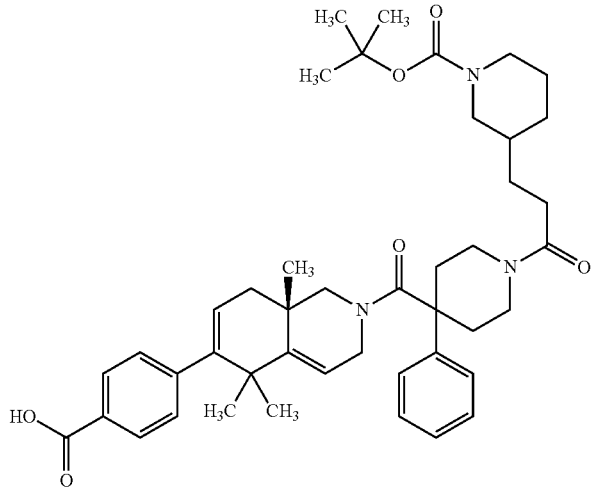 [SMILES: CC(C)(C)OC(=O)N1CCCC(CCC(=O)N2CCC(C(=O)N3CC=C4C(C)(C)C(c5ccc(C(=O)O)cc5)=CC[C@]4(C)C3)(c3ccccc3)CC2)C1] | 723.94 | 724.6 | 4.29 | M |
| A168 | 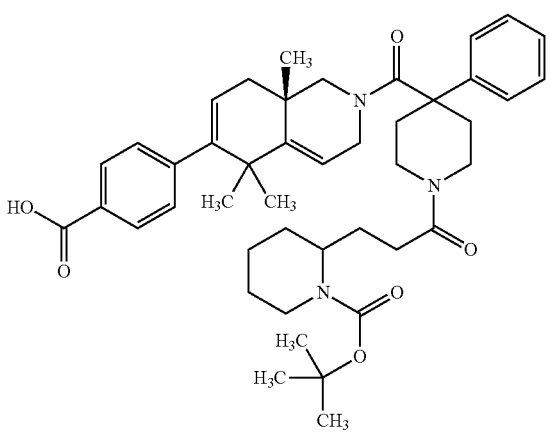 [SMILES: CC(C)(C)OC(=O)N1CCCCC1CCC(=O)N1CCC(C(=O)N2CC=C3C(C)(C)C(c4ccc(C(=O)O)cc4)=CC[C@]3(C)C2)(c2ccccc2)CC1] | 723.95 | 724.7 | 2.96 | A |

TABLE 12-continued

| Ex | Structure | MW | Obs Ion | RT | Met |
|---|---|---|---|---|---|
| A169 | 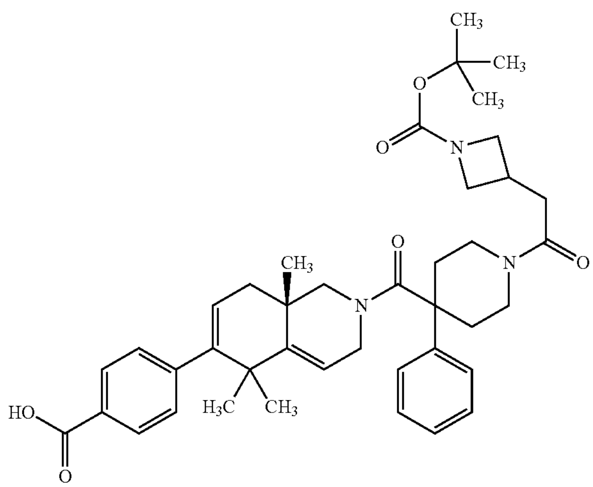 [SMILES: CC(C)(C)OC(=O)N1CC(CC(=O)N2CCC(C(=O)N3CC=C4C(C)(C)C(c5ccc(C(=O)O)cc5)=CC[C@]4(C)C3)(c3ccccc3)CC2)C1] | 681.86 | 682.6 | 2.69 | A |
| A170 | 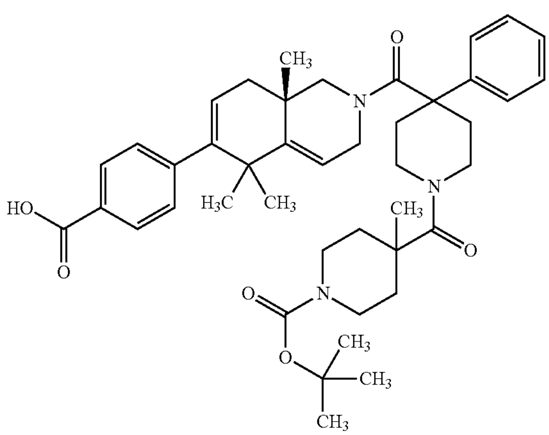 [SMILES: CC(C)(C)OC(=O)N1CCC(C)(C(=O)N2CCC(C(=O)N3CC=C4C(C)(C)C(c5ccc(C(=O)O)cc5)=CC[C@]4(C)C3)(c3ccccc3)CC2)CC1] | 709.91 | 710.6 | 4.28 | M |
| A171 | 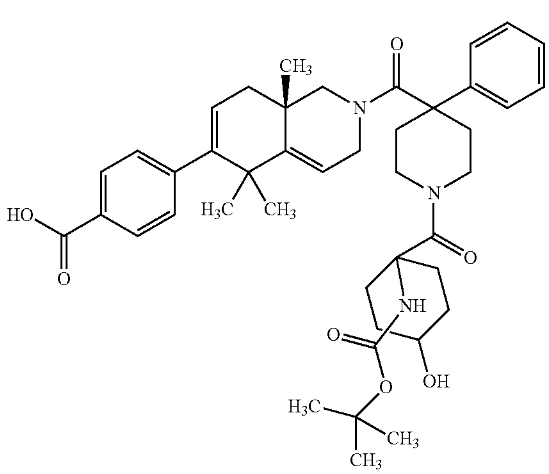 [SMILES: CC(C)(C)OC(=O)NC1(C(=O)N2CCC(C(=O)N3CC=C4C(C)(C)C(c5ccc(C(=O)O)cc5)=CC[C@]4(C)C3)(c3ccccc3)CC2)CCC(O)CC1] | 725.91 | 726.6 | 2.34 | A |

TABLE 12-continued

| Ex | Structure | MW | Obs Ion | RT | Met |
|---|---|---|---|---|---|
| A172 | 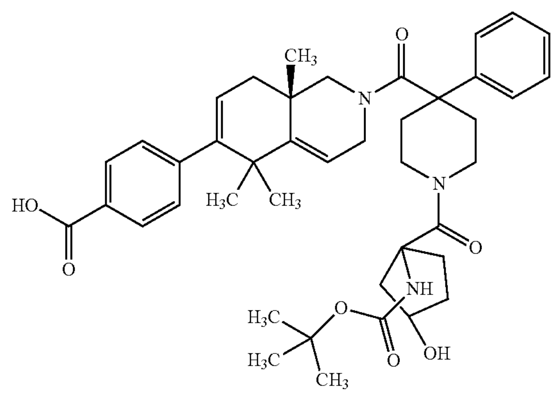 [SMILES: CC(C)(C)OC(=O)NC1(C(=O)N2CCC(C(=O)N3CC=C4C(C)(C)C(c5ccc(C(=O)O)cc5)=CC[C@]4(C)C3)(c3ccccc3)CC2)CCC(O)C1] | 711.89 | 712.6 | 3.83 | M |
| A173 | 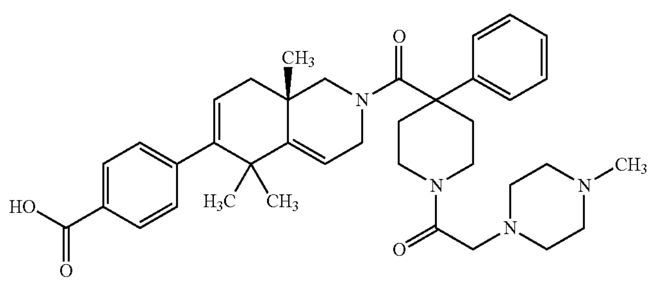 [SMILES: CN1CCN(CC(=O)N2CCC(C(=O)N3CC=C4C(C)(C)C(c5ccc(C(=O)O)cc5)=CC[C@]4(C)C3)(c3ccccc3)CC2)CC1] | 624.81 | 625.5 | 2.00 | A |
| A174 | 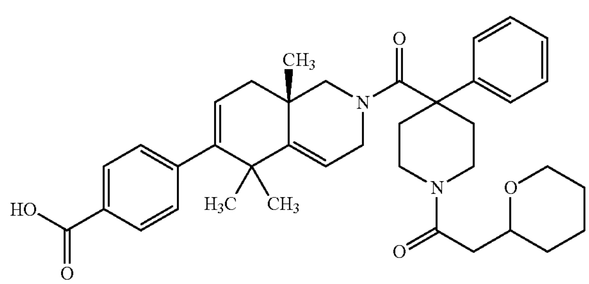 [SMILES: CC1(C)C(c2ccc(C(=O)O)cc2)=CC[C@]2(C)CN(C(=O)C3(c4ccccc4)CCN(C(=O)CC4CCCCO4)CC3)CC=C12] | 610.78 | 611.5 | 3.97 | M |
| A175 | 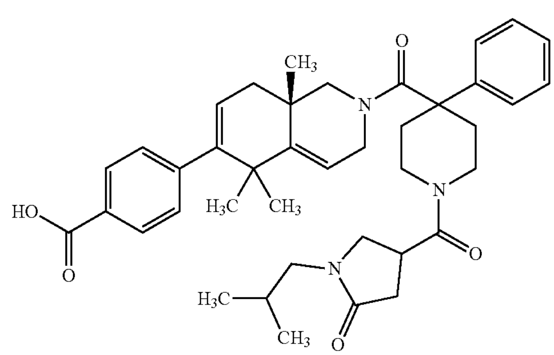 [SMILES: CC(C)CN1CC(C(=O)N2CCC(C(=O)N3CC=C4C(C)(C)C(c5ccc(C(=O)O)cc5)=CC[C@]4(C)C3)(c3ccccc3)CC2)CC1=O] | 651.83 | 652.6 | 2.43 | A |

TABLE 12-continued

| Ex | Structure | MW | Obs Ion | RT | Met |
|---|---|---|---|---|---|
| A176 | 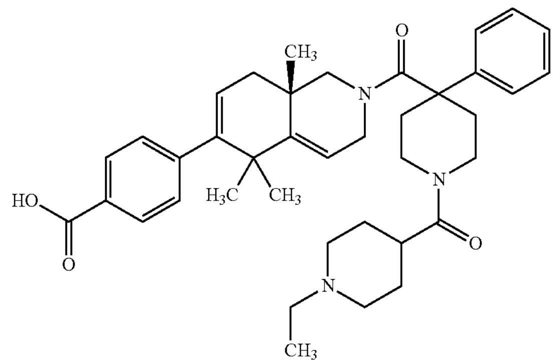 [SMILES: CCN1CCC(C(=O)N2CCC(C(=O)N3CC=C4C(C)(C)C(c5ccc(C(=O)O)cc5)=CC[C@]4(C)C3)(c3ccccc3)CC2)CC1] | 623.82 | 624.5 | 3.47 | M |
| A177 | 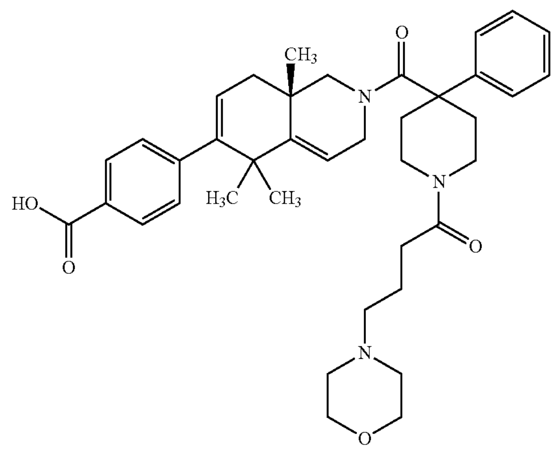 [SMILES: CC1(C)C(c2ccc(C(=O)O)cc2)=CC[C@]2(C)CN(C(=O)C3(c4ccccc4)CCN(C(=O)CCCN4CCOCC4)CC3)CC=C12] | 639.82 | 640.6 | 2.14 | A |
| A178 | 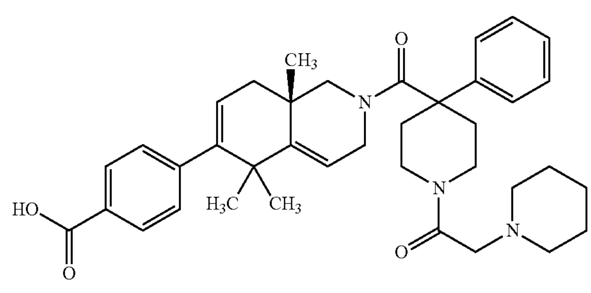 [SMILES: CC1(C)C(c2ccc(C(=O)O)cc2)=CC[C@]2(C)CN(C(=O)C3(c4ccccc4)CCN(C(=O)CN4CCCCC4)CC3)CC=C12] | 609.80 | 610.5 | 2.13 | M |
| A179 | 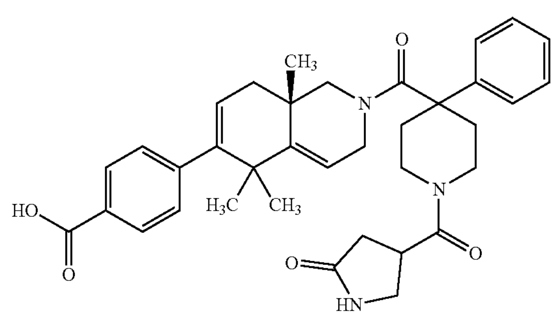 [SMILES: CC1(C)C(c2ccc(C(=O)O)cc2)=CC[C@]2(C)CN(C(=O)C3(c4ccccc4)CCN(C(=O)C4CNC(=O)C4)CC3)CC=C12] | 595.73 | 596.5 | 3.43 | M |

TABLE 12-continued

| Ex | Structure | MW | Obs Ion | RT | Met |
|---|---|---|---|---|---|
| A180 | 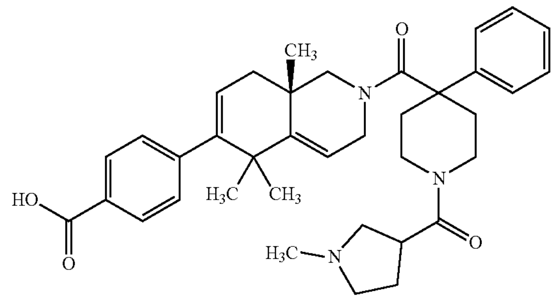 [SMILES: CN1CCC(C(=O)N2CCC(C(=O)N3CC=C4C(C)(C)C(c5ccc(C(=O)O)cc5)=CC[C@]4(C)C3)(c3ccccc3)CC2)C1] | 595.77 | 596.5 | 3.43 | M |
| A181 | 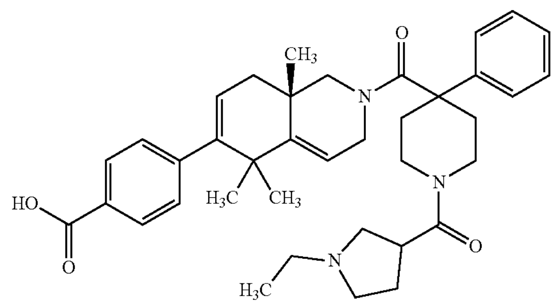 [SMILES: CCN1CCC(C(=O)N2CCC(C(=O)N3CC=C4C(C)(C)C(c5ccc(C(=O)O)cc5)=CC[C@]4(C)C3)(c3ccccc3)CC2)C1] | 609.80 | 610.5 | 3.45 | M |
| A182 | 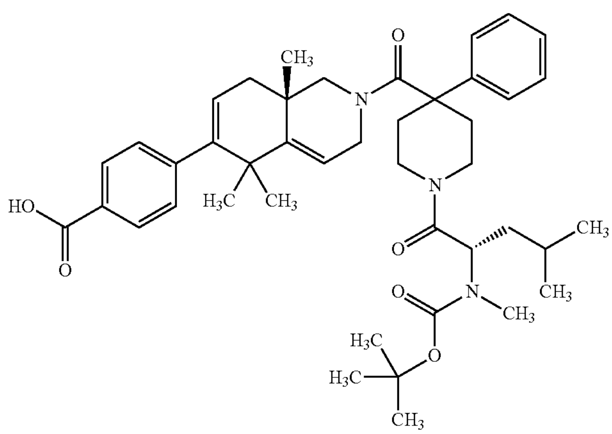 [SMILES: CC(C)C[C@@H](C(=O)N1CCC(C(=O)N2CC=C3C(C)(C)C(c4ccc(C(=O)O)cc4)=CC[C@]3(C)C2)(c2ccccc2)CC1)N(C)C(=O)OC(C)(C)C] | 711.93 | 712.6 | 4.43 | M |
| A183 | 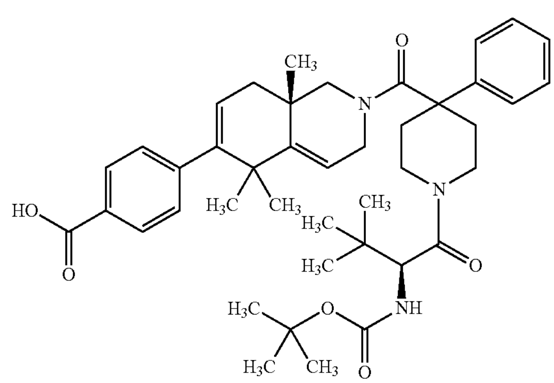 [SMILES: CC(C)(C)OC(=O)N[C@H](C(=O)N1CCC(C(=O)N2CC=C3C(C)(C)C(c4ccc(C(=O)O)cc4)=CC[C@]3(C)C2)(c2ccccc2)CC1)C(C)(C)C] | 697.90 | 698.6 | 3.02 | A |

TABLE 12-continued
| Ex | Structure | MW | Obs Ion | RT | Met |
|---|---|---|---|---|---|
| A184 | 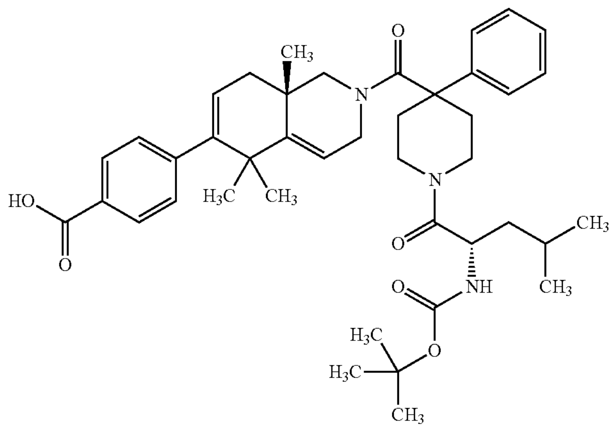 [SMILES: CC(C)C[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 697.90 | 698.6 | 4.30 | M |
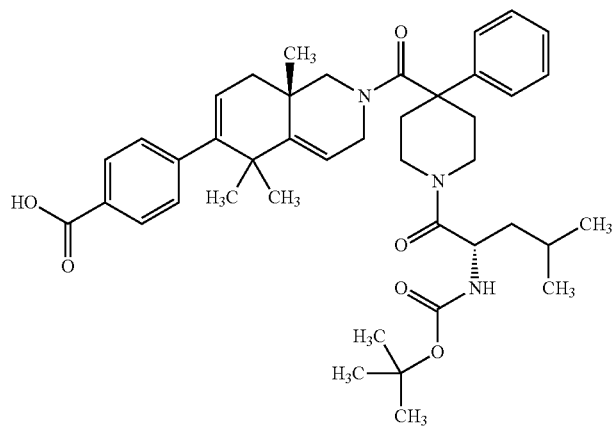
| A185 | | 741.97 | 742.7 | 4.34 | M |
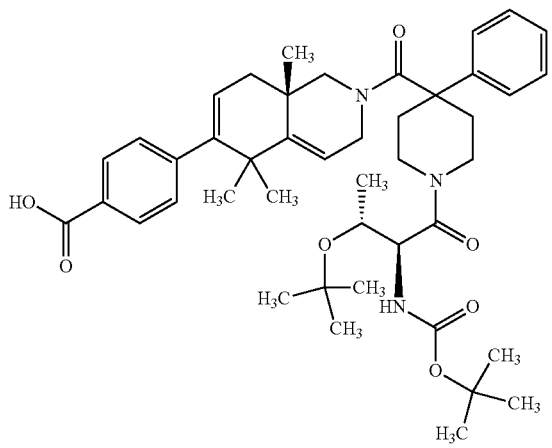 [SMILES: C[C@@H](OC(C)(C)C)[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1]
| A186 | | 685.85 | 686.6 | 4.00 | M |
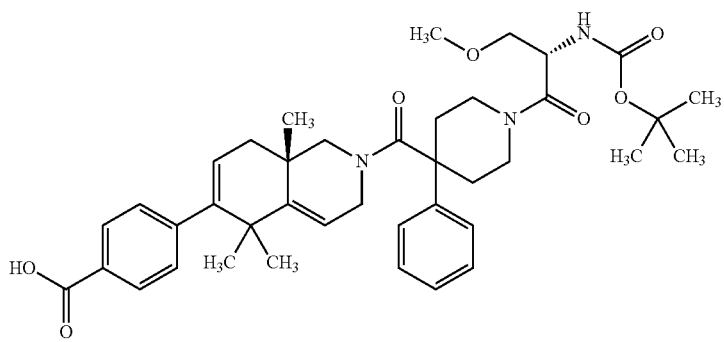 [SMILES: COC[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1]

TABLE 12-continued

| Ex | Structure | MW | Obs Ion | RT | Met |
|---|---|---|---|---|---|
| A187 | 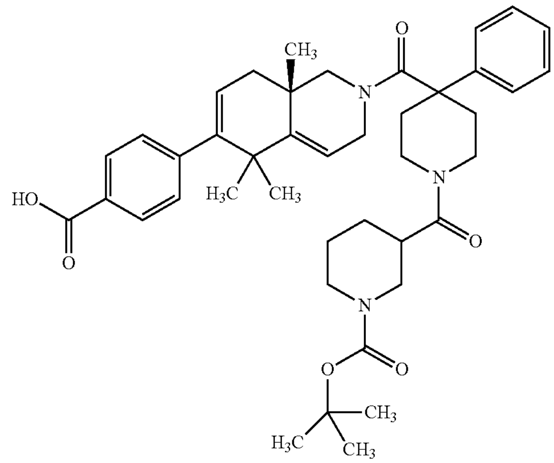 [SMILES: CC(C)(C)OC(=O)N1CCCC(C(=O)N2CCC(C(=O)N3CC=C4C(C)(C)C(c5ccc(C(=O)O)cc5)=CC[C@]4(C)C3)(c3ccccc3)CC2)C1] | 695.89 | 696.6 | 2.81 | A |
| A188 | 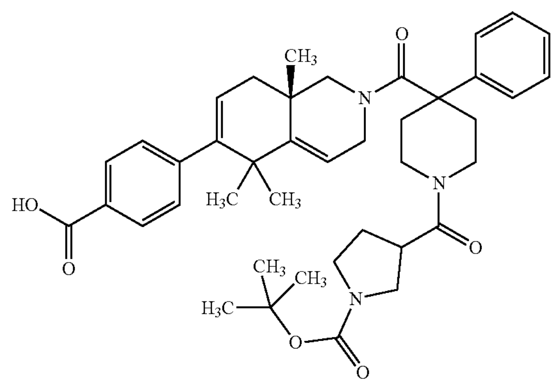 [SMILES: CC(C)(C)OC(=O)N1CCC(C(=O)N2CCC(C(=O)N3CC=C4C(C)(C)C(c5ccc(C(=O)O)cc5)=CC[C@]4(C)C3)(c3ccccc3)CC2)C1] | 681.86 | 682.6 | 2.73 | A |
| A189 | 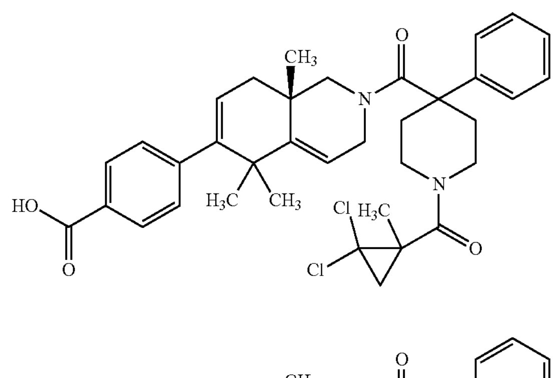 | 635.62 | 635.4 | 4.18 | M |
| A190 | 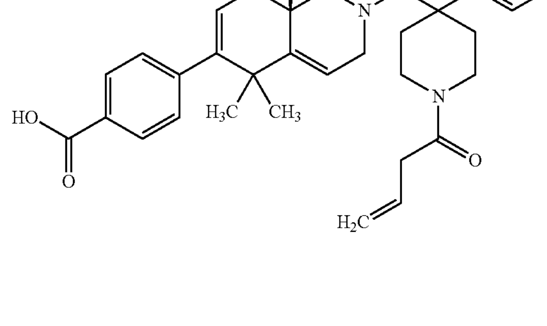 | 552.70 | 553.5 | 3.85 | M |

TABLE 12-continued

| Ex | Structure | MW | Obs Ion | RT | Met |
|---|---|---|---|---|---|
| A191 | 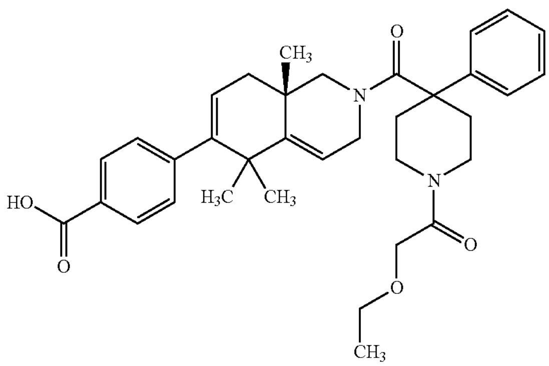 | 570.72 | 569.6 | 3.77 | M |
| A192 | 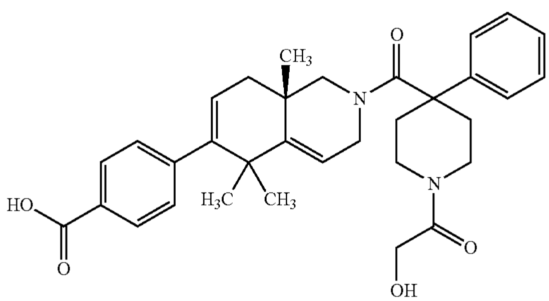 [SMILES: CC1(C)C(c2ccc(C(=O)O)cc2)=CC[C@]2(C)CN(C(=O)C3(c4ccccc4)CCN(C(=O)CO)CC3)CC=C12] | 542.67 | 543.4 | 3.49 | M |
| A193 | 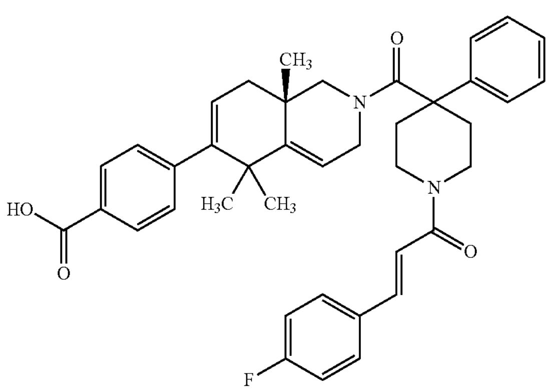 [SMILES: CC1(C)C(c2ccc(C(=O)O)cc2)=CC[C@]2(C)CN(C(=O)C3(c4ccccc4)CCN(C(=O)/C=C/c4ccc(F)cc4)CC3)CC=C12] | 632.76 | 633.5 | 2.79 | A |
| A194 | 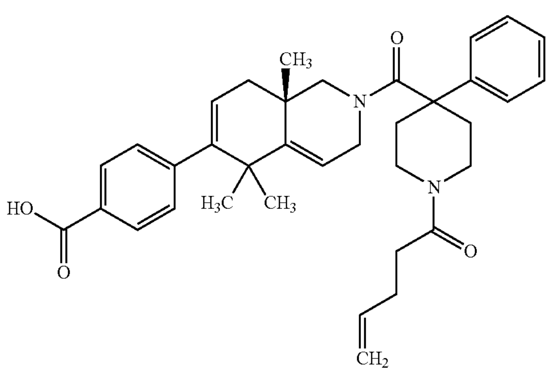 [SMILES: C=CCCC(=O)N1CCC(C(=O)N2CC=C3C(C)(C)C(c4ccc(C(=O)O)cc4)=CC[C@]3(C)C2)(c2ccccc2)CC1] | 566.73 | 567.5 | 2.55 | A |

TABLE 12-continued

| Ex | Structure | MW | Obs Ion | RT | Met |
|---|---|---|---|---|---|
| A195 | 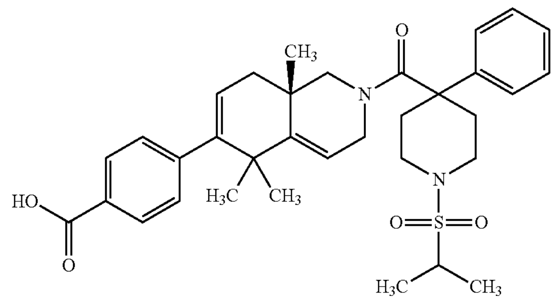 [SMILES: CC(C)S(=O)(=O)N1CCC(C(=O)N2CC=C3C(C)(C)C(c4ccc(C(=O)O)cc4)=CC[C@]3(C)C2)(c2ccccc2)CC1] | 590.78 | 591.5 | 2.58 | A |
| A196 | 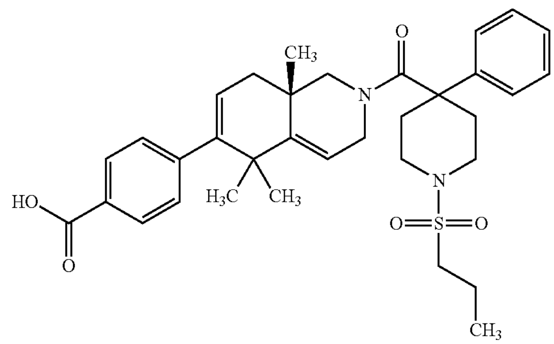 [SMILES: CCCS(=O)(=O)N1CCC(C(=O)N2CC=C3C(C)(C)C(c4ccc(C(=O)O)cc4)=CC[C@]3(C)C2)(c2ccccc2)CC1] | 590.77 | 591.4 | 3.86 | M |
| A197 | 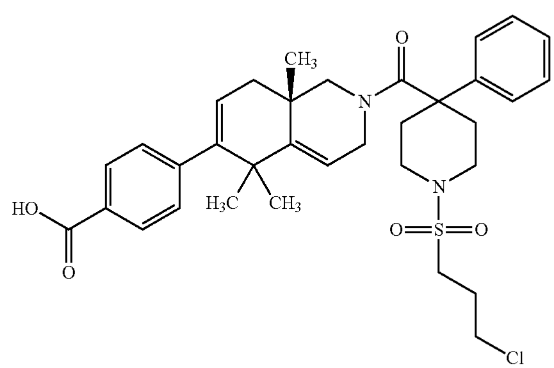 [SMILES: CC1(C)C(c2ccc(C(=O)O)cc2)=CC[C@]2(C)CN(C(=O)C3(c4ccccc4)CCN(S(=O)(=O)CCCCl)CC3)CC=C12] | 625.23 | 625.4 | 3.90 | M |
| A198 | 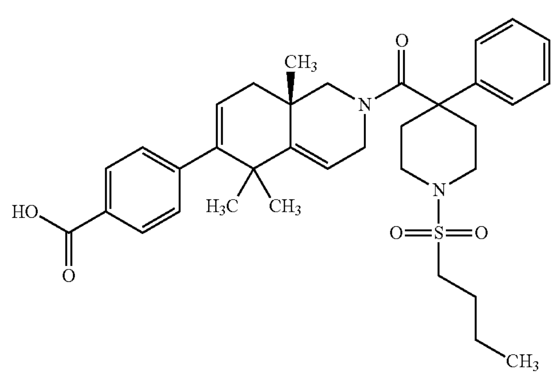 [SMILES: CCCCS(=O)(=O)N1CCC(C(=O)N2CC=C3C(C)(C)C(c4ccc(C(=O)O)cc4)=CC[C@]3(C)C2)(c2ccccc2)CC1] | 604.80 | 605.4 | 3.99 | M |

TABLE 12-continued

| Ex | Structure | MW | Obs Ion | RT | Met |
|---|---|---|---|---|---|
| A199 | 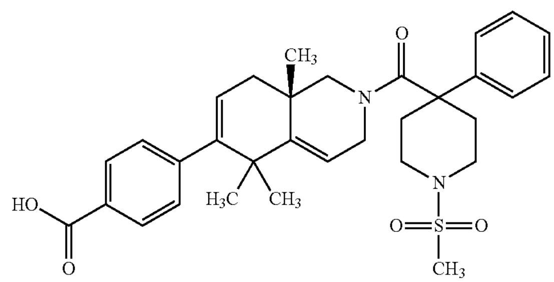 [SMILES: CC1(C)C(c2ccc(C(=O)O)cc2)=CC[C@]2(C)CN(C(=O)C3(c4ccccc4)CCN(S(C)(=O)=O)CC3)CC=C12] | 562.72 | 563.4 | 3.63 | M |
| A200 | 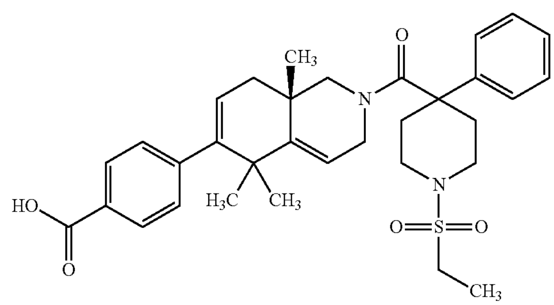 [SMILES: CCS(=O)(=O)N1CCC(C(=O)N2CC=C3C(C)(C)C(c4ccc(C(=O)O)cc4)=CC[C@]3(C)C2)(c2ccccc2)CC1] | 576.75 | 577.4 | 3.73 | M |
| A201 | 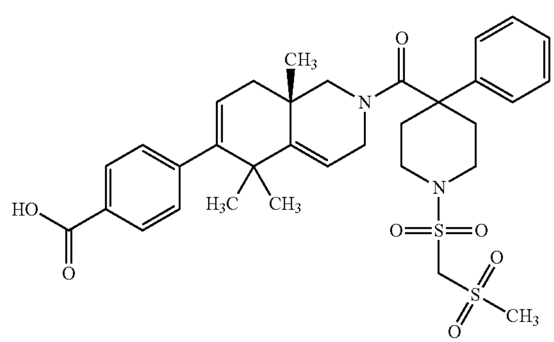 [SMILES: CC1(C)C(c2ccc(C(=O)O)cc2)=CC[C@]2(C)CN(C(=O)C3(c4ccccc4)CCN(S(=O)(=O)CS(C)(=O)=O)CC3)CC=C12] | 640.81 | 641.4 | 3.61 | M |
| A202 | 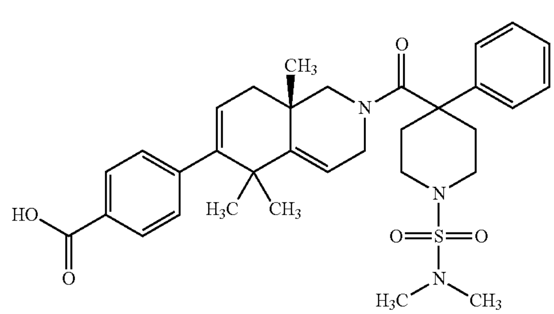 [SMILES: CN(C)S(=O)(=O)N1CCC(C(=O)N2CC=C3C(C)(C)C(c4ccc(C(=O)O)cc4)=CC[C@]3(C)C2)(c2ccccc2)CC1] | 591.76 | 592.4 | 3.81 | M |

TABLE 12-continued

| Ex | Structure | MW | Obs Ion | RT | Met |
|---|---|---|---|---|---|
| A203 | 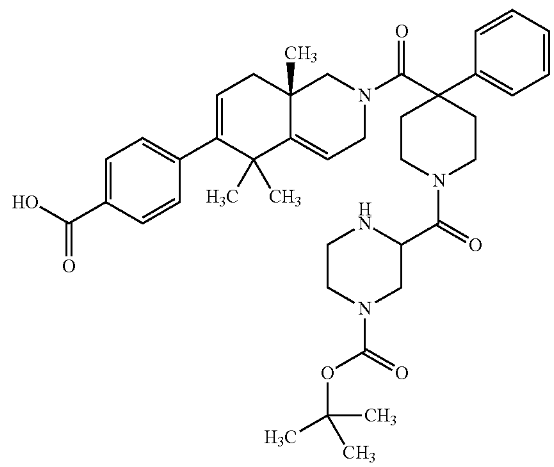 [SMILES: CC(C)(C)OC(=O)N1CCNC(C(=O)N2CCC(C(=O)N3CC=C4C(C)(C)C(c5ccc(C(=O)O)cc5)=CC[C@]4(C)C3)(c3ccccc3)CC2)C1] | 696.87 | 697.6 | 2.46 | A |
| A204 | 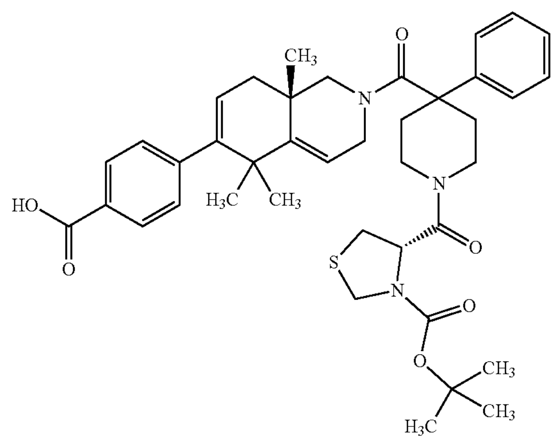 [SMILES: CC(C)(C)OC(=O)N1CSC[C@@H]1C(=O)N1CCC(C(=O)N2CC=C3C(C)(C)C(c4ccc(C(=O)O)cc4)=CC[C@]3(C)C2)(c2ccccc2)CC1] | 699.91 | 700.6 | 2.72 | A |
| A205 | 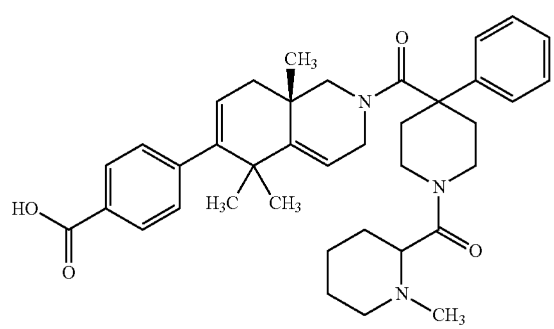 [SMILES: CN1CCCCC1C(=O)N1CCC(C(=O)N2CC=C3C(C)(C)C(c4ccc(C(=O)O)cc4)=CC[C@]3(C)C2)(c2ccccc2)CC1] | 609.80 | 610.5 | 3.59 | M |

TABLE 12-continued

| Ex | Structure | MW | Obs Ion | RT | Met |
|---|---|---|---|---|---|
| A206 | 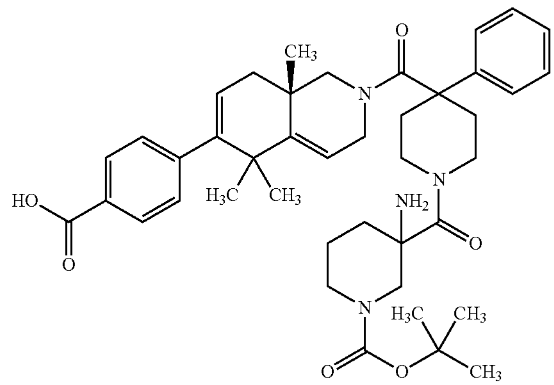 [SMILES: CC(C)(C)OC(=O)N1CCCC(N)(C(=O)N2CCC(C(=O)N3CC=C4C(C)(C)C(c5ccc(C(=O)O)cc5)=CC[C@]4(C)C3)(c3ccccc3)CC2)C1] | 710.90 | 711.5 | 4.05 | M |
| A207 | 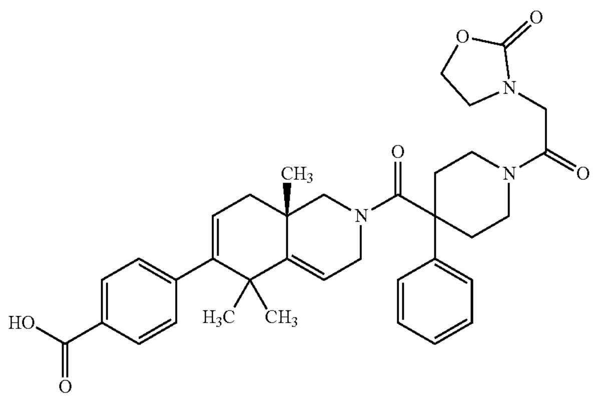 [SMILES: CC1(C)C(c2ccc(C(=O)O)cc2)=CC[C@]2(C)CN(C(=O)C3(c4ccccc4)CCN(C(=O)CN4CCOC4=O)CC3)CC=C12] | 611.73 | 612.3 | 3.32 | M |
| A208 | 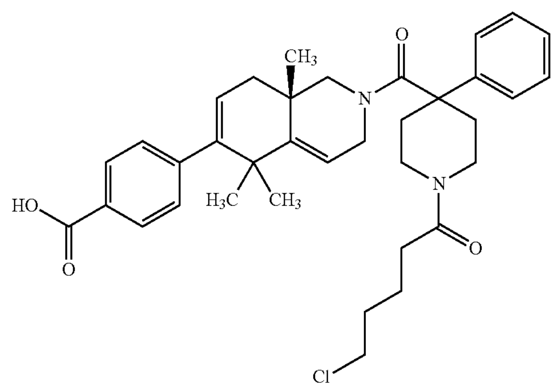 [SMILES: CC1(C)C(c2ccc(C(=O)O)cc2)=CC[C@]2(C)CN(C(=O)C3(c4ccccc4)CCN(C(=O)CCCCCl)CC3)CC=C12] | 603.19 | 603.3 | 3.95 | M |
| A209 | 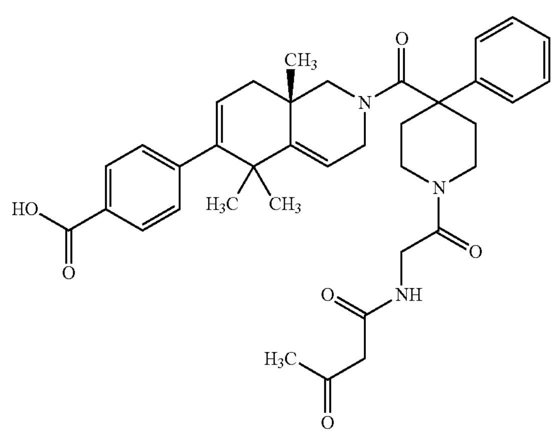 [SMILES: CC(=O)CC(=O)NCC(=O)N1CCC(C(=O)N2CC=C3C(C)(C)C(c4ccc(C(=O)O)cc4)=CC[C@]3(C)C2)(c2ccccc2)CC1] | 625.75 | 626.5 | 3.49 | M |

TABLE 12-continued
| Ex | Structure | MW | Obs Ion | RT | Met |
|----|-----------|-----|---------|-----|-----|
| A210 | 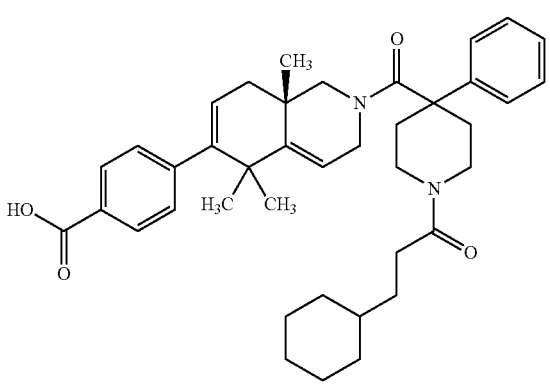 [SMILES: CC1(C)C(c2ccc(C(=O)O)cc2)=CC[C@]2(C)CN(C(=O)C3(c4ccccc4)CCN(C(=O)CCC4CCCCC4)CC3)CC=C12] | 622.84 | 623.5 | 3.13 | A |
| A211 | 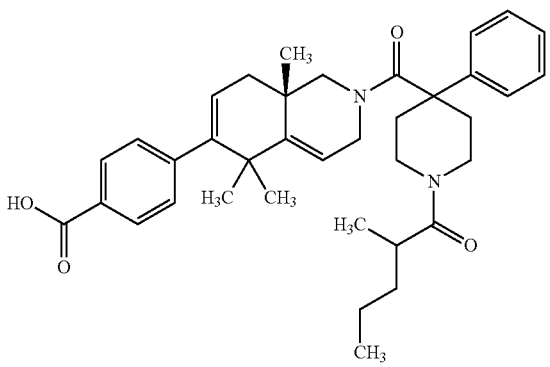 [SMILES: CCCC(C)C(=O)N1CCC(C(=O)N2CC=C3C(C)(C)C(c4ccc(C(=O)O)cc4)=CC[C@]3(C)C2)(c2ccccc2)CC1] | 582.77 | 583.5 | 2.78 | A |
| A212 | 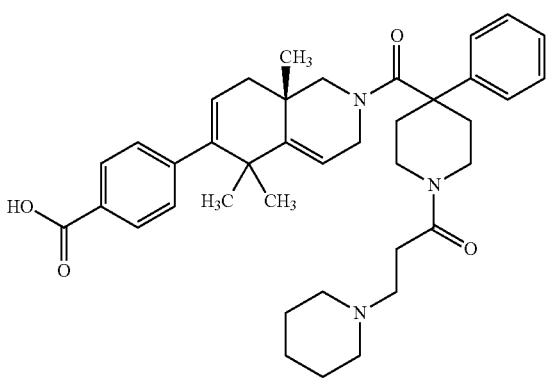 [SMILES: CC1(C)C(c2ccc(C(=O)O)cc2)=CC[C@]2(C)CN(C(=O)C3(c4ccccc4)CCN(C(=O)CCN4CCCCC4)CC3)CC=C12] | 623.82 | 624.5 | 3.53 | M |
| A213 | 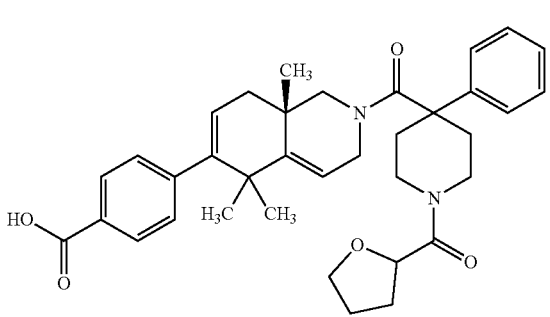 [SMILES: CC1(C)C(c2ccc(C(=O)O)cc2)=CC[C@]2(C)CN(C(=O)C3(c4ccccc4)CCN(C(=O)C4CCCO4)CC3)CC=C12] | 582.73 | 583.5 | 2.31 | A |

TABLE 12-continued

| Ex | Structure | MW | Obs Ion | RT | Met |
|---|---|---|---|---|---|
| A214 | 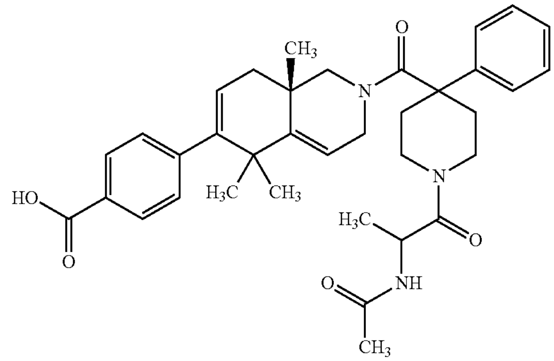 [SMILES: CC(=O)NC(C)C(=O)N1CCC(C(=O)N2CC=C3C(C)(C)C(c4ccc(C(=O)O)cc4)=CC[C@]3(C)C2)(c2ccccc2)CC1] | 597.74 | 598.5 | 3.55 | M |
| A215 | 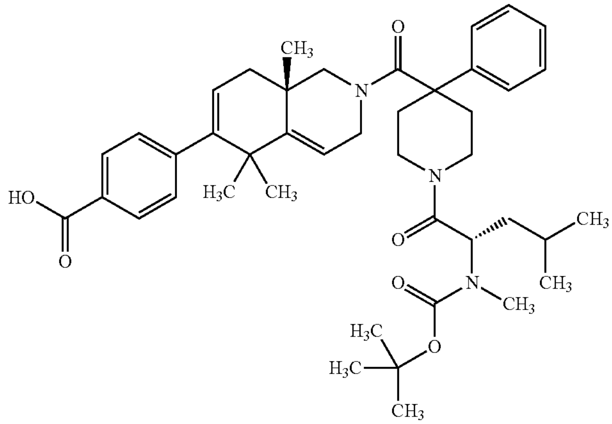 [SMILES: CC(C)C[C@@H](C(=O)N1CCC(C(=O)N2CC=C3C(C)(C)C(c4ccc(C(=O)O)cc4)=CC[C@]3(C)C2)(c2ccccc2)CC1)N(C)C(=O)OC(C)(C)C] | 711.93 | 712.6 | 3.19 | A |
| A216 | 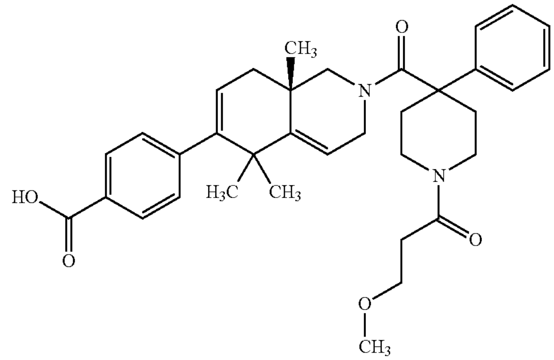 | 570.72 | 571.5 | 2.27 | A |
| A217 | 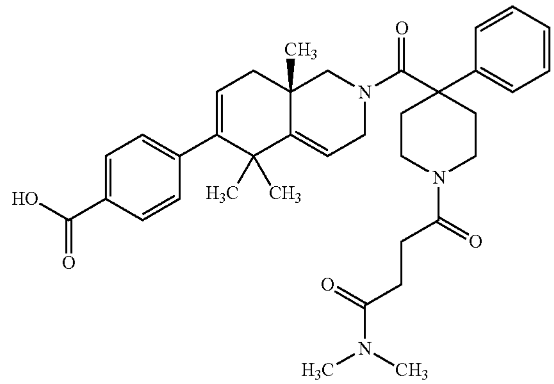 [SMILES: CN(C)C(=O)CCC(=O)N1CCC(C(=O)N2CC=C3C(C)(C)C(c4ccc(C(=O)O)cc4)=CC[C@]3(C)C2)(c2ccccc2)CC1] | 611.77 | 612.5 | 2.17 | A |

TABLE 12-continued

| Ex | Structure | MW | Obs Ion | RT | Met |
|---|---|---|---|---|---|
| A218 | 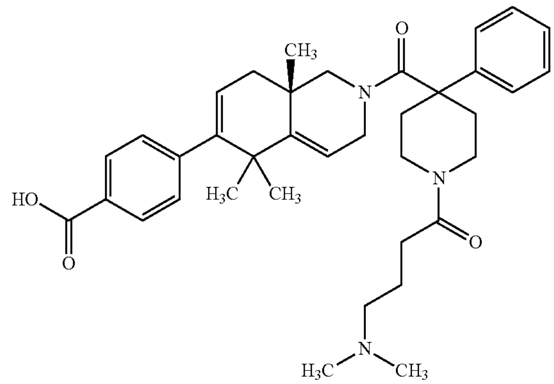 [SMILES: CN(C)CCCC(=O)N1CCC(C(=O)N2CC=C3C(C)(C)C(c4ccc(C(=O)O)cc4)=CC[C@]3(C)C2)(c2ccccc2)CC1] | 597.79 | 598.5 | 2.03 | A |
| A219 | 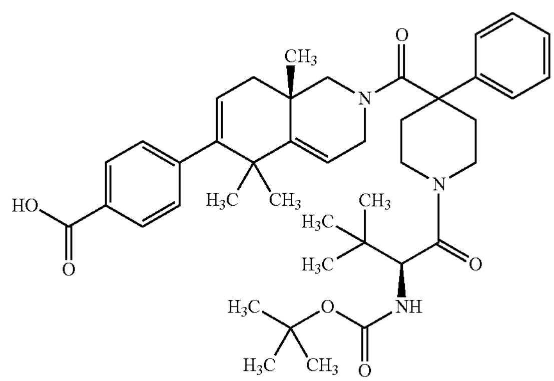 [SMILES: CC(C)(C)OC(=O)N[C@H](C(=O)N1CCC(C(=O)N2CC=C3C(C)(C)C(c4ccc(C(=O)O)cc4)=CC[C@]3(C)C2)(c2ccccc2)CC1)C(C)(C)C] | 697.92 | 698.6 | 3.03 | A |
| A220 | 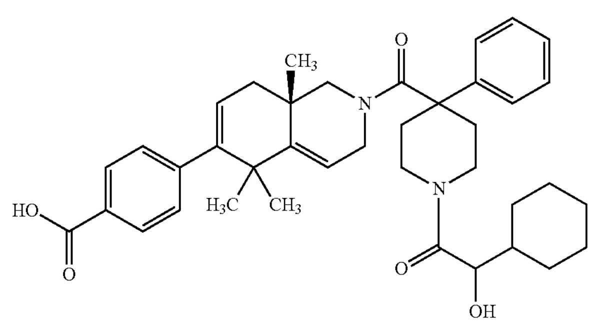 [SMILES: CC1(C)C(c2ccc(C(=O)O)cc2)=CC[C@]2(C)CN(C(=O)C3(c4ccccc4)CCN(C(=O)C(O)C4CCCCC4)CC3)CC=C12] | 624.81 | 625.5 | 2.76 | A |
| A221 | 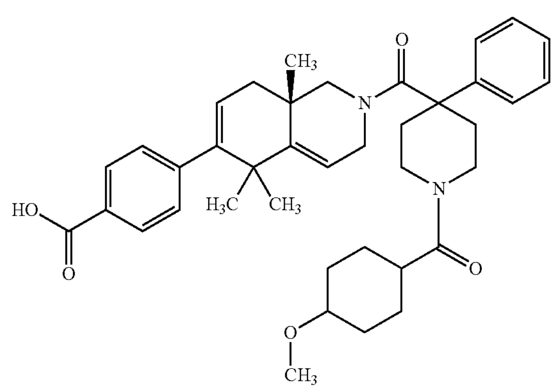 [SMILES: COC1CCC(C(=O)N2CCC(C(=O)N3CC=C4C(C)(C)C(c5ccc(C(=O)O)cc5)=CC[C@]4(C)C3)(c3ccccc3)CC2)CC1] | 624.81 | 625.5 | 2.57 | A |

TABLE 12-continued

| Ex | Structure | MW | Obs Ion | RT | Met |
|---|---|---|---|---|---|
| A222 | 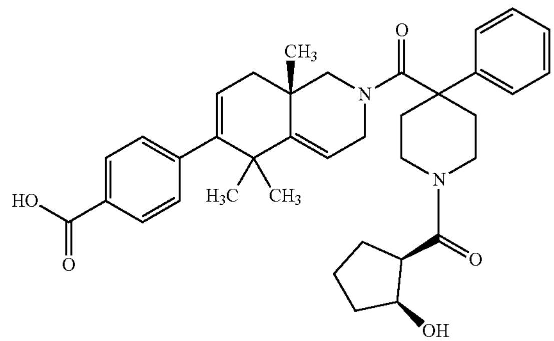 [SMILES: CC1(C)C(c2ccc(C(=O)O)cc2)=CC[C@]2(C)CN(C(=O)C3(c4ccccc4)CCN(C(=O)[C@@H]4CCC[C@@H]4O)CC3)CC=C12] | 596.76 | 597.5 | 2.41 | A |
| A223 | | 741.96 | 742.6 | 3.08 | A |
| A223 | | 685.85 | 686.6 | 2.62 | A |
| A224 | 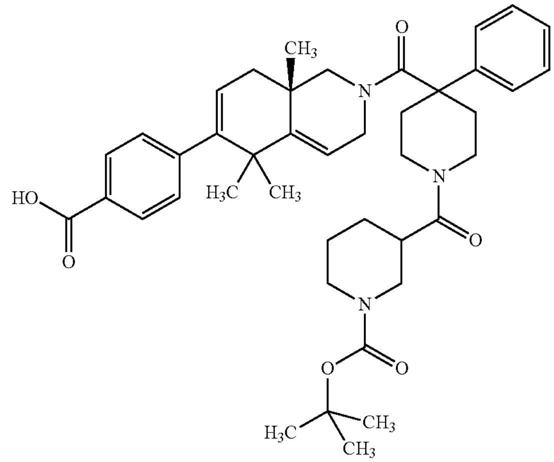 [SMILES: CC(C)(C)OC(=O)N1CCCC(C(=O)N2CCC(C(=O)N3CC=C4C(C)(C)C(c5ccc(C(=O)O)cc5)=CC[C@]4(C)C3)(c3ccccc3)CC2)C1] | 695.89 | 696.6 | 2.81 | A |

TABLE 12-continued

| Ex | Structure | MW | Obs Ion | RT | Met |
|---|---|---|---|---|---|
| A225 | 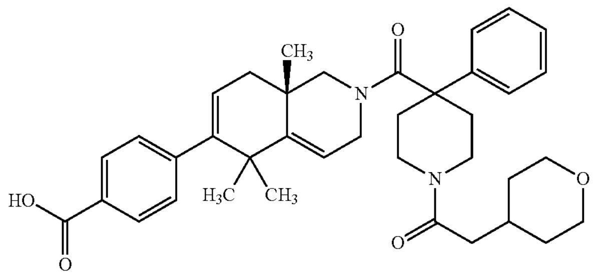 [SMILES: CC1(C)C(c2ccc(C(=O)O)cc2)=CC[C@]2(C)CN(C(=O)C3(c4ccccc4)CCN(C(=O)CC4CCOCC4)CC3)CC=C12] | 610.78 | 611.5 | 2.35 | A |
| A226 | 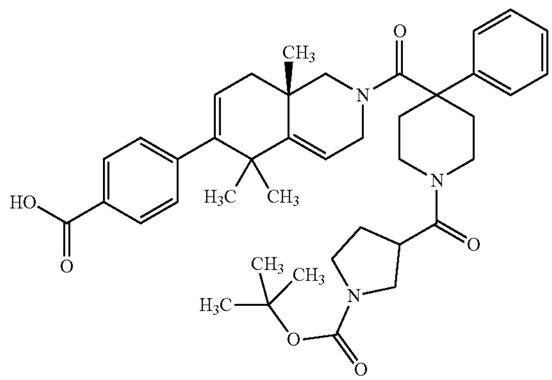 [SMILES: CC(C)(C)OC(=O)N1CCC(C(=O)N2CCC(C(=O)N3CC=C4C(C)(C)C(c5ccc(C(=O)O)cc5)=CC[C@]4(C)C3)(c3ccccc3)CC2)C1] | 681.86 | 682.6 | 2.73 | A |
| A227 | 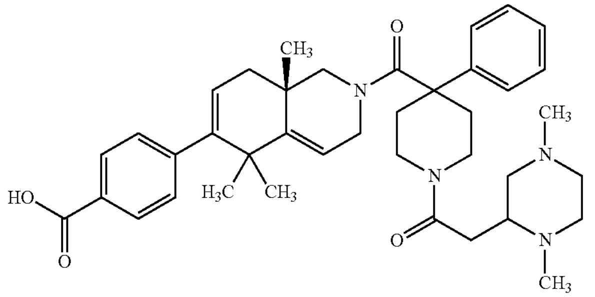 [SMILES: CN1CCN(C)C(CC(=O)N2CCC(C(=O)N3CC=C4C(C)(C)C(c5ccc(C(=O)O)cc5)=CC[C@]4(C)C3)(c3ccccc3)CC2)C1] | 638.84 | 639.5 | 2.04 | A |
| A228 | 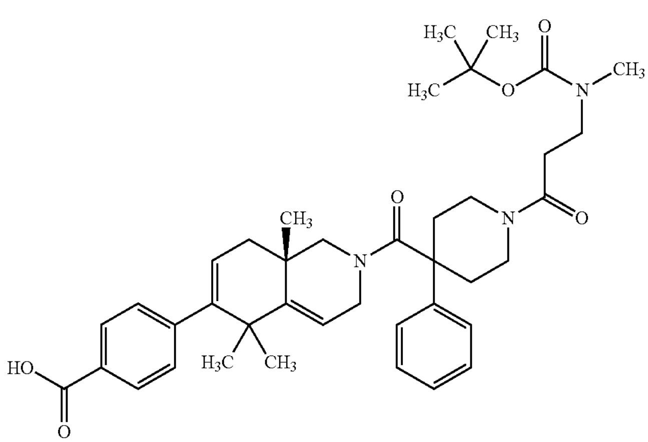 [SMILES: CN(CCC(=O)N1CCC(C(=O)N2CC=C3C(C)(C)C(c4ccc(C(=O)O)cc4)=CC[C@]3(C)C2)(c2ccccc2)CC1)C(=O)OC(C)(C)C] | 669.85 | 670.5 | 2.65 | A |

TABLE 12-continued

| Ex | Structure | MW | Obs Ion | RT | Met |
|---|---|---|---|---|---|
| A229 | 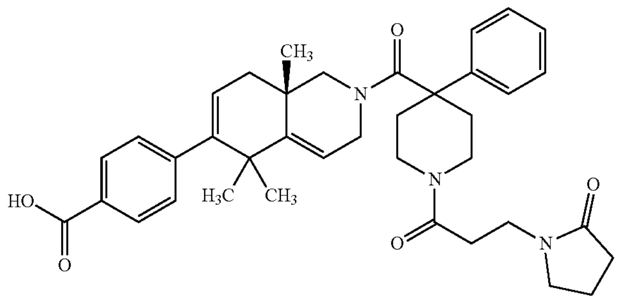 [SMILES: CC1(C)C(c2ccc(C(=O)O)cc2)=CC[C@]2(C)CN(C(=O)C3(c4ccccc4)CCN(C(=O)CCN4CCCC4=O)CC3)CC=C12] | 623.78 | 624.5 | 2.17 | A |
| A230 | 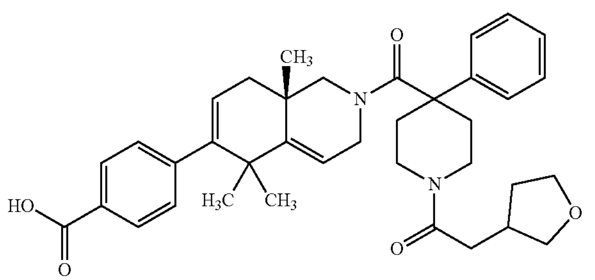 [SMILES: CC1(C)C(c2ccc(C(=O)O)cc2)=CC[C@]2(C)CN(C(=O)C3(c4ccccc4)CCN(C(=O)CC4CCOC4)CC3)CC=C12] | 596.76 | 597.4 | 3.70 | M |
| A231 | 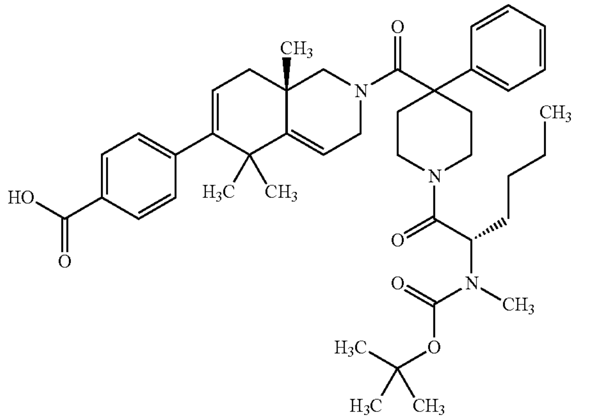 [SMILES: CCCC[C@@H](C(=O)N1CCC(C(=O)N2CC=C3C(C)(C)C(c4ccc(C(=O)O)cc4)=CC[C@]3(C)C2)(c2ccccc2)CC1)N(C)C(=O)OC(C)(C)C] | 711.93 | 712.6 | 3.20 | A |
| A232 | 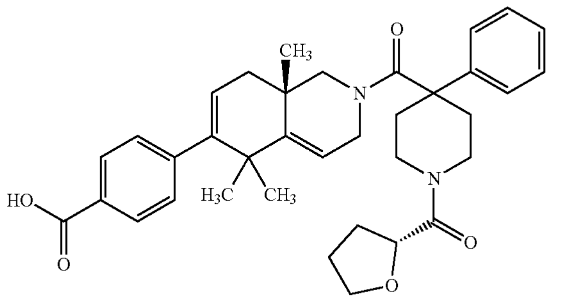 [SMILES: CC1(C)C(c2ccc(C(=O)O)cc2)=CC[C@]2(C)CN(C(=O)C3(c4ccccc4)CCN(C(=O)[C@H]4CCCO4)CC3)CC=C12] | 582.73 | 583.4 | 2.31 | A |

TABLE 12-continued

| Ex | Structure | MW | Obs Ion | RT | Met |
|---|---|---|---|---|---|
| A233 | 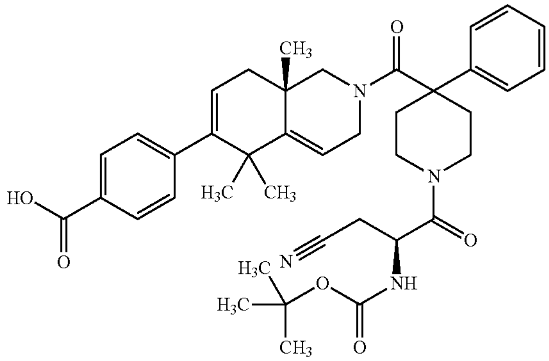 [SMILES: CC(C)(C)OC(=O)N[C@@H](CC#N)C(=O)N1CCC(C(=O)N2CC=C3C(C)(C)C(c4ccc(C(=O)O)cc4)=CC[C@]3(C)C2)(c2ccccc2)CC1] | 680.83 | 681.5 | 2.59 | A |
| A234 | 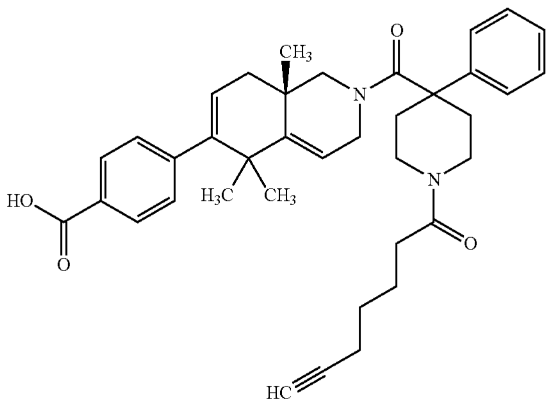 [SMILES: C#CCCCCC(=O)N1CCC(C(=O)N2CC=C3C(C)(C)C(c4ccc(C(=O)O)cc4)=CC[C@]3(C)C2)(c2ccccc2)CC1] | 592.77 | 593.5 | 2.60 | A |
| A235 | 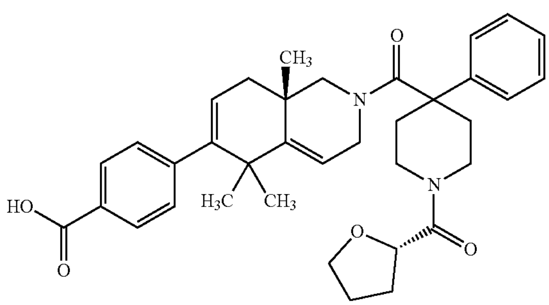 [SMILES: CC1(C)C(c2ccc(C(=O)O)cc2)=CC[C@]2(C)CN(C(=O)C3(c4ccccc4)CCN(C(=O)[C@@H]4CCCO4)CC3)CC=C12] | 582.73 | 583.4 | 3.73 | M |
| A236 | 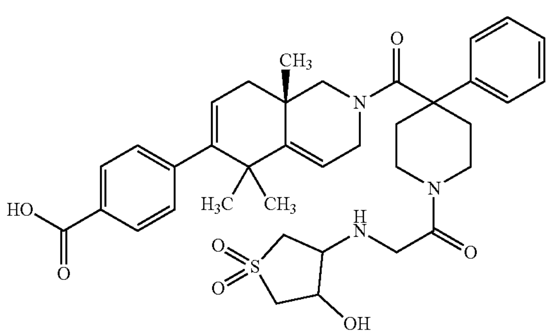 [SMILES: CC1(C)C(c2ccc(C(=O)O)cc2)=CC[C@]2(C)CN(C(=O)C3(c4ccccc4)CCN(C(=O)CNC4CS(=O)(=O)CC4O)CC3)CC=C12] | 675.83 | 676.5 | 2.07 | A |

TABLE 12-continued

| Ex | Structure | MW | Obs Ion | RT | Met |
|---|---|---|---|---|---|
| A237 | 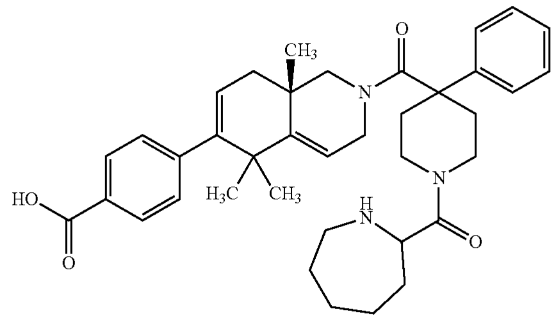 [SMILES: CC1(C)C(c2ccc(C(=O)O)cc2)=CC[C@]2(C)CN(C(=O)C3(c4ccccc4)CCN(C(=O)C4CCCCCN4)CC3)CC=C12] | 609.80 | 610.5 | 3.58 | M |
| A238 | 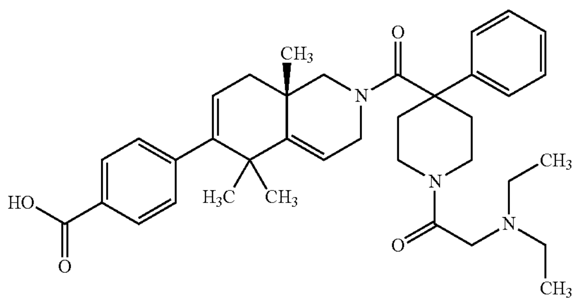 [SMILES: CCN(CC)CC(=O)N1CCC(C(=O)N2CC=C3C(C)(C)C(c4ccc(C(=O)O)cc4)=CC[C@]3(C)C2)(c2ccccc2)CC1] | 597.79 | 598.5 | 2.09 | A |
| A239 | 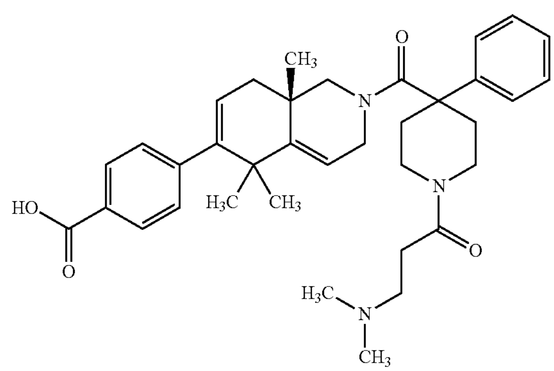 [SMILES: CN(C)CCC(=O)N1CCC(C(=O)N2CC=C3C(C)(C)C(c4ccc(C(=O)O)cc4)=CC[C@]3(C)C2)(c2ccccc2)CC1] | 583.76 | 584.5 | 3.39 | M |
| A240 | 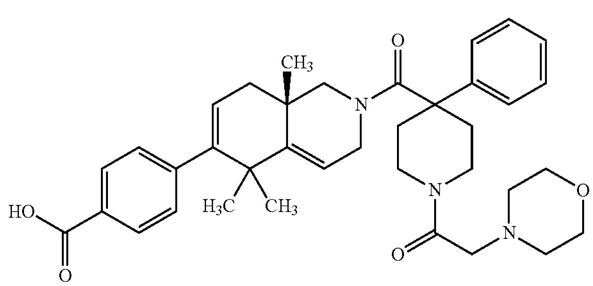 [SMILES: CC1(C)C(c2ccc(C(=O)O)cc2)=CC[C@]2(C)CN(C(=O)C3(c4ccccc4)CCN(C(=O)CN4CCOCC4)CC3)CC=C12] | 611.77 | 612.5 | 2.37 | A |

TABLE 12-continued

| Ex | Structure | MW | Obs Ion | RT | Met |
|---|---|---|---|---|---|
| A241 | 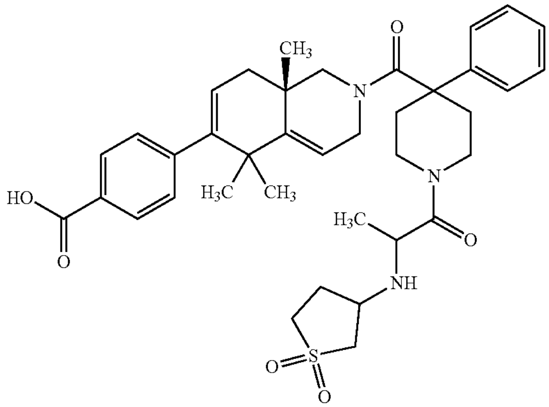 [SMILES: CC(NC1CCS(=O)(=O)C1)C(=O)N1CCC(C(=O)N2CC=C3C(C)(C)C(c4ccc(C(=O)O)cc4)=CC[C@]3(C)C2)(c2ccccc2)CC1] | 673.86 | 674.5 | 2.20 | A |
| A242 | 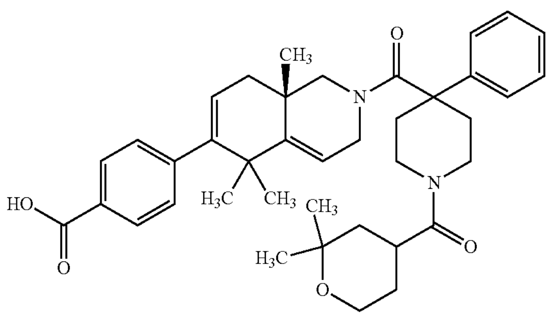 [SMILES: CC1(C)CC(C(=O)N2CCC(C(=O)N3CC=C4C(C)(C)C(c5ccc(C(=O)O)cc5)=CC[C@]4(C)C3)(c3ccccc3)CC2)CCO1] | 624.81 | 625.5 | 2.48 | A |
| A243 | 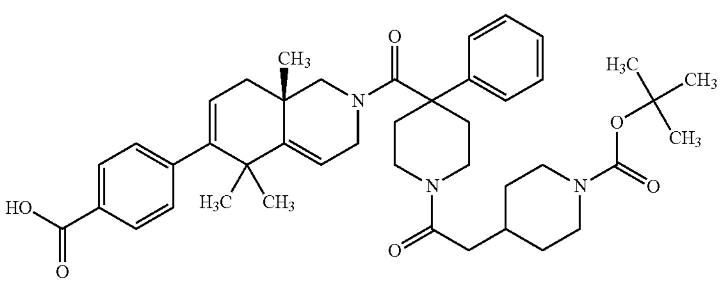 [SMILES: CC(C)(C)OC(=O)N1CCC(CC(=O)N2CCC(C(=O)N3CC=C4C(C)(C)C(c5ccc(C(=O)O)cc5)=CC[C@]4(C)C3)(c3ccccc3)CC2)CC1] | 709.91 | 710.6 | 4.18 | M |
| A244 | 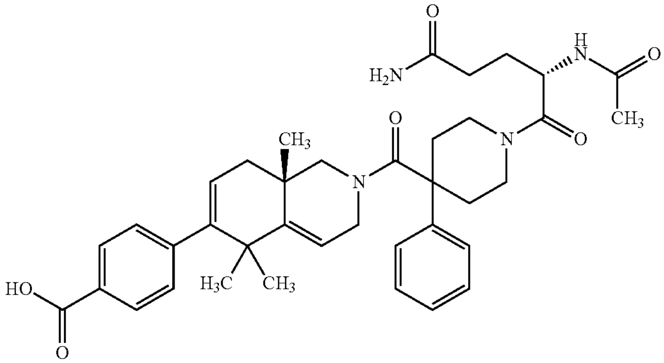 [SMILES: CC(=O)N[C@@H](CCC(N)=O)C(=O)N1CCC(C(=O)N2CC=C3C(C)(C)C(c4ccc(C(=O)O)cc4)=CC[C@]3(C)C2)(c2ccccc2)CC1] | 654.80 | 655.5 | 3.39 | M |

TABLE 12-continued

| Ex | Structure | MW | Obs Ion | RT | Met |
|---|---|---|---|---|---|
| A245 | 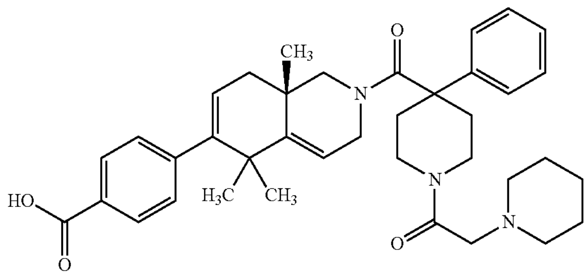 [SMILES: CC1(C)C(c2ccc(C(=O)O)cc2)=CC[C@]2(C)CN(C(=O)C3(c4ccccc4)CCN(C(=O)CN4CCCCC4)CC3)CC=C12] | 609.80 | 610.5 | 2.14 | A |
| A246 | 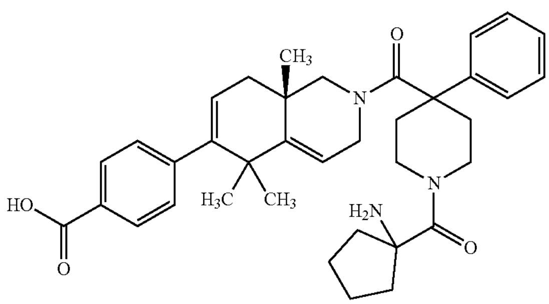 [SMILES: CC1(C)C(c2ccc(C(=O)O)cc2)=CC[C@]2(C)CN(C(=O)C3(c4ccccc4)CCN(C(=O)C4(N)CCCC4)CC3)CC=C12] | 595.77 | 596.4 | 3.45 | M |
| A247 | 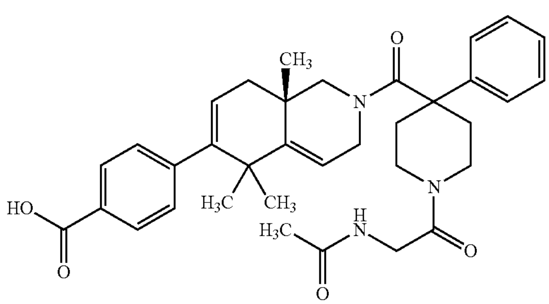 [SMILES: CC(=O)NCC(=O)N1CCC(C(=O)N2CC=C3C(C)(C)C(c4ccc(C(=O)O)cc4)=CC[C@]3(C)C2)(c2ccccc2)CC1] | 583.72 | 584.3 | 3.30 | M |
| A248 | 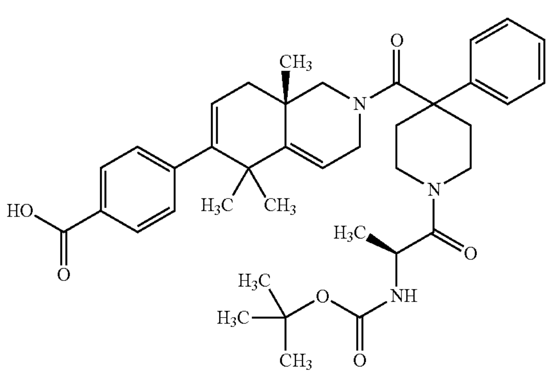 [SMILES: C[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 655.82 | 656.5 | 4.00 | M |

TABLE 12-continued
| Ex | Structure | MW | Obs Ion | RT | Met |
|---|---|---|---|---|---|
| A249 | 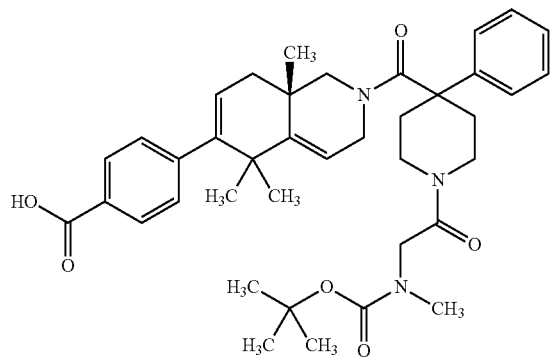 [SMILES: CN(CC(=O)N1CCC(C(=O)N2CC=C3C(C)(C)C(c4ccc(C(=O)O)cc4)=CC[C@]3(C)C2)(c2ccccc2)CC1)C(=O)OC(C)(C)C] | 655.82 | 656.5 | 3.98 | M |
| A250 | 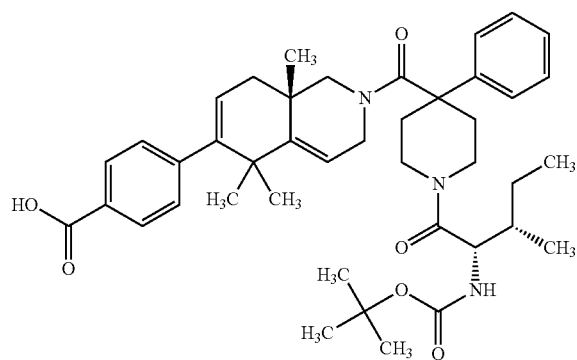 [SMILES: CC[C@H](C)[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 697.90 | 698.5 | 4.28 | M |
| A251 | 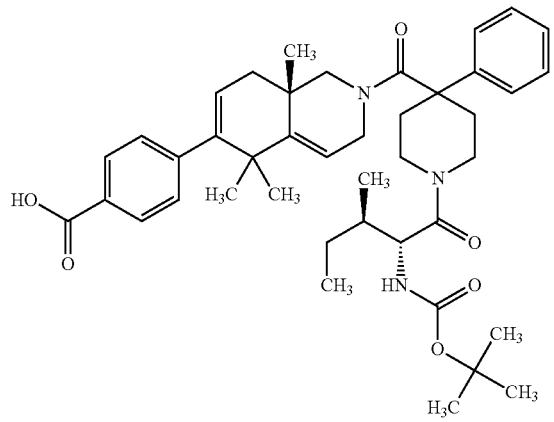 [SMILES: CC[C@@H](C)[C@@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 697.90 | 698.6 | 4.29 | M |

TABLE 12-continued

| Ex | Structure | MW | Obs Ion | RT | Met |
|---|---|---|---|---|---|
| A252 | 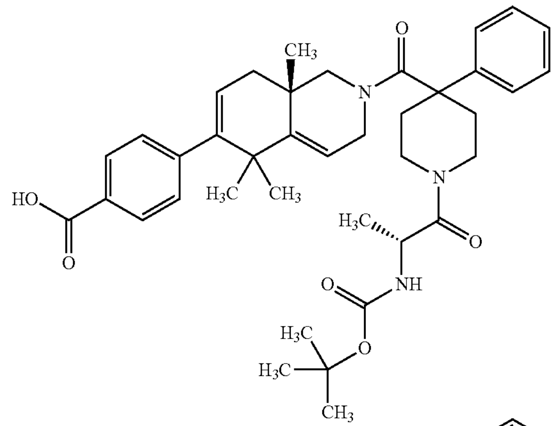 [SMILES: C[C@@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 655.82 | 656.5 | 4.00 | M |
| A253 | 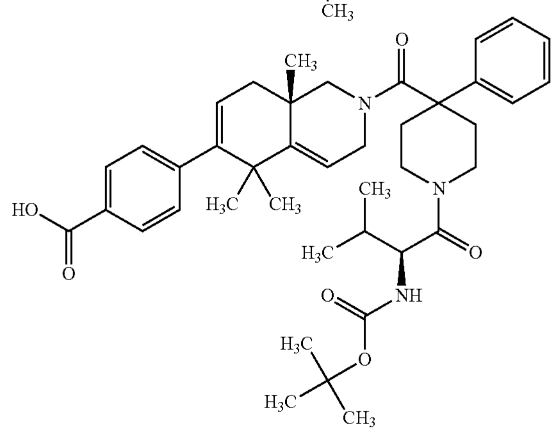 | 683.88 | 684.5 | 4.19 | M |

Examples A254-A338 were prepared from intermediate 3 and commercially available diamines by the following general method:

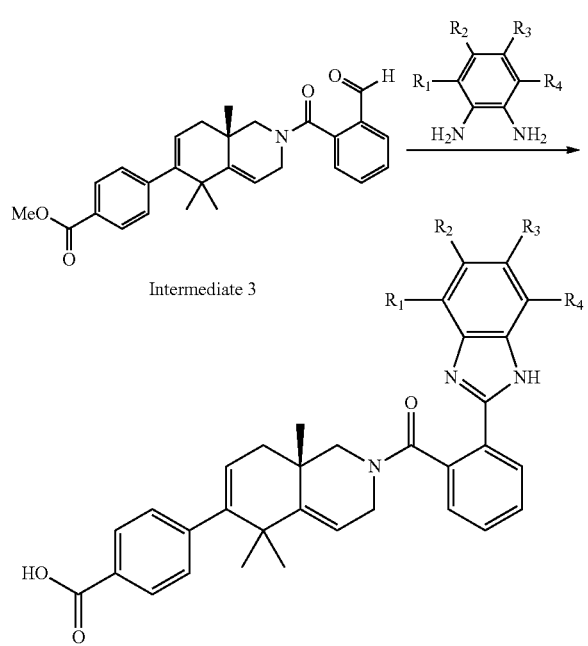

Intermediate 3

Prepared a solution of (S)-methyl 4-(2-(2-formylbenzoyl)-5,5,8a-trimethyl-1,2,3,5,8,8a-hexahydroisoquinolin-6-yl)benzoate (190 mg, 432 µmol) in NMP (6.0 mL). To each of the 16×48 mm threaded vials containing the diamines was added 0.5 mL of the (S)-methyl 4-(2-(2-formylbenzoyl)-5,5,8a-trimethyl-1,2,3,5,8,8a-hexahydroisoquinolin-6-yl)benzoate solution followed by the sodium metabisulfite (7.4 mg). Added a stir bar to each vial, capped and allowed to stir at room temp for 10 minutes before heating to 110° C. w/stirring for 18 hrs. Samples were blown down in the Zymark tabletop dryer at 40° C. for 3 hrs. Prepared a solution of Lithium Hydroxide (143.4 mg, 3.4 mmol) in water (2.4 mL). To each of the reaction vials was added 800 µL Dioxane and 200 µL Lithium Hydroxide solution. Capped vial and heated to 70° C. w/stirring. After 5 hrs, reaction mixtures were blown down in the Zymark tabletop dryer at 40° C. for 2 hrs. Added 1.0 mL DMF to each vial. Vortexed to dissolve. Transferred contents to empty SPE cartridges for filtration, collecting into 16×48 mm round bottom vials. Rinsed reaction vials w/500 µL DMF each, and transferred rinses to the corresponding SPE cartridges. Submitted for HPLC purification, and LCMS analyses, results are shown in the spreadsheet. See Table 13.

TABLE 13

| Ex | Structure | MW | Obs Ion | RT | Met |
|---|---|---|---|---|---|
| A254 | 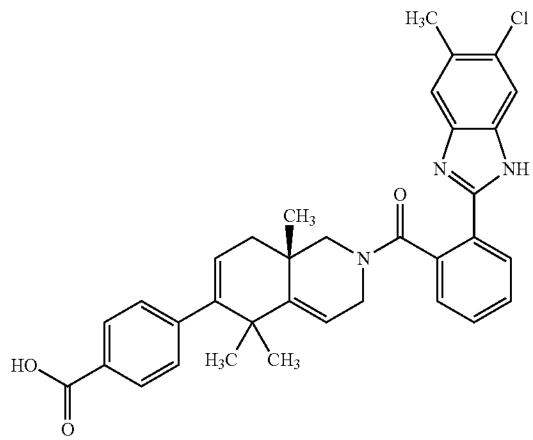 | 566.10 | 566.3 | 4.00 | M |
| A255 | 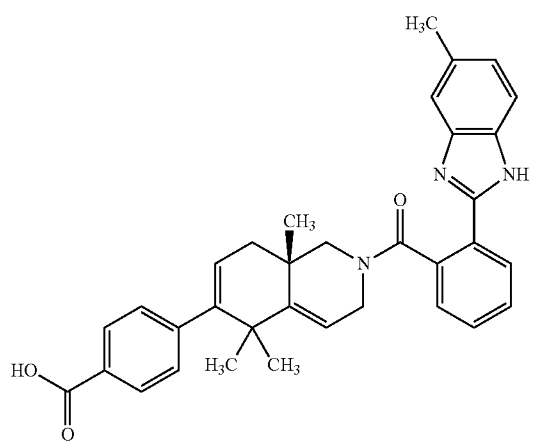 [SMILES: Cc1ccc2[nH]c(-c3ccccc3C(=O)N3CC=C4C(C)(C)C(c5ccc(C(=O)O)cc5)=CC[C@]4(C)C3)nc2c1] | 531.64 | 532.3 | 3.77 | M |
| A256 | 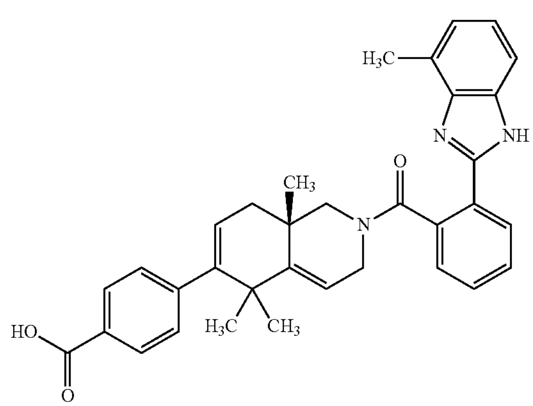 [SMILES: Cc1cccc2[nH]c(-c3ccccc3C(=O)N3CC=C4C(C)(C)C(c5ccc(C(=O)O)cc5)=CC[C@]4(C)C3)nc12] | 531.64 | 532.3 | 3.80 | M |

TABLE 13-continued

| Ex | Structure | MW | Obs Ion | RT | Met |
|---|---|---|---|---|---|
| A257 | 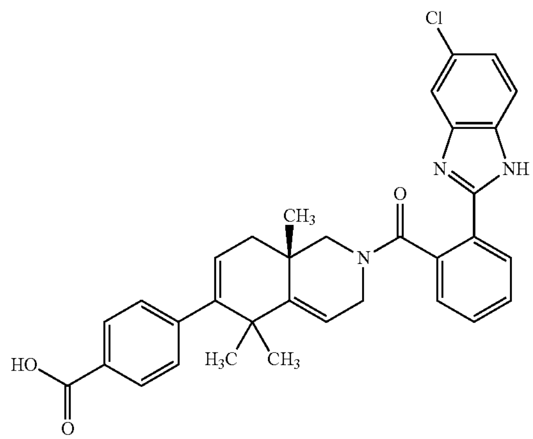 | 552.06 | 550.3 | 2.52 | A |
| A258 | 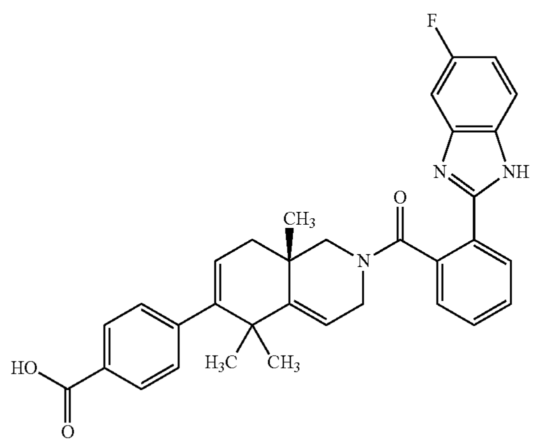 [SMILES: CC1(C)C(c2ccc(C(=O)O)cc2)=CC[C@]2(C)CN(C(=O)c3ccccc3-c3nc4cc(F)ccc4[nH]3)CC=C12] | 535.61 | 534.3 | 2.33 | A |
| A259 | 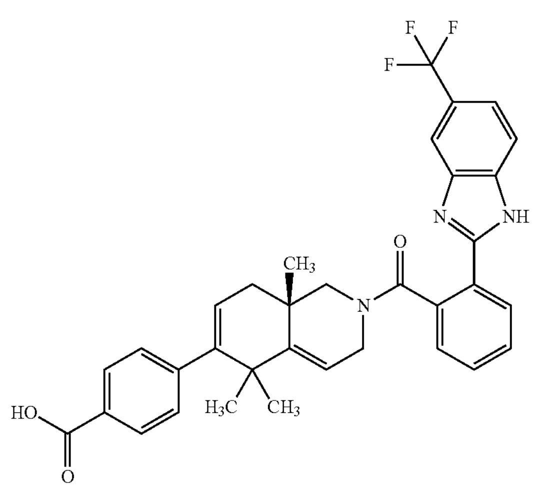 [SMILES: CC1(C)C(c2ccc(C(=O)O)cc2)=CC[C@]2(C)CN(C(=O)c3ccccc3-c3nc4cc(C(F)(F)F)ccc4[nH]3)CC=C12] | 585.62 | 586.3 | 2.60 | A |

TABLE 13-continued

| Ex | Structure | MW | Obs Ion | RT | Met |
|---|---|---|---|---|---|
| A260 | 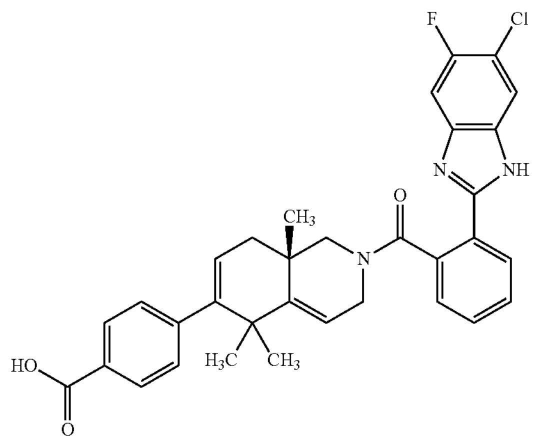 [SMILES: CC1(C)C(c2ccc(C(=O)O)cc2)=CC[C@]2(C)CN(C(=O)c3ccccc3-c3nc4cc(F)c(Cl)cc4[nH]3)CC=C12] | 570.06 | 570.2 | 3.93 | M |
| A261 | 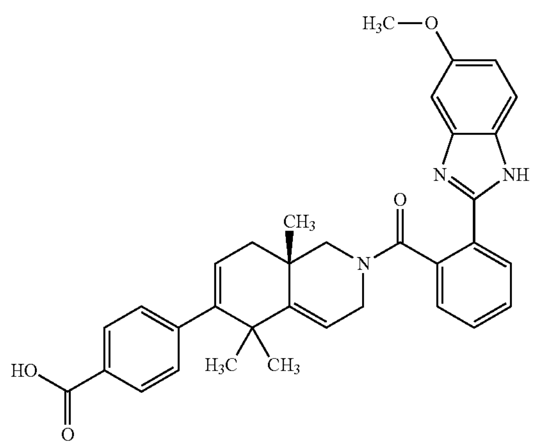 [SMILES: COc1ccc2[nH]c(-c3ccccc3C(=O)N3CC=C4C(C)(C)C(c5ccc(C(=O)O)cc5)=CC[C@]4(C)C3)nc2c1] | 547.64 | 548.4 | 2.24 | A |
| A262 | 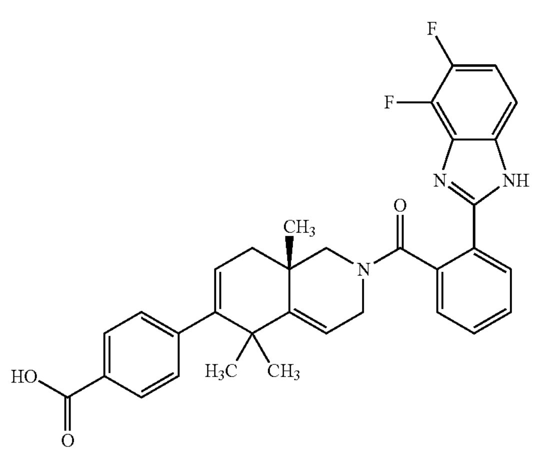 [SMILES: CC1(C)C(c2ccc(C(=O)O)cc2)=CC[C@]2(C)CN(C(=O)c3ccccc3-c3nc4c(F)c(F)ccc4[nH]3)CC=C12] | 553.60 | 553.9 | 2.43 | A |

TABLE 13-continued
| Ex | Structure | MW | Obs Ion | RT | Met |
|---|---|---|---|---|---|
| A263 | 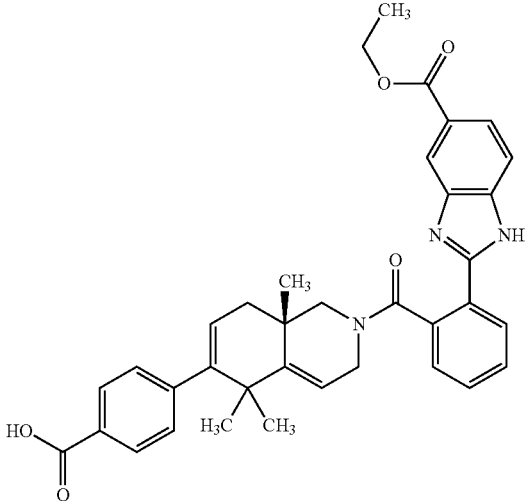 [SMILES: CCOC(=O)c1ccc2[nH]c(-c3ccccc3C(=O)N3CC=C4C(C)(C)C(c5ccc(C(=O)O)cc5)=CC[C@]4(C)C3)nc2c1] | 589.68 | 590.2 | 3.79 | M |
| A264 | 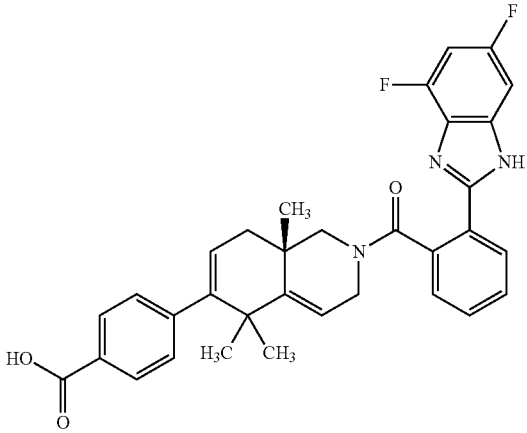 | 553.60 | 554.3 | 3.80 | M |
| A265 | 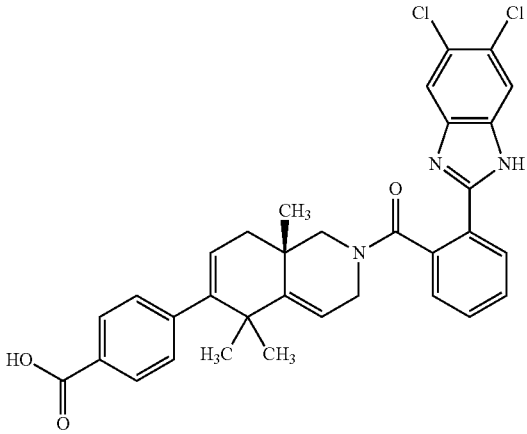 | 586.52 | 586.2 | 4.04 | M |

TABLE 13-continued

| Ex | Structure | MW | Obs Ion | RT | Met |
|---|---|---|---|---|---|
| A266 | 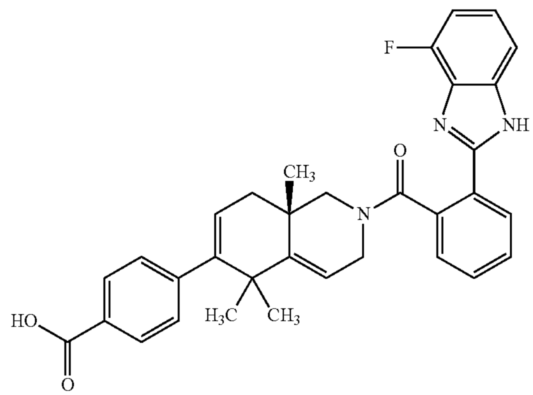 [SMILES: CC1(C)C(c2ccc(C(=O)O)cc2)=CC[C@]2(C)CN(C(=O)c3ccccc3-c3nc4c(F)cccc4[nH]3)CC=C12] | 535.62 | 536.3 | 2.22 | A |
| A267 | 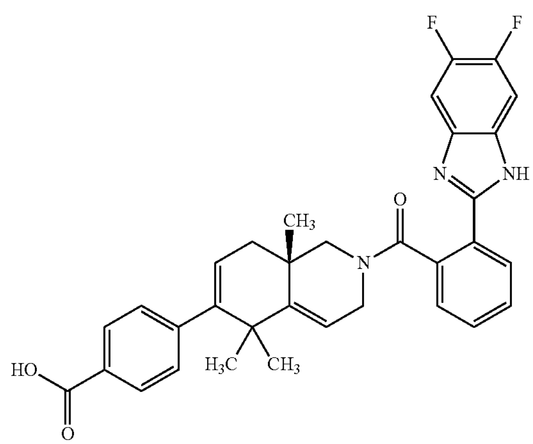 [SMILES: CC1(C)C(c2ccc(C(=O)O)cc2)=CC[C@]2(C)CN(C(=O)c3ccccc3-c3nc4cc(F)c(F)cc4[nH]3)CC=C12] | 553.61 | 554.2 | 2.24 | A |
| A268 | 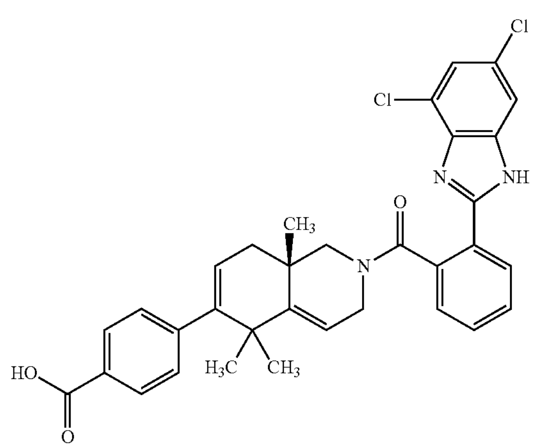 | 586.52 | 584.1 | 4.13 | M |

TABLE 13-continued
| Ex | Structure | MW | Obs Ion | RT | Met |
|---|---|---|---|---|---|
| A269 | 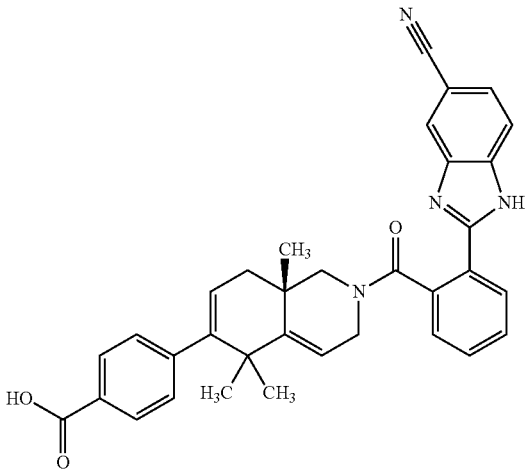 [SMILES: CC1(C)C(c2ccc(C(=O)O)cc2)=CC[C@]2(C)CN(C(=O)c3ccccc3-c3nc4cc(C#N)ccc4[nH]3)CC=C12] | 542.63 | 543.2 | 2.09 | A |
| A270 | 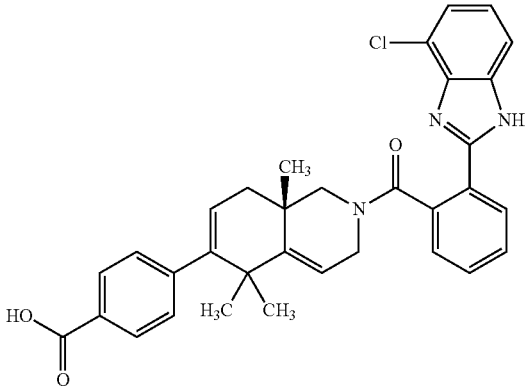 [SMILES: CC1(C)C(c2ccc(C(=O)O)cc2)=CC[C@]2(C)CN(C(=O)c3ccccc3-c3nc4c(Cl)cccc4[nH]3)CC=C12] | 552.07 | 552.2 | 2.33 | A |
| A271 | 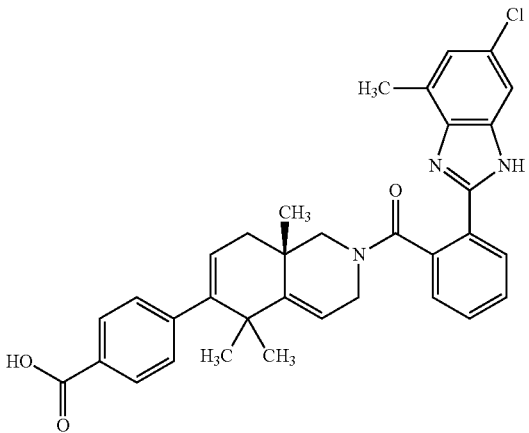 | 566.10 | 566.3 | 3.98 | M |

TABLE 13-continued

| Ex | Structure | MW | Obs Ion | RT | Met |
|---|---|---|---|---|---|
| A272 | 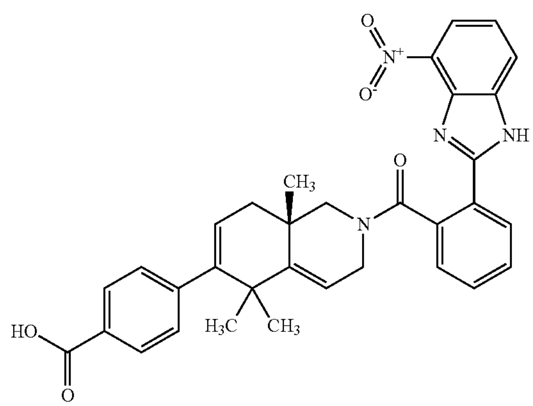 | 562.63 | 563.2 | 2.30 | A |
| A273 | 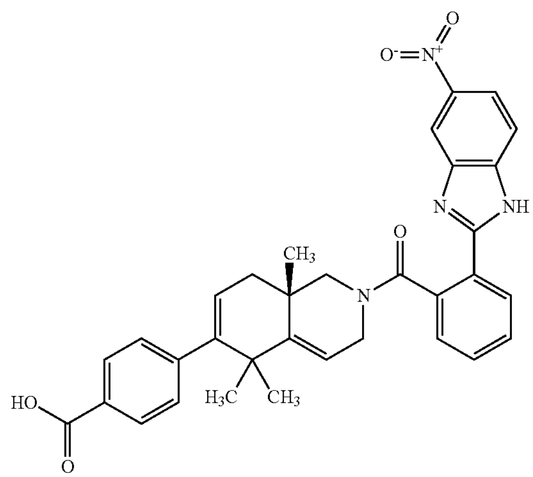 | 562.63 | 563.2 | 3.64 | M |
| A274 | 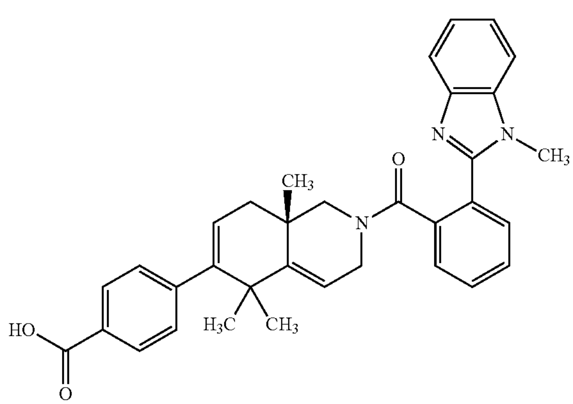 [SMILES: Cn1c(-c2ccccc2C(=O)N2CC=C3C(C)(C)C(c4ccc(C(=O)O)cc4)=CC[C@]3(C)C2)nc2ccccc21] | 531.65 | 532.3 | 2.17 | A |

TABLE 13-continued

| Ex | Structure | MW | Obs Ion | RT | Met |
|---|---|---|---|---|---|
| A275 | 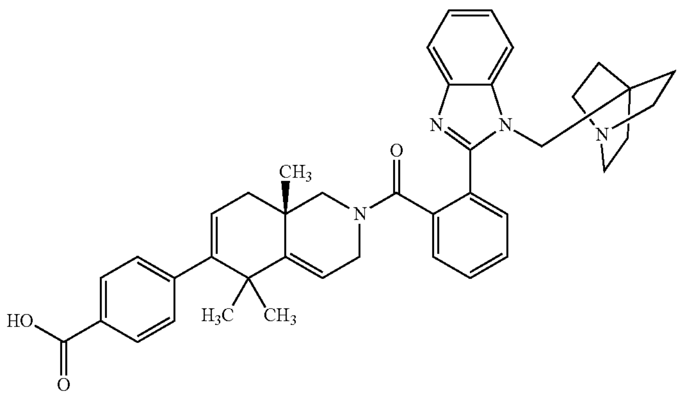 [SMILES: CC1(C)C(c2ccc(C(=O)O)cc2)=CC[C@]2(C)CN(C(=O)c3ccccc3-c3nc4ccccc4n3CC34CCN(CC3)CC4)CC=C12] | 640.83 | 641.7 | 3.25 | M |
| A276 | 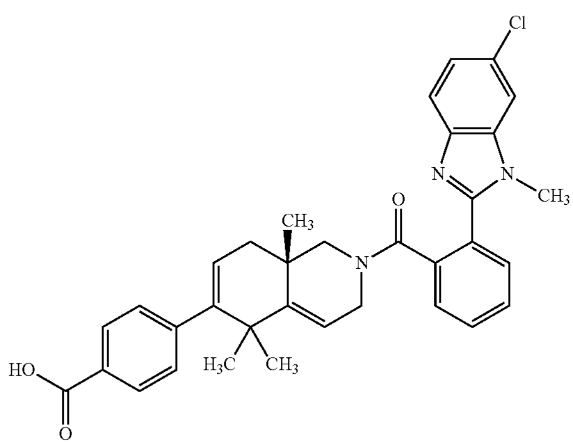 [SMILES: Cn1c(-c2ccccc2C(=O)N2CC=C3C(C)(C)C(c4ccc(C(=O)O)cc4)=CC[C@]3(C)C2)nc2ccc(Cl)cc21] | 566.09 | 566.5 | 3.83 | M |
| A277 | 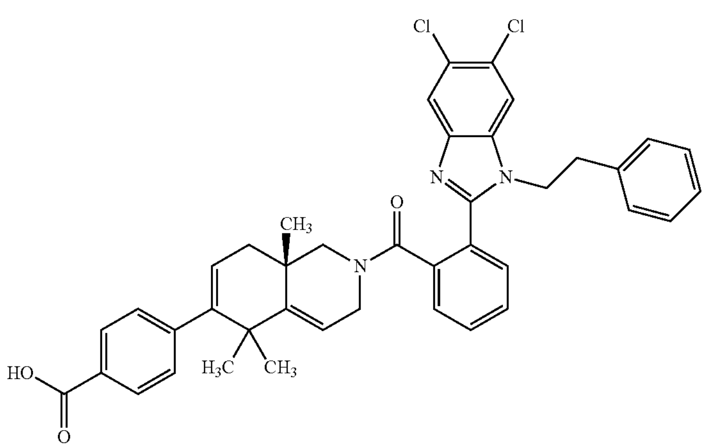 [SMILES: CC1(C)C(c2ccc(C(=O)O)cc2)=CC[C@]2(C)CN(C(=O)c3ccccc3-c3nc4cc(Cl)c(Cl)cc4n3CCc3ccccc3)CC=C12] | 690.67 | 690.3 | 4.28 | M |

TABLE 13-continued

| Ex | Structure | MW | Obs Ion | RT | Met |
|---|---|---|---|---|---|
| A278 | 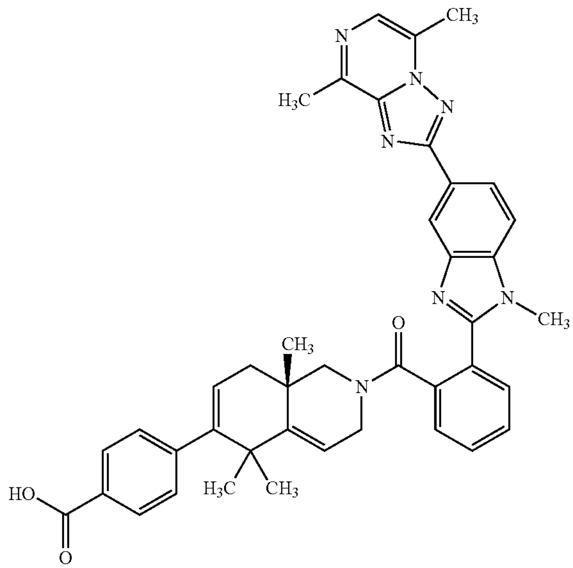 [SMILES: Cc1ncc(C)n2nc(-c3ccc4c(c3)nc(-c3ccccc3C(=O)N3CC=C5C(C)(C)C(c6ccc(C(=O)O)cc6)=CC[C@]5(C)C3)n4C)nc12] | 677.81 | 678.4 | 3.72 | M |
| A279 | 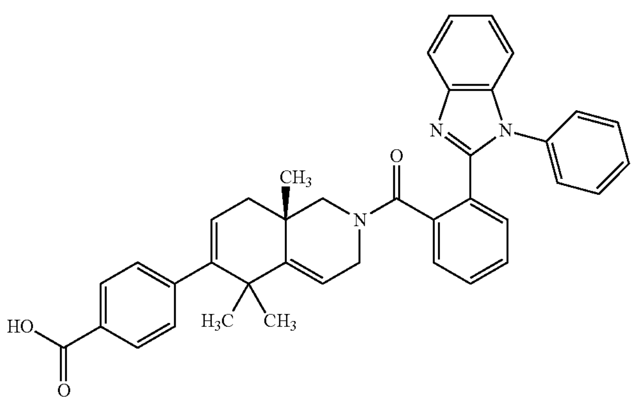 [SMILES: CC1(C)C(c2ccc(C(=O)O)cc2)=CC[C@]2(C)CN(C(=O)c3ccccc3-c3nc4ccccc4n3-c3ccccc3)CC=C12] | 593.73 | 594.3 | 2.67 | A |
| A280 | 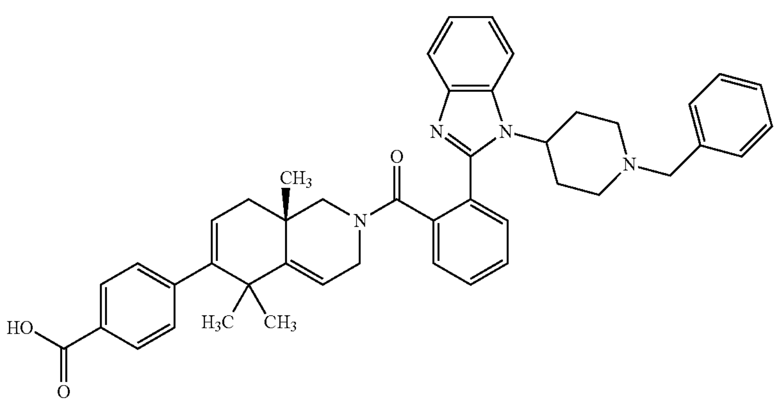 [SMILES: CC1(C)C(c2ccc(C(=O)O)cc2)=CC[C@]2(C)CN(C(=O)c3ccccc3-c3nc4ccccc4n3C3CCN(Cc4ccccc4)CC3)CC=C12] | 690.89 | 691.5 | 2.58 | A |

TABLE 13-continued

| Ex | Structure | MW | Obs Ion | RT | Met |
|---|---|---|---|---|---|
| A281 | 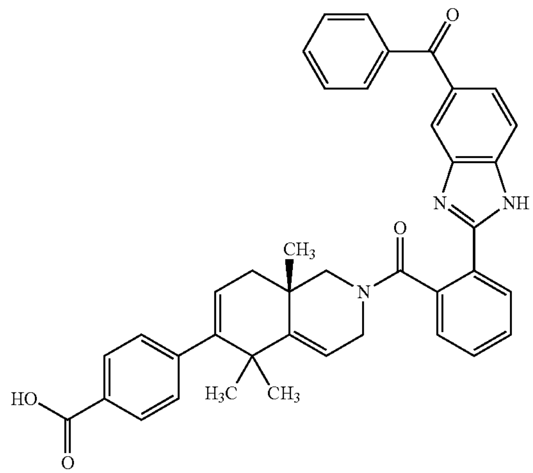 [SMILES: CC1(C)C(c2ccc(C(=O)O)cc2)=CC[C@]2(C)CN(C(=O)c3ccccc3-c3nc4cc(C(=O)c5ccccc5)ccc4[nH]3)CC=C12] | 621.74 | 622.6 | 3.83 | M |
| A282 | 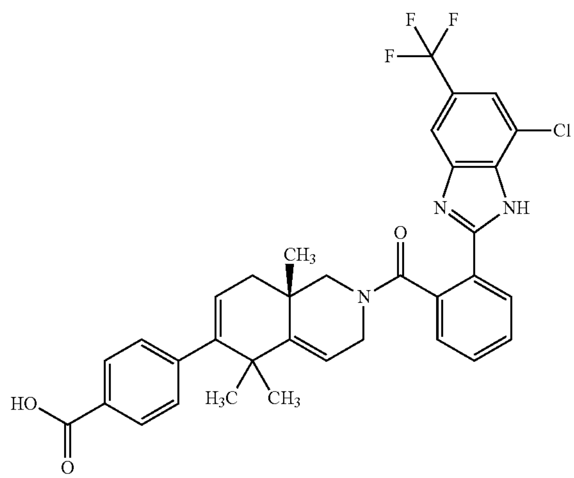 [SMILES: CC1(C)C(c2ccc(C(=O)O)cc2)=CC[C@]2(C)CN(C(=O)c3ccccc3-c3nc4cc(C(F)(F)F)cc(Cl)c4[nH]3)CC=C12] | 620.06 | 620.6 | 2.87 | A |
| A283 | 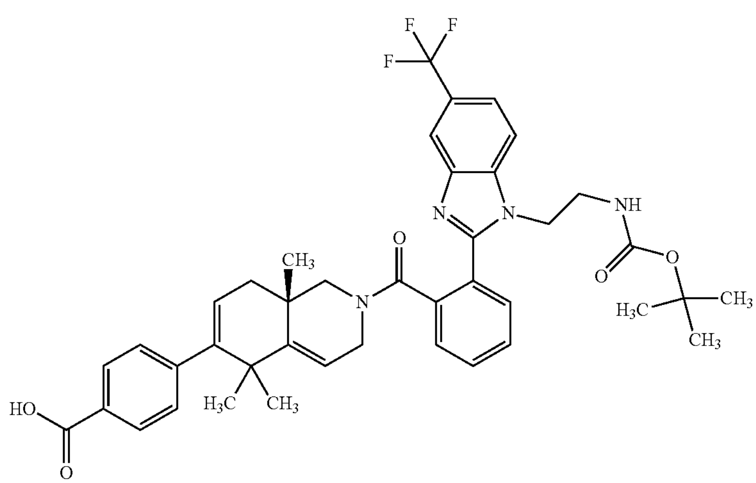 [SMILES: CC(C)(C)OC(=O)NCCn1c(-c2ccccc2C(=O)N2CC=C3C(C)(C)C(c4ccc(C(=O)O)cc4)=CC[C@]3(C)C2)nc2cc(C(F)(F)F)ccc21] | 728.81 | 729.7 | 4.02 | M |

TABLE 13-continued

| Ex | Structure | MW | Obs Ion | RT | Met |
|---|---|---|---|---|---|
| A284 | 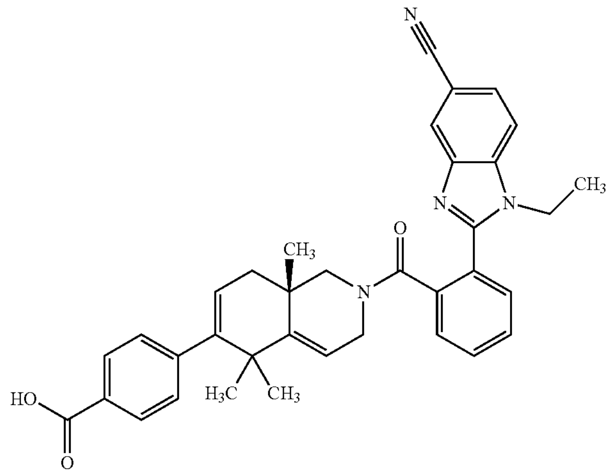 [SMILES: CCn1c(-c2ccccc2C(=O)N2CC=C3C(C)(C)C(c4ccc(C(=O)O)cc4)=CC[C@]3(C)C2)nc2cc(C#N)ccc21] | 570.68 | 571.6 | 3.61 | M |
| A285 | 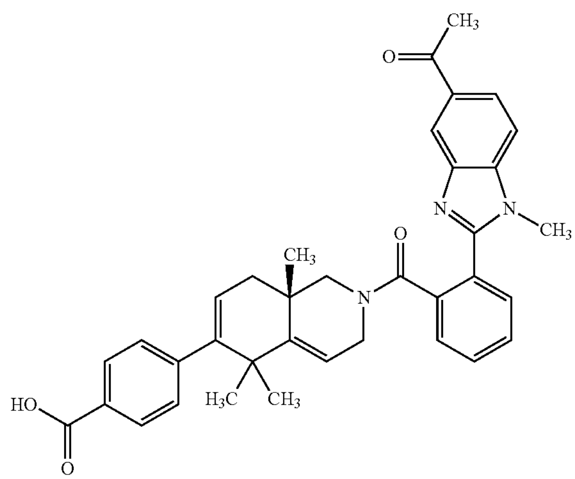 [SMILES: CC(=O)c1ccc2c(c1)nc(-c1ccccc1C(=O)N1CC=C3C(C)(C)C(c4ccc(C(=O)O)cc4)=CC[C@]3(C)C1)n2C] | 573.68 | 574.6 | 3.45 | M |
| A286 | 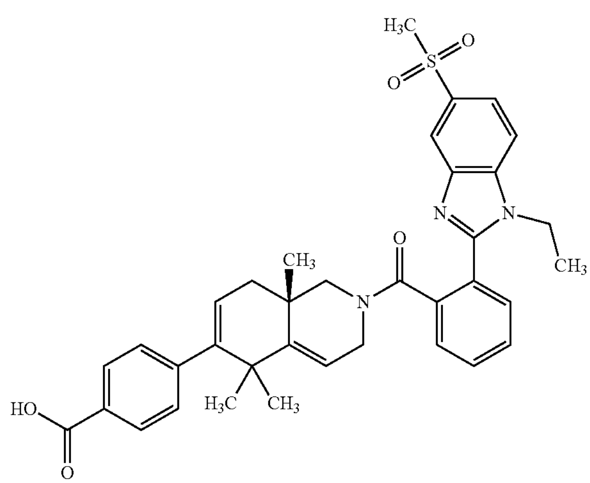 [SMILES: CCn1c(-c2ccccc2C(=O)N2CC=C3C(C)(C)C(c4ccc(C(=O)O)cc4)=CC[C@]3(C)C2)nc2cc(S(C)(=O)=O)ccc21] | 623.77 | 624.3 | 2.07 | A |

TABLE 13-continued

| Ex | Structure | MW | Obs Ion | RT | Met |
|---|---|---|---|---|---|
| A287 | 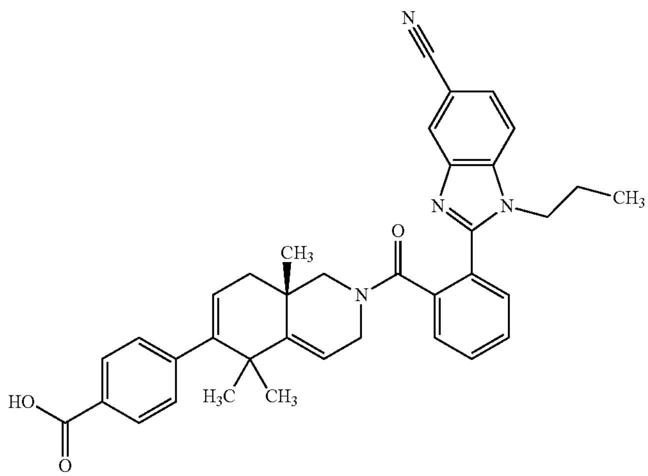 [SMILES: CCCn1c(-c2ccccc2C(=O)N2CC=C3C(C)(C)C(c4ccc(C(=O)O)cc4)=CC[C@]3(C)C2)nc2cc(C#N)ccc21] | 584.71 | 585.6 | 2.55 | A |
| A288 | 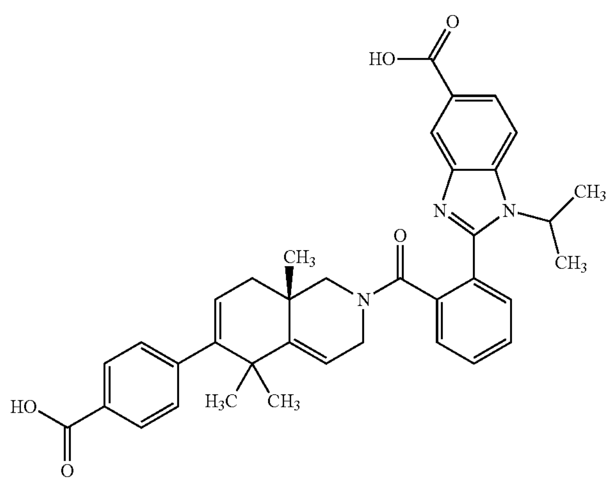 [SMILES: CC(C)n1c(-c2ccccc2C(=O)N2CC=C3C(C)(C)C(c4ccc(C(=O)O)cc4)=CC[C@]3(C)C2)nc2cc(C(=O)O)ccc21] | 603.71 | 604.3 | 1.87 | A |
| A289 | 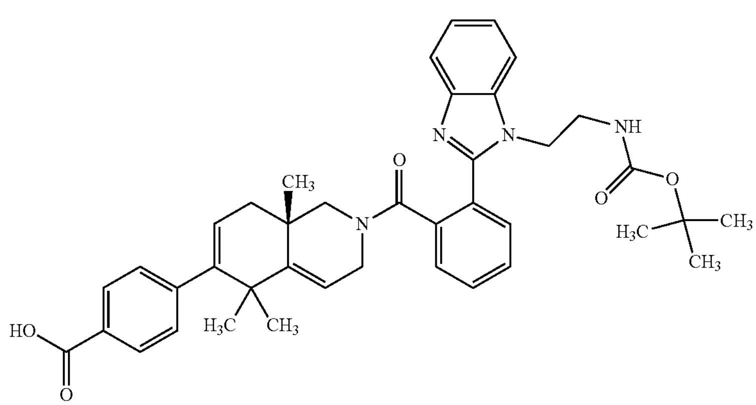 [SMILES: CC(C)(C)OC(=O)NCCn1c(-c2ccccc2C(=O)N2CC=C3C(C)(C)C(c4ccc(C(=O)O)cc4)=CC[C@]3(C)C2)nc2ccccc21] | 660.80 | 661.4 | 3.79 | M |

TABLE 13-continued

| Ex | Structure | MW | Obs Ion | RT | Met |
|---|---|---|---|---|---|
| A290 | 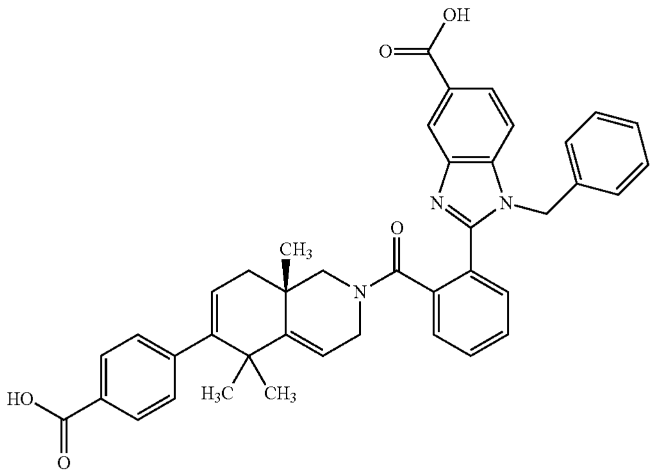 [SMILES: CC1(C)C(c2ccc(C(=O)O)cc2)=CC[C@]2(C)CN(C(=O)c3ccccc3-c3nc4cc(C(=O)O)ccc4n3Cc3ccccc3)CC=C12] | 651.76 | 652.3 | 2.07 | A |
| A291 | 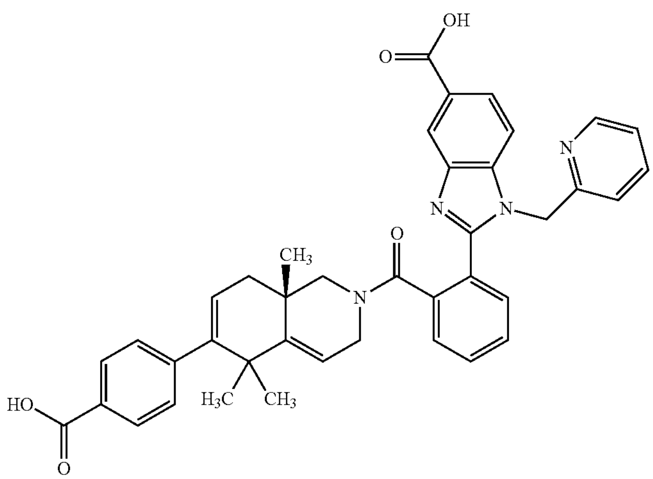 [SMILES: CC1(C)C(c2ccc(C(=O)O)cc2)=CC[C@]2(C)CN(C(=O)c3ccccc3-c3nc4cc(C(=O)O)ccc4n3Cc3ccccn3)CC=C12] | 652.74 | 653.3 | 3.11 | M |
| A292 | 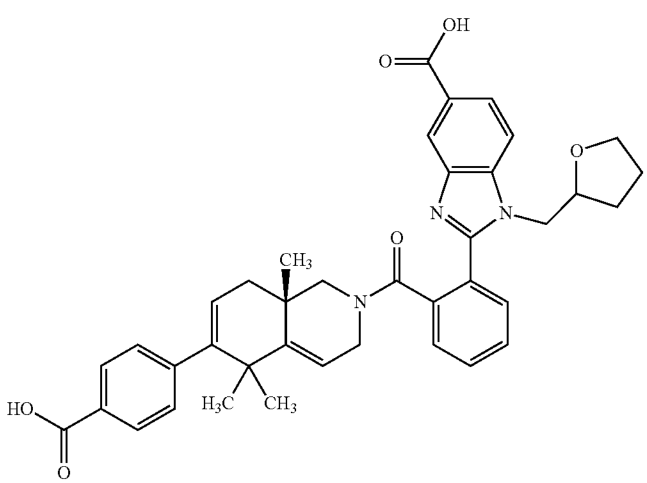 [SMILES: CC1(C)C(c2ccc(C(=O)O)cc2)=CC[C@]2(C)CN(C(=O)c3ccccc3-c3nc4cc(C(=O)O)ccc4n3CC3CCCO3)CC=C12] | 645.74 | 646.3 | 1.87 | A |

TABLE 13-continued

| Ex | Structure | MW | Obs Ion | RT | Met |
|---|---|---|---|---|---|
| A293 | 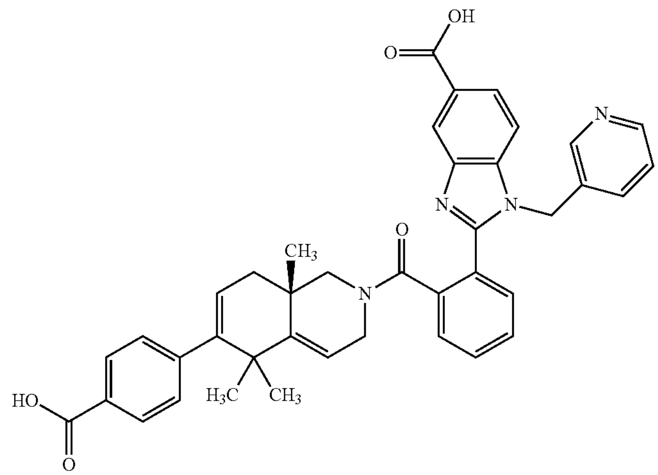 [SMILES: CC1(C)C(c2ccc(C(=O)O)cc2)=CC[C@]2(C)CN(C(=O)c3ccccc3-c3nc4cc(C(=O)O)ccc4n3Cc3cccnc3)CC=C12] | 652.75 | 653.3 | 3.01 | M |
| A294 | 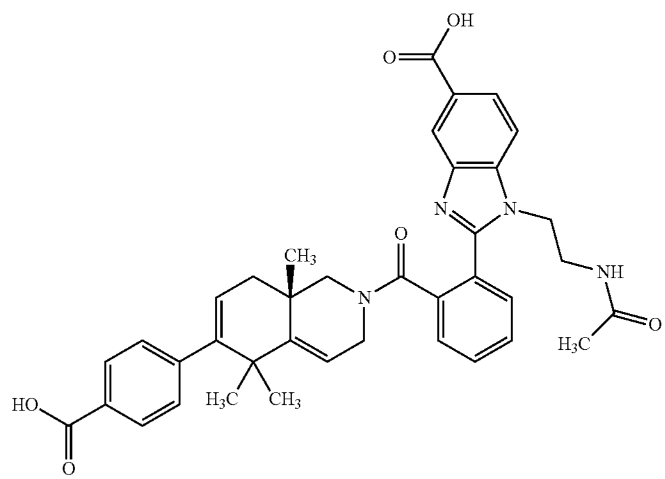 [SMILES: CC(=O)NCCn1c(-c2ccccc2C(=O)N2CC=C3C(C)(C)C(c4ccc(C(=O)O)cc4)=CC[C@]3(C)C2)nc2cc(C(=O)O)ccc21] | 646.74 | 647.3 | 1.59 | A |
| A295 | 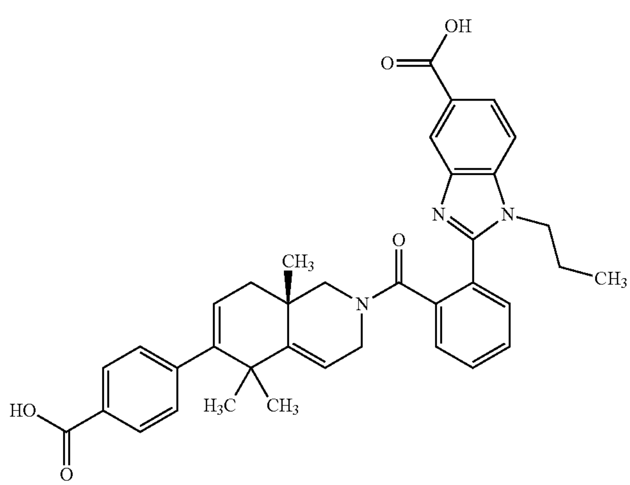 [SMILES: CCCn1c(-c2ccccc2C(=O)N2CC=C3C(C)(C)C(c4ccc(C(=O)O)cc4)=CC[C@]3(C)C2)nc2cc(C(=O)O)ccc21] | 603.71 | 604.6 | 2.23 | A |

TABLE 13-continued

| Ex | Structure | MW | Obs Ion | RT | Met |
|---|---|---|---|---|---|
| A296 | 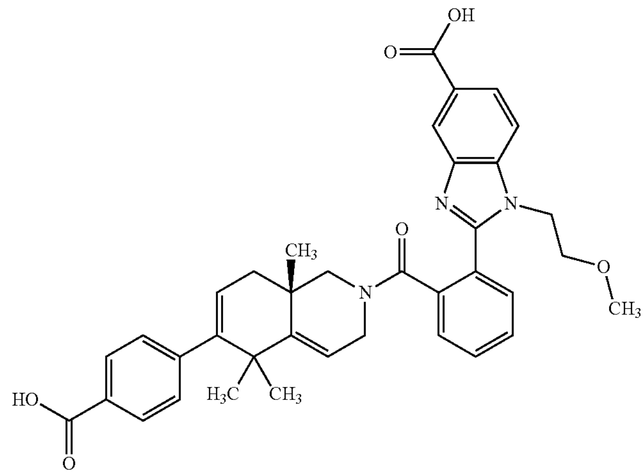 [SMILES: COCCn1c(-c2ccccc2C(=O)N2CC=C3C(C)(C)C(c4ccc(C(=O)O)cc4)=CC[C@]3(C)C2)nc2cc(C(=O)O)ccc21] | 619.72 | 620.3 | 3.04 | M |
| A297 | 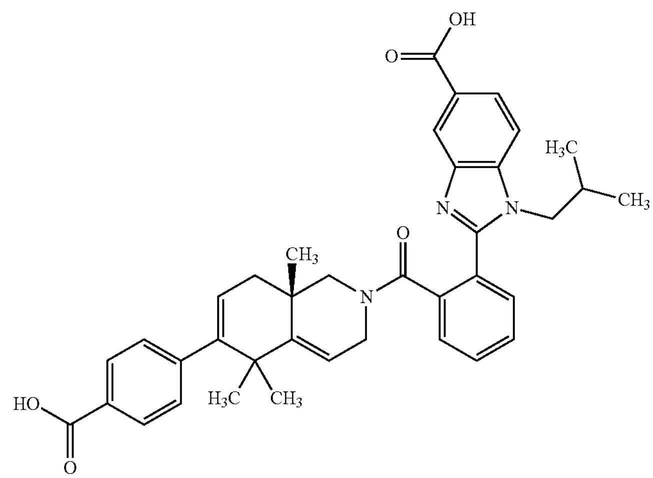 [SMILES: CC(C)Cn1c(-c2ccccc2C(=O)N2CC=C3C(C)(C)C(c4ccc(C(=O)O)cc4)=CC[C@]3(C)C2)nc2cc(C(=O)O)ccc21] | 617.73 | 618.6 | 2.27 | A |
| A298 | 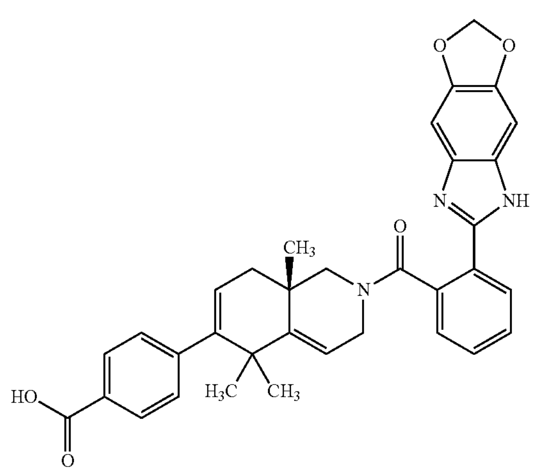 [SMILES: CC1(C)C(c2ccc(C(=O)O)cc2)=CC[C@]2(C)CN(C(=O)c3ccccc3-c3nc4cc5c(cc4[nH]3)OCO5)CC=C12] | 561.64 | 562.3 | 2.11 | A |

TABLE 13-continued
| Ex | Structure | MW | Obs Ion | RT | Met |
|---|---|---|---|---|---|
| A299 | 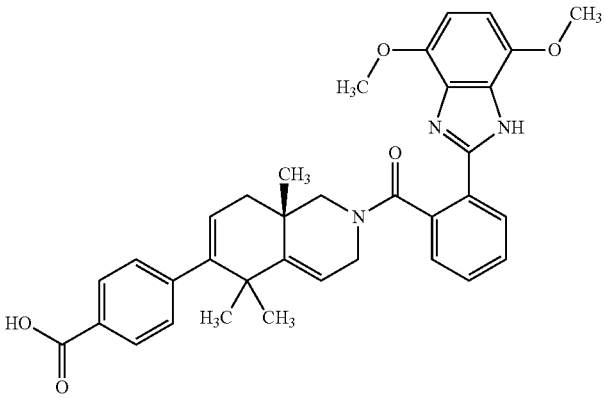 [SMILES: COc1ccc(OC)c2[nH]c(-c3ccccc3C(=O)N3CC=C4C(C)(C)C(c5ccc(C(=O)O)cc5)=CC[C@]4(C)C3)nc12] | 577.68 | 578.3 | 2.20 | A |
| A300 | 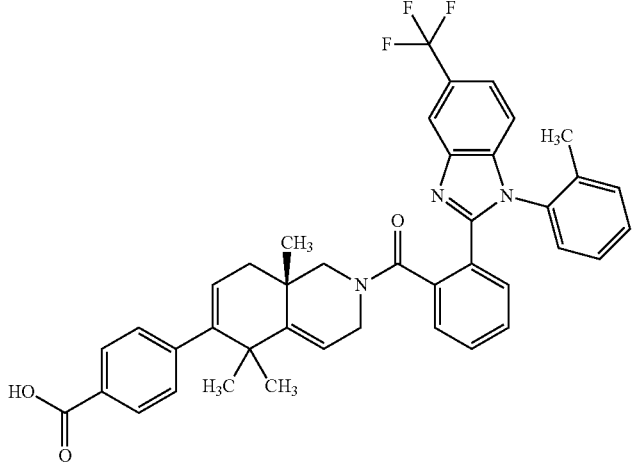 [SMILES: Cc1ccccc1-n1c(-c2ccccc2C(=O)N2CC=C3C(C)(C)C(c4ccc(C(=O)O)cc4)=CC[C@]3(C)C2)nc2cc(C(F)(F)F)ccc21] | 675.74 | 676.1 | 3.31 | A |
| A301 | 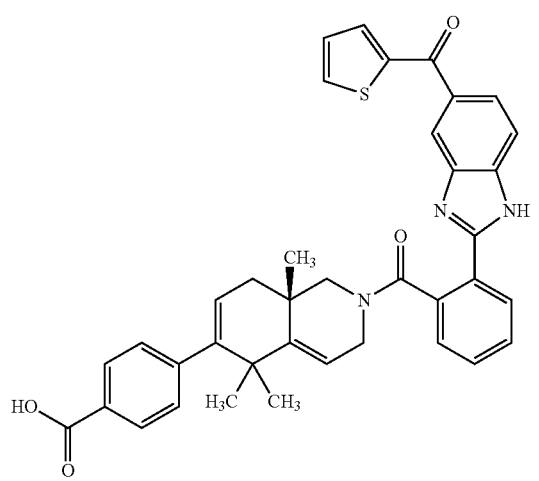 [SMILES: CC1(C)C(c2ccc(C(=O)O)cc2)=CC[C@]2(C)CN(C(=O)c3ccccc3-c3nc4cc(C(=O)c5cccs5)ccc4[nH]3)CC=C12] | 627.75 | 628.2 | 2.32 | A |

TABLE 13-continued

| Ex | Structure | MW | Obs Ion | RT | Met |
|---|---|---|---|---|---|
| A302 | 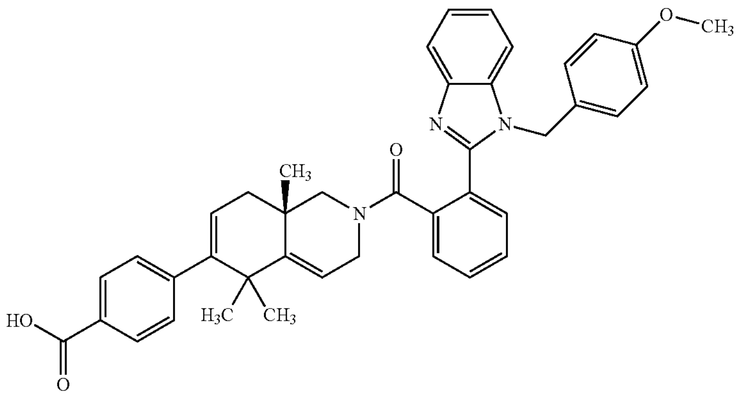 [SMILES: COc1ccc(Cn2c(-c3ccccc3C(=O)N3CC=C4C(C)(C)C(c5ccc(C(=O)O)cc5)=CC[C@]4(C)C3)nc3ccccc32)cc1] | 637.77 | 638.1 | 3.11 | M |
| A303 | 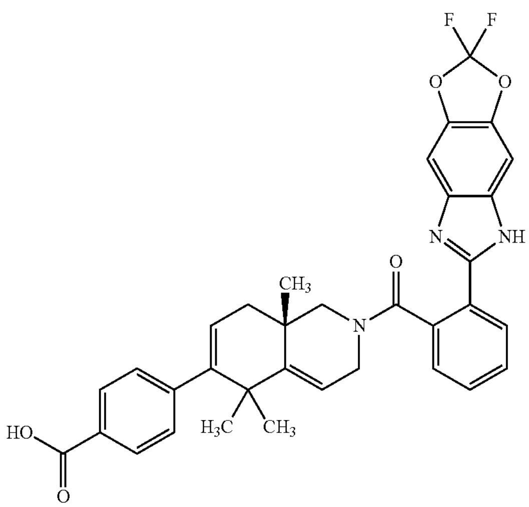 [SMILES: CC1(C)C(c2ccc(C(=O)O)cc2)=CC[C@]2(C)CN(C(=O)c3ccccc3-c3nc4cc5c(cc4[nH]3)OC(F)(F)O5)CC=C12] | 597.61 | 598.3 | 2.46 | A |
| A304 | 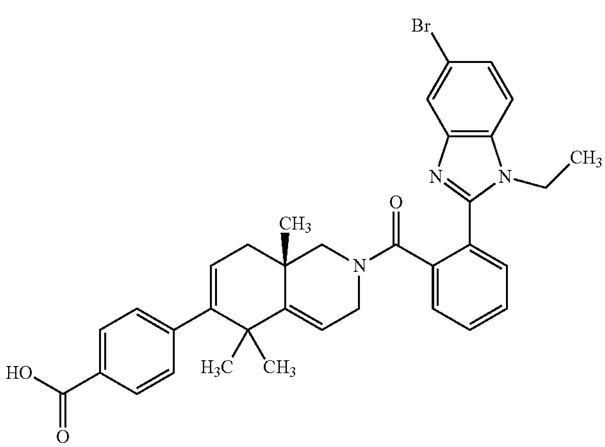 [SMILES: CCn1c(-c2ccccc2C(=O)N2CC=C3C(C)(C)C(c4ccc(C(=O)O)cc4)=CC[C@]3(C)C2)nc2cc(Br)ccc21] | 624.57 | 624.3 | 2.59 | A |

TABLE 13-continued

| Ex | Structure | MW | Obs Ion | RT | Met |
|---|---|---|---|---|---|
| A305 | 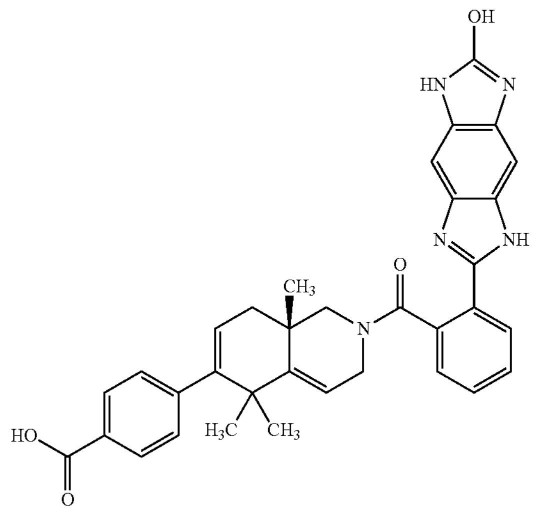 [SMILES: CC1(C)C(c2ccc(C(=O)O)cc2)=CC[C@]2(C)CN(C(=O)c3ccccc3-c3nc4cc5[nH]c(O)nc5cc4[nH]3)CC=C12] | 573.64 | 574.3 | 3.20 | M |
| A306 | 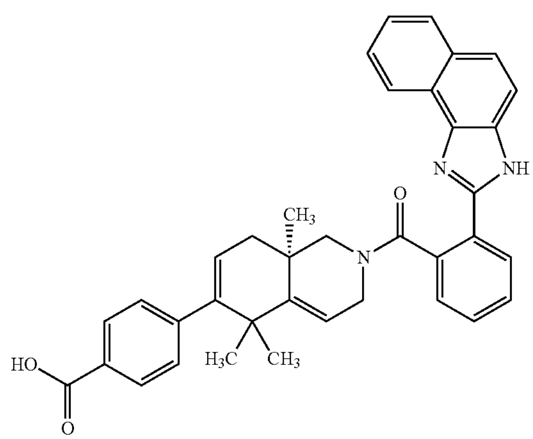 [SMILES: CC1(C)C(c2ccc(C(=O)O)cc2)=CC[C@@]2(C)CN(C(=O)c3ccccc3-c3nc4c(ccc5ccccc54)[nH]3)CC=C12] | 567.68 | 568.3 | 3.88 | M |
| A307 | 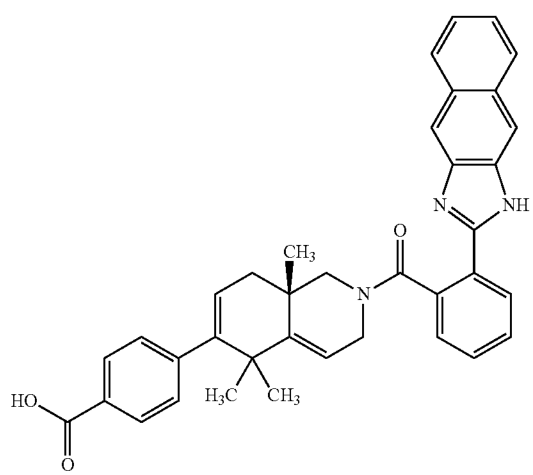 [SMILES: CC1(C)C(c2ccc(C(=O)O)cc2)=CC[C@]2(C)CN(C(=O)c3ccccc3-c3nc4cc5ccccc5cc4[nH]3)CC=C12] | 567.68 | 568.3 | 2.41 | A |

TABLE 13-continued
| Ex | Structure | MW | Obs Ion | RT | Met |
|---|---|---|---|---|---|
| A308 | 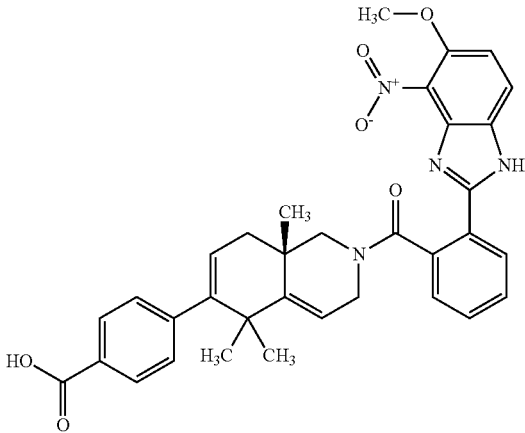 [SMILES: COc1ccc2[nH]c(-c3ccccc3C(=O)N3CC=C4C(C)(C)C(c5ccc(C(=O)O)cc5)=CC[C@]4(C)C3)nc2c1[N+](=O)[O-]] | 592.64 | 593.3 | 2.29 | A |
| A309 | 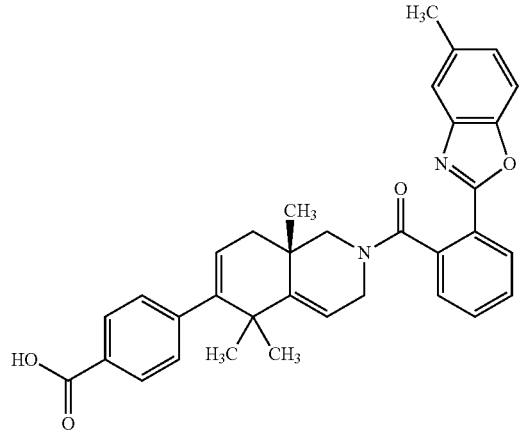 [SMILES: Cc1ccc2oc(-c3ccccc3C(=O)N3CC=C4C(C)(C)C(c5ccc(C(=O)O)cc5)=CC[C@]4(C)C3)nc2c1] | 532.64 | 533.3 | 4.13 | M |
| A310 | 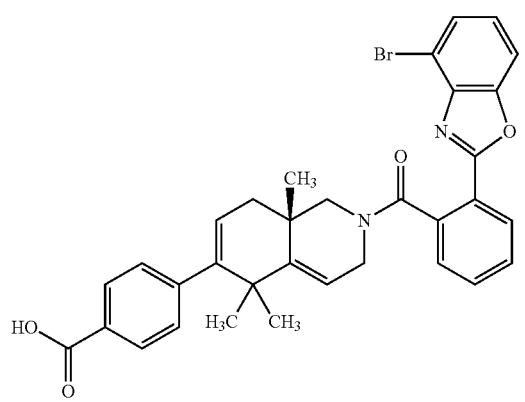 | 597.50 | 597.4 | 2.74 | A |

TABLE 13-continued

| Ex | Structure | MW | Obs Ion | RT | Met |
|---|---|---|---|---|---|
| A311 | 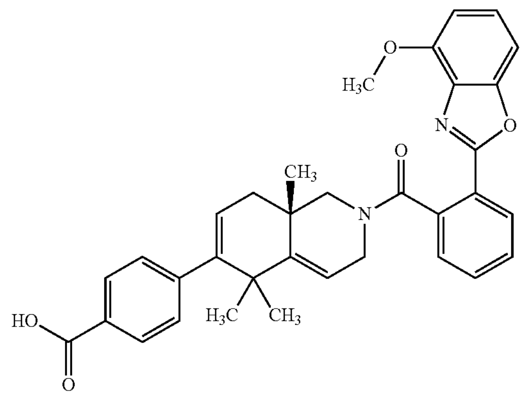 [SMILES: COc1cccc2oc(-c3ccccc3C(=O)N3CC=C4C(C)(C)C(c5ccc(C(=O)O)cc5)=CC[C@]4(C)C3)nc12] | 548.64 | 549.4 | 2.55 | A |
| A312 | 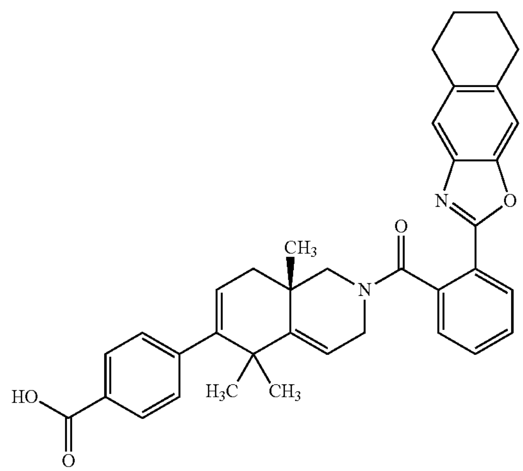 [SMILES: CC1(C)C(c2ccc(C(=O)O)cc2)=CC[C@]2(C)CN(C(=O)c3ccccc3-c3nc4cc5c(cc4o3)CCCC5)CC=C12] | 572.69 | 573.5 | 4.39 | M |
| A313 | 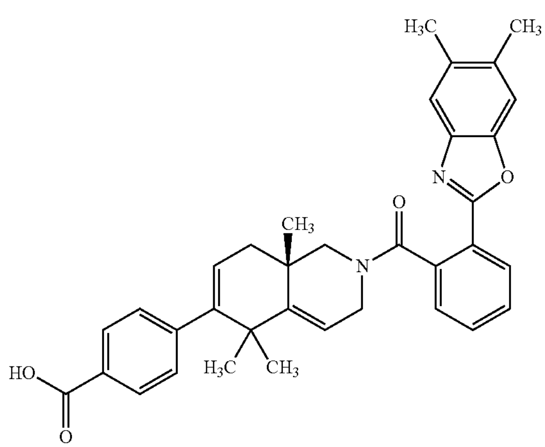 [SMILES: Cc1cc2nc(-c3ccccc3C(=O)N3CC=C4C(C)(C)C(c5ccc(C(=O)O)cc5)=CC[C@]4(C)C3)oc2cc1C] | 546.66 | 547.4 | 2.82 | A |

TABLE 13-continued

| Ex | Structure | MW | Obs Ion | RT | Met |
|---|---|---|---|---|---|
| A314 | 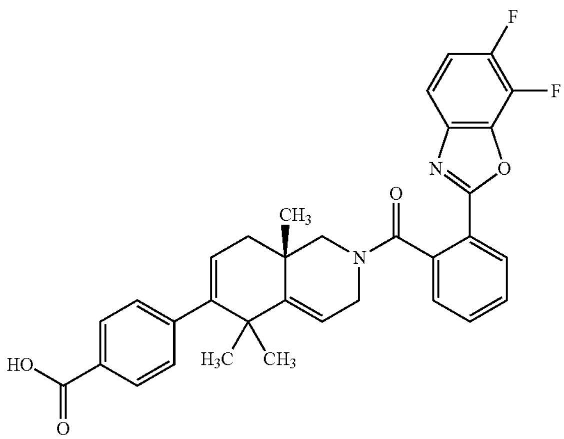 [SMILES: CC1(C)C(c2ccc(C(=O)O)cc2)=CC[C@]2(C)CN(C(=O)c3ccccc3-c3nc4ccc(F)c(F)c4o3)CC=C12] | 554.59 | 555.3 | 4.10 | M |
| A315 | 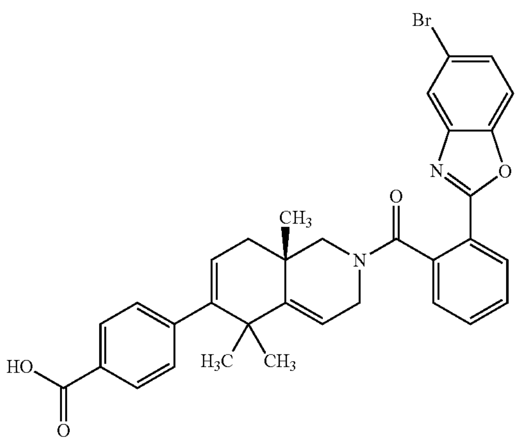 [SMILES: CC1(C)C(c2ccc(C(=O)O)cc2)=CC[C@]2(C)CN(C(=O)c3ccccc3-c3nc4cc(Br)ccc4o3)CC=C12] | 597.51 | 597.3 | 2.80 | A |
| A316 | 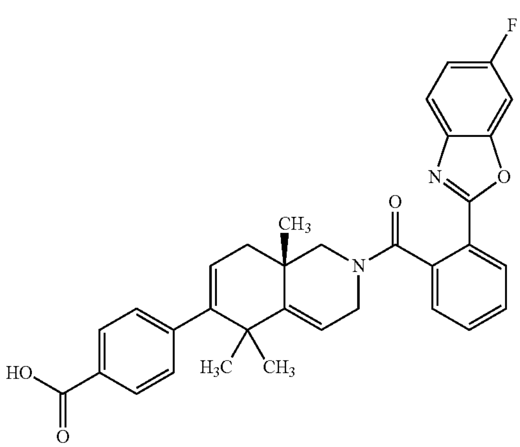 [SMILES: CC1(C)C(c2ccc(C(=O)O)cc2)=CC[C@]2(C)CN(C(=O)c3ccccc3-c3nc4ccc(F)cc4o3)CC=C12] | 536.60 | 537.4 | 2.61 | A |

TABLE 13-continued

| Ex | Structure | MW | Obs Ion | RT | Met |
|---|---|---|---|---|---|
| A317 | 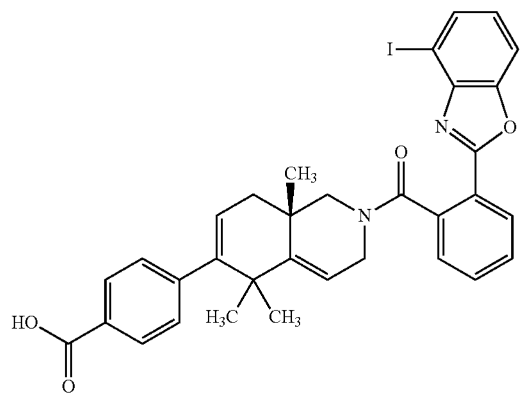 [SMILES: CC1(C)C(c2ccc(C(=O)O)cc2)=CC[C@]2(C)CN(C(=O)c3ccccc3-c3nc4c(I)cccc4o3)CC=C12] | 644.50 | 645.3 | 4.17 | M |
| A318 | 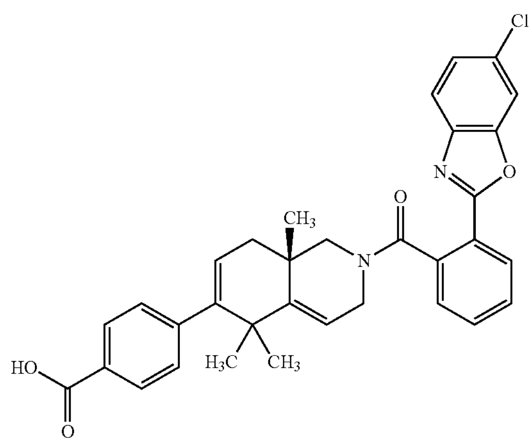 [SMILES: CC1(C)C(c2ccc(C(=O)O)cc2)=CC[C@]2(C)CN(C(=O)c3ccccc3-c3nc4ccc(Cl)cc4o3)CC=C12] | 553.06 | 553.3 | 2.78 | A |
| A319 | 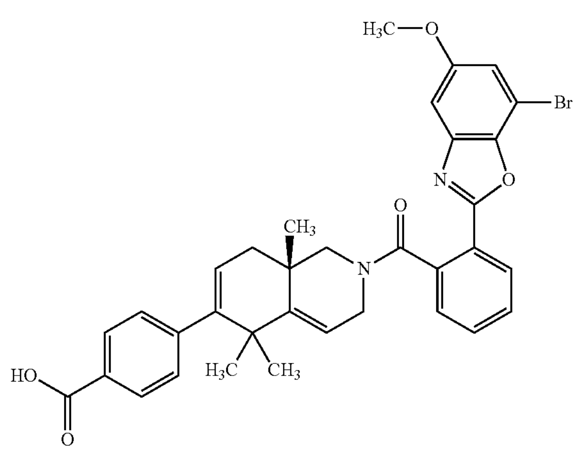 [SMILES: COc1cc(Br)c2oc(-c3ccccc3C(=O)N3CC=C4C(C)(C)C(c5ccc(C(=O)O)cc5)=CC[C@]4(C)C3)nc2c1] | 627.52 | 627.1 | 4.19 | M |

TABLE 13-continued

| Ex | Structure | MW | Obs Ion | RT | Met |
|---|---|---|---|---|---|
| A320 | 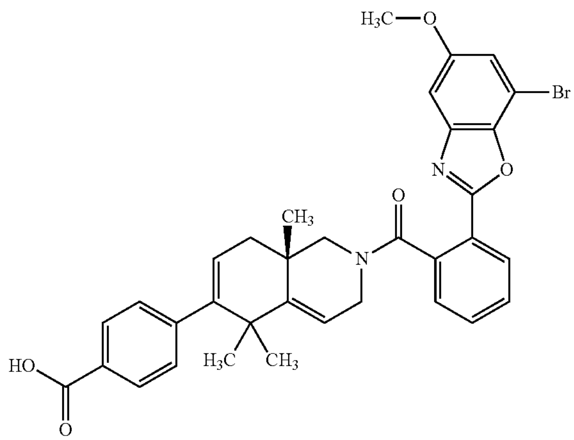 [SMILES: COc1cc(Br)c2oc(-c3ccccc3C(=O)N3CC=C4C(C)(C)C(c5ccc(C(=O)O)cc5)=CC[C@]4(C)C3)nc2c1] | 548.64 | 549.4 | 3.92 | M |
| A321 | 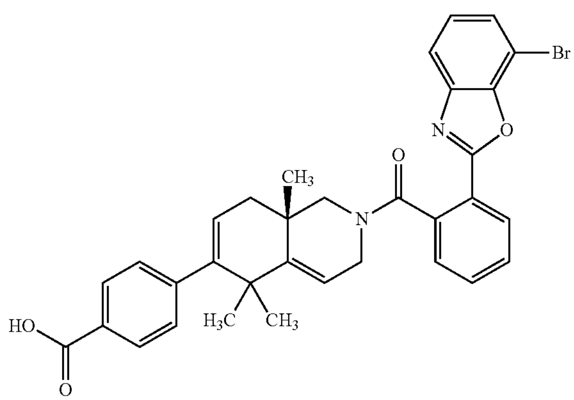 [SMILES: CC1(C)C(c2ccc(C(=O)O)cc2)=CC[C@]2(C)CN(C(=O)c3ccccc3-c3nc4cccc(Br)c4o3)CC=C12] | 597.50 | 597.1 | 4.12 | M |
| A322 | 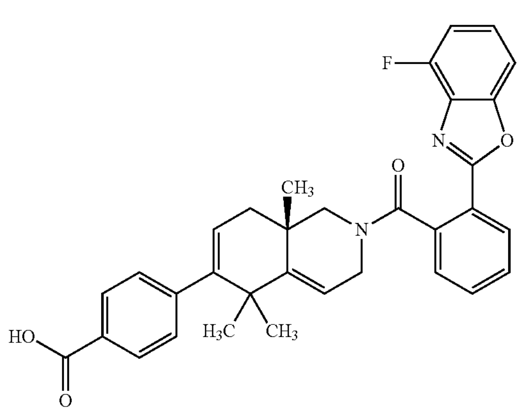 [SMILES: CC1(C)C(c2ccc(C(=O)O)cc2)=CC[C@]2(C)CN(C(=O)c3ccccc3-c3nc4c(F)cccc4o3)CC=C12] | 536.59 | 537.3 | 3.92 | M |

TABLE 13-continued
| Ex | Structure | MW | Obs Ion | RT | Met |
|---|---|---|---|---|---|
| A323 | 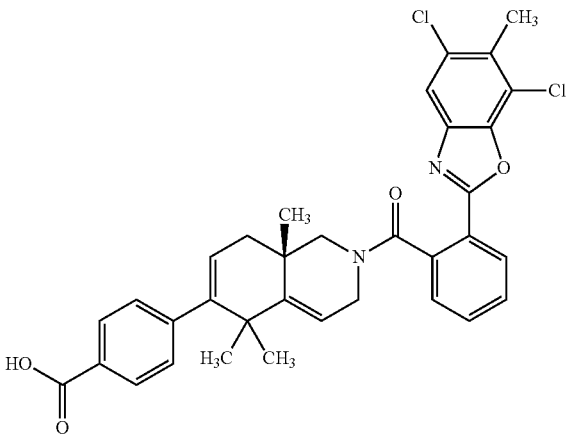 [SMILES: Cc1c(Cl)cc2nc(-c3ccccc3C(=O)N3CC=C4C(C)(C)C(c5ccc(C(=O)O)cc5)=CC[C@]4(C)C3)oc2c1Cl] | 601.52 | 601.3 | 4.53 | M |
| A324 | 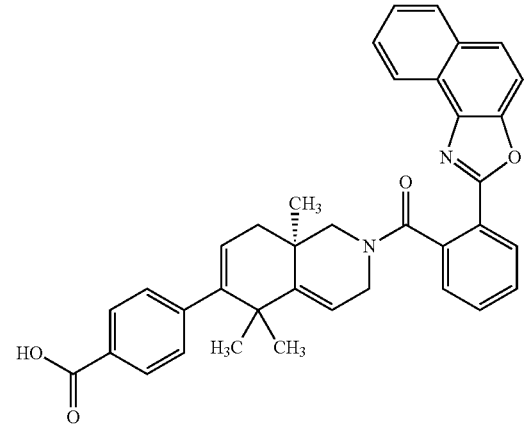 [SMILES: CC1(C)C(c2ccc(C(=O)O)cc2)=CC[C@@]2(C)CN(C(=O)c3ccccc3-c3nc4c(ccc5ccccc54)o3)CC=C12] | 568.66 | 569.4 | 4.26 | M |
| A325 | 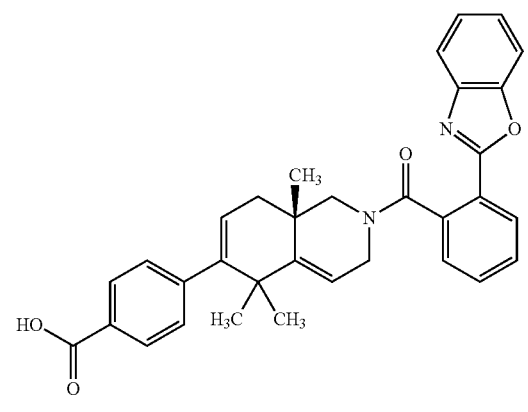 [SMILES: CC1(C)C(c2ccc(C(=O)O)cc2)=CC[C@]2(C)CN(C(=O)c3ccccc3-c3nc4ccccc4o3)CC=C12] | 518.61 | 519.3 | 3.92 | M |

TABLE 13-continued

| Ex | Structure | MW | Obs Ion | RT | Met |
|---|---|---|---|---|---|
| A326 | 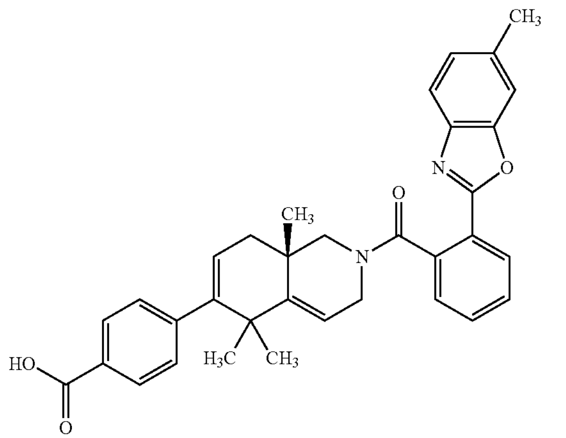 [SMILES: Cc1ccc2nc(-c3ccccc3C(=O)N3CC=C4C(C)(C)C(c5ccc(C(=O)O)cc5)=CC[C@]4(C)C3)oc2c1] | 532.64 | 533.4 | 4.06 | M |
| A327 | 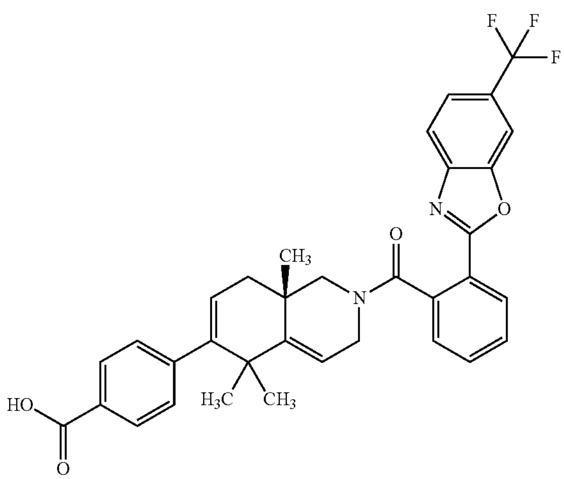 [SMILES: CC1(C)C(c2ccc(C(=O)O)cc2)=CC[C@]2(C)CN(C(=O)c3ccccc3-c3nc4ccc(C(F)(F)F)cc4o3)CC=C12] | 586.60 | 587.3 | 2.85 | A |
| A328 | 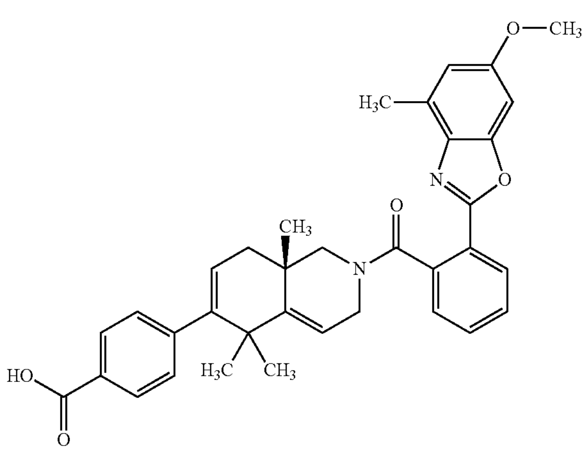 [SMILES: COc1cc(C)c2nc(-c3ccccc3C(=O)N3CC=C4C(C)(C)C(c5ccc(C(=O)O)cc5)=CC[C@]4(C)C3)oc2c1] | 562.65 | 563.4 | 2.79 | A |

TABLE 13-continued

| Ex | Structure | MW | Obs Ion | RT | Met |
|---|---|---|---|---|---|
| A329 | 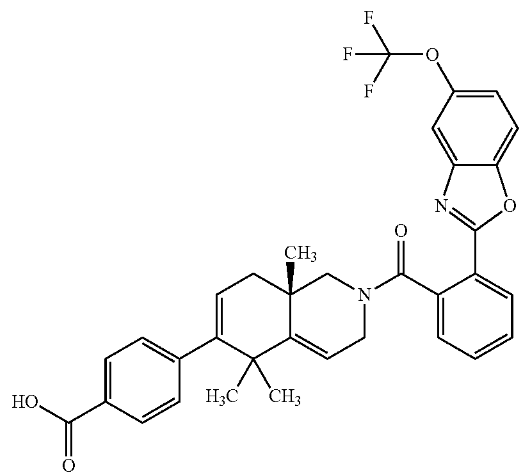 [SMILES: CC1(C)C(c2ccc(C(=O)O)cc2)=CC[C@]2(C)CN(C(=O)c3ccccc3-c3nc4cc(OC(F)(F)F)ccc4o3)CC=C12] | 602.60 | 603.3 | 4.19 | M |
| A330 | 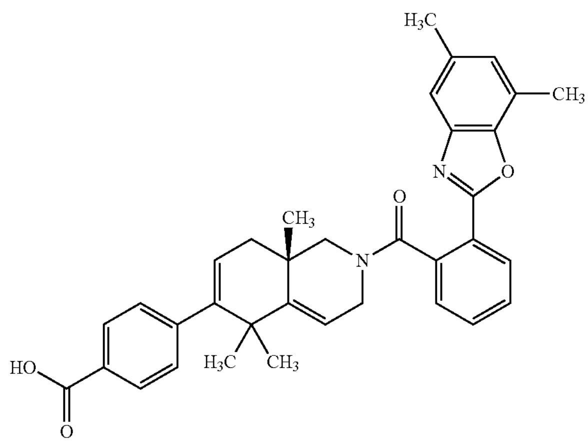 [SMILES: Cc1cc(C)c2oc(-c3ccccc3C(=O)N3CC=C4C(C)(C)C(c5ccc(C(=O)O)cc5)=CC[C@]4(C)C3)nc2c1] | 546.66 | 547.2 | 4.16 | M |
| A331 | 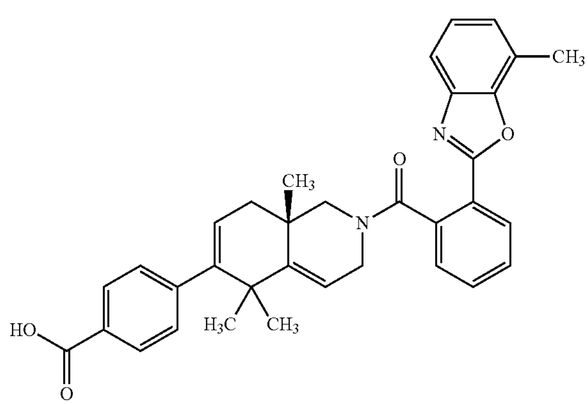 [SMILES: Cc1cccc2nc(-c3ccccc3C(=O)N3CC=C4C(C)(C)C(c5ccc(C(=O)O)cc5)=CC[C@]4(C)C3)oc12] | 532.63 | 533.2 | 4.01 | M |

TABLE 13-continued

| Ex | Structure | MW | Obs Ion | RT | Met |
|---|---|---|---|---|---|
| A332 | 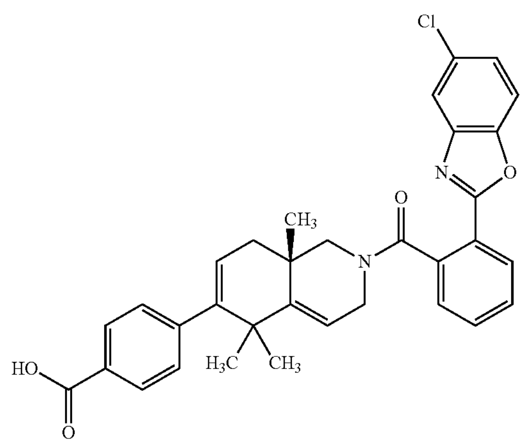 [SMILES: CC1(C)C(c2ccc(C(=O)O)cc2)=CC[C@]2(C)CN(C(=O)c3ccccc3-c3nc4cc(Cl)ccc4o3)CC=C12] | 553.06 | 553.3 | 2.79 | A |
| A333 | 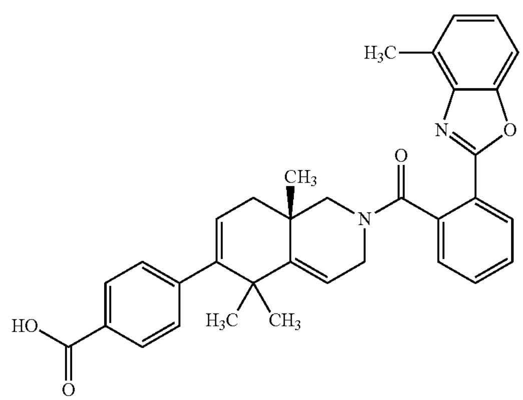 [SMILES: Cc1cccc2oc(-c3ccccc3C(=O)N3CC=C4C(C)(C)C(c5ccc(C(=O)O)cc5)=CC[C@]4(C)C3)nc12] | 532.63 | 533.4 | 4.13 | M |
| A334 | 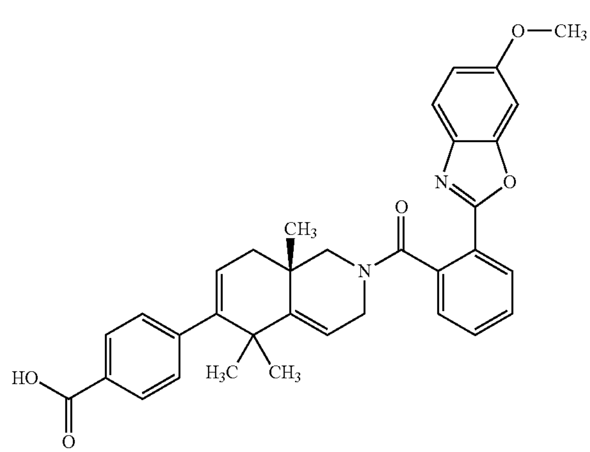 [SMILES: COc1ccc2nc(-c3ccccc3C(=O)N3CC=C4C(C)(C)C(c5ccc(C(=O)O)cc5)=CC[C@]4(C)C3)oc2c1] | 548.64 | 549.4 | 3.92 | M |

TABLE 13-continued

| Ex | Structure | MW | Obs Ion | RT | Met |
|---|---|---|---|---|---|
| A335 | 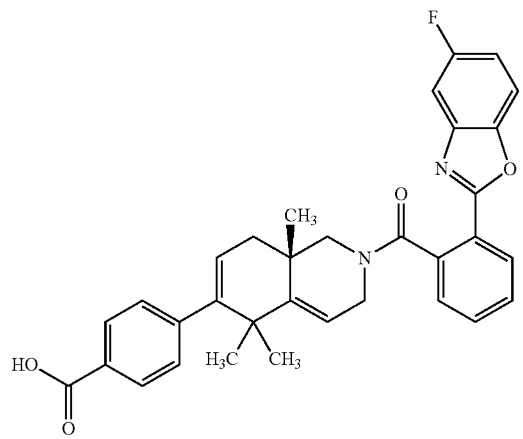 [SMILES: CC1(C)C(c2ccc(C(=O)O)cc2)=CC[C@]2(C)CN(C(=O)c3ccccc3-c3nc4cc(F)ccc4o3)CC=C12] | 536.59 | 537.4 | 3.96 | M |
| A336 | 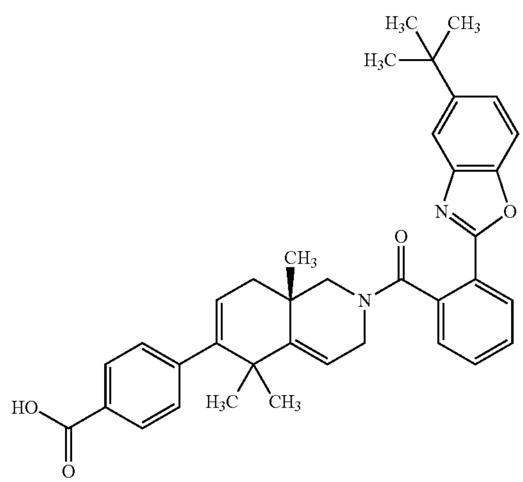 [SMILES: CC1(C)C(c2ccc(C(=O)O)cc2)=CC[C@]2(C)CN(C(=O)c3ccccc3-c3nc4cc(C(C)(C)C)ccc4o3)CC=C12] | 574.71 | 575.5 | 4.38 | M |
| A337 | 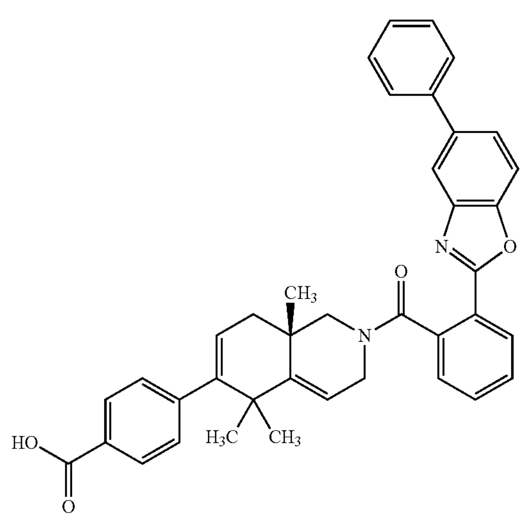 [SMILES: CC1(C)C(c2ccc(C(=O)O)cc2)=CC[C@]2(C)CN(C(=O)c3ccccc3-c3nc4cc(-c5ccccc5)ccc4o3)CC=C12] | 594.70 | 595.5 | 3.04 | A |

TABLE 13-continued

| Ex | Structure | MW | Obs Ion | RT | Met |
|---|---|---|---|---|---|
| A338 | 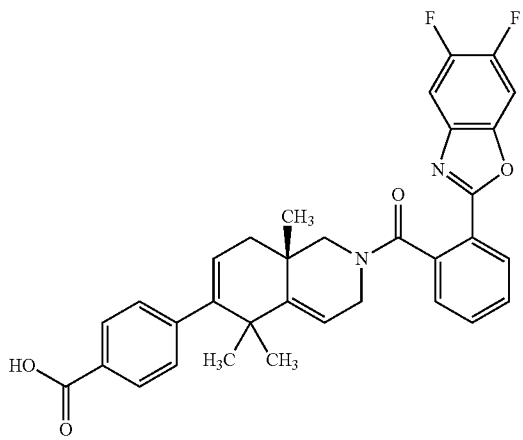 [SMILES: CC1(C)C(c2ccc(C(=O)O)cc2)=CC[C@]2(C)CN(C(=O)c3ccccc3-c3nc4cc(F)c(F)cc4o3)CC=C12] | 554.59 | 555.3 | 2.68 | A |

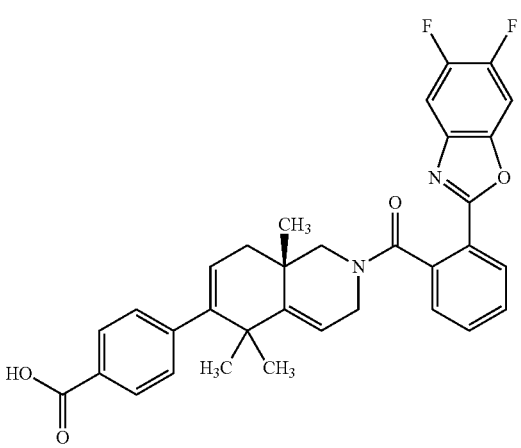

Section 3
LCMS Methods
Method B
Start % B=0, Final % B=100
Gradient Time=2 min
Flow Rate=1.0 mL/min
Wavelength=220
Solvent A=10% MeOH-90% H₂O-0.1% TFA
Solvent B=90% MeOH-10% H₂O-0.1% TFA
Column=PHENOMENEX-LUNA 2.0×30 mm 3 um
Method C
Start % B=0
Final % B=100
Gradient Time=4 min
Flow Rate=0.8 mL/min
Wavelength=220
Solvent A=10% MeOH-90% H₂O-0.1% TFA
Solvent B=90% MeOH-10% H₂O-0.1% TFA
Column=Xbridge Phenyl 2.1×50 mm 2.5 um
Method D
Start % B=0, Final % B=100
Gradient Time=2 min
Flow Rate=1.0 mL/min
Wavelength=220
Solvent A=5% MeOH: 95% Water: 10 mM Ammonium Actetate
Solvent B=95% MeOH: 5% Water: 10 mM Ammonium Actetate
Column=PHENOMENEX-LUNA C18, 2.0×30 mm 3 um Preparation of Compounds Examples B1 and B2

Preparation of Compound B1 (S)-4-(2-(3-(2-(2-(1,1-dioxidothiomorpholino)ethyl)-2H-tetrazol-5-yl)-5-nitrophenyl)-5,5,8a-trimethyl-1,2,3,5,8,8a-hexahydroisoquinolin-6-yl)benzoic acid and Compound B2 (S)-4-(2-(3-(1-(2-(1,1-dioxidothiomorpholino)ethyl)-1H-tetrazol-5-yl)-5-nitrophenyl)-5,5,8a-trimethyl-1,2,3,5,8,8a-hexahydroisoquinolin-6-yl)benzoic acid

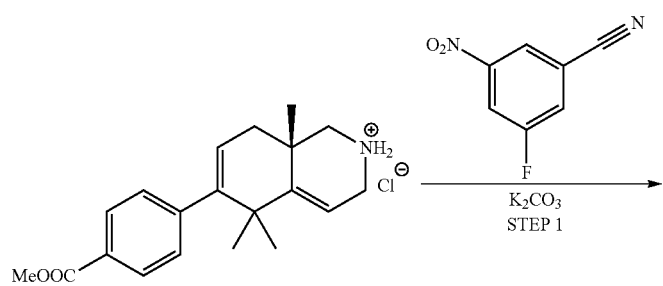

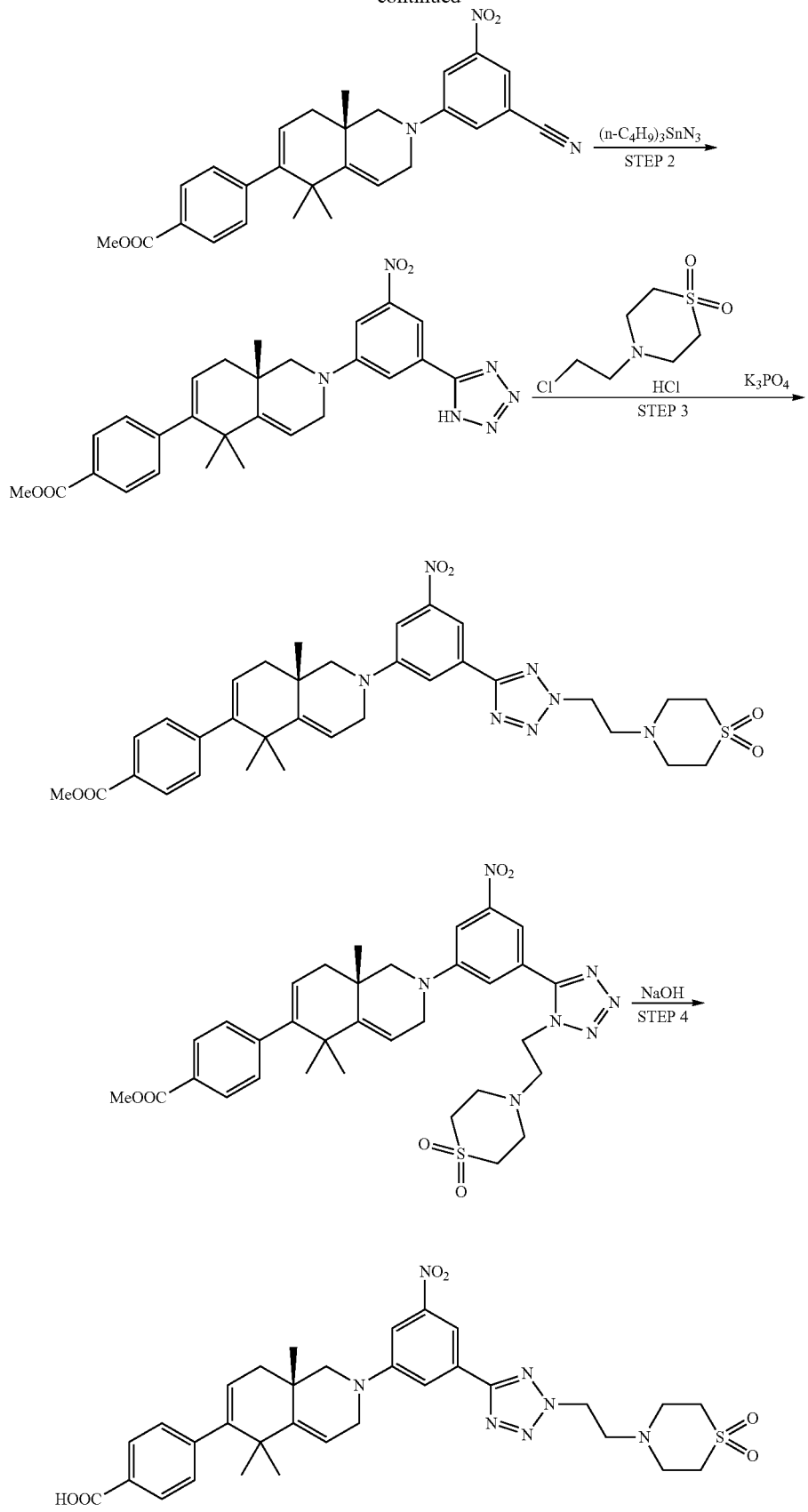

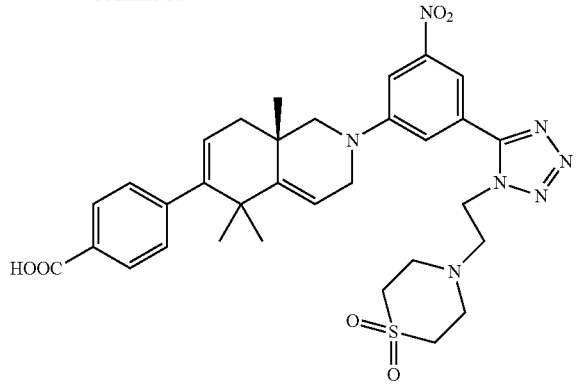

Example B2

Step 1: Preparation of (S)-methyl 4-(2-(3-cyano-5-nitrophenyl)-5,5,8a-trimethyl-1,2,3,5,8,8a-hexahydroisoquinolin-6-yl)benzoate To a mixture of (S)-6-(4-(methoxycarbonyl)phenyl)-5,5,8a-trimethyl-1,2,3,5,8,8a-hexahydroisoquinolin-2-ium chloride (119 mg, 0.342 mmol) and 3-fluoro-5-nitrobenzonitrile (398 mg, 2.395 mmol) in the presence of anhydrous potassium carbonate (284 mg, 2.052 mmol) in a resealable pressure tube was added DMF (4 mL), followed by flushing with nitrogen. The tube was sealed, placed in an oil bath at 125° C. for overnight. The resulted mixture was diluted with 50 mL of ethyl acetate and washed twice with water (2×20 mL). The organic layers were collected and evaporated to yield a solid which was purified by flash chromatography. The fractions containing desired the product were collected and dried under reduced pressure to give 65 mg of the title compound (41.5%) as a solid. LC/MS m/z 458.29 (M+H)+, 2.74 min (Method B). $^1$H NMR (400 MHz, CHLOROFORM-d) δ 8.03-7.94 (m, 2H), 7.86 (t, J=2.3 Hz, 1H), 7.81-7.77 (m, 1H), 7.33 (dd, J=2.6, 1.1 Hz, 1H), 7.29-7.24 (m, 2H), 5.76 (t, J=3.4 Hz, 1H), 5.64 (dd, J=6.0, 3.0 Hz, 1H), 4.11-4.04 (m, 1H), 3.94 (s, 3H), 3.80 (dd, J=16.6, 2.8 Hz, 1H), 3.63 (d, J=12.0 Hz, 1H), 2.99 (d, J=12.0 Hz, 1H), 2.18-2.12 (m, 2H), 1.35 (s, 3H), 1.30-1.26 (m, 3H), 1.17 (s, 3H).

Step 2: Preparation of (S)-methyl 4-(5,5,8a-trimethyl-2-(3-nitro-5-(1H-tetrazol-5-yl)phenyl)-1,2,3,5,8,8a-hexahydroisoquinolin-6-yl)benzoate To a resealable tube was added (S)-methyl 4-(2-(3-cyano-5-nitrophenyl)-5,5,8a-trimethyl-1,2,3,5,8,8a-hexahydroisoquinolin-6-yl)benzoate (50 mg, 0.109 mmol) and azidotributylstannane (0.079 mL, 0.287 mmol) in toluene (1 mL) under nitrogen. The pressure tube was sealed and warmed to 130° C. overnight. The crude reaction mixture was evaporated, washed with water and extracted with ethyl acetate (2×10 mL). The organic layers were combined and evaporated to dryness. The resulted solid was purified by flash chromatography. The fractions containing the desired product were collected and dried under reduced pressure to give 50 mg of the title compound (91%) as a solid. LC/MS m/z 501.26 (M+H)+, 2.52 min (method B).

Step 3: Preparation of (S)-methyl 4-(2-(3-(1-(2-(1,1-dioxidothiomorpholino)ethyl)-1H-tetrazol-5-yl)-5-nitrophenyl)-5,5,8a-trimethyl-1,2,3,5,8,8a-hexahydroisoquinolin-6-yl)benzoate and (S)-methyl 4-(2-(3-(2-(2-(1,1-dioxidothiomorpholino)ethyl)-2H-tetrazol-5-yl)-5-nitrophenyl)-5,5,8a-trimethyl-1,2,3,5,8,8a-hexahydroisoquinolin-6-yl)benzoate A mixture of (S)-methyl 4-(5,5,8a-trimethyl-2-(3-nitro-5-(1H-tetrazol-5-yl)phenyl)-1,2,3,5,8,8a-hexahydroisoquinolin-6-yl)benzoate (50 mg, 0.100 mmol), 4-(2-chloroethyl)thiomorpholine 1,1-dioxide hydrochloride (94 mg, 0.400 mmol), potassium phosphate (93 mg, 0.440 mmol) and NaI (44.8 mg, 0.270 mmol) in Acetonitrile (5 mL) was heated up at 120° C. for 19 hours in a seal tube. The resulted mixture was diluted with 20 ml of ethyl acetate and washed with water. The organic layer was collected and evaporated to dryness under reduced pressure, used in next step without further purification. LCMS showed two peaks with the same molecular weight as the desired products. LC/MS m/z 662.4 (M+H)+, 2.39 min, 2.59 min (method B).

Step 4

To a solution of (S)-methyl 4-(2-(3-(1-(2-(1,1-dioxidothiomorpholino)ethyl)-1H-tetrazol-5-yl)-5-nitrophenyl)-5,5,8a-trimethyl-1,2,3,5,8,8a-hexahydroisoquinolin-6-yl)benzoate and (S)-4-(2-(3-(2-(2-(1,1-dioxidothiomorpholino)ethyl)-2H-tetrazol-5-yl)-5-nitrophenyl)-5,5,8a-trimethyl-1,2,3,5,8,8a-hexahydroisoquinolin-6-yl)benzoate (total 66.1 mg, 0.1 mmole) in dioxane (1.0 mL), THF (1.0 mL), MeOH (1.0 mL) was added sodium hydroxide (1.0 mL). A yellow solution was formed. The mixture was stirred at 70° C. for 3 hours. The resulted solution was purified by prep. HPLC. Two fractions with molecular weight of the desired product but different retention times were collected separately and evaporated to dryness to give S)-4-(2-(3-(1-(2-(1,1-dioxidothiomorpholino)ethyl)-1H-tetrazol-5-yl)-5-nitrophenyl)-5,5,8a-trimethyl-1,2,3,5,8,8a-hexahydroisoquinolin-6-yl)benzoic acid (3 mg, 4.2%) and (S)-4-(2-(3-(2-(2-(1,1-dioxidothiomorpholino)ethyl)-2H-tetrazol-5-yl)-5-nitrophenyl)-5,5,8a-trimethyl-1,2,3,5,8,8a-hexahydroisoquinolin-6-yl)benzoic acid (20 mg, 29.0%). LC/MS m/z 648.4 (M+H)+, 2.06 min (method B). $^1$H NMR (400 MHz, CHLOROFORM-d) δ 8.07 (d, J=8.3 Hz, 2H), 7.89 (t, J=2.1 Hz, 1H), 7.81 (s, 1H), 7.60 (s, 1H), 7.32 (d, J=8.3 Hz, 2H), 5.78 (t, J=3.3 Hz, 1H), 5.65 (dd, J=6.0, 2.8 Hz, 1H), 4.64 (t, J=5.9 Hz, 2H), 4.17 (dd, J=16.8, 4.0 Hz, 1H), 3.89-3.82 (m, 1H), 3.75-3.70 (m, 1H), 3.22 (d, J=6.0 Hz, 2H), 3.04 (d, J=6.0 Hz, 5H), 2.98-2.93 (m, 4H), 2.21-2.10 (m, 2H), 1.36 (s, 3H), 1.27 (s, 3H), 1.20 (s, 3H). LC/MS m/z 648.3 (M+H)$^+$, 2.23 min (method B). $^1$H NMR (400 MHz, CHLOROFORM-d) Symbol 8.31 (dd, J=1.9, 1.1 Hz, 1H), 8.08 (d, J=8.3 Hz, 2H), 7.99 (d, J=1.3 Hz, 1H), 7.80 (t, J=2.1 Hz, 1H), 7.33 (d, J=8.5 Hz, 2H), 5.79 (t, J=3.3 Hz, 1H), 5.66 (dd, J=6.1, 2.9 Hz, 1H), 4.86 (t, J=6.1 Hz, 2H), 4.19 (dd, J=16.7, 3.9 Hz, 1H), 3.85 (dd, J=16.7, 2.6 Hz, 1H), 3.75 (d, J=12.3 Hz, 1H), 3.31 (t, J=6.3 Hz, 2H), 3.21-3.14 (m, 4H), 3.09-3.03 (m, 4H), 3.00 (d, J=12.3 Hz, 1H), 2.24-2.11 (m, 2H), 1.40 (s, 3H), 1.31 (s, 3H), 1.21 (s, 3H)

Example B3

Preparation of (S)-4-(2-(3-amino-5-(2-(2-(1,1-dioxidothiomorpholino)ethyl)-2H-tetrazol-5-yl)phenyl)-5,5,8a-trimethyl-1,2,3,5,8,8a-hexahydroisoquinolin-6-yl)benzoic acid

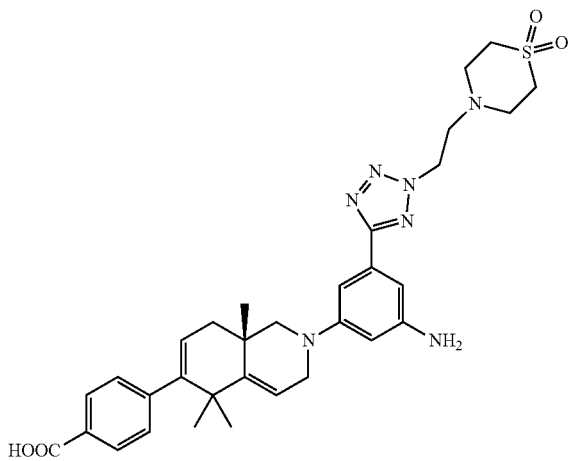 [SMILES: CC1(C)C(c2ccc(C(=O)O)cc2)=CC[C@]2(C)CN(c3cc(N)cc(-c4nnn(CCN5CCS(=O)(=O)CC5)n4)c3)CC=C12]

To a medium yellow solution of (S)-4-(2-(3-(2-(2-(1,1-dioxidothiomorpholino)ethyl)-2H-tetrazol-5-yl)-5-nitrophenyl)-5,5,8a-trimethyl-1,2,3,5,8,8a-hexahydroisoquinolin-6-yl)benzoic acid (20 mg, 0.031 mmol) in absolute ethanol (900 μL) at RT was added tin(II) chloride dihydrate (34.8 mg, 0.154 mmol) in a single portion. The mixture was warmed to 70-72° C. in an oil bath for an hour. Rapid discoloration was observed and the mixture turned into pale lemon yellow color. The resulted mixture was diluted with ethyl acetate, washed with a saturated aqueous solution of sodium bicarbonate. The aqueous phase was then extracted three times with CH$_2$Cl$_2$. The organic layers were combined and dried over sodium sulfate. The solvent was removed and the residue was purified by prepHPLC. The fractions containing desired product were collected and dried under reduced pressure to give the title compound (1 mg, 4.98%) as a solid. LC/MS m/z 618.41 (M+H)$^+$, 2.01 min (method B). $^1$H NMR (400 MHz, METHANOL-d4) δ 8.00 (d, J=8.3 Hz, 2H), 7.72 (s, 1H), 7.43 (s, 1H), 7.33 (d, J=8.3 Hz, 2H), 6.97 (s, 1H), 5.89 (t, J=3.3 Hz, 1H), 5.66 (dd, J=5.6, 3.4 Hz, 1H), 4.92 (m, 2H), 4.13 (dd, J=16.8, 4.0 Hz, 1H), 3.82-3.78 (m, 1H), 3.76 (s, 1H), 3.27 (t, J=6.0 Hz, 2H), 3.13-3.09 (m, 4H), 3.05 (d, J=6.5 Hz, 4H), 2.94 (d, J=12.0 Hz, 1H), 2.19 (d, J=6.0 Hz, 2H), 1.42 (s, 3H), 1.32 (s, 3H), 1.22 (s, 3H).

Example B4

Preparation of (S)-4-(2-(3-(2-(2-(1,1-dioxidothiomorpholino)ethyl)-2H-tetrazol-5-yl)-5-(3-(1,1-dioxidothiomorpholino)propanamido)phenyl)-5,5,8a-trimethyl-1,2,3,5,8,8a-hexahydroisoquinolin-6-yl) benzoic acid

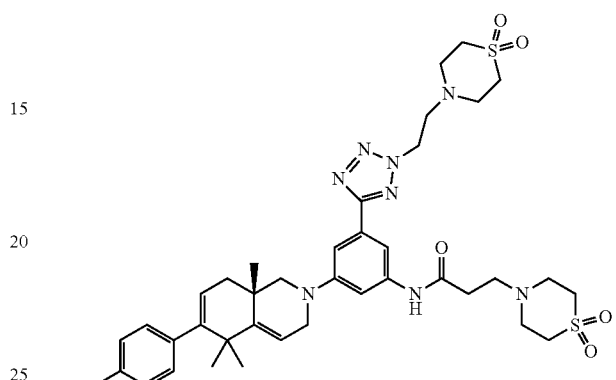

To a medium yellow solution of (S)-4-(2-(3-amino-5-(2-(2-(1,1-dioxidothiomorpholino)ethyl)-2H-tetrazol-5-yl)phenyl)-5,5,8a-trimethyl-1,2,3,5,8,8a-hexahydroisoquinolin-6-yl)benzoic acid (20 mg, 0.032 mmol) in CH$_2$Cl$_2$ (1 ml) at RT was added 3-(1,1-dioxidothiomorpholino)propanoic acid (6.71 mg, 0.032 mmol) and HATU (24.62 mg, 0.065 mmol) followed by DIEA (16.96 μl, 0.097 mmol) and the mixture was stirred for 3 h. The mixture was diluted with ethyl acetate, washed with a saturated aqueous solution of sodium bicarbonate. The aqueous phase was then extracted three times with CH$_2$Cl$_2$. The organic layers were combine and dried over sodium sulfate. The solvent was removed and the residue was purified by prepHPLC. The fractions containing desired product were collected and dried under reduced pressure to give the title compound (2 mg, 7.66%) as a solid. LC/MS m/z 808.53 (M+H)$^+$, 2.13 min (method B).

Likewise the examples in Table 14 were prepared by the analogous aromatic nucleophilic substitution route as illustrated above in preparations of examples B1 and B2 using (S)-6-(4-(methoxycarbonyl)phenyl)-5,5,8a-trimethyl-1,2,3,5,8,8a-hexahydroisoquinolin-2-ium chloride as the common starting material, and commercially available electrophiles instead of 3-fluoro-5-nitrobenzonitrile as indicated in the table, followed by subsequent steps, 2, 3, 4.

TABLE 14

| Ex | Reagent | MW | Obs (M + 1)$^+$ | RT | Met |
|---|---|---|---|---|---|
| B5 | 4-fluorobenzonitrile | 602.27 | 603.38 | 2.30 | B |
| B6 | 2-fluorobenzonitrile | 602.27 | 603.35 | 2.20 | B |
| B7 | 3,5-difluorobenzonitrile | 459.21 | 460.40 | 1.99 | D |
| B8 | 3,5-difluorobenzonitrile | 620.26 | 621.33 | 2.27 | D |
| B9 | 3,5-difluorobenzonitrile | 618.26 | 619.32 | 1.80 | D |

Ex = Example;
MW = Molecular weight;
Obs = Observed;
RT = Retention time;
Met = LC/MS Method.

Example B10

Preparation of (S)-4,4'-(5,5,8a-trimethyl-3,5,8,8a-tetrahydroisoquinoline-2,6(1H)-diyl)dibenzoic acid

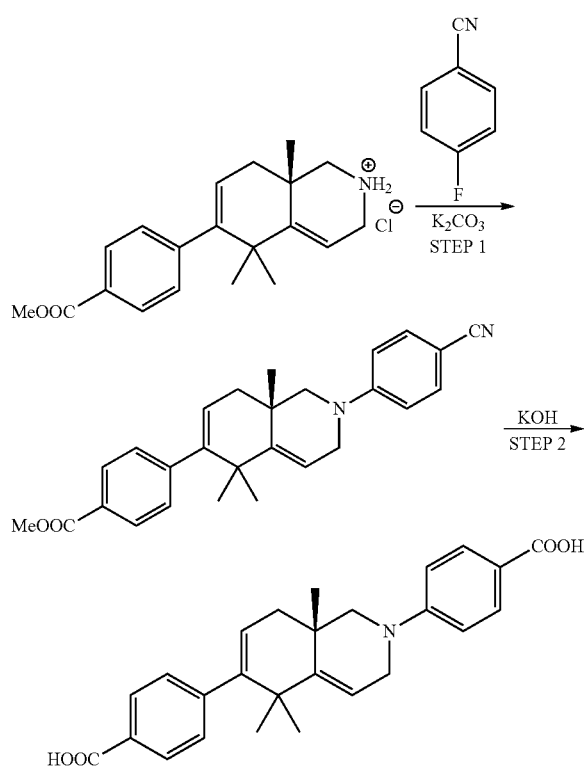

Example B10

Step 1: Preparation of methyl (S)-4-(2-(4-cyanophenyl)-5,5,8a-trimethyl-1,2,3,5,8,8a-hexahydroisoquinolin-6-yl)benzoate To a mixture of (S)-6-(4-(methoxycarbonyl)phenyl)-5,5,8a-trimethyl-1,2,3,5,8,8a-hexahydroisoquinolin-2-ium chloride (119 mg, 0.342 mmol) and 4-fluorobenzonitrile (317 mg, 2.62 mmol) in the presence of anhydrous potassium carbonate (320 mg, 2.3 mmol) in a resealable pressure tube was added DMF (4 mL), followed by flushing with nitrogen. The tube was sealed, placed in an oil bath at 125° C. overnight. The resulted mixture was diluted with 50 mL of ethyl acetate and washed twice with water (2×20 mL). The organic layers were collected and evaporated to yield a solid which was purified by flash chromatography. The fractions containing desired product were collected and dried under reduced pressure to give 130 mg of the title compound (88%) as a solid. LC/MS m/z 413.35 (M+H)$^+$, 4.485 min (method C). $^1$H NMR (400 MHz, CHLOROFORM-d) δ 8.04-7.94 (m, 2H), 7.56-7.47 (m, 2H), 7.31-7.20 (m, 2H), 6.85 (d, J=9.0 Hz, 2H), 5.73 (t, J=3.3 Hz, 1H), 5.61 (dd, J=6.4, 2.6 Hz, 1H), 4.05 (dd, J=16.8, 3.5 Hz, 1H), 3.94 (s, 3H), 3.75 (dd, J=16.9, 2.9 Hz, 1H), 3.66 (d, J=12.5 Hz, 1H), 2.91 (d, J=12.5 Hz, 1H), 2.17-2.02 (m, 2H), 1.32 (s, 3H), 1.26 (s, 3H), 1.15 (s, 3H).

Step 2

To a suspension of (S)-methyl 4-(2-(4-cyanophenyl)-5,5,8a-trimethyl-1,2,3,5,8,8a-hexahydroisoquinolin-6-yl)benzoate (15 mg, 0.036 mmol) in ethanol (1 mL) was added a 40% w/w solution of KOH (2 mL). The mixture was warmed to 80° C. for 7 hours. The resulted solution was purified by prep. HPLC. The fractions containing desired product were collected and dried under reduced pressure to give (S)-4,4'-(5,5,8a-trimethyl-3,5,8,8a-tetrahydroisoquinoline-2,6(1H)-diyl)dibenzoic acid (7 mg, 44.7%). LC/MS m/z 418.27 (M+H)$^+$, 2.53 min (Method B). $^1$H NMR (400 MHz, METHANOL-d$_4$) δ7.93-7.83 (m, 4H), 7.26-7.15 (m, 2H), 6.89 (d, J=8.8 Hz, 2H), 5.83 (t, J=3.4 Hz, 1H), 5.59 (dd, J=6.1, 2.9 Hz, 1H), 4.04 (dd, J=17.1, 4.0 Hz, 1H), 3.79-3.56 (m, 2H), 2.78 (d, J=12.3 Hz, 1H), 2.25-1.97 (m, 2H), 1.38 (s, 3H), 1.28 (s, 3H), 1.17 (s, 3H).

Likewise the examples in Table 15 were prepared by the analogous aromatic nucleophilic substitution route as illustrated above using (S)-6-(4-(methoxycarbonyl)phenyl)-5,5,8a-trimethyl-1,2,3,5,8,8a-hexahydroisoquinolin-2-ium chloride as the common starting material, and commercially available electrophiles instead of 4-fluorobenzonitrile indicated in the table.

TABLE 15

| Ex | Reagent | MW | Obs (M + 1)$^+$ | RT | Met |
|---|---|---|---|---|---|
| B11 | 2-chloropyrimidine | 375.20 | 376.23 | 2.21 | B |
| B12 | ethyl 2-bromothiazole-5-carboxylate | 424.15 | 425.14 | 2.19 | B |
| B13 | 2-chloro-4-methoxypyrimidine | 405.21 | 406.20 | 1.94 | B |
| B14 | ethyl 2-bromothiazole-5-carboxylate* | 452.18 | 453.11 | 2.39 | B |
| B15 | 3-fluoro-5-nitrobenzonitrile | 462.18 | 463.21 | 2.43 | B |
| B16 | ethyl 2-bromothiazole-4-carboxylate | 424.15 | 425.14 | 2.18 | D |
| B17 | 4-fluorobenzonitrile | 416.21 | 417.25 | 2.21 | B |

Ex = Example;
MW = Molecular weight;
Obs = Observed;
RT = Retention time;
Met = LC/MS Method.
*same as B12 except that a selective hydrolysis step to hydrolyze the methyl ester in the presence of an ethyl ester as described in Helv. Chim. Acta. 1974, 57, 987 was used.

Section 4

Method E

Start % B=0, Final % B=100 over 2 minute gradient, hold at 100% B

Flow Rate=0.8 mL/min

Wavelength=220 nm

Solvent A=95% water, 5% methanol, 10 mM ammonium acetate

Solvent B=5% water, 95% methanol, 10 mM ammonium acetate

Column=Xbridge C18, 3.5 μm, 2.1×50 mm

Method F

Start % B=0, Final % B=100 over 2 minute gradient, hold at 100% B

Flow Rate=1 mL/min

Wavelength=220 nm

Solvent A=90% water, methanol, 0.1% TFA

Solvent B=10% water, 90% methanol, 0.1% TFA

Column=Phenomenex Luna C18, 3 μm, 2.0×30 mm

Example C1
Preparation of 4-((4aS,8aS)-2-(2-((S)-2-((2-(1,1-dioxidothiomorpholino)ethyl)carbamoyl)pyrrolidin-1-yl)-2-oxoacetyl)-5,5,8a-trimethyl-1,2,3,4,4a,5,8,8a-octahydroisoquinolin-6-yl)benzoic acid
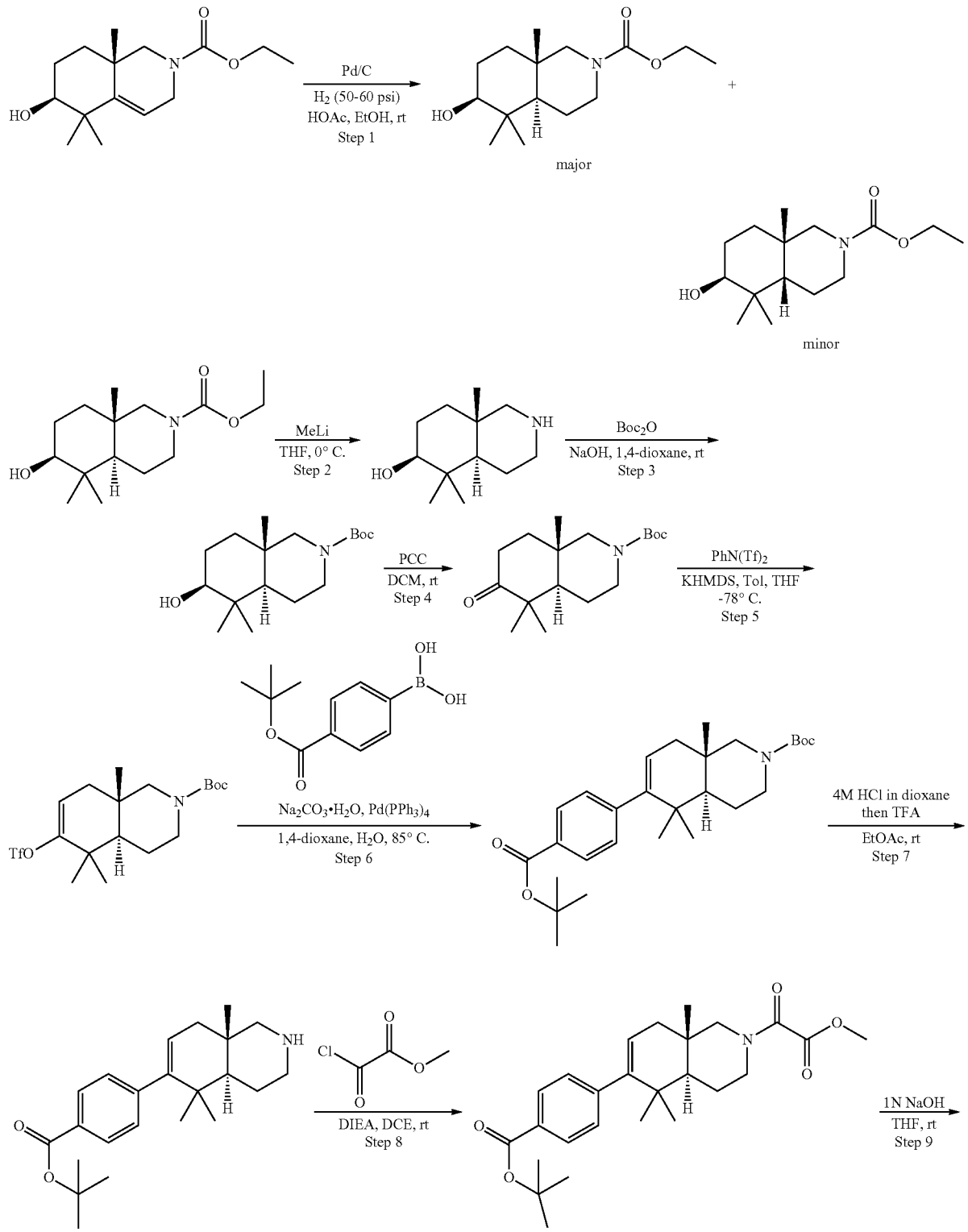

-continued
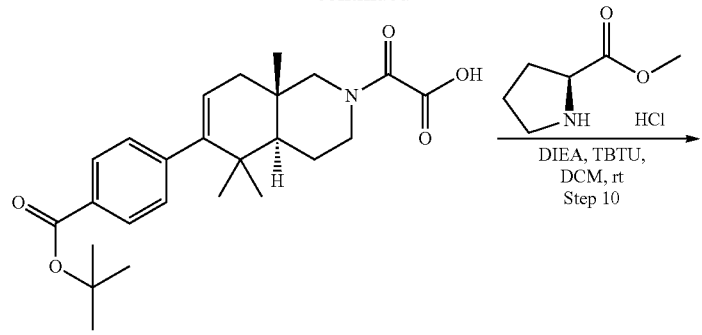
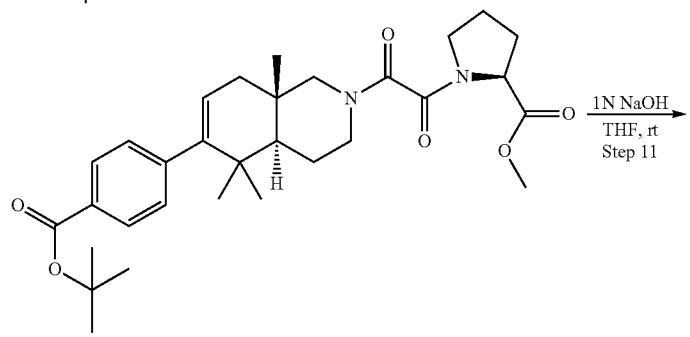
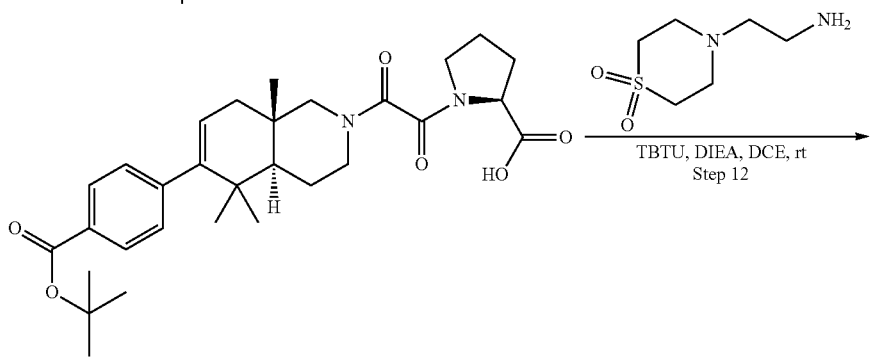
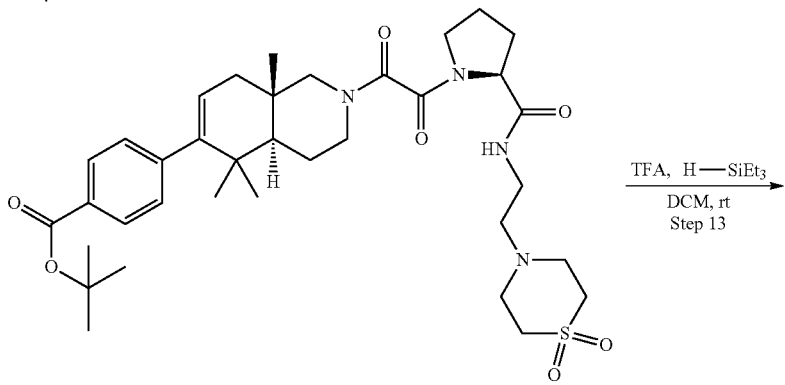
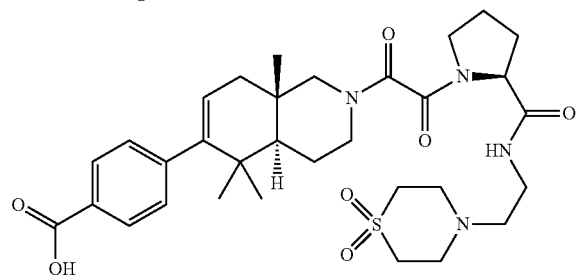
Example C1

Step 1: Preparation of (4aR,6S,8aS)-ethyl 6-hydroxy-5,5,8a-trimethyloctahydroisoquinoline-2(1H)-carboxylate and (4aS,6S,8aS)-ethyl 6-hydroxy-5,5,8a-trimethyloctahydroisoquinoline-2(1H)-carboxylate To a solution of (6S,8aS)-ethyl 6-hydroxy-5,5,8a-trimethyl-3,5,6,7,8,8a-hexahydroisoquinoline-2(1H)-carboxylate (5.2 g, 19.45 mmol) in ethanol (100 mL) was added acetic acid (1.1 mL, 19.5 mmol) and Pd/C (2.07 g, 1.95 mmol). The mixture was attached to a PARR shaker and was pressurized to 50 psi with hydrogen. After 24 h the mixture was removed from the PARR shaker. TLC indicated some starting material still remained so the mixture was degassed, the sides of the flask were washed with 10 mL of MeOH and an additional 2.0 g of Pd/C were added. The mixture was again put on the PARR shaker under 60 psi of hydrogen. The mixture was filtered through a pad of celite to remove the solids and the filtrate was concentrated under reduced pressure. The residue was purified by flash chromatography using a 300 g silica gel column and a 0-30% EtOAc in toluene gradient. The fractions containing the expected product were combined and concentrated under reduced pressure to give 2.55 g of the major product as a clear, colorless oil (Rf=0.23, 2:8 EtOAc/toluene, stained with Hanessian's stain) and 0.69 g of the minor product as a clear, colorless oil, which upon standing partially crystallized. The fractions containing a mixture of diastereomers were combined and were concentrated under reduced pressure then were repurified by flash chromatography using a 0-30% EtOAc in toluene gradient and a 240 g silica gel column. The fractions containing each diastereomer were combined and concentrated under reduced pressure. To give an additional 0.59 g of the major product, (4aR,6S,8aS)-ethyl 6-hydroxy-5,5,8a-trimethyloctahydroisoquinoline-2(1H)-carboxylate (3.14 g total, 60% yield), and 0.51 g of the minor product, (4aS,6S,8aS)-ethyl 6-hydroxy-5,5,8a-trimethyloctahydroisoquinoline-2(1H)-carboxylate (1.2 g total, 23% yield). Major product: $^1$H NMR (500 MHz, chloroform-d) δ 4.42-4.21 (m, 1H), 4.19-4.06 (m, 2H), 3.86-3.61 (m, 1H), 3.30-3.23 (m, 1H), 2.76-2.57 (m, 1H), 2.36-2.21 (m, 1H), 1.76-1.60 (m, 2H), 1.58-1.49 (m, 2H), 1.49-1.35 (m, 2H), 1.32-1.12 (m, 4H), 0.99 (s, 3H), 0.98-0.92 (m, 4H), 0.79 (s, 3H). Minor product: $^1$H NMR (500 MHz, chloroform-d) δ 4.20-3.96 (m, 3H), 3.63-3.44 (m, 2H), 2.75-2.53 (m, 2H), 1.77-1.62 (m, 4H), 1.51 (qd, J=12.6, 4.7 Hz, 1H), 1.33-1.15 (m, 6H), 1.12 (s, 3H), 1.08 (s, 3H), 1.02 (s, 3H).

Step 2: Preparation of (4aR,6S,8aS)-5,5,8a-trimethyldecahydroisoquinolin-6-ol A solution of (4aR,6S,8aS)-ethyl 6-hydroxy-5,5,8a-trimethyloctahydroisoquinoline-2(1H)-carboxylate (0.585 g, 2.17 mmol) in THF (15 mL) was cooled to 0° C. To the solution was added methyllithium (1.6M in ether, 6.79 mL, 10.86 mmol). The mixture was stirred at 0° C. for 3 h then was carefully quenched with water (15 mL) and extracted with dichloromethane (3×25 mL). The combined organic layers were dried over sodium sulfate, filtered and concentrated under reduced pressure to give the crude product as an orange solid. The crude product was used in the next step with no additional purification.

Step 3: Preparation of (4aR,6S,8aS)-tert-butyl 6-hydroxy-5,5,8a-trimethyloctahydroisoquinoline-2(1H)-carboxylate To a solution of the crude (4aR,6S,8aS)-5,5,8a-trimethyldecahydroisoquinolin-6-ol in 1,4-dioxane (7 mL) was added 1 M NaOH (7.30 mL, 7.30 mmol) followed by Boc$_2$O (1.24 mL, 5.35 mmol). The mixture was stirred at rt for 16.5 h then was diluted with 20 mL of water and extracted with dichloromethane (3×40 mL). The combined organic layers were dried over sodium sulfate, filtered and concentrated under reduced pressure to give the title product. The crude product was used in the next step with no additional purification. LCMS: m/e 298.06 (M+H)$^+$, 1.70 min (Method E).

Step 4: Preparation of (4aR,8aS)-tert-butyl 5,5,8a-trimethyl-6-oxooctahydroisoquinoline-2(1H)-carboxylate To a solution of the crude (4aR,6S,8aS)-tert-butyl 6-hydroxy-5,5,8a-trimethyloctahydroisoquinoline-2(1H)-carboxylate (0.66 g, 2.219 mmol) from the previous step in dichloromethane (15 mL) was added pyridinium chlorochromate (0.717 g, 3.33 mmol). The mixture was stirred at rt for 3 h, then was filtered through a pad of silica gel and celite (washed with 1:1 ethyl acetate:hexanes). The filtrate was concentrated under reduced pressure to give the title product (0.47 g, 1.59 mmol, 73% over 3 steps). $^1$H NMR (400 MHz, chloroform-d) δ 4.51-4.17 (m, 1H), 4.01-3.66 (m, 1H), 2.80-2.53 (m, 2H), 2.46-2.22 (m, 2H), 1.47 (s, 9H), 1.75-1.23 (m, 5H), 1.13 (s, 3H), 1.09 (s, 3H), 1.04 (s, 3H). $^{13}$C NMR (101 MHz, chloroform-d) δ 215.5, 154.9, 79.5, 59.3, 52.5, 47.4, 36.3, 34.9, 34.4, 28.5, 27.4, 25.2, 22.2, 21.4, 17.2.

Step 5: Preparation of (4aR,8aS)-tert-butyl 5,5,8a-trimethyl-6-(trifluoromethylsulfonyloxy)-3,4,4a,5,8,8a-hexahydroisoquinoline-2(1H)-carboxylate A solution of (4aR,8aS)-tert-butyl 5,5,8a-trimethyl-6-oxooctahydroisoquinoline-2(1H)-carboxylate (0.464 g, 1.571 mmol) in THF (10 mL) was cooled to −78° C. To the solution was added KHMDS (0.5 M in toluene, 6.28 mL, 3.14 mmol). The mixture was stirred for 15 minutes at −78° C. and a solution of N-phenylbis(trifluoromethanesulphonimide) (0.617 g, 1.728 mmol) in THF (5 mL) and toluene (5 mL) was added. The mixture was stirred at −78° C. for 3 h then an additional 0.1 g of N-Phenylbis(trifluoromethanesulphonimide) was added. After 1 h of additional stirring, the reaction was quenched with water (30 mL) and extracted with ethyl acetate (3×50 mL). The combined organic layers were dried over sodium sulfate, filtered and concentrated under reduced pressure. The residue was adsorbed to silica gel and was purified by flash chromatography using a 0-20% ethyl acetate in hexanes gradient and a 40 g silca gel colmn. The fractions containing the expected product were combined and concentrated under reduced pressure. The title product was isolated as a clear, colorless oil (0.468 g, 1.095 mmol, 69.7% yield). NMR (500 MHz, chloroform-d) δ 5.68 (dd, J=6.0, 2.9 Hz, 1H), 4.46-4.16 (m, 1H), 4.02-3.74 (m, 1H), 2.77-2.25 (m, 2H), 2.01-1.89 (m, 2H), 1.47 (s, 9H), 1.68-1.41 (m, 3H), 1.14 (s, 3H), 1.02 (s, 3H), 1.01 (s, 3H).

Step 6: Preparation of (4aS,8aS)-tert-butyl 6-(4-(tert-butoxycarbonyl)phenyl)-5,5,8a-trimethyl-3,4,4a,5,8,8a-hexahydroisoquinoline-2(1H)-carboxylate To a solution of (4aR,8aS)-tert-butyl 5,5,8a-trimethyl-6-(trifluoromethylsulfonyloxy)-3,4,4a,5,8,8a-hexahydroisoquinoline-2(1H)-carboxylate (0.46 g, 1.08 mmol) in 1,4-dioxane (8.0 mL) was added sodium carbonate monohydrate (0.40 g, 3.23 mmol), 4-tert-butoxycarbonylphenylboronic acid (0.30 g, 1.35 mmol), and palladium tetrakis (0.037 g, 0.032 mmol). The mixture was diluted with water (2.0 mL), flushed with nitrogen and heated to 85° C. After 3 h of heating, the mixture was cooled to rt, diluted with 25 mL of water and was extracted with dichloromethane (3×30 mL). The combined organic layers were dried over sodium sulfate, filtered and concentrated under reduced pressure. The residue was adsorbed to silica gel and was purified by flash chromatography using a 0-25% ethyl acetate in hexanes gradient and a 25 g silica gel column. The fractions containing the expected product were combined and concentrated under reduced pressure to give the title product as a clear, colorless film. LCMS: m/e 456.2 (M+H)$^+$, 2.76 min (Method E). $^1$H NMR (400 MHz, chloroform-d) δ 7.90 (d, J=8.3 Hz, 2H), 7.21-7.16 (m, 2H), 5.38 (dd, J=5.3, 3.0 Hz, 1H), 4.49-4.16 (m, 1H), 4.02-3.72 (m, 1H), 2.85-2.30 (m, 2H), 1.96-1.81 (m, 2H), 1.60 (s, 9H), 1.49 (s, 9H), 1.71-1.42 (m, 3H), 1.09 (s, 3H), 0.96 (s, 3H), 0.90 (s, 3H).

Step 7: Preparation of tert-butyl 4-((4aS,8aS)-5,5, 8a-trimethyl-1,2,3,4,4a,5,8,8a-octahydroisoquinolin-6-yl)benzoate To a solution of (4aS,8aS)-tert-butyl 6-(4-(tert-butoxycarbonyl)phenyl)-5,5,8a-trimethyl-3,4,4a,5,8,8a-hexahydroisoquinoline-2(1H)-carboxylate (0.32 g, 0.702 mmol) in ethyl acetate (3 mL) was added HCl (4M in dioxane, 1 mL, 4.00 mmol). The mixture was stirred at rt in a sealed vessel for 5 h, then the vessel was uncapped and was stirred overnight at rt. LC/MS indicated the reaction was not yet complete so an additional 5 mL of EtOAc and HCl (4M in dioxane) (1 mL, 4.00 mmol) was added and the mixture was stirred for a second night. After stirring overnight, LC/MS was inconclusive, so TFA was added (0.271 mL, 3.51 mmol) and the mixture was stirred at rt for three days. The mixture was concentrated under reduced pressure then was used in the next step with no additional purification. LCMS: m/e 356.23 (M+H)$^+$, 2.16 min (Method E).

Step 8: Preparation of tert-butyl 4-((4aS,8aS)-2-(2-methoxy-2-oxoacetyl)-5,5,8a-trimethyl-1,2,3,4,4a,5,8,8a-octahydroisoquinolin-6-yl)benzoate To a suspension of tert-butyl 4-((4aS,8aS)-5,5,8a-trimethyl-1,2,3,4,4a,5,8,8a-octahydroisoquinolin-6-yl)benzoate, HCl (0.27 g, 0.689 mmol) in DCE (5 mL) was added DIEA (0.602 mL, 3.44 mmol) and methyl oxalyl chloride (127 mL, 1.378 mmol). Upon addition of the methyl oxalyl chloride, the solids dissolved. The sides of the flask were rinsed with an additional 3 mL of DCE and the clear, yellow solution was stirred at 11 for 30 minutes. HPLC showed complete consumption of the starting material so the mixture was diluted with water (20 mL) and was extracted with dichloromethane (3×20 mL). The combined organic layers were dried over sodium sulfate, filtered and concentrated under reduced pressure. The mixture was filtered through a pad of celite and silica gel (washed with 1:1 ethyl acetate:hexanes) and the filtrate was concentrated under reduced pressure to give the title product as a colorless foam (0.29 g, 0.657 mmol, 94% yield over two steps). LCMS: m/e 442.26 (M+H)$^+$, 2.48 min (Method E).

Step 9: Preparation of 2-((4aS,8aS)-6-(4-(tert-butoxycarbonyl)phenyl)-5,5,8a-trimethyl-3,4,4a,5,8,8a-hexahydroisoquinolin-2(1H)-yl)-2-oxoacetic acid To a solution of tert-butyl 4-((4aS,8aS)-2-(2-methoxy-2-oxoacetyl)-5,5,8a-trimethyl-1,2,3,4,4a,5,8,8a-octahydroiso-quinolin-6-yl)benzoate (0.283 g, 0.641 mmol) in THF (5 mL) was added NaOH (1N, 3.2 mL, 3.2 mmol). The mixture was stirred at rt for 3.5 h then was neutralized with 10 mL 1N HCl and extracted with dichloromethane (3×15 mL). The combined organic layers were dried over sodium sulfate, filtered and concentrated under reduced pressure. The title product was isolated as a colorless foam (0.275 g, 0.643 mmol, 100% yield). LCMS: m/e 428.22 (M+H)$^+$, 2.24 min (Method E).

Step 10: Preparation of (S)-methyl 1-(2-((4aS,8aS)-6-(4-(tert-butoxycarbonyl)phenyl)-5,5,8a-trimethyl-3,4,4a,5,8,8a-hexahydroisoquinolin-2(1H)-yl)-2-oxoacetyl)pyrrolidine-2-carboxylate To a solution of 2-((4a5,8aS)-6-(4-(tert-butoxycarbonyl)phenyl)-5,5,8a-trimethyl-3,4,4a,5,8,8a-hexahydroisoquinolin-2(1H)-yl)-2-oxoacetic acid (0.27 g, 0.632 mmol) in dichloromethane (6 mL) was added DIEA (0.551 mL, 3.16 mmol), L-proline methyl ester hydrochloride (0.126 g, 0.758 mmol), and o-Benzotriazol-1-yl-N,N,N',N'-tetramethyluronium tetrafluoroborate (0.304 g, 0.947 mmol). The mixture was stirred at for 15.5 h, then was diluted with 15 mL of water and extracted with dichloromethane (3×15 mL). The combined organic layers were dried over sodium sulfate, filtered and concentrated under reduced pressure. The residue was adsorbed to silica gel and was purified by flash chromatography using a 0-65% ethyl acetate in hexanes gradient and a 25 g silica gel column. The fractions containing the expected product were combined and concentrated under reduced pressure to give the title product product as a white foam (0.212 g, 0.394 mmol, 62.3% yield). LCMS: m/e 538.98 (M+H)$^+$, 2.48 min (Method E).

Step 11: Preparation of (S)-1-(2-((4aS,8aS)-6-(4-(tert-butoxycarbonyl)phenyl)-5,5,8a-trimethyl-3,4,4a,5,8,8a-hexahydroisoquinolin-2(1H)-yl)-2-oxoacetyl)pyrrolidine-2-carboxylic acid To a solution of (S)-methyl 1-(2-((4aS,8aS)-6-(4-(tert-butoxycarbonyl)phenyl)-5,5,8a-trimethyl-3,4,4a,5,8,8a-hexahydroisoquinolin-2(1H)-yl)-2-oxoacetyl)pyrrolidine-2-carboxylate (0.212 g, 0.394 mmol) in THF (5 mL) was added NaOH (1N, 2 ml, 2.000 mmol). The mixture was stirred at rt for 16 h then was diluted with 10 mL of 1N HCl and extracted with dichloromethane (3×15 mL). The combined organic layers were dried over sodium sulfate, filtered and concentrated under reduced pressure. The drying agent was removed by filtration, and the filtrate was concentrated under reduced pressure to give the title compound as a white solid (0.188 g, 0.358 mmol, 91% yield). LCMS: m/e 525.30 (M+H)$^+$, 2.27 min (Method E).

Step 12: Preparation of tert-butyl 4-((4aS,8aS)-2-(2-((S)-2-((2-(1,1-dioxidothiomorpholino)ethyl)carbamoyl)pyrrolidin-1-yl)-2-oxoacetyl)-5,5,8a-trimethyl-1,2,3,4,4a,5,8,8a-octahydroisoquinolin-6-yl)benzoate To a solution of (S)-1-(2-((4aS,8aS)-6-(4-(tert-butoxycarbonyl)phenyl)-5,5,8a-trimethyl-3,4,4a,5,8,8a-hexahydroisoquinolin-2(1H)-yl)-2-oxoacetyl)pyrrolidine-2-carboxylic acid (0.02 g, 0.038 mmol) in DCE (1 mL) was added DIEA (0.033 mL, 0.191 mmol) followed by N-(2-aminoethyl) thiomorpholine 1,1-dioxide (10.19 mg, 0.057 mmol) and o-Benzotriazol-1-yl-N,N,N',N'-tetramethyluronium tetrafluoroborate (0.018 g, 0.057 mmol). The mixture was stirred at rt over the weekend for 64 h then was diluted with 5 mL of water and extracted with dichloromethane (3×5 mL). The combined organic layers were dried over sodium sulfate, filtered and concentrated under reduced pressure. The residue was purified by prep HPLC. The fractions containing the expected product were combined and concentrated under reduced pressure to give the title product as an off-white solid (16.5 mg, 0.024 mmol, 63% yield). LCMS: m/e 685.38 (M+H)$^+$, 2.36 min (Method E).

Step 13

To a solution of tert-butyl 4-((4aS,8aS)-2-(2-((S)-2-(2-(1,1-dioxidothiomorpholino)ethyl)carbamoyl)pyrrolidin-1-yl)-2-oxoacetyl)-5,5,8a-trimethyl-1,2,3,4,4a,5,8,8a-octahydroisoquinolin-6-yl)benzoate (16.5 mg, 0.024 mmol) in DCM (1 mL) was added TFA (9.28 µl, 0.120 mmol) and triethylsilane (3.85 µl, 0.024 mmol). The mixture was stirred at rt. After 1 h an additional 0.1 mL of TFA was added. After 3 h of stirring the mixture was concentrated under a stream of nitrogen. The residue was purified by prep HPLC. The fractions containing the expected product were combined and concentrated under reduced pressure to give 4-((4aS,8aS)-2-(2-((S)-2-((2-(1,1-dioxidothiomorpholino)ethyl)carbamoyl)pyrrolidin-1-yl)-2-oxoacetyl)-5,5,8a-trimethyl-1,2,3,4,4a,5,8,8a-octahydroisoquinolin-6-yl)benzoic acid as a clear, colorless foam (13.1 mg, 0.021 mmol, 88% yield). LCMS: m/e 629.24 (M+H)$^+$, 1.56 min (Method E).

Example C2

Preparation of 4-((4aS,8aS)-2-(2-((S)-2-((3-(1,1-dioxidothiomorpholino)propyl)carbamoyl)pyrrolidin-1-yl)-2-oxoacetyl)-5,5,8a-trimethyl-1,2,3,4,4a,5,8,8a-octahydroisoquinolin-6-yl)benzoic acid

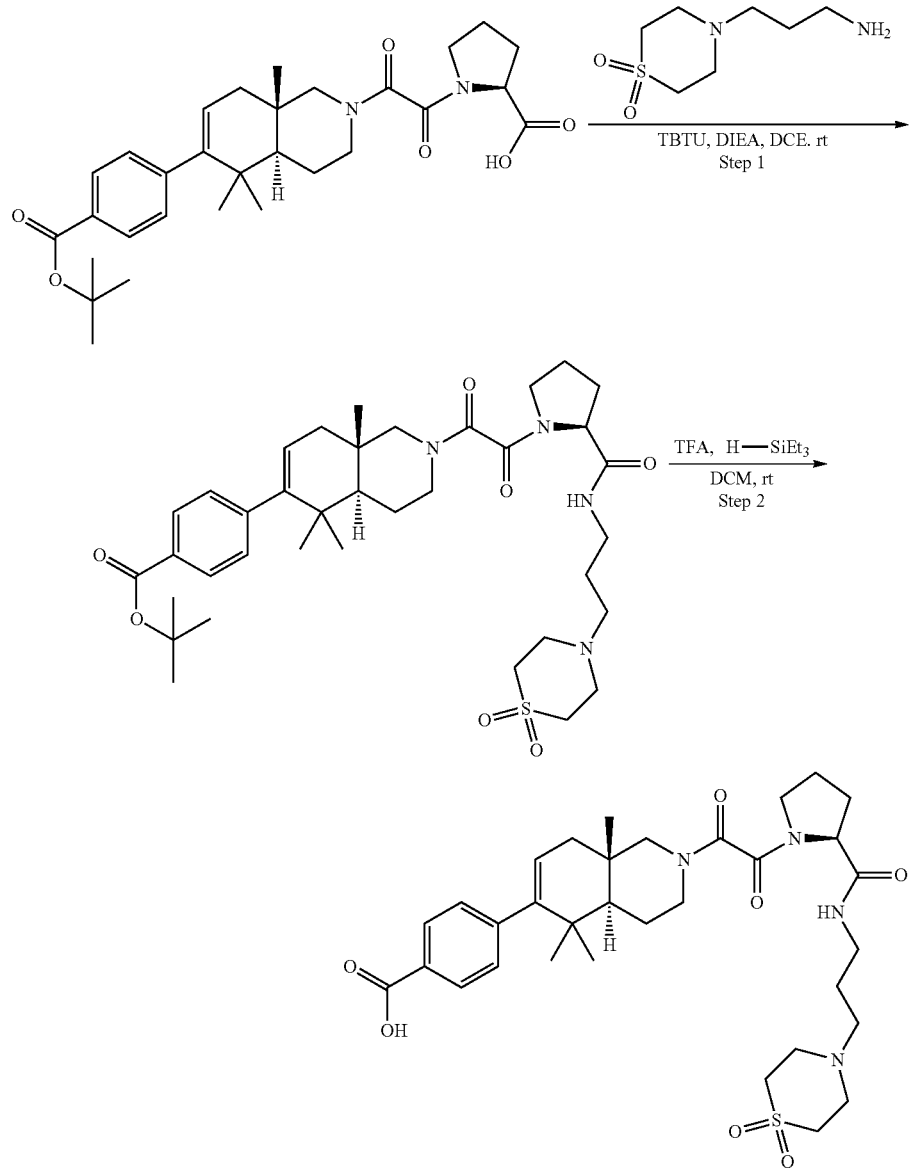

Example C2

Step 1: Preparation of tert-butyl 4-((4aS,8aS)-2-(2-((S)-2-((3-(1,1-dioxidothiomorpholino)propyl)carbamoyl)pyrrolidin-1-yl)-2-oxoacetyl)-5,5,8a-trimethyl-1,2,3,4,4a,5,8,8a-octahydroisoquinolin-6-yl)benzoate To a solution of (S)-1-(2-((4aS,8aS)-6-(4-(tert-butoxycarbonyl)phenyl)-5,5,8a-trimethyl-3,4,4a,5,8,8a-hexahydroisoquinolin-2(1H)-yl)-2-oxoacetyl)pyrrolidine-2-carboxylic acid (0.02 g, 0.038 mmol) in DCE (1 mL) was added DIEA (0.033 mL, 0.191 mmol) followed by thiomorpholine, 4-(3-aminopropyl)-1,1-dioxide (10.99 mg, 0.057 mmol) and o-benzotriazol-1-yl-N,N,N',N'-tetramethyluronium tetrafluoroborate (0.018 g, 0.057 mmol). The mixture was stirred at rt for 64 h, then was diluted with 5 mL of water and extracted with dichloromethane (3×5 mL). The combined organic layers were dried over sodium sulfate, filtered and concentrated under reduced pressure. The residue was purified by prep HPLC. The fractions containing the expected product were combined and concentrated under reduced pressure to give the title product (18.5 mg, 0.026 mmol, 69% yield). LCMS: m/e 699.46 (M+H)+, 2.37 min (Method E).

Step 2

To a solution of tert-butyl 4-((4aS,8aS)-2-(2-((S)-2-((3-(1,1-dioxidothiomorpholino)propyl)carbamoyl)pyrrolidin-1-yl)-2-oxoacetyl)-5,5,8a-trimethyl-1,2,3,4,4a,5,8,8a-octahydroisoquinolin-6-yl)benzoate (18.5 mg, 0.026 mmol) in DCM (1 mL) was added triethylsilane (4.23 µl, 0.026 mmol) and TFA (10.20 µl, 0.132 mmol). The mixture was stirred at rt. After 1 h of stirring an additional 0.1 mL of TFA was added. After 3 h of stirring, the mixture was concentrated under a stream of nitrogen. The residue was purified by prep HPLC. The fractions containing the expected product were combined and concentrated under reduced pressure to give the title product as a clear, colorless foam. (10.8 mg, 0.017 mmol, 65% yield). LCMS: m/e 643.23 (M+H)+, 1.59 min (Method E).

Example C3

Preparation of (S)-4-(2-(4-(aminomethyl)-4-phenylcyclohexyl)-5,5,8a-trimethyl-1,2,3,5,8,8a-hexahydroisoquinolin-6-yl)benzoic acid

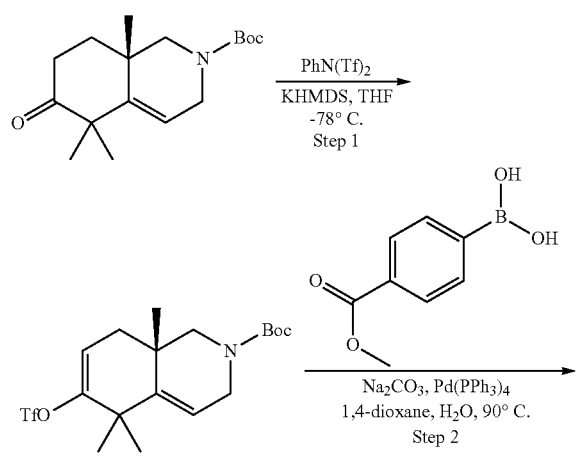

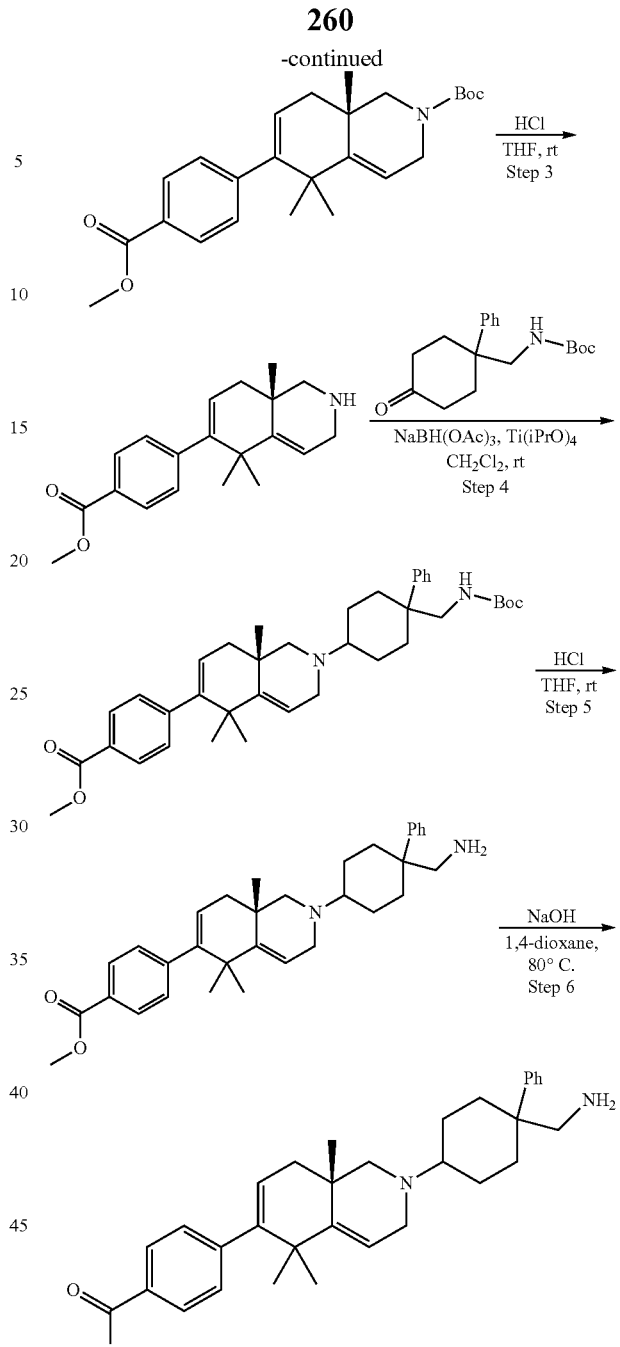

Example C3

Step 1: Preparation of (S)-tert-butyl 5,5,8a-trimethyl-6-(((trifluoromethyl)sulfonyl)oxy)-3,5,8,8a-tetrahydroisoquinoline-2(1H)-carboxylate To a solution of (S)-tert-butyl 5,5,8a-trimethyl-6-oxo-1,5,6,7,8,8a-hexahydroisoquinoline-2(3H)-carboxylate (5.4 g, 18.40 mmol) in THF (100 mL) at −78° C. was added KHMDS (0.91M in THF, 30.3 mL, 27.6 mmol). The mixture was stirred for 1 hour, then 1,1,1-trifluoro-N-phenyl-N-((trifluoromethyl)sulfonyl)methanesulfonamide (7.23 g, 20.25 mmol) in THF (20 ml) was added and the reaction stirred at −78° C. for 2 hour. TLC indicated sm was consumed so the reaction mixture was quenched with water and extracted with ethyl acetate. The combined organic layers were dried over sodium sulfate, filtered and concentrated under reduced pressure. The residue was purified using flash chromatography with a 20-50% ethyl acetate/hexanes mobile phase. The fractions containing the product were combine and concentrated under reduced pressure to give the title product as yellow oil (5.0 g, 11.75 mmol, 64% yield). $^1$H NMR (400 MHz, chloroform-d) δ 5.79 (dd, J=6.0, 3.3 Hz, 1H), 5.69-5.55 (m, 1H), 4.45-4.15 (m, 1H), 4.00-3.58 (m, 2H), 2.75-2.54 (m, 1H), 2.05 (br. s., 2H), 1.49 (s, 9H), 1.30 (s, 3H), 1.27 (br. s., 3H), 1.19 (s, 3H).

Step 2: Preparation of (S)-tert-butyl 6-(4-(methoxycarbonyl)phenyl)-5,5,8a-trimethyl-3,5,8,8a-tetrahydroisoquinoline-2(1H)-carboxylate A mixture of (S)-tert-butyl 5,5,8a-trimethyl-6-(((trifluoromethyl)sulfonyl)oxy)-3,5,8,8a-tetrahydroisoquinoline-2(1H)-carboxylate (2.0 g, 4.70 mmol), (4-(methoxycarbonyl)phenyl)boronic acid (1.27 g, 7.05 mmol), Pd(PPh$_3$)$_4$ (0.163 g, 0.141 mmol) and sodium carbonate (4.98 g, 47.0 mmol) in 1,4-dioxane (20 mL) and water (20.00 mL) was stirred at 90° C. for 1 hour. The reaction mixture was worked up and the residue was purified by flash chromatography to provide the title product as white solid (1.3 g, 3.16 mmol, 67% yield). LCMS: m/e 412.19 (M+H)$^+$, 2.49 min (Method F).

Step 3: Preparation of (S)-methyl 4-(5,5,8a-trimethyl-1,2,3,5,8,8a-hexahydroisoquinolin-6-yl)benzoate A mixture of (S)-tert-butyl 6-(4-(methoxycarbonyl)phenyl)-5,5,8a-trimethyl-3,5,8,8a-tetrahydroisoquinoline-2(1H)-carboxylate (1.3 g, 3.16 mmol) and HCl (4M, 7.90 mL, 31.6 mmol) in THF (20 mL) was stirred at 20° C. for 40 hour. LCMS indicated the formation of desired product so the reaction mixture was concentrated under reduced pressure to provide the desired product as white solid (0.9 g, 2.89 mmol, 91% yield). LCMS: m/e 312.23 (M+H)$^+$, 1.79 min (Method F).

Step 4: Preparation of (S)-methyl 4-(2-(4-(((tert-butoxycarbonyl)amino)methyl)-4-phenylcyclohexyl)-5,5,8a-trimethyl-1,2,3,5,8,8a-hexahydroisoquinolin-6-yl)benzoate A mixture of (S)-methyl 4-(5,5,8a-trimethyl-1,2,3,5,8,8a-hexahydroisoquinolin-6-yl)benzoate (360 mg, 1.156 mmol), tert-butyl ((4-oxo-1-phenylcyclohexyl)methyl)carbamate (421 mg, 1.387 mmol) and titanium(IV) isopropoxide (0.339 mL, 1.156 mmol) in dichloromethane (100 mL) was stirred at 20° C. for 1 h, then sodium triacetoxyhydroborate (490 mg, 2.312 mmol) was added. The reaction mixture was stirred for 20 hours at room temperature, then was worked up. The residue was purified by flash chromatography using a 0-30% ethyl acetate/hexanes gradient to provide the title product as white solid (0.120 g, 0.200 mmol, 17% yield). LCMS: m/e 599.4 (M+H)$^+$, 2.16 min (Method F).

Step 5: Preparation of (S)-methyl 4-(2-(4-(aminomethyl)-4-phenylcyclohexyl)-5,5,8a-trimethyl-1,2,3,5,8,8a-hexahydroisoquinolin-6-yl)benzoate A mixture of (S)-methyl 4-(2-(4-(((tert-butoxycarbonyl)amino)methyl)-4-phenylcyclohexyl)-5,5,8a-trimethyl-1,2,3,5,8,8a-hexahydroisoquinolin-6-yl)benzoate (120 mg, 0.200 mmol) and HCl (4M, 0.501 mL, 2.004 mmol) in THF (2 mL) was stirred at 20° C. for 35 h. The reaction mixture was concentrated under reduced pressure to provide the title product as white solid (0.060 g, 0.120 mmol, 60%). LCMS: m/e 499.3 (M+H)$^+$, 1.85 min (Method F).

Step 6

A mixture of (S)-methyl 4-(2-(4-(aminomethyl)-4-phenylcyclohexyl)-5,5,8a-trimethyl-1,2,3,5,8,8a-hexahydroisoquinolin-6-yl)benzoate (6 mg, 0.012 mmol) and NaOH (1M, 0.120 mL, 0.120 mmol) in 1,4-dioxane (1.0 mL) was stirred at 80° C. for 3 h. The reaction mixture was filtered and purified by preparative HPLC to provide (S)-4-(2-(4-(aminomethyl)-4-phenylcyclohexyl)-5,5,8a-trimethyl-1,2,3,5,8,8a-hexahydroisoquinolin-6-yl)benzoic acid as white solid (2.0 mg, 0.004 mmol, 33% yield). LCMS: m/e 485.27 (M+H)$^+$, 1.74 min (method F).

Example C4

Preparation of (S)-4-(2-(4-((bis(2-(1,1-dioxidothiomorpholino)ethyl)amino)methyl)-4-phenylcyclohexyl)-5,5,8a-trimethyl-1,2,3,5,8,8a-hexahydroisoquinolin-6-yl)benzoic acid

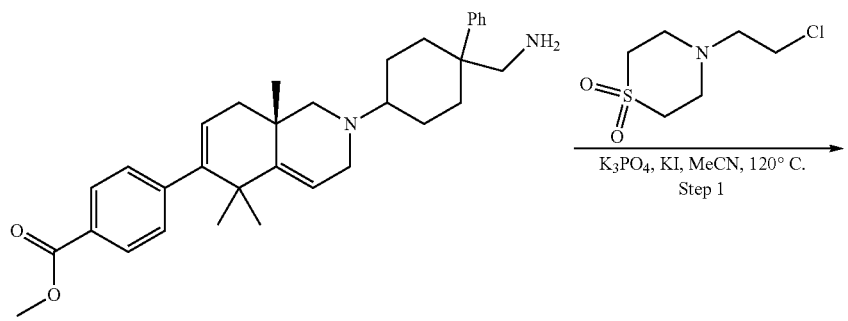

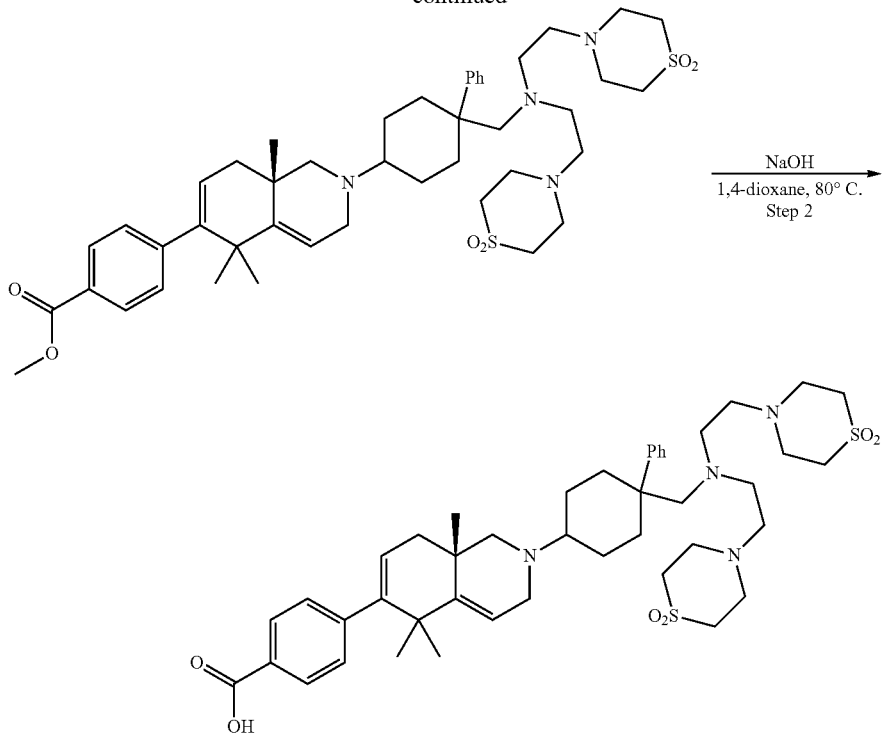

Example C4

Step 1: Preparation of (S)-methyl 4-(2-(4-((bis(2-(1,1-dioxidothiomorpholino)ethyl)amino)methyl)-4-phenylcyclohexyl)-5,5,8a-trimethyl-1,2,3,5,8,8a-hexahydroisoquinolin-6-yl)benzoate A mixture of (S)-methyl 4-(2-(4-(aminomethyl)-4-phenylcyclohexyl)-5,5,8a-trimethyl-1,2,3,5,8,8a-hexahydroisoquinolin-6-yl)benzoate (92526-066) (10 mg, 0.020 mmol), 4-(2-chloroethyl)thiomorpholine 1,1-dioxide (7.93 mg, 0.040 mmol), potassium phosphate (17.03 mg, 0.080 mmol) and potassium iodide (6.66 mg, 0.040 mmol) in acetonitrile (1 mL) was heated to 120° C. in a sealed pressure vessel for 4 hour. The reaction mixture was worked up. The title product was isolated as a yellow oil (10 mg, 0.012 mmol, 60% yield). LCMS: m/e 821.39 (M+H)$^+$, 1.86 min (Method F).

Step 2

A mixture of (S)-methyl 4-(2-(4-((bis(2-(1,1-dioxidothiomorpholino)ethyl)amino)methyl)-4-phenylcyclohexyl)-5,5,8a-trimethyl-1,2,3,5,8,8a-hexahydroisoquinolin-6-yl)benzoate (10 mg, 0.012 mmol) and NaOH (1M, 0.122 mL, 0.122 mmol) in 1,4-dioxane (1.0 mL) was stirred at 80° C. for 3 h. The mixture was cooled to rt, filtered and purified by preparative HPLC to provide (S)-4-(2-(4-((bis(2-(1,1-dioxidothiomorpholino)ethyl)amino)methyl)-4-phenylcyclohexyl)-5,5,8a-trimethyl-1,2,3,5,8,8a-hexahydroisoquinolin-6-yl)benzoic acid as a white solid (3.6 mg, 0.0044 mmol, 37% yield). LCMS: m/e 807.39 (M+H)$^+$, 1.68 min (Method F).

Example C5

Preparation of (S)-4-(2-(4-(((tert-butoxycarbonyl)amino)methyl)-4-phenylcyclohexyl)-5,5,8a-trimethyl-1,2,3,5,8,8a-hexahydroisoquinolin-6-yl)benzoic acid

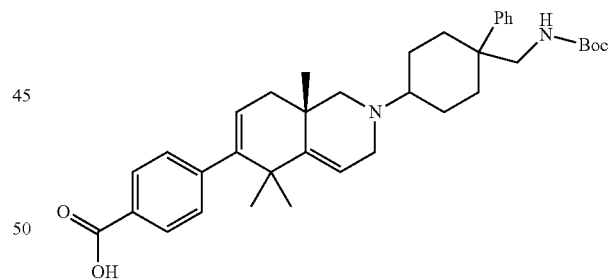

A mixture of (S)-methyl 4-(2-(4-(((tert-butoxycarbonyl)amino)methyl)-4-phenylcyclohexyl)-5,5,8a-trimethyl-1,2,3,5,8,8a-hexahydroisoquinolin-6-yl)benzoate (32 mg, 0.027 mmol) and NaOH (1M, 0.267 ml, 0.267 mmol) in 1,4-dioxane (1.0 ml) was stirred heated to 80° C. for 3 h. The reaction mixture was filtered and purified by preparative HPLC to provide the desired product as white solid (3.5 mg, 0.0059 mmol, 22% yield). LCMS: m/e 585.45 (M+H)$^+$, 2.09 min (Method F).

Results
Biology Data for the Examples
"μM" means micromolar;
"mL" means milliliter;
"μl" means microliter;

"mg" means milligram;
"μg" means microgram;

The materials and experimental procedures used to obtain the results reported in Tables 16 and 17 are described below.

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 μg/ml penicillin G and up to 100 units/ml streptomycin. The 293T cells were propagated in DMEM media supplemented with 10% heat inactivated fetal bovine serum (FBS), 100 units/ml penicillin G and 100 μg/ml streptomycin. The proviral DNA clone of $NL_{4-3}$ was obtained from the NIH AIDS Research and Reference Reagent Program. A recombinant $NL_{4-3}$ virus, in which a section of the nef gene from $NL_{4-3}$ was replaced with the *Renilla* luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 17. Table 16 is the key for the data in Table 17.

Results:

TABLE 16

Biological Data Key for $EC_{50}$

| Compounds with $EC_{50}$ <0.5 μM | Compounds with EC50 >0.5 μM and <3 μM | Compounds with EC50 >3 μM |
|---|---|---|
| Group "A" | Group "B" | Group "C" |

TABLE 17

Biological data

| Ex | Structure | 10% FBS $EC_{50}$ (uM) |
|---|---|---|
| 1 | 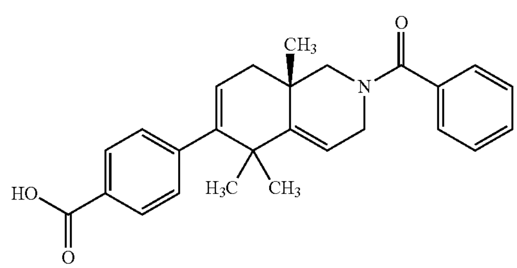 [SMILES: CC1(C)C(c2ccc(C(=O)O)cc2)=CC[C@]2(C)CN(C(=O)c3ccccc3)CC=C12] | C |
| 2 | 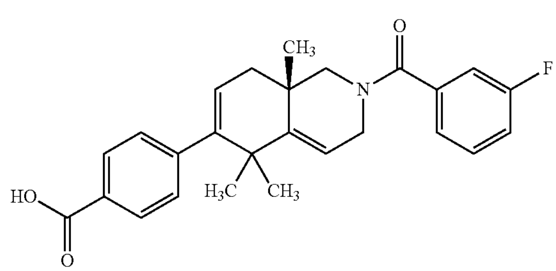 [SMILES: CC1(C)C(c2ccc(C(=O)O)cc2)=CC[C@]2(C)CN(C(=O)c3cccc(F)c3)CC=C12] | C |
| 3 | 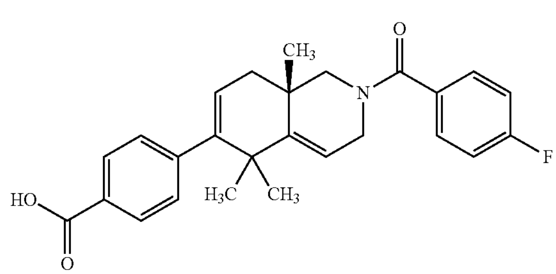 [SMILES: CC1(C)C(c2ccc(C(=O)O)cc2)=CC[C@]2(C)CN(C(=O)c3ccc(F)cc3)CC=C12] | C |

TABLE 17-continued

| | | Biological data | |
|---|---|---|---|
| Ex | Structure | | 10% FBS EC$_{50}$ (uM) |
| 4 | | | C |
| 5 | | | C |
| 6 | | | C |
| 7 | | | C |
| 8 | | | C |

TABLE 17-continued

| | Biological data | |
|---|---|---|
| Ex | Structure | 10% FBS EC$_{50}$ (uM) |
| 9 | | C |
| 10 | | C |
| 11 | | 0.46 |
| 12 | | C |

TABLE 17-continued

| | Biological data | |
|---|---|---|
| Ex | Structure | 10% FBS EC$_{50}$ (uM) |
| 13 | | C |
| 14 | | C |
| 15 | | C |
| 16 | | C |
| 17 | | 1.69 |

TABLE 17-continued

| | | Biological data | |
|---|---|---|---|
| Ex | Structure | | 10% FBS EC$_{50}$ (uM) |
| 18 | | | C |
| 19 | | | C |
| 20 | | | C |
| 21 | | | C |
| 22 | | | C |

TABLE 17-continued

| | Biological data | |
|---|---|---|
| Ex | Structure | 10% FBS EC$_{50}$ (uM) |
| 23 | | C |
| 24 | | C |
| 25 | | C |
| 26 | | 0.63 |
| 27 | | C |

TABLE 17-continued
| | | Biological data | |
|---|---|---|---|
| Ex | | Structure | 10% FBS EC$_{50}$ (uM) |
| 28 | | 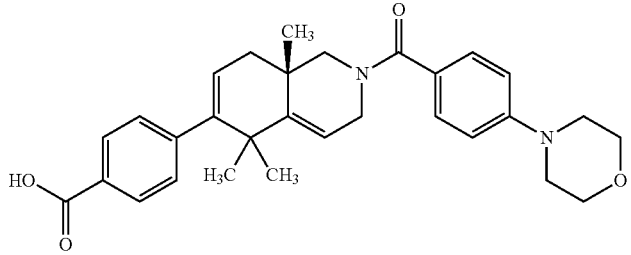 [SMILES: CC1(C)C(c2ccc(C(=O)O)cc2)=CC[C@]2(C)CN(C(=O)c3ccc(N4CCOCC4)cc3)CC=C12] | C |
| 29 | | 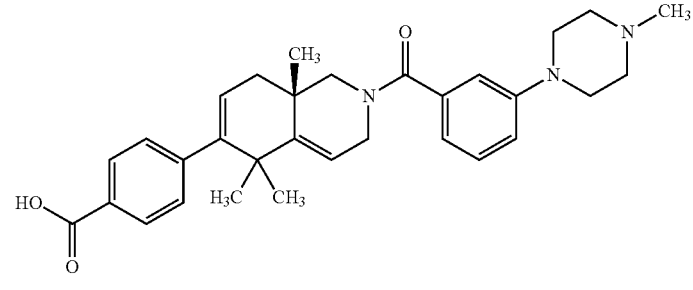 [SMILES: CN1CCN(c2cccc(C(=O)N3CC=C4C(C)(C)C(c5ccc(C(=O)O)cc5)=CC[C@]4(C)C3)c2)CC1] | C |
| 30 | | 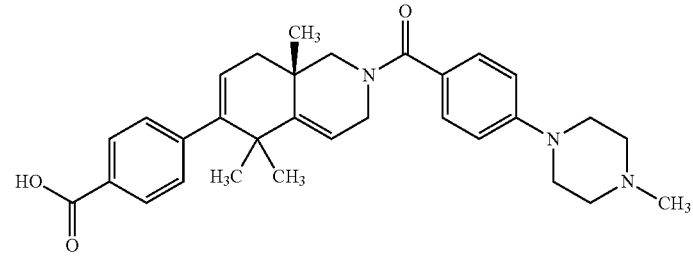 [SMILES: CN1CCN(c2ccc(C(=O)N3CC=C4C(C)(C)C(c5ccc(C(=O)O)cc5)=CC[C@]4(C)C3)cc2)CC1] | 2.27 |
| 31 | | 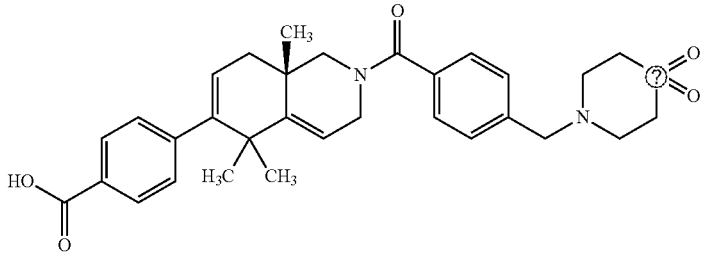 [SMILES: CC1(C)C(c2ccc(C(=O)O)cc2)=CC[C@]2(C)CN(C(=O)c3ccc(CN4CCS(=O)(=O)CC4)cc3)CC=C12] | C |
| 32 | | 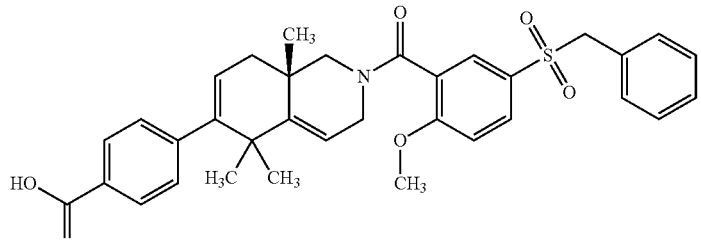 | 0.66 |

TABLE 17-continued
| | Biological data | |
|---|---|---|
| Ex | Structure | 10% FBS EC$_{50}$ (uM) |
| 33 | 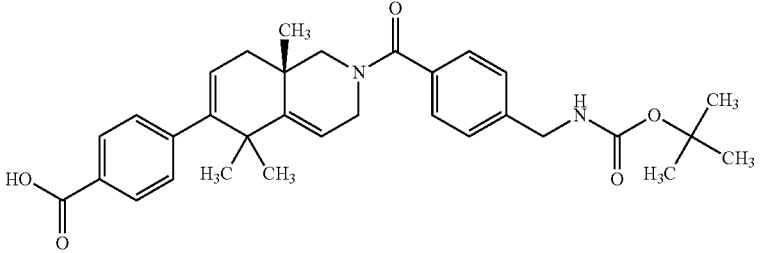 [SMILES: CC(C)(C)OC(=O)NCc1ccc(C(=O)N2CC=C3C(C)(C)C(c4ccc(C(=O)O)cc4)=CC[C@]3(C)C2)cc1] | C |
| 34 | 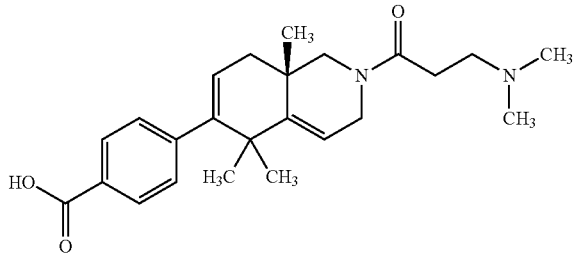 [SMILES: CN(C)CCC(=O)N1CC=C2C(C)(C)C(c3ccc(C(=O)O)cc3)=CC[C@]2(C)C1] | C |
| 35 | 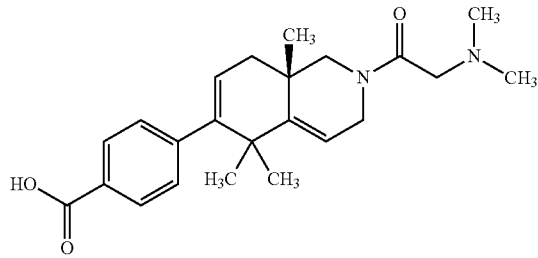 [SMILES: CN(C)CC(=O)N1CC=C2C(C)(C)C(c3ccc(C(=O)O)cc3)=CC[C@]2(C)C1] | C |
| 36 | 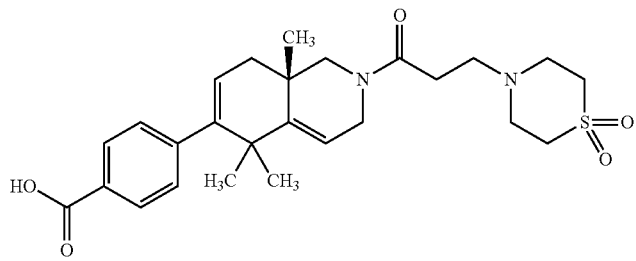 [SMILES: CC1(C)C(c2ccc(C(=O)O)cc2)=CC[C@]2(C)CN(C(=O)CCN3CCS(=O)(=O)CC3)CC=C12] | C |
| 37 | 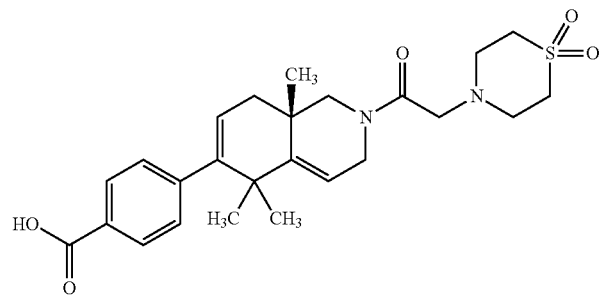 [SMILES: CC1(C)C(c2ccc(C(=O)O)cc2)=CC[C@]2(C)CN(C(=O)CN3CCS(=O)(=O)CC3)CC=C12] | C |

TABLE 17-continued

Biological data

| Ex | Structure | 10% FBS EC$_{50}$ (uM) |
|---|---|---|
| 38 | 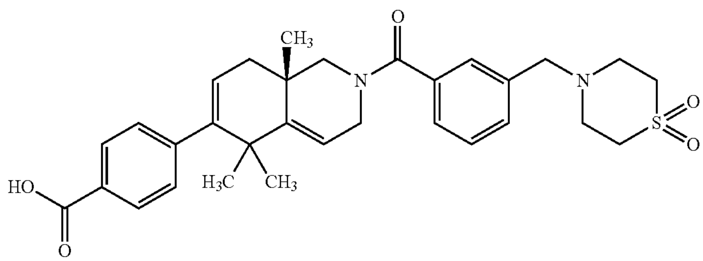 [SMILES: CC1(C)C(c2ccc(C(=O)O)cc2)=CC[C@]2(C)CN(C(=O)c3cccc(CN4CCS(=O)(=O)CC4)c3)CC=C12] | C |
| 39 | 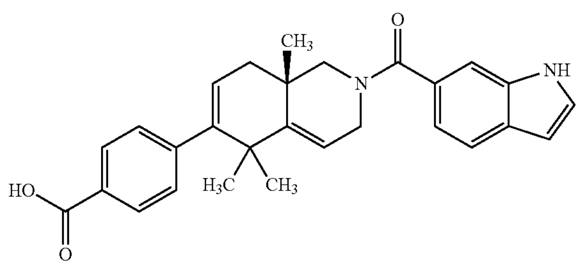 [SMILES: CC1(C)C(c2ccc(C(=O)O)cc2)=CC[C@]2(C)CN(C(=O)c3ccc4cc[nH]c4c3)CC=C12] | 1.49 |
| 40 | 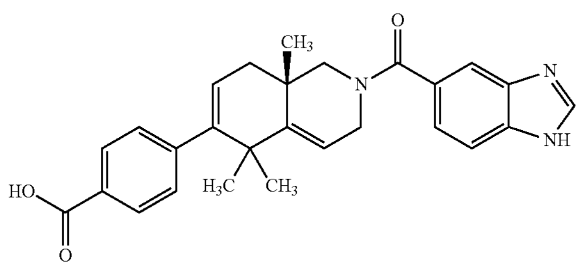 [SMILES: CC1(C)C(c2ccc(C(=O)O)cc2)=CC[C@]2(C)CN(C(=O)c3ccc4[nH]cnc4c3)CC=C12] | C |
| 41 | 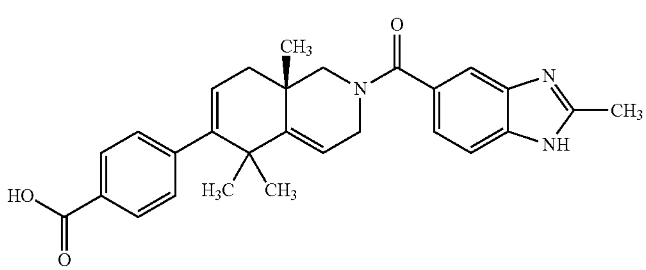 [SMILES: Cc1nc2cc(C(=O)N3CC=C4C(C)(C)C(c5ccc(C(=O)O)cc5)=CC[C@]4(C)C3)ccc2[nH]1] | C |
| 42 | 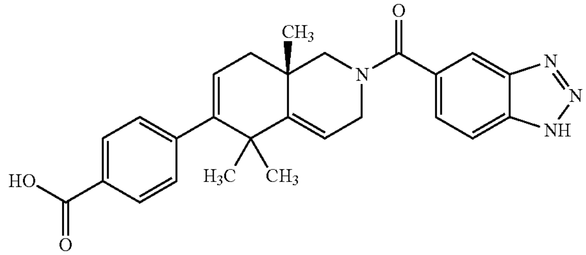 [SMILES: CC1(C)C(c2ccc(C(=O)O)cc2)=CC[C@]2(C)CN(C(=O)c3ccc4[nH]nnc4c3)CC=C12] | C |

TABLE 17-continued

Biological data

| Ex | Structure | 10% FBS EC$_{50}$ (uM) |
|---|---|---|
| 43 | 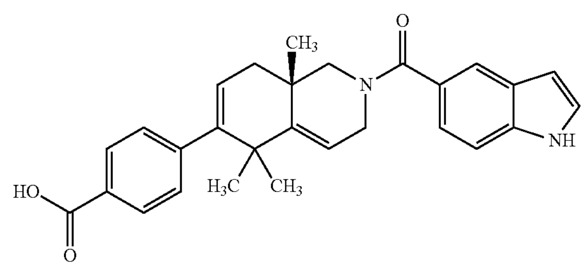 [SMILES: CC1(C)C(c2ccc(C(=O)O)cc2)=CC[C@]2(C)CN(C(=O)c3ccc4[nH]ccc4c3)CC=C12] | C |
| 44 | 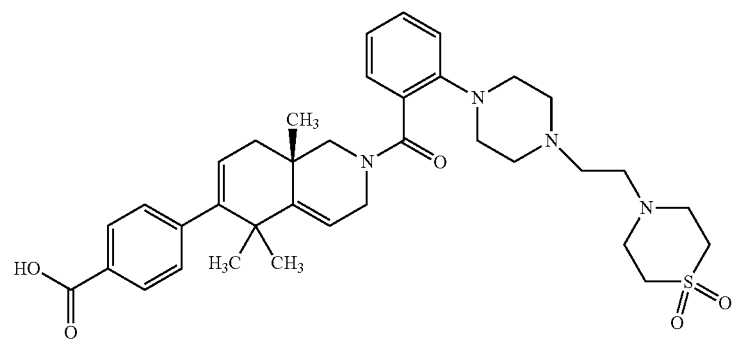 [SMILES: CC1(C)C(c2ccc(C(=O)O)cc2)=CC[C@]2(C)CN(C(=O)c3ccccc3N3CCN(CCN4CCS(=O)(=O)CC4)CC3)CC=C12] | 0.52 |
| 45 | 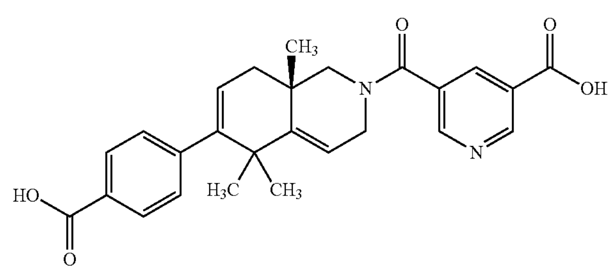 [SMILES: CC1(C)C(c2ccc(C(=O)O)cc2)=CC[C@]2(C)CN(C(=O)c3cncc(C(=O)O)c3)CC=C12] | C |
| 46 | 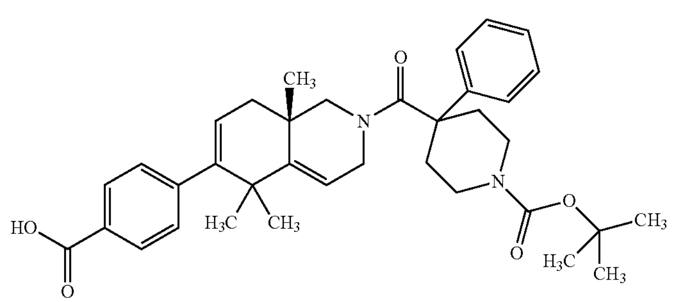 [SMILES: CC(C)(C)OC(=O)N1CCC(C(=O)N2CC=C3C(C)(C)C(c4ccc(C(=O)O)cc4)=CC[C@]3(C)C2)(c2ccccc2)CC1] | 0.25 |

TABLE 17-continued

Biological data

| Ex | Structure | 10% FBS EC$_{50}$ (uM) |
|---|---|---|
| 47 | 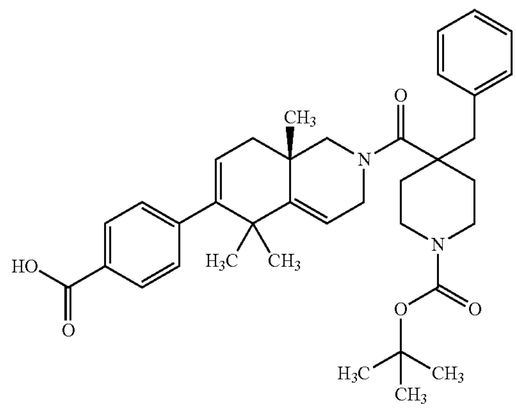 [SMILES: CC(C)(C)OC(=O)N1CCC(Cc2ccccc2)(C(=O)N2CC=C3C(C)(C)C(c4ccc(C(=O)O)cc4)=CC[C@]3(C)C2)CC1] | 1.07 |
| 48 | 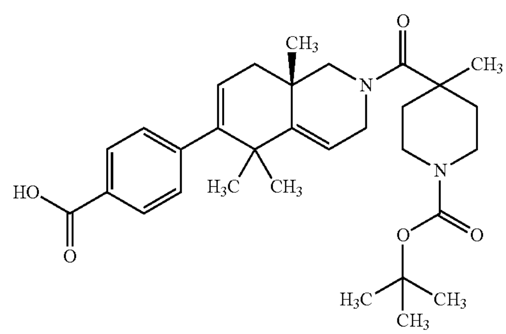 [SMILES: CC(C)(C)OC(=O)N1CCC(C)(C(=O)N2CC=C3C(C)(C)C(c4ccc(C(=O)O)cc4)=CC[C@]3(C)C2)CC1] | 0.27 |
| 49 | 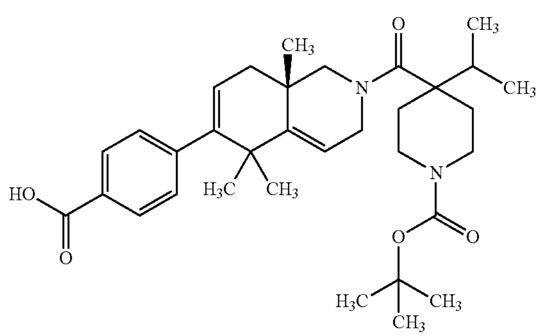 [SMILES: CC(C)C1(C(=O)N2CC=C3C(C)(C)C(c4ccc(C(=O)O)cc4)=CC[C@]3(C)C2)CCN(C(=O)OC(C)(C)C)CC1] | 1.18 |
| 50 | 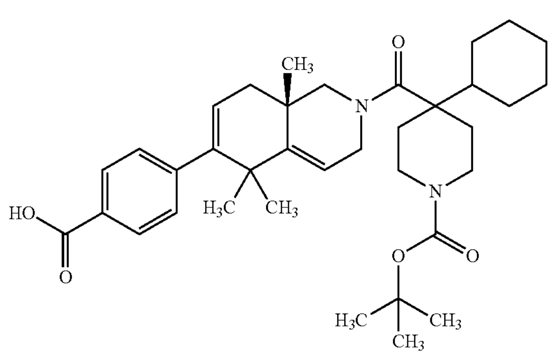 [SMILES: CC(C)(C)OC(=O)N1CCC(C(=O)N2CC=C3C(C)(C)C(c4ccc(C(=O)O)cc4)=CC[C@]3(C)C2)(C2CCCCC2)CC1] | 0.29 |

TABLE 17-continued
| | Biological data | |
|---|---|---|
| Ex | Structure | 10% FBS EC$_{50}$ (uM) |
| 51 | 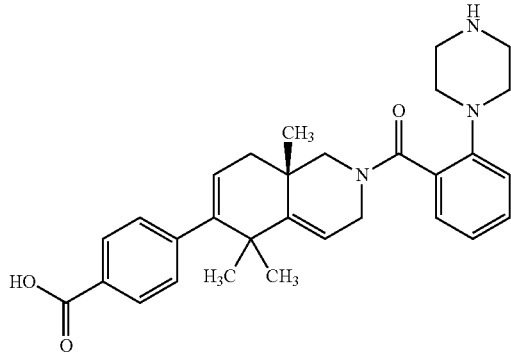 [SMILES: CC1(C)C(c2ccc(C(=O)O)cc2)=CC[C@]2(C)CN(C(=O)c3ccccc3N3CCNCC3)CC=C12] | 0.87 |
| 52 | 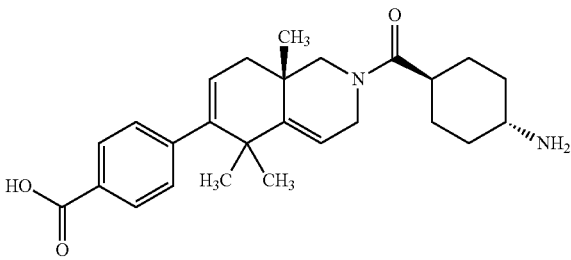 [SMILES: CC1(C)C(c2ccc(C(=O)O)cc2)=CC[C@]2(C)CN(C(=O)[C@H]3CC[C@H](N)CC3)CC=C12] | 3.62 |
| 53 | 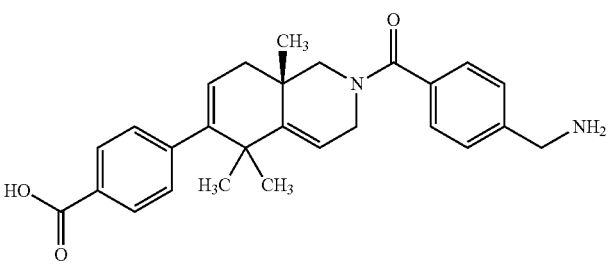 [SMILES: CC1(C)C(c2ccc(C(=O)O)cc2)=CC[C@]2(C)CN(C(=O)c3ccc(CN)cc3)CC=C12] | C |
| 54 | 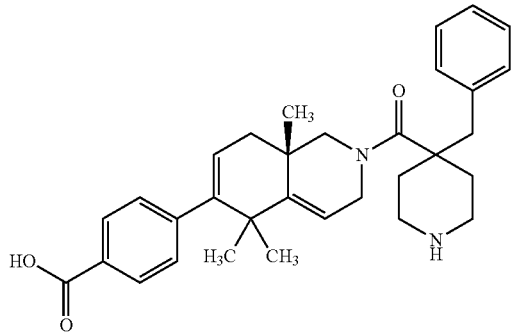 [SMILES: CC1(C)C(c2ccc(C(=O)O)cc2)=CC[C@]2(C)CN(C(=O)C3(Cc4ccccc4)CCNCC3)CC=C12] | 0.610 |

TABLE 17-continued
Biological data
| Ex | Structure | 10% FBS EC$_{50}$ (uM) |
|---|---|---|
| 55 | 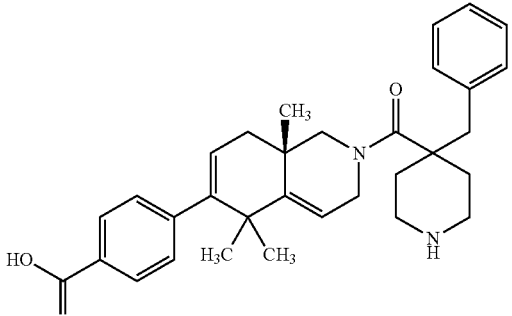 | 3.04 |
| 56 | 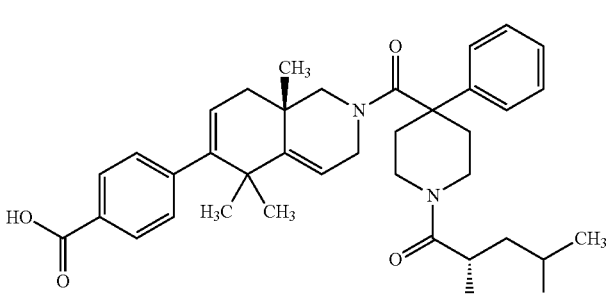 | A |
| 57 | 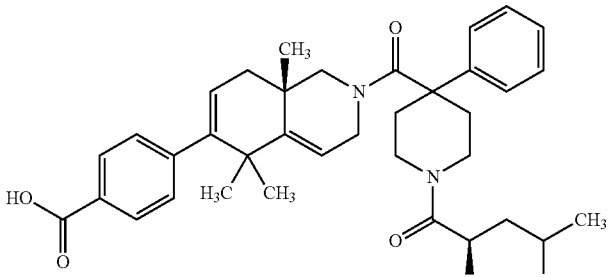 | 0.148 |
| 58 | 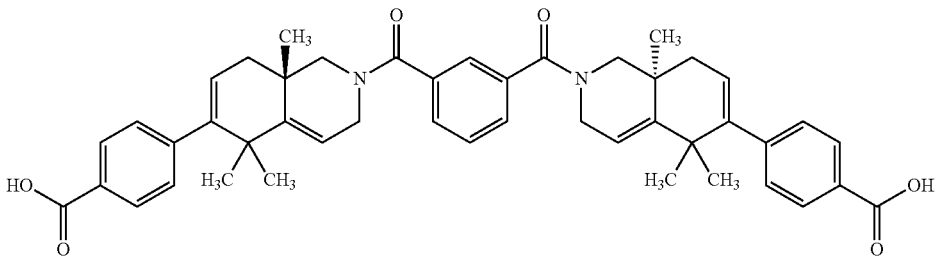 [SMILES: CC1(C)C(c2ccc(C(=O)O)cc2)=CC[C@]2(C)CN(C(=O)c3cccc(C(=O)N4CC=C5C(C)(C)C(c6ccc(C(=O)O)cc6)=CC[C@]5(C)C4)c3)CC=C12] | A |
| 59 | 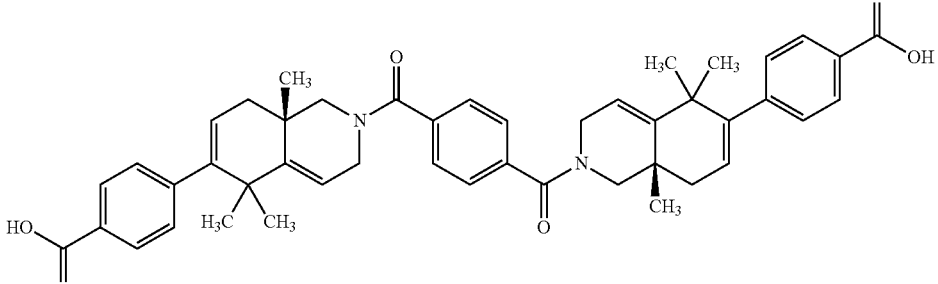 | 1.047 |

TABLE 17-continued

Biological data

| Ex | Structure | 10% FBS EC$_{50}$ (uM) |
|---|---|---|
| 60 | 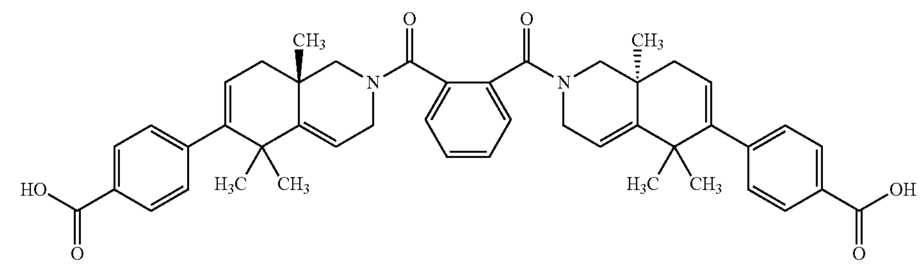 [SMILES: CC1(C)C(c2ccc(C(=O)O)cc2)=CC[C@]2(C)CN(C(=O)c3ccccc3C(=O)N3CC=C4C(C)(C)C(c5ccc(C(=O)O)cc5)=CC[C@]4(C)C3)CC=C12] | B |
| 61 | 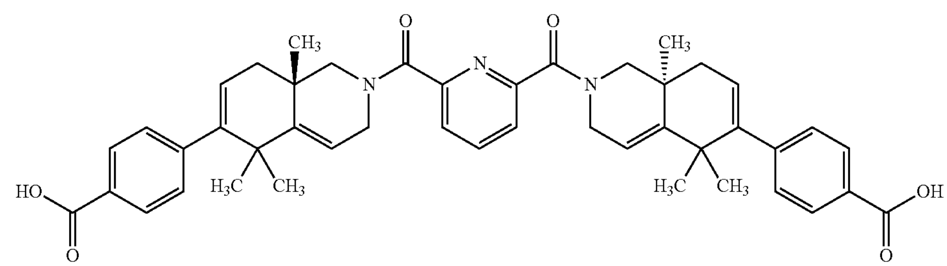 [SMILES: CC1(C)C(c2ccc(C(=O)O)cc2)=CC[C@]2(C)CN(C(=O)c3cccc(C(=O)N4CC=C5C(C)(C)C(c6ccc(C(=O)O)cc6)=CC[C@]5(C)C4)n3)CC=C12] | C |
| 62 | 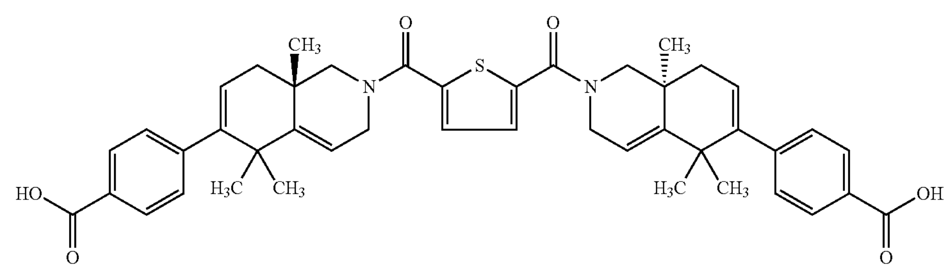 [SMILES: CC1(C)C(c2ccc(C(=O)O)cc2)=CC[C@]2(C)CN(C(=O)c3ccc(C(=O)N4CC=C5C(C)(C)C(c6ccc(C(=O)O)cc6)=CC[C@]5(C)C4)s3)CC=C12] | C |
| 63 | 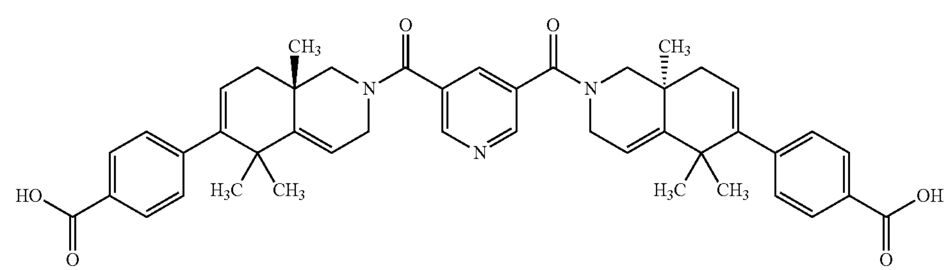 [SMILES: CC1(C)C(c2ccc(C(=O)O)cc2)=CC[C@]2(C)CN(C(=O)c3cncc(C(=O)N4CC=C5C(C)(C)C(c6ccc(C(=O)O)cc6)=CC[C@]5(C)C4)c3)CC=C12] | C |
| 64 | 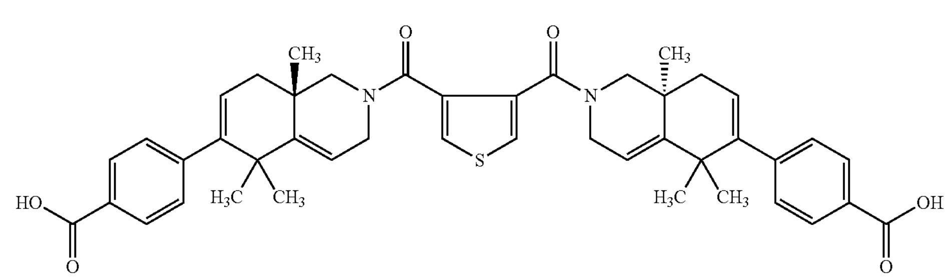 [SMILES: CC1(C)C(c2ccc(C(=O)O)cc2)=CC[C@]2(C)CN(C(=O)c3cscc3C(=O)N3CC=C4C(C)(C)C(c5ccc(C(=O)O)cc5)=CC[C@]4(C)C3)CC=C12] | 1.06 |

TABLE 17-continued

Biological data

| Ex | Structure | 10% FBS EC$_{50}$ (uM) |
|---|---|---|
| 65 | 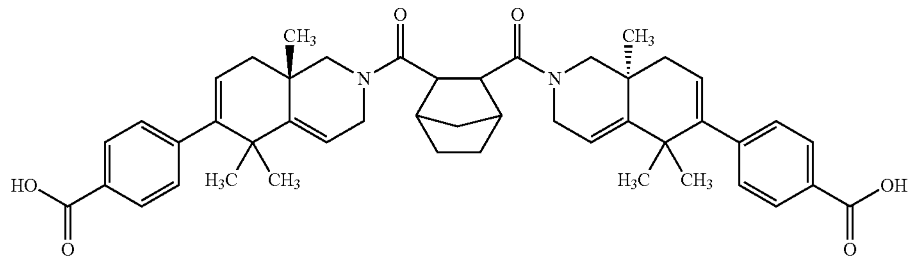 [SMILES: CC1(C)C(c2ccc(C(=O)O)cc2)=CC[C@]2(C)CN(C(=O)C3C4CCC(C4)C3C(=O)N3CC=C4C(C)(C)C(c5ccc(C(=O)O)cc5)=CC[C@]4(C)C3)CC=C12] | 2.81 |
| 66 | 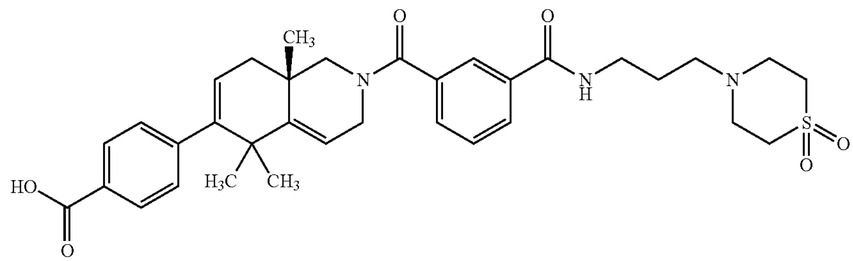 [SMILES: CC1(C)C(c2ccc(C(=O)O)cc2)=CC[C@]2(C)CN(C(=O)c3cccc(C(=O)NCCCN4CCS(=O)(=O)CC4)c3)CC=C12] | C |
| 67 | 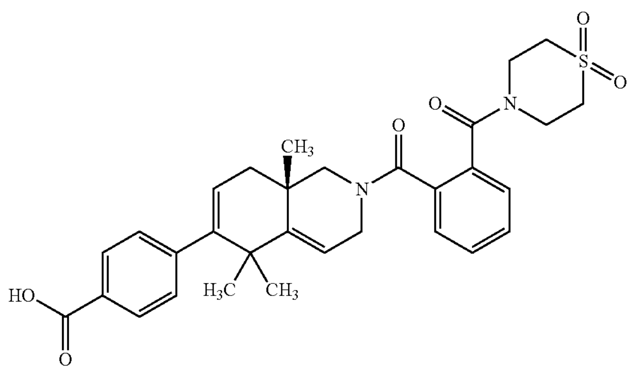 [SMILES: CC1(C)C(c2ccc(C(=O)O)cc2)=CC[C@]2(C)CN(C(=O)c3ccccc3C(=O)N3CCS(=O)(=O)CC3)CC=C12] | C |
| 68 | 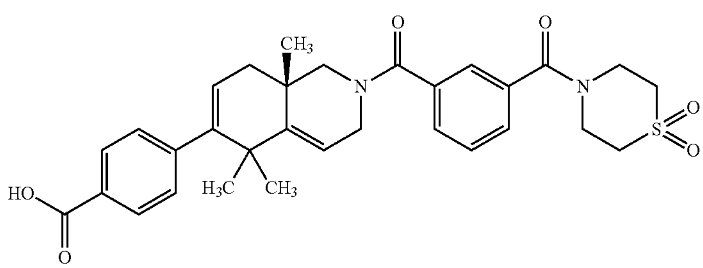 [SMILES: CC1(C)C(c2ccc(C(=O)O)cc2)=CC[C@]2(C)CN(C(=O)c3cccc(C(=O)N4CCS(=O)(=O)CC4)c3)CC=C12] | C |
| 69 | 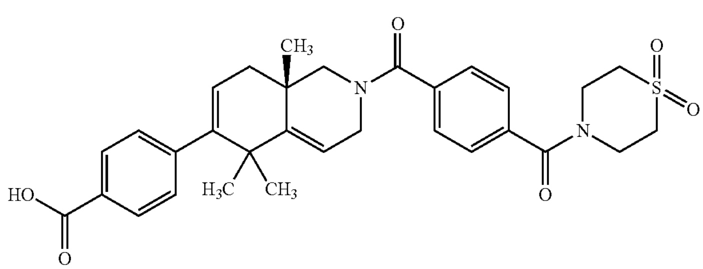 [SMILES: CC1(C)C(c2ccc(C(=O)O)cc2)=CC[C@]2(C)CN(C(=O)c3ccc(C(=O)N4CCS(=O)(=O)CC4)cc3)CC=C12] | C |

TABLE 17-continued

Biological data

| Ex | Structure | 10% FBS EC$_{50}$ (uM) |
|---|---|---|
| 70 | 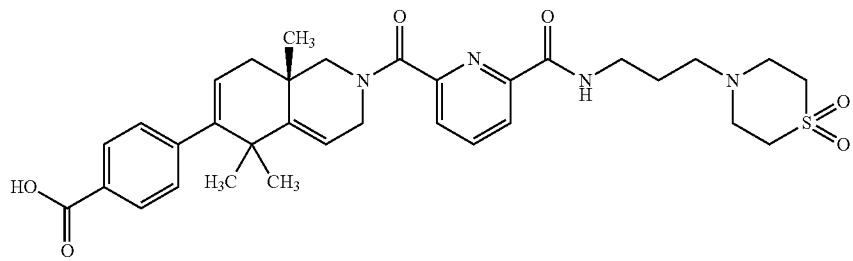 [SMILES: CC1(C)C(c2ccc(C(=O)O)cc2)=CC[C@]2(C)CN(C(=O)c3cccc(C(=O)NCCCN4CCS(=O)(=O)CC4)n3)CC=C12] | C |
| 71 | 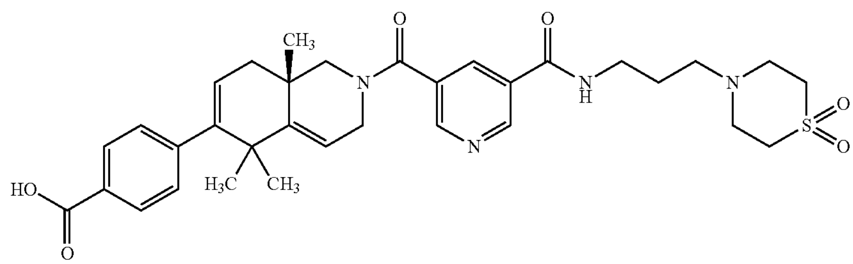 [SMILES: CC1(C)C(c2ccc(C(=O)O)cc2)=CC[C@]2(C)CN(C(=O)c3cncc(C(=O)NCCCN4CCS(=O)(=O)CC4)c3)CC=C12] | C |
| 72 | 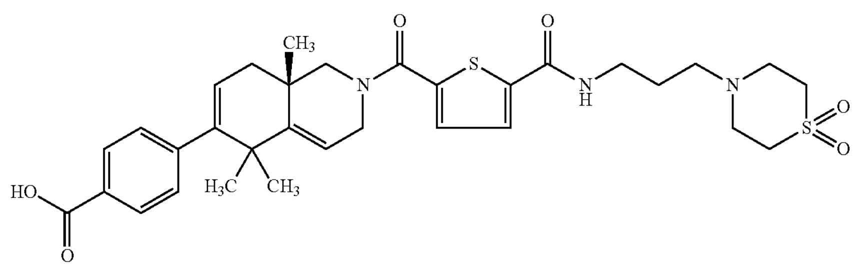 [SMILES: CC1(C)C(c2ccc(C(=O)O)cc2)=CC[C@]2(C)CN(C(=O)c3ccc(C(=O)NCCCN4CCS(=O)(=O)CC4)s3)CC=C12] | C |
| 73 | 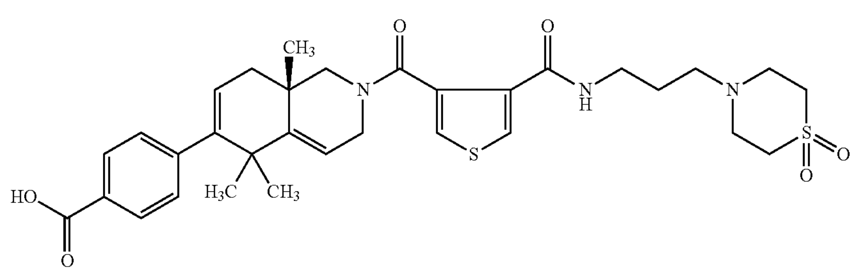 [SMILES: CC1(C)C(c2ccc(C(=O)O)cc2)=CC[C@]2(C)CN(C(=O)c3cscc3C(=O)NCCCN3CCS(=O)(=O)CC3)CC=C12] | C |
| 74 | 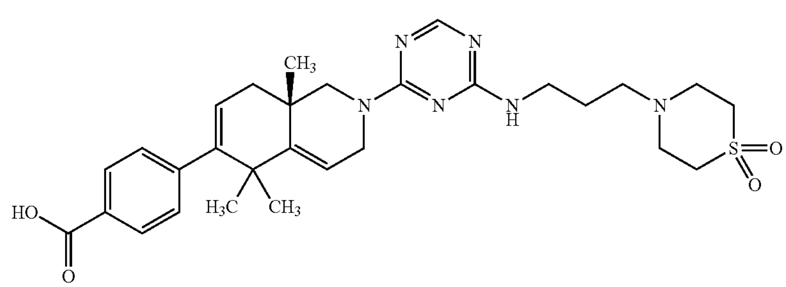 [SMILES: CC1(C)C(c2ccc(C(=O)O)cc2)=CC[C@]2(C)CN(c3ncnc(NCCCN4CCS(=O)(=O)CC4)n3)CC=C12] | 0.34 |

TABLE 17-continued

| Ex | Structure | 10% FBS EC$_{50}$ (uM) |
|---|---|---|
| 75 | 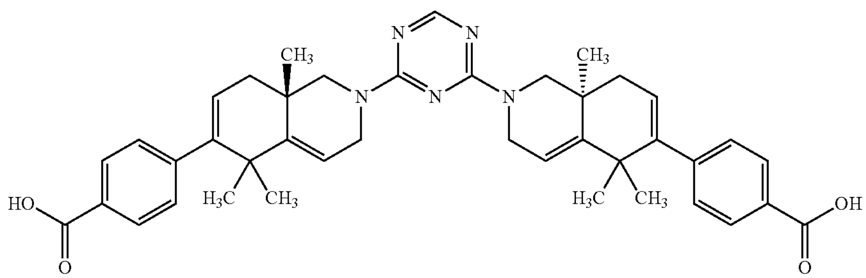 [SMILES: CC1(C)C(c2ccc(C(=O)O)cc2)=CC[C@]2(C)CN(c3ncnc(N4CC=C5C(C)(C)C(c6ccc(C(=O)O)cc6)=CC[C@]5(C)C4)n3)CC=C12] | 0.19 |
| 76 | 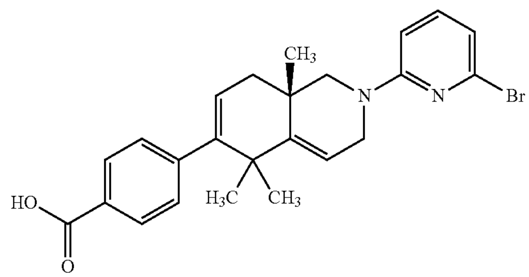 [SMILES: CC1(C)C(c2ccc(C(=O)O)cc2)=CC[C@]2(C)CN(c3cccc(Br)n3)CC=C12] | 0.98 |
| 77 | 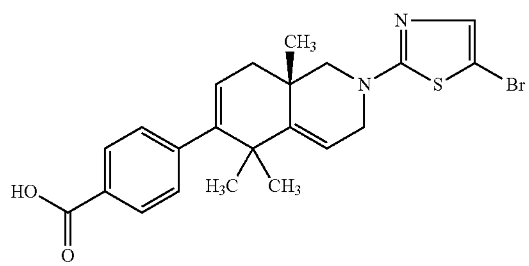 [SMILES: CC1(C)C(c2ccc(C(=O)O)cc2)=CC[C@]2(C)CN(c3ncc(Br)s3)CC=C12] | C |
| 78 | 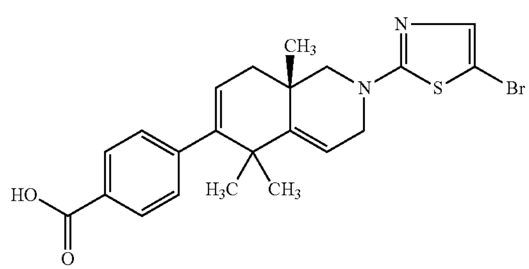 [SMILES: CC1(C)C(c2ccc(C(=O)O)cc2)=CC[C@]2(C)CN(c3ncc(Br)s3)CC=C12] | 0.27 |
| 79 | 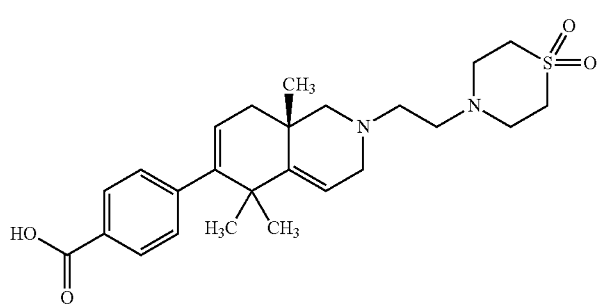 [SMILES: CC1(C)C(c2ccc(C(=O)O)cc2)=CC[C@]2(C)CN(CCN3CCS(=O)(=O)CC3)CC=C12] | C |

TABLE 17-continued

| | Biological data | |
|---|---|---|
| Ex | Structure | 10% FBS EC$_{50}$ (uM) |
| 80 | | 0.179 |
| 81 | | B |
| 82 | | A |
| 83 | | A |

TABLE 17-continued
| | | Biological data | |
|---|---|---|---|
| Ex | Structure | | 10% FBS EC$_{50}$ (uM) |
| 84 | 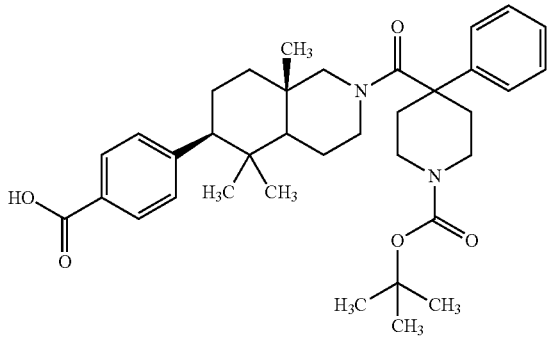 [SMILES: CC(C)(C)OC(=O)N1CCC(C(=O)N2CCC3C(C)(C)[C@@H](c4ccc(C(=O)O)cc4)CC[C@]3(C)C2)(c2ccccc2)CC1] | | 0.050 |
| 85 | 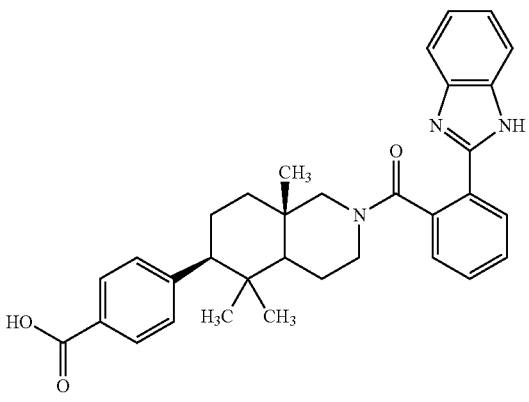 [SMILES: CC1(C)C2CCN(C(=O)c3ccccc3-c3nc4ccccc4[nH]3)C[C@@]2(C)CC[C@@H]1c1ccc(C(=O)O)cc1] | | A |
| 86 | 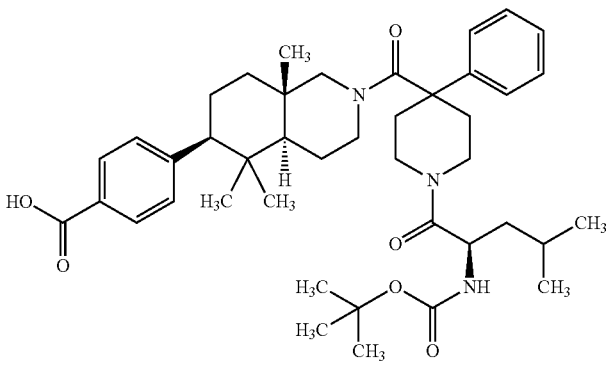 [SMILES: CC(C)C[C@@H](NC(=O)OC(C)(C)C)C(=O)N1CCC(C(=O)N2CC[C@H]3C(C)(C)[C@@H](c4ccc(C(=O)O)cc4)CC[C@]3(C)C2)(c2ccccc2)CC1] | | A |
| 87 | 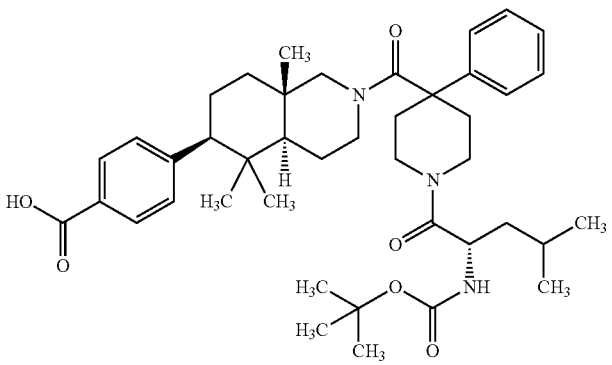 [SMILES: CC(C)C[C@H](NC(=O)OC(C)(C)C)C(=O)N1CCC(C(=O)N2CC[C@H]3C(C)(C)[C@@H](c4ccc(C(=O)O)cc4)CC[C@]3(C)C2)(c2ccccc2)CC1] | | 0.101 |

TABLE 17-continued

| | | Biological data | |
|---|---|---|---|
| Ex | | Structure | 10% FBS EC$_{50}$ (uM) |
| 88 | | | A |
| 89 | | | 0.067 |
| 90 | | | C |
| 91 | | | C |

TABLE 17-continued

Biological data

| Ex | Structure | 10% FBS EC$_{50}$ (uM) |
|---|---|---|
| 92 | 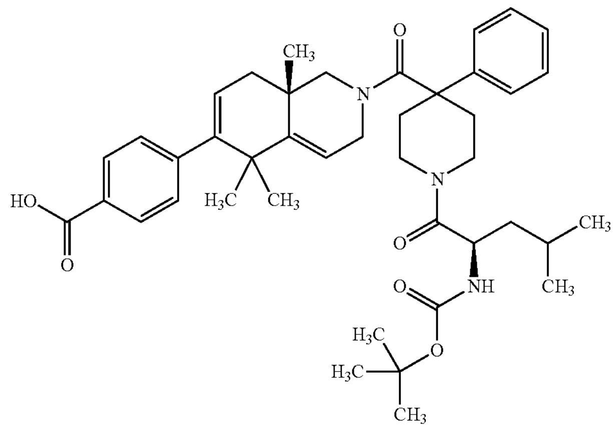 [SMILES: CC(C)C[C@@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 0.008 |
| 93 | 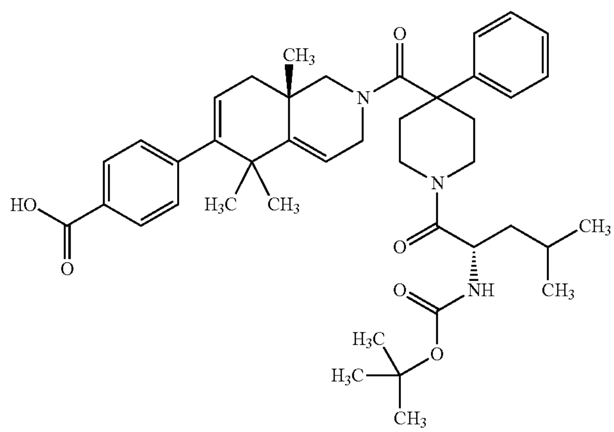 [SMILES: CC(C)C[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | A |
| 94 | 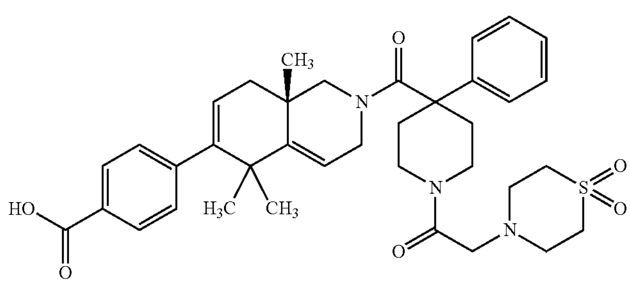 [SMILES: CC1(C)C(c2ccc(C(=O)O)cc2)=CC[C@]2(C)CN(C(=O)C3(c4ccccc4)CCN(C(=O)CN4CCS(=O)(=O)CC4)CC3)CC=C12] | 1.37 |
| 95 | 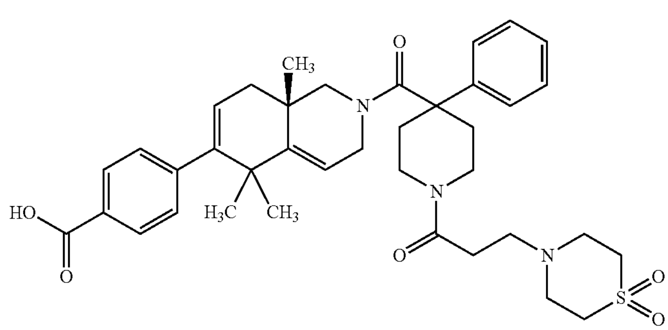 [SMILES: CC1(C)C(c2ccc(C(=O)O)cc2)=CC[C@]2(C)CN(C(=O)C3(c4ccccc4)CCN(C(=O)CCN4CCS(=O)(=O)CC4)CC3)CC=C12] | 2.70 |

TABLE 17-continued

| | Biological data | |
|---|---|---|
| Ex | Structure | 10% FBS EC$_{50}$ (uM) |
| 96 | | 1.35 |
| 97 | | 0.051 |
| 98 | | A |

TABLE 17-continued

| | Biological data | |
|---|---|---|
| Ex | Structure | 10% FBS EC$_{50}$ (uM) |
| 99 | | 0.016 |
| 100 | | 2.81 |
| 101 | | 2.98 |

TABLE 17-continued

| | Biological data | |
|---|---|---|
| Ex | Structure | 10% FBS EC$_{50}$ (uM) |
| A1 | | C |
| A30 | | 1.08 |
| A36 | | 0.38 |
| A40 | | C |

TABLE 17-continued

| | Biological data | |
|---|---|---|
| Ex | Structure | 10% FBS EC$_{50}$ (uM) |
| A46 | | 1.32 |
| A58 | | 1.85 |
| A66 | | C |
| A71 | | 1.30 |

TABLE 17-continued
| | Biological data | |
|---|---|---|
| Ex | Structure | 10% FBS EC$_{50}$ (uM) |
| A79 | 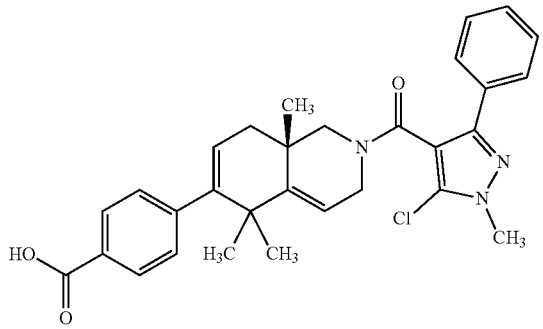 [SMILES: Cn1nc(-c2ccccc2)c(C(=O)N2CC=C3C(C)(C)C(c4ccc(C(=O)O)cc4)=CC[C@]3(C)C2)c1Cl] | 0.87 |
| A86 | 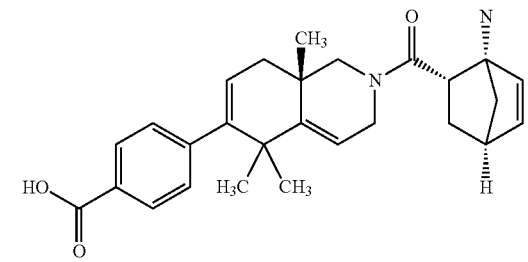 [SMILES: CC1(C)C(c2ccc(C(=O)O)cc2)=CC[C@]2(C)CN(C(=O)[C@H]3C[C@@H]4C=C[C@@]3(N)C4)CC=C12] | C |
| A91 | 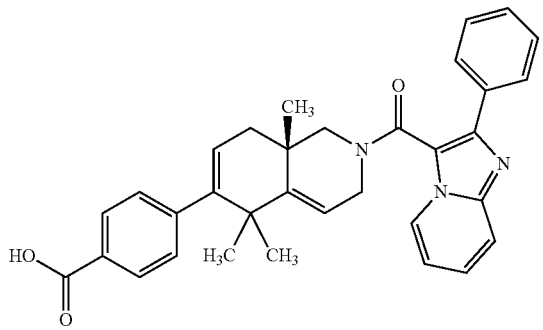 [SMILES: CC1(C)C(c2ccc(C(=O)O)cc2)=CC[C@]2(C)CN(C(=O)c3c(-c4ccccc4)nc4ccccn34)CC=C12] | 0.711 |
| A111 | 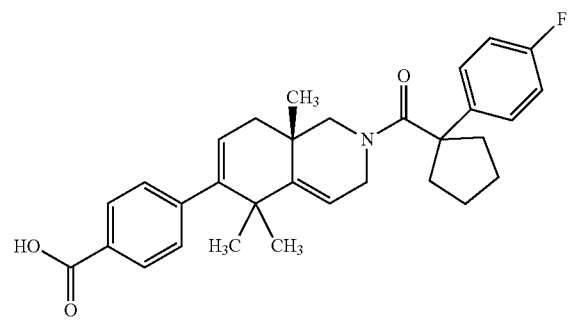 [SMILES: CC1(C)C(c2ccc(C(=O)O)cc2)=CC[C@]2(C)CN(C(=O)C3(c4ccc(F)cc4)CCCC3)CC=C12] | C |

TABLE 17-continued

| | Biological data | |
|---|---|---|
| Ex | Structure | 10% FBS EC$_{50}$ (uM) |
| A112 | | 1.104 |
| A114 | | 0.052 |
| A168 | | A |

TABLE 17-continued

| Ex | Structure | 10% FBS EC$_{50}$ (uM) |
|---|---|---|
| A185 | 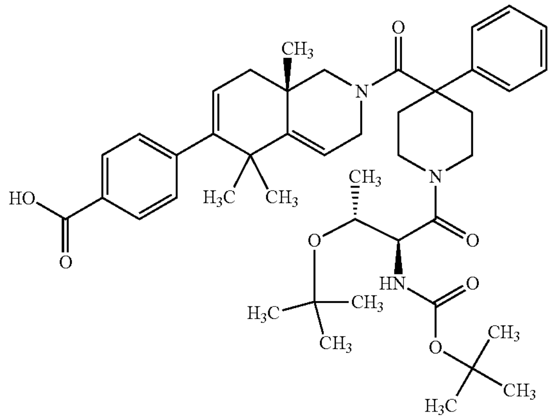 [SMILES: C[C@@H](OC(C)(C)C)[C@H](NC(=O)OC(C)(C)C)C(=O)N1CCC(C(=O)N2CC=C3C(C)(C)C(c4ccc(C(=O)O)cc4)=CC[C@]3(C)C2)(c2ccccc2)CC1] | 0.123 |
| A195 | 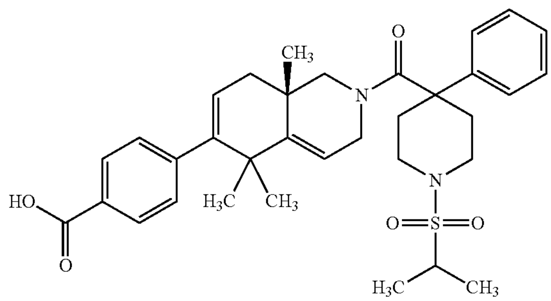 | A |
| A197 | 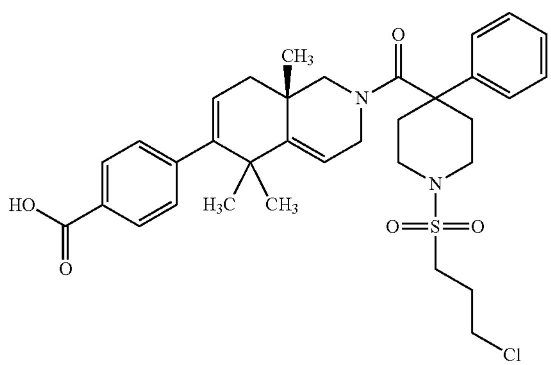 [SMILES: CC1(C)C(c2ccc(C(=O)O)cc2)=CC[C@]2(C)CN(C(=O)C3(c4ccccc4)CCN(S(=O)(=O)CCCCl)CC3)CC=C12] | 0.147 |
| A204 | 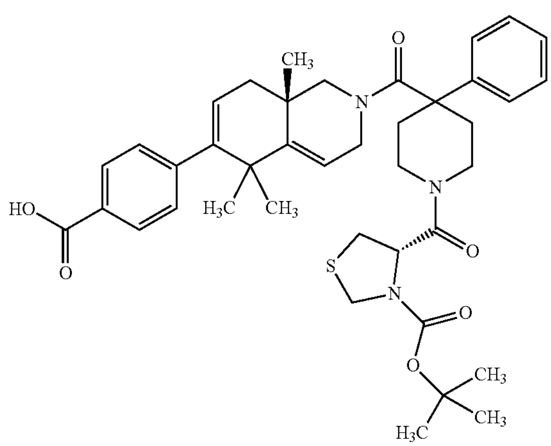 [SMILES: CC(C)(C)OC(=O)N1CSC[C@@H]1C(=O)N1CCC(C(=O)N2CC=C3C(C)(C)C(c4ccc(C(=O)O)cc4)=CC[C@]3(C)C2)(c2ccccc2)CC1] | 0.309 |

TABLE 17-continued

Biological data

| Ex | Structure | 10% FBS EC$_{50}$ (uM) |
|---|---|---|
| A219 | 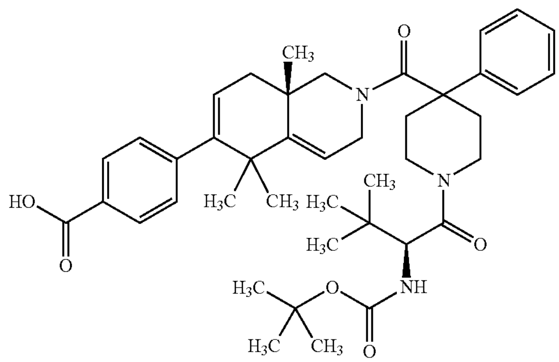 [SMILES: CC(C)(C)OC(=O)N[C@H](C(=O)N1CCC(C(=O)N2CC=C3C(C)(C)C(c4ccc(C(=O)O)cc4)=CC[C@]3(C)C2)(c2ccccc2)CC1)C(C)(C)C] | 0.150 |
| A254 | 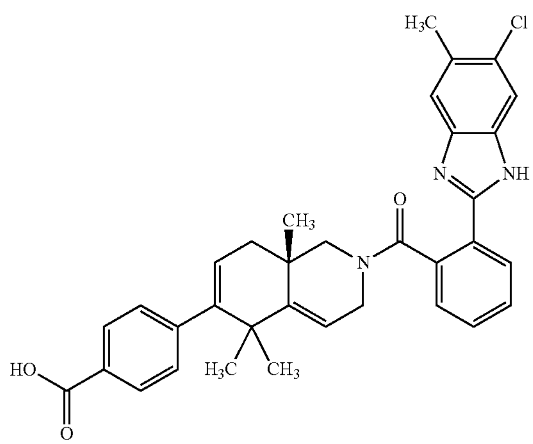 | A |
| A260 | 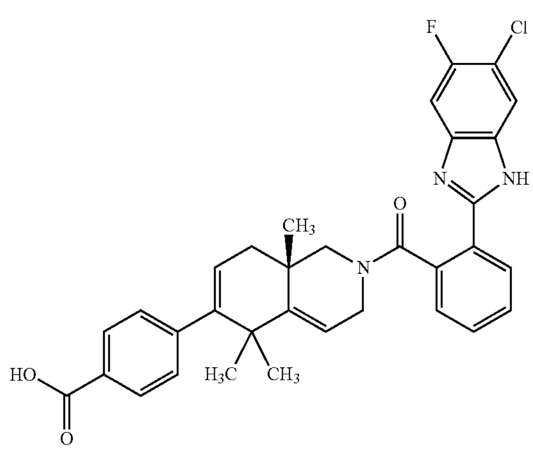 | 0.298 |

TABLE 17-continued
| | Biological data | |
|---|---|---|
| Ex | Structure | 10% FBS EC$_{50}$ (uM) |
| A265 | 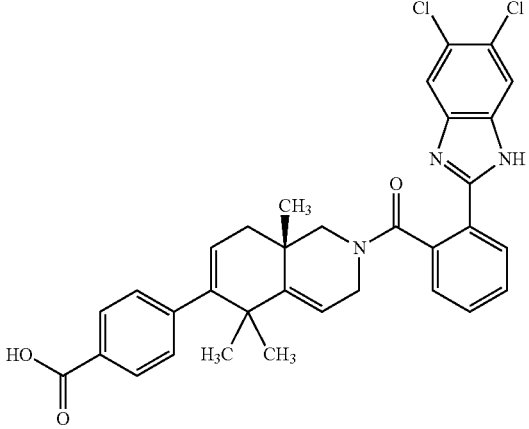 | A |
| A266 | 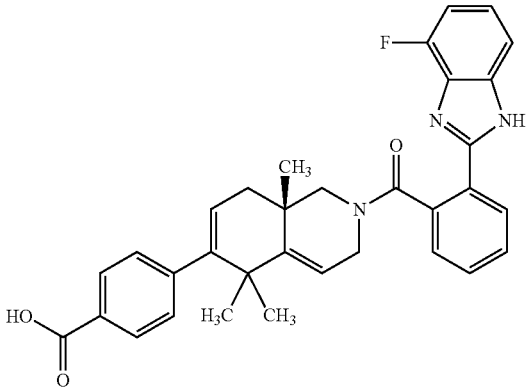 | A |
| A267 | 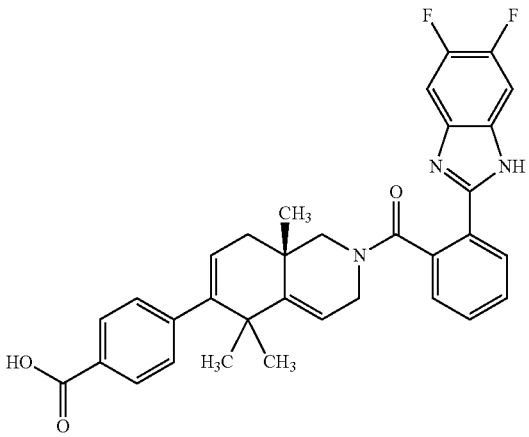 [SMILES: CC1(C)C(c2ccc(C(=O)O)cc2)=CC[C@]2(C)CN(C(=O)c3ccccc3-c3nc4cc(F)c(F)cc4[nH]3)CC=C12] | B |

TABLE 17-continued

| | Biological data | |
|---|---|---|
| Ex | Structure | 10% FBS EC$_{50}$ (uM) |
| A268 | | 0.014 |
| A270 | | 0.014 |
| A271 | | A |

TABLE 17-continued

| | Biological data | |
|---|---|---|
| Ex | Structure | 10% FBS EC$_{50}$ (uM) |
| A272 | | A |
| A273 | | 0.063 |
| A274 | | C |

TABLE 17-continued

Biological data

| Ex | Structure | 10% FBS EC$_{50}$ (uM) |
|---|---|---|
| A275 | 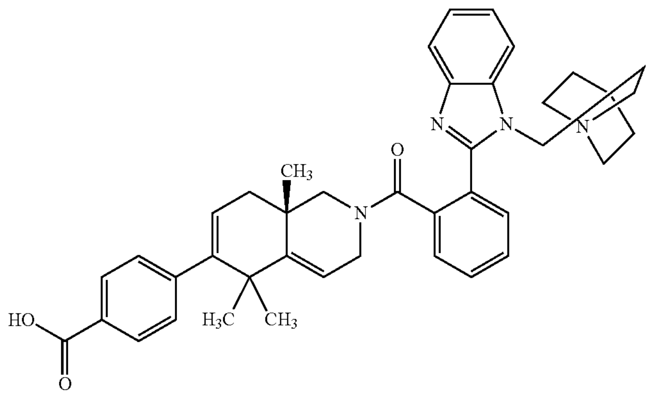 [SMILES: CC1(C)C(c2ccc(C(=O)O)cc2)=CC[C@]2(C)CN(C(=O)c3ccccc3-c3nc4ccccc4n3CCCN3CCCCC3)CC=C12] | 1.70 |
| A277 | 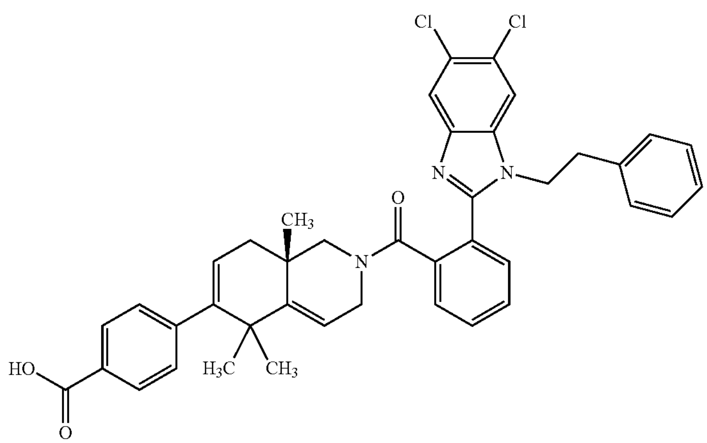 [SMILES: CC1(C)C(c2ccc(C(=O)O)cc2)=CC[C@]2(C)CN(C(=O)c3ccccc3-c3nc4cc(Cl)c(Cl)cc4n3CCc3ccccc3)CC=C12] | 2.25 |
| A278 | 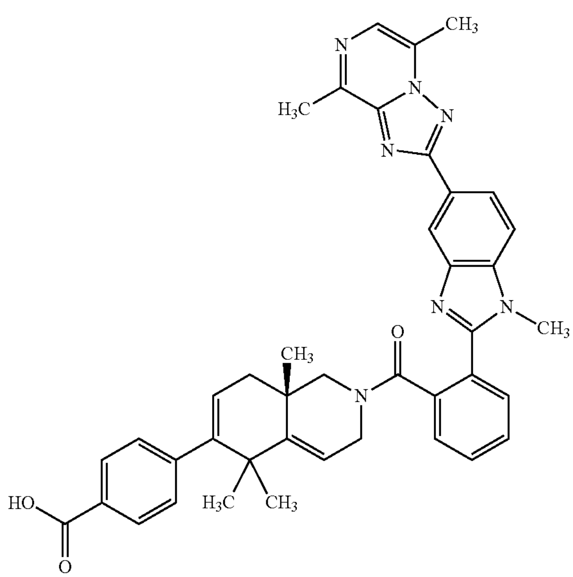 [SMILES: Cc1ncc(C)n2nc(-c3ccc4c(c3)nc(-c3ccccc3C(=O)N3CC=C5C(C)(C)C(c6ccc(C(=O)O)cc6)=CC[C@]5(C)C3)n4C)nc12] | 4.96 |

TABLE 17-continued

| | Biological data | |
|---|---|---|
| Ex | Structure | 10% FBS EC$_{50}$ (uM) |
| A279 | | 0.39 |
| A280 | | 0.55 |
| A281 | | 0.95 |

TABLE 17-continued
| | Biological data | |
|---|---|---|
| Ex | Structure | 10% FBS EC$_{50}$ (uM) |
| A283 | 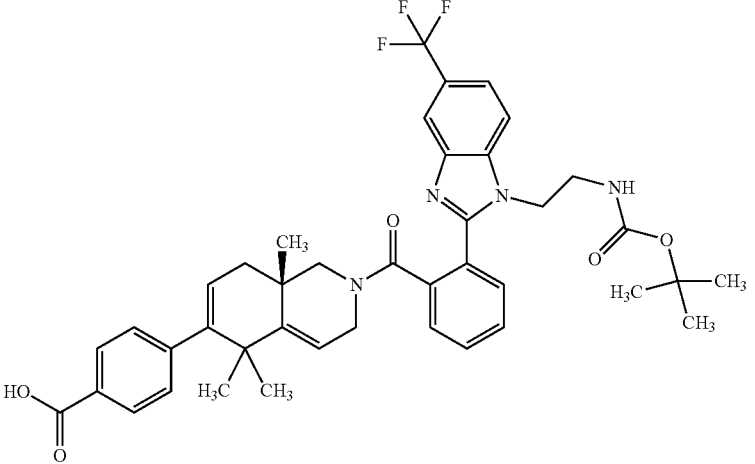 [SMILES: CC(C)(C)OC(=O)NCCn1c(-c2ccccc2C(=O)N2CC=C3C(C)(C)C(c4ccc(C(=O)O)cc4)=CC[C@]3(C)C2)nc2cc(C(F)(F)F)ccc21] | 1.37 |
| A286 | 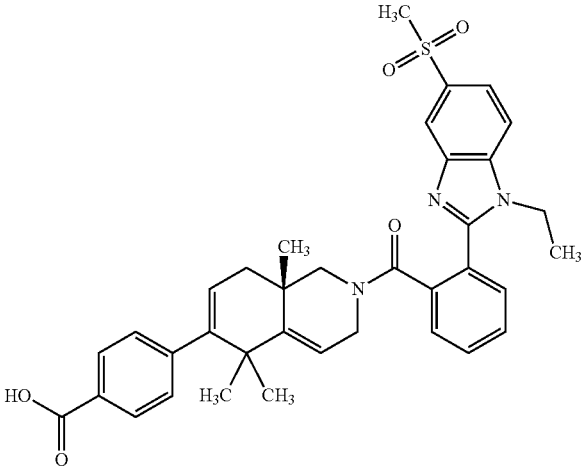 [SMILES: CCn1c(-c2ccccc2C(=O)N2CC=C3C(C)(C)C(c4ccc(C(=O)O)cc4)=CC[C@]3(C)C2)nc2cc(S(C)(=O)=O)ccc21] | C |
| A290 | 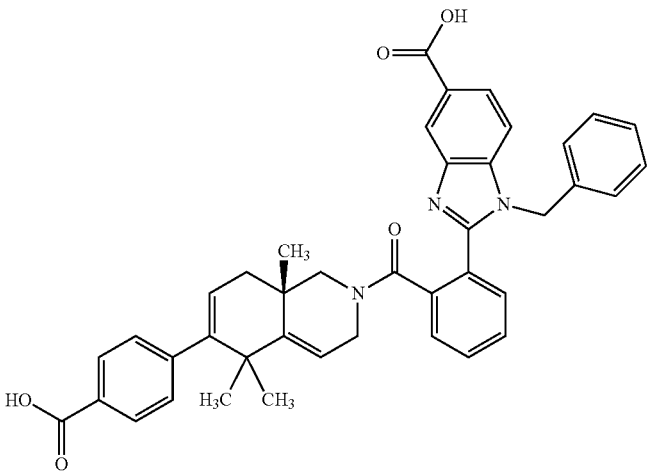 [SMILES: CC1(C)C(c2ccc(C(=O)O)cc2)=CC[C@]2(C)CN(C(=O)c3ccccc3-c3nc4cc(C(=O)O)ccc4n3Cc3ccccc3)CC=C12] | C |

TABLE 17-continued

|  | Biological data | |
|---|---|---|
| Ex | Structure | 10% FBS EC$_{50}$ (uM) |
| A293 | (structure) | C |
| A294 | (structure) | C |
| A296 | (structure) | C |

TABLE 17-continued

| | Biological data | |
|---|---|---|
| Ex | Structure | 10% FBS EC$_{50}$ (uM) |
| A298 | | 0.060 |
| A299 | | A |
| A309 | | 0.171 |

TABLE 17-continued

| | Biological data | |
|---|---|---|
| Ex | Structure | 10% FBS EC$_{50}$ (uM) |
| A311 | | 0.218 |
| A314 | | B |
| A315 | | 0.127 |

TABLE 17-continued

| | Biological data | |
|---|---|---|
| Ex | Structure | 10% FBS EC$_{50}$ (uM) |
| A318 | | A |
| A320 | | 0.183 |
| A324 | | A |

TABLE 17-continued
| | Biological data | |
|---|---|---|
| Ex | Structure | 10% FBS EC$_{50}$ (uM) |
| A325 | 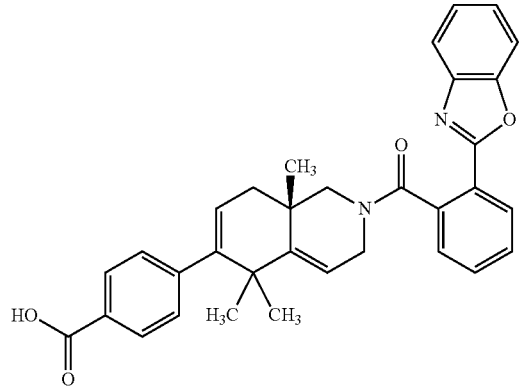 [SMILES: CC1(C)C(c2ccc(C(=O)O)cc2)=CC[C@]2(C)CN(C(=O)c3ccccc3-c3nc4ccccc4o3)CC=C12] | 0.235 |
| A326 | 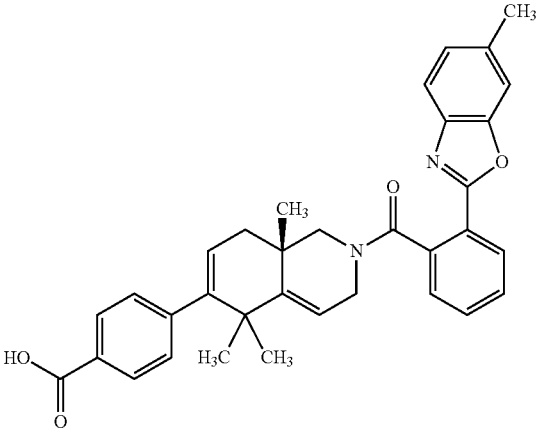 [SMILES: Cc1ccc2nc(-c3ccccc3C(=O)N3CC=C4C(C)(C)C(c5ccc(C(=O)O)cc5)=CC[C@]4(C)C3)oc2c1] | 0.257 |
| A332 | 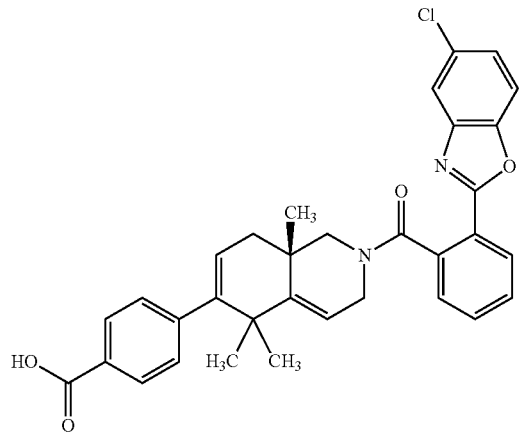 [SMILES: CC1(C)C(c2ccc(C(=O)O)cc2)=CC[C@]2(C)CN(C(=O)c3ccccc3-c3nc4cc(Cl)ccc4o3)CC=C12] | A |

TABLE 17-continued

| | Biological data | |
|---|---|---|
| Ex | Structure | 10% FBS EC$_{50}$ (uM) |
| A334 | | A |
| A338 | | B |
| B1 | | 0.024 |

TABLE 17-continued

Biological data

| Ex | Structure | 10% FBS EC$_{50}$ (uM) |
|---|---|---|
| B2 | 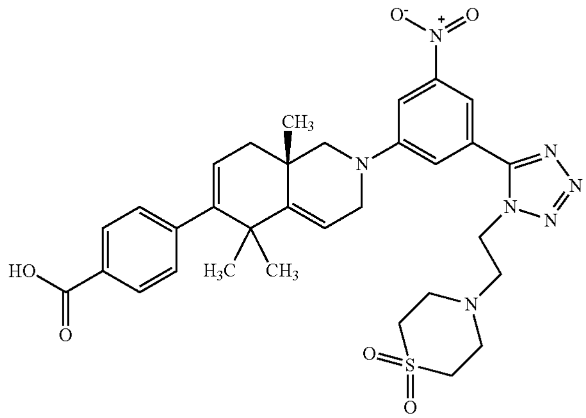 [SMILES: CC1(C)C(c2ccc(C(=O)O)cc2)=CC[C@]2(C)CN(c3cc(-c4nnnn4CCN4CCS(=O)(=O)CC4)cc([N+](=O)[O-])c3)CC=C12] | 0.760 |
| B3 | 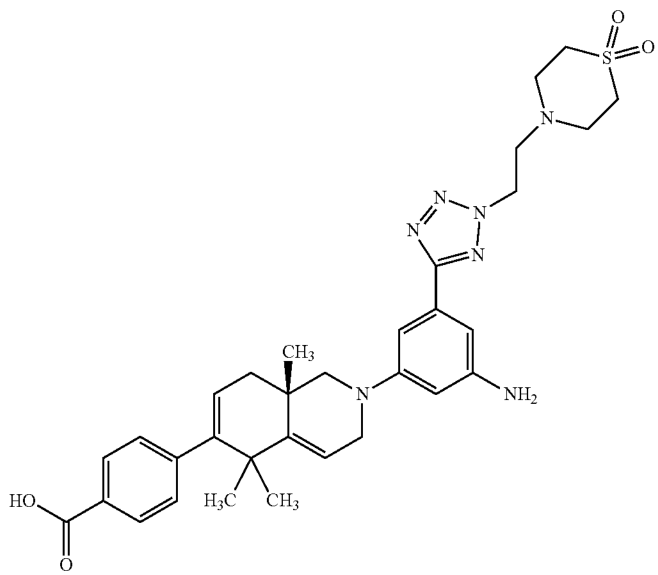 [SMILES: CC1(C)C(c2ccc(C(=O)O)cc2)=CC[C@]2(C)CN(c3cc(N)cc(-c4nnn(CCN5CCS(=O)(=O)CC5)n4)c3)CC=C12] | C |
| B4 | 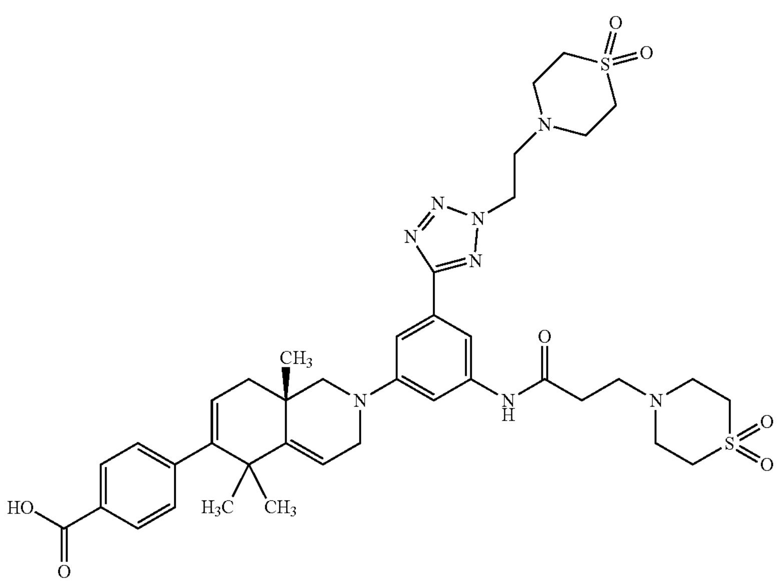 [SMILES: CC1(C)C(c2ccc(C(=O)O)cc2)=CC[C@]2(C)CN(c3cc(NC(=O)CCN4CCS(=O)(=O)CC4)cc(-c4nnn(CCN5CCS(=O)(=O)CC5)n4)c3)CC=C12] | 1.702 |

TABLE 17-continued
Biological data
| Ex | Structure | 10% FBS EC$_{50}$ (uM) |
|---|---|---|
| B5 | 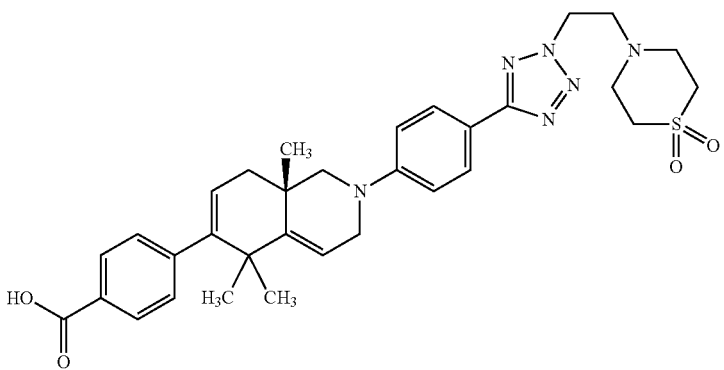 [SMILES: CC1(C)C(c2ccc(C(=O)O)cc2)=CC[C@]2(C)CN(c3ccc(-c4nnn(CCN5CCS(=O)(=O)CC5)n4)cc3)CC=C12] | C |
| B6 | 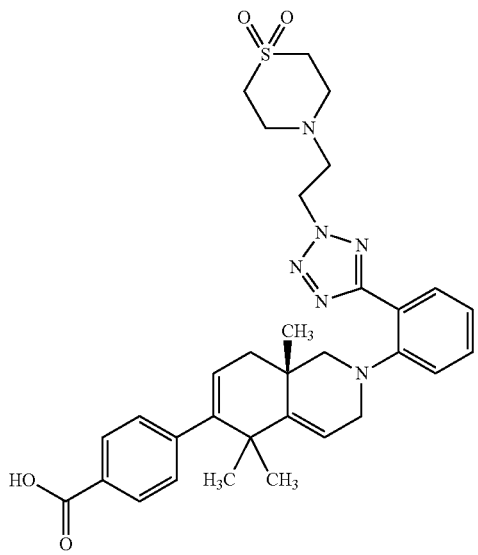 [SMILES: CC1(C)C(c2ccc(C(=O)O)cc2)=CC[C@]2(C)CN(c3ccccc3-c3nnn(CCN4CCS(=O)(=O)CC4)n3)CC=C12] | 0.045 |
| B7 | 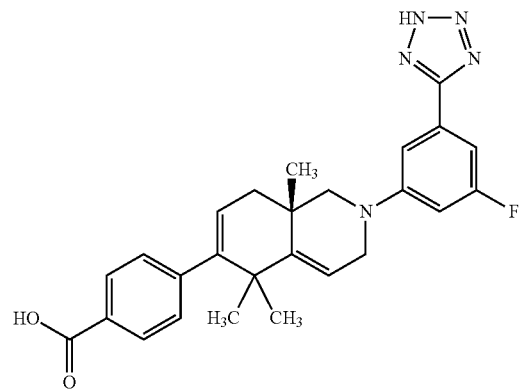 [SMILES: CC1(C)C(c2ccc(C(=O)O)cc2)=CC[C@]2(C)CN(c3cc(F)cc(-c4nn[nH]n4)c3)CC=C12] | C |

TABLE 17-continued
Biological data
| Ex | Structure | 10% FBS EC$_{50}$ (uM) |
|---|---|---|
| B8 | 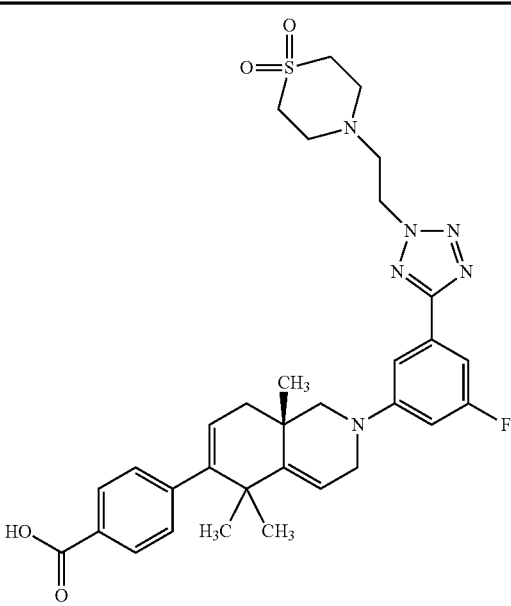 | A |
| B9 | 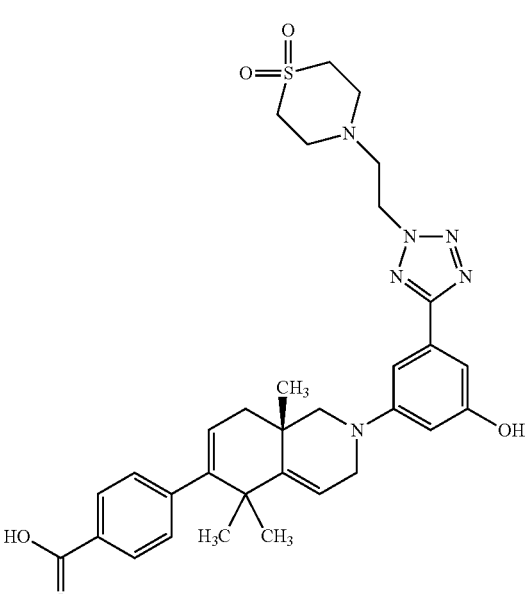 | 1.17 |
| B10 | 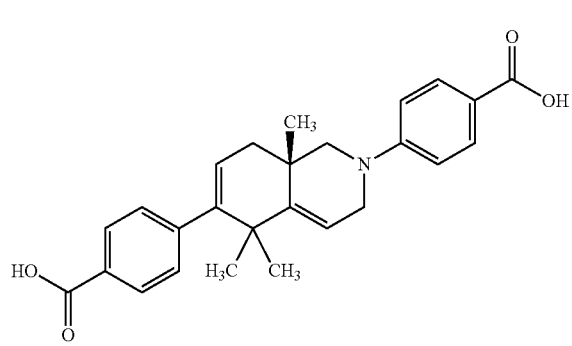 [SMILES: CC1(C)C(c2ccc(C(=O)O)cc2)=CC[C@]2(C)CN(c3ccc(C(=O)O)cc3)CC=C12] | C |

TABLE 17-continued
| | Biological data | |
|---|---|---|
| Ex | Structure | 10% FBS EC$_{50}$ (uM) |
| B11 | 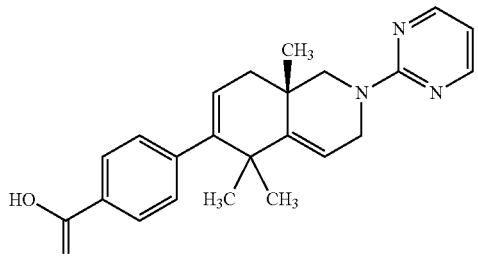 | C |
| B12 | 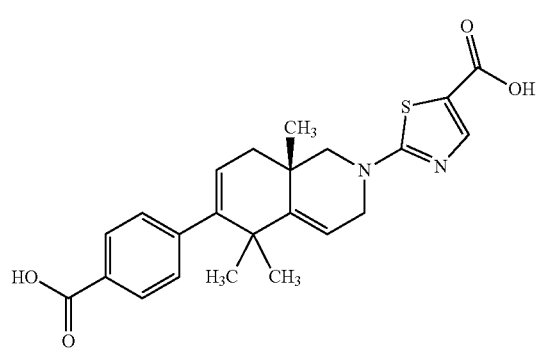 [SMILES: CC1(C)C(c2ccc(C(=O)O)cc2)=CC[C@]2(C)CN(c3ncc(C(=O)O)s3)CC=C12] | C |
| B13 | 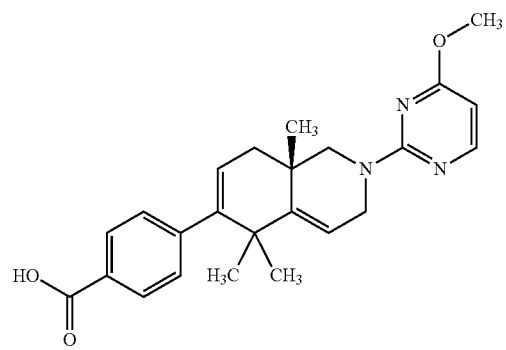 [SMILES: COc1ccnc(N2CC=C3C(C)(C)C(c4ccc(C(=O)O)cc4)=CC[C@]3(C)C2)n1] | 2.7 |
| B14 | 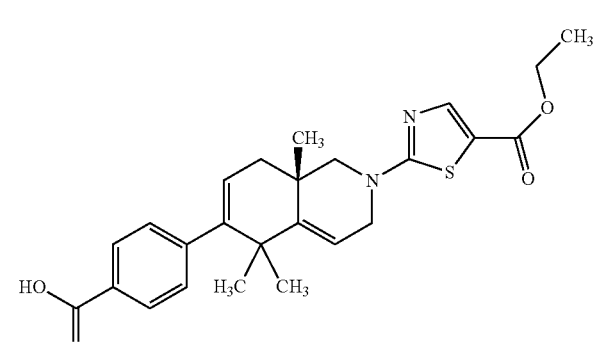 | B |

TABLE 17-continued

| | Biological data | |
|---|---|---|
| Ex | Structure | 10% FBS EC$_{50}$ (uM) |
| B15 | | C |
| B16 | | 1.478 |
| B17 | | C |
| C1 | | C |

TABLE 17-continued

| | Biological data | |
|---|---|---|
| Ex | Structure | 10% FBS EC$_{50}$ (uM) |
| C2 | | C |
| C3 | | 0.1504 |
| C4 | | >3 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:
1. A compound of Formula X:

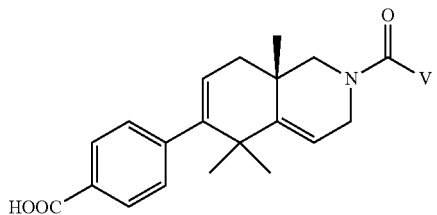

Formula X or a pharmaceutically acceptable salt thereof wherein;
V is selected from —$C_{1-6}$alkyl, -substituted $C_{1-6}$alkyl, —$C_{3-16}$ carbocycle, -substituted $C_{3-16}$ carbocycle, —$C_{3-16}$ heterocycle, -substituted $C_{3-16}$ heterocycle, -aryl, -substituted aryl, -heteroaryl, -substituted heteroaryl,
wherein said carbocycles, heterocycles, aryls, and heteroaryls defined herein for V are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —$NO_2$, —CN, —$C_{1-6}$ alkyl, —$C_{1-6}$ alkoxy, —$OQ_1$, —$CF_3$, —$COOR_2$, —$NR_3R_4$; —COR, —COOR, —$SO_2$, —$SO_2NR_3R_4$, and —$C_{1-6}$ alkyl$Q_1$, —$C_{1-6}$ alkyl-CO—$C_{1-6}$ alkyl $Q_1$, —$C_{1-6}$ alkyl-$NR_3$—$C_{1-6}$ alkyl $Q_1$, —$C_{1-6}$ alkyl-$SO_2C_{1-6}$ alkyl $Q_1$, —$C_{1-6}$ alkyl-$SO_2NR_3$— $C_{1-6}$ alkyl $Q_1$, —$C_{1-6}$ alkyl-$NR_3SO_2$— $C_{1-6}$ alkyl $Q_1$, —$C_{1-6}$ alkyl-$NR_3CO$— $C_{1-6}$ alkyl $Q_1$, —$C_{1-6}$ alkyl-$CONR_3$— $C_{1-6}$ alkyl $Q_1$, —$C_{2-6}$ alkyl-O— $C_{1-6}$ alkyl $Q_1$;
$Q_1$ is selected from $C_{3-16}$ carbocycle, substituted $C_{3-16}$ carbocycle, $C_{3-16}$ heterocycle, substituted $C_{3-16}$ heterocycle, aryl, substituted aryl, heteroaryl, substituted heteroaryl wherein said carbocycles, heterocycles, aryls, and heteroaryls are further selected from monocyclic, bicyclic, and tricyclic systems, wherein the bicyclic and tricyclic systems are further selected from fused, non-fused, and spiro systems and wherein said substituents are further selected from —H, -halo, -hydroxyl, —$NO_2$, —CN, —$C_{1-6}$ alkyl, —$C_{1-6}$ alkoxy, —$CF_3$, —$COOR_2$, —$NR_3R_4$; —COR, —COOR, —$SO_2$, and —$SO_2NR_3R_4$;
and $R_3$ and $R_4$ are independently selected from —H, —$C_{1-6}$ alkyl, —$C_{1-6}$ substituted alkyl, aryl, heteroaryl, substituted aryl, substituted heteroaryl, and —$COOR_2$;
alternatively $R_3$ and $R_4$ are taken together with the adjacent N to form a cycle selected from:

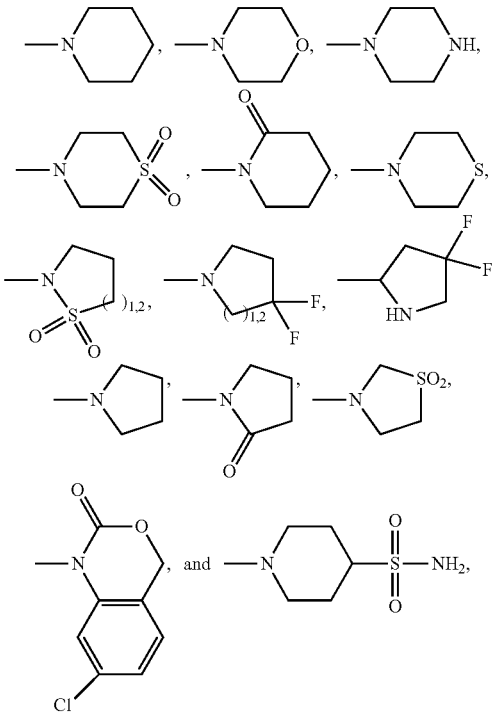

with the proviso that only one of $R_3$ or $R_4$ can be —$COOR_2$.

2. A pharmaceutical composition comprising a compound or salt of claim 1 and a pharmaceutically acceptable carrier.

3. The composition of claim 2 further comprising at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

4. The composition of claim 3 wherein the other agent is dolutegravir.

5. A method for treating HIV infection comprising administering a compound of claim 1, or a pharmaceutically acceptable salt thereof, to a patient in need thereof.

6. The method of claim 5 further comprising administering at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

7. The method of claim 6 wherein the other agent is dolutegravir.

8. The method of claim 6 wherein the other agent is administered to the patient prior to, simultaneously with, or subsequently to the compound of claim 1.

* * * * *